United States Patent
Kazlauskas et al.

(10) Patent No.: US 6,667,173 B2
(45) Date of Patent: Dec. 23, 2003

(54) NUCLEIC ACIDS ENCODING PLATELET DERIVED GROWTH FACTOR-ALPHA RECEPTORS

(75) Inventors: Andrius Kazlauskas, Winchester, MA (US); Yasushi Ikuno, Suita Osaka (JP)

(73) Assignee: The Schepens Eye Research Institute, Boston, MA (US)

( * ) Notice: Subject to any disclaimer, the term of this patent is extended or adjusted under 35 U.S.C. 154(b) by 0 days.

(21) Appl. No.: 09/866,510

(22) Filed: May 25, 2001

(65) Prior Publication Data

US 2002/0111304 A1 Aug. 15, 2002

Related U.S. Application Data

(60) Provisional application No. 60/250,747, filed on Dec. 1, 2000, and provisional application No. 60/289,103, filed on May 7, 2001.

(51) Int. Cl.⁷ .......................... C12N 15/11; C12N 15/12; C12N 15/63

(52) U.S. Cl. ................................. 435/320.1; 536/23.1

(58) Field of Search ................. 536/23.1; 435/69.1, 435/320.1

(56) References Cited

U.S. PATENT DOCUMENTS

| | | |
|---|---|---|
| 5,268,358 A | 12/1993 | Fretto |
| 5,371,205 A | 12/1994 | Kelly et al. |
| 5,444,151 A | 8/1995 | Vassbotn et al. |
| 5,686,572 A | 11/1997 | Wolf et al. |

OTHER PUBLICATIONS

Omura et al., 1997, J. Biol. Vhem. 272:12676–12682.*
Balciunaite et al. (2000), *PDGF Initiates Two Distinct Phases of protein Kinase C Activity That Make Unequal Contributions to the G0 to S Transition*, Curr. Biol. 10:261.
Ikuno et al. (2000), *Attenuation of Experimental Proliferative Vitreoretinopathy by Inhibiting the Platelet–Derived Growth Factor Receptor*, Invest. Ophthal. & Visual Sci. 41(10):3107.
Bae et al. (2000), *Platelet–Derived Growth Factor–Induced $H_2O_2$ Production Requires the Activation of Phosphatidylinositol 3–Kinase*, J. Biol. Chem. 275(14):10527.
Schlesinger et al. (1999), *Platelet–Derived Growth Factor–Dependent Association of the GTPase–Activating Protein of Ras and Src*, Biochem. J. 344:519.
Andrews et al. (1999), *Platelet–Derived Growth Factor Plays a Key Role in Proliferative Vitreoretinopathy*, Invest. Ophthal. & Visual Sci. 40(11):2683.
.DeMali et al. (1999), *Integrins Enhance Platelet–Derived Growth Factor (PDGF)–Dependent Responses By Altering The Signal Relay Enzymes That Are Recruited to the PDGFβ Receptor*, J. Biol. Chem 274(28):19551.

Montmayeur et al. (1977), *The Platelet–Derived Growth Factor β Receptor Triggers Multiple Cytoplasmic Signaling Cascades That Arrive at the Nucleus as Distinguished Inputs*, J. Biol. Chem. 272(51):32670.
Bazenet et al. (1996), *Phosphorylation of Tyrosine 720 in the Platelet–Derived Growth Factor α Receptor is Required for Binding of Grb2 and SHP–2 but Not for Activation of Ras or Cell Proliferation*, Molec. & Cell. Biol. 16(12):6926.
DeMali et al. (1997), *Platelet–Derived Growth Factor–Dependent Cellular Transformation Requires Either Phospholipase CY or Phosphatidylinositol 3 Kinase*, J. Biol. Chem. 272(14):9011.
Rosenkranz et al. (2000), *Src Family Kinases Negatively Regulate Platelet–Derived Growth Factor α Receptor–Dependent Signaling and Disease Progression*, J. Biol. Chem. 275(13):9620.
Pastor (1998), *Proliferative Vitreoretinopathy: An Overview*, Survey of Ophthal. 43(1):3.
Grinnell, et al. (1999), *Differences in the Regulation of Fibroblast Contraction of Floating Versus Stressed Collagen Matrices*, J. Biol. Chem. 274(2):918.
Grisanti et al. (1996), *Kontraktion Extrazellularer Matrix Durch Transdifferenzierte Retinale Pigmentepithelzellen: Induktoren und Inhibitoren*, Opthalmologe 93:709.
Skuta et al. (1999), *Increased Myosin Light Chain Phosphorylation is not Required for Growth Factor Stimulation of Collagen Matrix Contraction*, J. Biol. Chem. 274(42):30163.
Rayan et al. (1996), *Pharmacologic Regulation of Dupuytren's Fibroblast Contract in Vitro*, J. of Hand Surgery 21A(6):1065.
Yang et al. (1996), *Inhibition of Retinal Pigment Epithelial Cell–Induced Tractional Retinal Detachment by Disintegrins, a Group of Arg–GLY–Asp–Containing Peptides From Viper Venom*, Invest. Ophthal. & Vis. Sci. 37(5):843.

(List continued on next page.)

*Primary Examiner*—Elizabeth Kemmerer
(74) *Attorney, Agent, or Firm*—Foley Hoag LLP; Isabelle M. Clause; Laurent T. Knapp

(57) ABSTRACT

The invention provides methods and compositions for treating diseases and conditions, which are associated with an abnormal PDGF level or response, such as cell proliferation, cell migration, extracellular matrix synthesis and secretion, and cell contraction. Exemplary diseases or disorders include cell proliferative diseases and fibrotic diseases. Exemplary fibrotic diseases include those resulting from a wound healing process, such as excessive scarring and PVR. Generally, the method comprise administering to a subject in need thereof a pharmaceutically efficient amount of a nucleic acid encoding a mutated PDGFR. The invention further provides gel contraction assays for identifying compounds for treating or preventing the development of diseases involving cell contraction, e.g., fibrotic diseases.

40 Claims, 15 Drawing Sheets

OTHER PUBLICATIONS

Hunt et al. (1994), *Cytokines and Serum Cause $\alpha_2\beta_1$ Integrin–Mediated Contraction of Collagen Gels by Cultured Retinal Pigment Epithelial Cells*, Invest. Ophthal. & Vis. Sci. 35(3):955.

Yang et al. (1997), *Inhibition of RPE Cell–Mediated Matrix Adhesion and Collagen Gel Contraction by Crovidisin, a Collagen–Binding Snake Venom Protein*, Curr. Eye Res. 16(11):1119.

Heldin (1992), *Structural and Functional Studies on Platelet–Derived Growth Factor*, The Embo J. 11(12):4251.

Ikuno et al. (2000), *Attenuation of Experimental Proliferative Vitreoretinopathy by Inihibiting the Platelet–Derived Growth Factor Receptor*, Invest. Ophthal. & Vis. Sci. 41(10):3107.

Matsui et al. (1989), *Isolation of a Novel Receptor cDNA Establishes the Existence of Two PDGF Receptor Genes*, Science 243:800.

Kelly et al. (1991), *Platelet–Derived Growth Factor (PDGF) Stimulates PDGF Receptor Subunit Dimerization and Intersubunit Trans–Phosphorylation*, J. of Biol. Chem. 266(14):8987.

Gronwald et al. (1988), *Cloning and Expression of a cDNA Coding for the Human Platelet–Derived Growth Factor Receptor: Evidence for More Than One Receptor Class*, Proc. Natl. Acad. Sci. USA 85:3435.

Ataliatis et al. (1995), *PDGF Signaling is Required for Gastrulation of Xenopus Laevis*, Development 121:3099.

Ueno et al. (1991), *Inhibition of PDGF β Receptor Signal Transduction by Coexpression of a Truncated Receptor*, Science 252:844.

Alimandi et al. (1997), *PLC–Gamma Activation is Required for PDGF–betaR–Mediated Mitogenesis and Monocytic Differentiation of Myeloid Progenitor Cells*, Oncogene 15(5):585.

Rosenkranz et al. (1999), *Evidence for Distinct Signaling Properties and Biological Responses Induced by the PDGF Receptor Alpha and Beta Subtypes*, Growth Factors 16(3):201.

Jones et al. (1999), *PDGF Induces an Early and a Late Wave of PI 3–Kinase Activity, and Only the Late Wave is Required for Progression Through G1*, Curr. Biol. 9(10):512.

Lashkari et al (1999), *Hepatocyte Growth Factor Receptor in Human RPE Cells: Implications in Proliferative Vitreoretinopathy*, Invest. Ophthalmol. 40(1):149.

Olivera et al. (1999), *Platelet–Derived Growth Factor–Induced Activation of Sphingosine Kinase Phosphorylation of the PDGF Receptor Tyrosine Residue Responsible for Binding of PCLY*, The Faseb J. 13:1593.

Rosenkrantz et al. (1999), *Identification of the Receptor–Associated Signaling Enzymes that are Required for Platelet–Derived Growth Factor–AA–Dependent Chemotaxis and DNA Synthesis*, J. Biol. Chem. 274(40):28335.

Rosenkrantz et al. (1999), *Pathophysiologic Significance of Growth Factors and New Therapeutic Concepts in Cardiovascular Disease*, Med. Klin. 94(9):496.

Bernard et al. (1999), *Phosphospecific Antibodies Reveal Temporal Regulation of Platelet–Derived Growth Factor Beta Receptor Signaling*, Exp. Cell Res. 253(2):704.

DeMali et al. (1999), *Multiple Roles for Src in a PDGF–Stimulated Cell*, Exp. Cell. Res. 253(1):271.

Lin et al. (1995), *Treatment of Human Fibroblasts with Vanadate and Platelet–Derived Growth factor in the Presence of Serum Inhibits Collagen Matrix Contraction*, Exp. Cell Res. 221(1):73.

Lin et al. (1997), *Fibroblasts Contracting Matrices Form Transient Plasma Membrane Passages Through Which the Cells Take Up Fluorescein Isothiocyanate–Dextran and Ca2+*, Molecular Biol. of the Cell, 8(1):59.

\* cited by examiner

NUCLEIC ACIDS ENCODING PLATELET DERIVED GROWTH FACTOR-ALPHA RECEPTORS

CROSS-REFERENCE TO RELATED APPLICATIONS

This application claims the benefit of U.S. Provisional Applications No. 60/250,747, filed Dec. 1, 2000 and No. 60/289,103, filed May 7, 2001, the contents of which is specifically incorporated herein.

BACKGROUND OF THE INVENTION

Fibrosis, the formation of excessive amounts of fibrotic or scar tissue, is a central issue in medicine. Scar tissue blocks arteries, immobilizes joints and damages internal organs, wreaking havoc on the body's ability to maintain vital functions. Every year, about 1.3 million people are hospitalized due to the damaging effects of fibrosis, yet doctors have few therapeutics to help them control this dangerous condition. As a result, they often see patients crippled, disfigured or killed by unwanted masses of uncontrollable scars.

Fibrosis can follow surgery in the form of adhesions, keloid tumors or hypertrophic (very severe) scarring. Fibrosis causes contractures and joint dislocation following severe burns, wounds or orthopaedic injuries; it can occur in any organ and accompanies many disease states, such as hepatitis (liver cirrhosis), hypertension (heart failure), tuberculosis (pulmonary fibrosis), scleroderma (fibrotic skin and internal organs), diabetes (nephropathy) and atherosclerosis (fibrotic blood vessels).

Ironically, the very process designed to repair the body can lead to dangerous complications. Like epoxy, scar tissue serves only a structural role. It fills in the gaps, but cannot contribute to the function of the organ in which it appears. For example, as fibrotic scar tissue replaces heart muscle damaged by hypertension, the heart becomes less elastic and thus less able to do its job. Similarly, pulmonary fibrosis causes the lungs to stiffen and decrease in size, a condition that can become life-threatening. Fibrotic growth can also proliferate and invade the healthy tissue that surrounds it even after the original injury heals. Too much scar tissue thus causes physiological roadblocks that disfigure, cripple or kill.

In most cases, fibrosis is a reactive process, and several different factors can apparently modulate the pathways leading to tissue fibrosis. Such factors include the early inflammatory responses, local increase in fibroblast cell populations, modulation of the synthetic function of fibroblasts, and altered regulation of the biosynthesis and degradation of collagen.

One treatment approach, therefore, has been to target the early inflammatory response. Treatment with topical corticosteroids has achieved limited success, if used early in fibrosis. However, steroid therapy has little or no effect once scar tissue has already formed. Furthermore, prolonged administration of hydrocortisone, in pulmonary fibrotic disease for example, may actually worsen the condition.

The second approach involves slowing the proliferation of those cells responsible for the increased collagen synthesis. Generally, this involves fibroblast cells, except in the vasculature where smooth muscle cells are responsible for collagen deposition. Compounds that have been used to inhibit fibroblast proliferation include benzoic hydrazide, as taught by U.S. Pat. No. 5,374,660. Benzoic hydrazide has been shown to suppress collagen synthesis and fibroblast proliferation, at least in tissue culture cells. U.S. Pat. No. 5,358,959 teaches the use of imidazole derivatives to inhibit the growth of fibroblasts by blocking the calcium-activated potassium channel. This particular agent also inhibits the proliferation of endothelial cells and vascular smooth muscle cells.

Likewise, a number of agents which affect smooth muscle cell proliferation have been tested. These compositions have included heparin, coumarin, aspirin, fish oils, calcium antagonists, steroids, prostacyclin, rapamycin, dipyridamole, ultraviolet irradiation, gamma (.gamma.)-interferon, serotonin inhibitors, methotrexate and mycophenolic acid, either alone or in various combinations.

A number of treatments have been devised that are based on the modulation of the synthetic function of fibroblast or smooth muscle cells. Like most cells, fibroblasts and smooth muscles cells are modulated by cytokines (factors secreted in response to infection that modify the function of target cells). Gamma interferon is a lymphokine (a cytokine that is produced by lymphocytes) known to inhibit fibroblast proliferation and collagen synthesis. Likewise, the monokine (a cytokine that is produced by macrophages) beta-interferon serves the same function. Thus, U.S. Pat. No. 5,312,621 teaches the use of these cytokines in the treatment of fibrosis. Similarly, certain cytokines have been tested for their effect on the proliferation and stimulation of collagen synthesis in smooth muscle cells. For example, U.S. Pat. No. 5,268,358 is directed to the use of peptides that block the binding of platelet-derived growth factors to their receptors. U.S. Pat. No. 5,304,541 is directed to chimeric transforming growth factor-beta (TGF-.beta.) peptides which block cell proliferation. U.S. Pat. No. 5,308,622 is directed to conjugates comprising fibroblastic growth factor (FGF) and cytotoxic agents. U.S. Pat. No. 5,326,559 is directed to interleukin-2 targeted molecules. Although promising, many of these agents and compositions have known and serious side effects and, consequently, limited effectiveness.

The final treatment strategy involves directly influencing the metabolism of collagen and the other components of fibrotic tissue. Thus, drugs that interfere with the biosynthesis, accumulation and catabolism of collagen have been used in the treatment of fibrosis. Many drugs are used to inhibit collagen synthesis, including derivatives of pyridone, alkadiene, benzoquinone, pyridine, oxalylamino acid and proline analogs. However, all of these drugs suffer from the drawback of also inhibiting the normal, and required, synthesis of collagen as well as the detrimental synthesis that occurs during fibrosis.

One of the most important pathologies for which fibrosis is a contributing factor is cardiovascular disease. Cardiovascular disease is the leading cause of death in the Western world. In the United States it accounted for 930,000 deaths in 1990. There are an estimated 1.5 million heart attacks per year in the U.S. that result in more than 500,000 deaths annually.

Another fibrotic disease is proliferative vitreoretinopathy (PVR), which is characterized by the formation of a membrane in front and/or behind the retina, which is composed of ECM and cells. Some of the events thought to contribute to pathogenesis include migration of the retinal pigment epithelial (RPE) cells and retinal glial cells (Muller cells), and synthesis of extracellular molecules such as collagen. Pastor, J. C. (1998) *Surv. Ophthalmol.* 43:3. Extracellular matrix (ECM) components such as collagen bind to cells via integrins such as $\alpha 2\beta 1$, and this interaction is likely to be integral to contraction. Schiro, J. A. et al. (1991) *Cell* 67:403; Gullberg, D. A. et al. (1990) *Exp. Cell Res.* 186:264. The typical PVR membrane is mainly composed of collagen I, II, and III, Jerdan, J. A. et al. (1989) *Ophthalmology* 96:801, and is found on the inner or outer surface of the retina, or along the posterior portion of the vitreous, Michels, R. G. et al. (1990) *Retinal Detachment* 1990:669.

Contraction of the epiretinal membrane results in tractional retinal detachment (TRD). Michels, R. G. et al. (1990) *Retinal Detachment* 1990:669; Pastor, J. C. (1998) *Surv. Opthalmol.* 43:3. Once the retina loses its functional contact with the underlying layer of retinal pigment epithelial (RPE) cells, it is irreversibly damaged due to apoptosis of the photoreceptors. Berglin, L. et al. (1997) *Graefes Arch. Clin. Exp. Ophthalmol.* 235:306; Cook, B. et al. (1995) *Invest. Ophthalmol. Vis. Sci.* 36:990. PVR occurs in up to 10% of patients undergoing surgery to reattach the retina. The Retina Society Terminology Committee (1983) *Opthalmology* 90:121. The prognosis for an individual afflicted by PVR is generally poor, and 20 to 40% of the patients lose their vision despite additional retinal reattachment surgeries. Michels, R. G. et al. (1990) *Retinal Detachment* 1990:669.

Growth factors such as transforming growth factor-β (TGF-β), Connor, T. B. et al. (1989) *J. Clin. Invest.* 83:1661; Kon, C. H. et al. (1999) *Invest. Ophthalmol. Vis. Sci.* 40:705, and platelet-derived growth factor (PDGF), Robbins, S. G. et al. (1994) *Invest. Ophthalmol. Vis. Sci.* 35:3649; Campochiaro, P. A. et al. (1985) *Arch. Ophthalmol.* 103:576; Campochiaro, P. A. et al. (1994) *J. Cell Sci.* 107:2459; Cassidy, L. et al (1998) *Br. J. Ophthalmol.* 82:181; Garcia-Layana, A. et al. (1997) *Curr. Eye Res.* 16:556, are believed to play an important role in promoting the events which contribute to fibrotic diseases, such as PVR. Other growth factors, such as hepatocyte growth factor (HGF), Lashkari, K. et al. (1999) *Invest. Ophthalmol. Vis. Sci.* 40:149, basic fibroblast growth factor (bFGF), or interleukin-6 (IL-6), Kon, C. H. et al. (1999) *Invest. Ophthalmol. Vis. Sci.* 40:705; Cassidy, L. et al. (1998) *Br. J. Ophthalmol.* 82:181, have also been implicated.

PDGF is a potent mitogen for fibroblasts, and induces DNA synthesis, chemotaxis, and sometimes serves as a survival factor. Two PDGF gene have been identified, and they encode the PDGF-A and PDGF-B chain. Biologically active PDGF is either a homo- or heterodimer, therefore there are three kinds of combinations, PDGF-AA, -AB, and -BB. The receptor for PDGF is a homo- or heterodimer of the α and β subunits. The receptor subunits differ in their affinity for ligand, and hence the composition of receptor subunits is in part dependent on the isoform of PDGF. For instance, PDGF-AA only binds to αα homodimer, -AB to αα homo- or αβ heterodimer, and -BB binds to any subunit combination. In the studies described herein, we focus on the PDGF α receptor (αPDGFR), which is a homodimer of the α subunits, and can be assembled by any of the three PDGF isoforms. PDGF dimerizes the αPDGFR, leading to activation of the receptor's tyrosine activity, which is encoded in the intracellular domain of the receptor. Activation of the receptor's kinase as a prerequisite for subsequent signal relay and biological responses, such as cell migration, proliferation, synthesis and secretion of ECM, as well as contraction. The αPDGFR can be activated by any of the PDGF isoforms (AA, AB, BB), including the newly discovered PDGF-CC isoform. Li, X. et al. (2000) *Nat. Cell Biol.* 2:302. Ligand binding activates the receptor, whereupon it becomes tyrosine phosphorylated and associates with a variety of SH2 domain-containing signaling enzymes. These include Src family kinases, the phosphotyrosine phosphatase SHP-2, phosphoinositide 3-kinase (PI3K), and phospholipase C-γ1 (PLCγ). These signaling enzymes are required to mediate PDGF-dependent cellular responses, and different pathways seem to be involved in different biological reactions. For instance, PI3K is required to drive cells into S phase, whereas the combination of Src family kinase, PI3K, and PLCγ are necessary for PDGF-dependent chemotaxis. Rosenkranz, S. et al. (1999) *J. Biol. Chem.* 274:28335.

Thus, it is desirable to have efficient agents for treating fibrotic diseases, such as PVR, as well as methods for identifying agents for treating fibrotic diseases.

SUMMARY OF THE INVENTION

In one embodiment, the invention provides methods and compositions for treating or preventing diseases that are associated with an abnormal PDGF level or PDGF-indcued biological response, such as cell proliferation, cell migration, extracellular matrix synthesis or secretion, and cell contraction. In a preferred embodiment, the invention provides methods and compositions for treating or preventing proliferative diseases, such as fibrotic diseases, e.g., proliferative vitreoretinopath (PVR), liver cirrhosis, pulmonary fibrosis, kidney fibrosis, scleroderma, keloids, hypertrophic scars, skin wound healing and atherosclerosis. The method preferably includes administering to a subject in need thereof, an amount of an agent sufficient to reduce a biological activity of PDGF. For example, the agent may inhibit receptor tyrosine kinases, e.g., platelet derived growth factor receptor (PDGFR). In an even more preferred embodiment, the agent inhibits at least part of the signal transduction from the αPDGFR. For example, the agent inhibits activation of a Src family kinase, e.g., phosphoinositide 3-kinase (PI3K) and phospholipase C-γ1 (PLCγ).

The agent for use in the methods of the invention can be a compound which inhibits receptor tyrosine kinases, e.g., PDGFRs. A preferred agent is a compound which prevents at least part of the signal transduction from such a receptor. The agent can be a small molecule, a peptide, or a nucleic acid. A preferred agent is a mutated form of a receptor tyrosine kinase, which acts, e.g., by competition with the wildtype receptor. Even more preferred agents are mutants of αPDGFR or βPDGFR, such as those further described herein. Other agents that can be used include ligands which compete with the naturally occurring ligand, e.g., with PDGF.

The agents can be administered together with a pharmaceutical carrier or excipient. In a preferred embodiment, the agent is administered locally to a subject in need thereof, e.g., in the eye in the case of proliferative vitreoretinopathy.

If the agent is a peptide or protein, e.g., a mutant of αPDGFR, the agent can be administered to a subject as a nucleic acid encoding the peptide or protein. The nucleic acid can be administered as naked DNA, or it can be combined with an agent facilitating its delivery, e.g., liposomes. A preferred method of administering a nucleic acid is by administering a viral vector containing the nucleic acid. The viral vector can be, e.g., an adenovirus, an adenovirus-associated virus (AAV), a herpes virus, a papillomavirus, or a retrovirus. In a preferred embodiment, a viral vector encoding a truncated αPDGFR is administered to a subject having or being likely to develop, a fibrotic disease.

In some embodiments, it may be desirable to target the agent or the vector encoding the agent to a specific tissue, e.g., retina. This can be acccomplished by various means, e.g., by using a viral vector that is specific for the desired target tissue. Alternatively, the viral vector or liposome or other carrier can be modified to express on its surface a molecule that will interact with a molecule on the surface of the target tissue.

The agents for use in the methods are also within the scope of the invention. Preferred agents include mutant αPDGFRs and mutant βPDGFRs and nucleic acids encoding such. For example, the invention provides polypeptides comprising an amino acid sequence having the general structure X-Y-Z, wherein Y consists of a portion of platelet derived growth factor-alpha receptor (PDGFαR) consisting essentially of amino acids 1 to about 589; amino acids 21 to about 589; or amino acids 25 to about 589 of SEQ ID NO: 2; X and Z consist of at least one amino acid, wherein, if Z is more than one amino acid, Z does not have the amino acid sequence of human PDGFαR located downstream of about amino acid 589. Y can also be amino acids 1 to about 561 of SEQ ID NO: 25 (beta PDGFR). In one embodiment, X and Z are absent. In another embodiment, the invention provides polypeptides consisting essentially of, comprising or consisting of, the amino acid sequence set forth in SEQ ID NO: 4, 6, 8, or 10 (PDGFRalpha mutants) or SEQ ID NO: 16, 18, 20, 22, or 24 (PDGFR beta mutants). These polypeptides may lack the signal peptide.

Other preferred agents of the invention are nucleic acids encoding a mutant PDGFR polypeptide, e.g., nucleic acids comprising or consisting of the nucleotide sequence set forth in SEQ ID NO: 3, 5, 7, 9, 15, 17, 19, 21 and 23. These nucleic acids are preferably operably linked to at least one transcriptional regulatory element, and may be part of a vector. The invention further provides pharmaceutical compositions including a nucleic acid or polypeptide of the invention, and methods for preparing such pharmaceutical compositions.

The invention further provides assays for identifying agents which can be used to treat fibrotic diseases and/or diseases associated with an abnormal contraction of cells. In a preferred embodiment, the assay comprises contacting cells, e.g., fibroblasts, with an agent and determining whether the cells contracted. In an even more preferred embodiment, the cells and the agent are suspended in a matrix, e.g., a collagen matrix. It has been shown herein that use of this in vitro assay correlates with in vivo tests of activity of compounds.

11) in response to PDGF-BB. The correlation between PDGF-dependent contraction and the PVR score was of borderline significance (P=0.0512).

Figure 14:
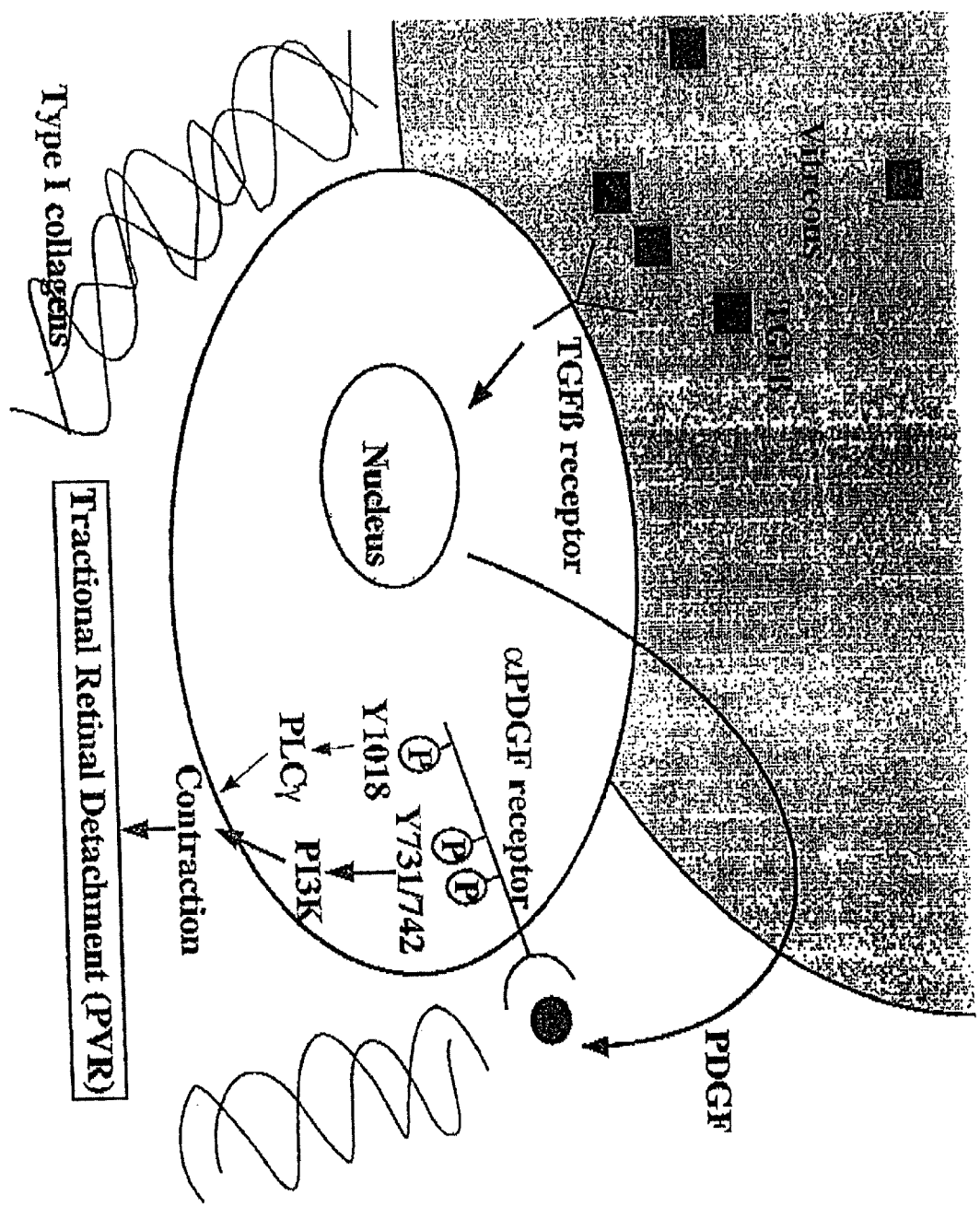

FIG. 14 shows a model for the relationship between TGFβ and αPDGFR-driven PVR.

DETAILED DESCRIPTION OF THE INVENTION

General

The invention is based at least in part on the observation that mutated PDGFR polypeptides can inhibit the development of PVR in an animal model of PVR. This inhibitory effect occurs even in the presence of wild type receptors. Thus, expression of such mutated PDGFR polypeptides can inhibit the development or progression of diseases associated with an abnormal PDGF level or response, such as fibrotic diseases, of which PVR is one example. The invention is also based on the demonstration that PLCγ and PI3K are involved in the development of PVR. The invention is also based on the development of a gel contraction assay and the observation that there is a strong correlation between the ability of test compounds to prevent cell contraction is the gel contraction assay and their ability to prevent PVR. It has also been shown that cell lines, as opposed to primary cell cultures can be used for this assay.

Accordingly, in one embodiment, the invention provides methods and compositions for treating diseases and conditions, which are associated with an abnormal PDGF level or response, such as cell proliferation, cell migration, extracellular matrix synthesis and secretion, and cell contraction. Exemplary diseases or disorders include cell proliferative diseases and fibrotic diseases. Exemplary fibrotic diseases include those resulting from a wound healing process, such as excessive scarring and PVR. Generally, the method comprise administering to a subject in need thereof a pharmaceutically efficient amount of a compound which inhibits a PDGF-induced biological response, such as cell proliferation, cell migration, extracellular matrix synthesis and secretion, and cell contraction, such that at least certain symptoms of the disease have ameliorated. For example, a compound is injected into the eye of a subject having PVR, such that PVR is prevented or treated.

In one embodiment of the invention, the compositions of the invention comprise a mutated PDGFR polypeptide, e.g., a mutated αPDGFR polypeptide. The mutated polypeptide can be a truncated receptor or a receptor having a mutation in one or more amino acids. In a preferred embodiment, the compositions of the invention comprise a nucleic acid encoding a mutated PDGFR polypeptide. The nucleic acid is preferably operably linked to transcriptional regulatory elements, and may be part of a vector. Other compounds within the invention include those identified by the gel contraction assay described herein.

In yet another embodiment, the invention provides methods for treating or preventing fibrotic diseases, e.g., PVR, comprising contacting target cells with compounds that inhibit PLCγ and PI3K.

The invention further provides gel contraction assays for identifying compounds which prevent the development of fibrotic diseases. Generally, the assays comprise contacting cells with a test compound and a substance known to stimulate contaction of the cells and determining whether the contraction of the cells is inhibited or not in the presence of the test compound relative to the absence of the test compound.

Definitions

For convenience, the meaning of certain terms and phrases employed in the specification, examples, and appended claims are provided below. It is also to be understood that the terminology used herein is for the purpose of describing particular embodiments only and is not intended to be limiting.

It must be noted that, as used in the specification and the appended claims, the singular forms "a," "an" and "the" include plural referents unless the context clearly dictates otherwise. Thus, for example, reference to "a mutation" includes two or more such mutations, and the like.

The term "PDGFR" or "Platelet Derived Growth Factor Receptor" is used interchangeably herein with PDGFR chain" and refers to a polypeptide to which PDGF binds and causes the receptor or chain to associate with another receptor or chain. In a preferred embodiment, a PDGFR is αPDGFR having the amino acid sequence set forth in SEQ ID NO: 2 or βPDGFR having the amino acid sequence set forth in SEQ ID NO: 14. The term PDGFR also encompasses naturally occuring alleles of PDGFR. In certain situations, which should be obvious from the context, a PDGFR refers to a complex of two PDGFR chains.

The terms "PDGFR alpha", "αPDGFR", "PDGFRα", and "PDGFαR" are used interchangeably herein. The terms "PDGFR beta", "βPDGFR", "PDGFRβ", and "PDGFβR" are used interchangeably herein.

The term "mutated PDGFR chain" or "mutated PDGFR" refers to a PDGFR which contains at least one mutation. The mutated PDGFR, also referred to as "mutant" can be a truncation mutation, a dominant negative mutant, or a PDGFR in which one or more amino acids are substituted, deleted or added. When refering to a mutated receptor having two chains, a mutated receptor refers to a receptor in which at least one of the two chains contains at least one mutation.

"Cell proliferative disorders" refers to disorders wherein unwanted cell proliferation of one or more subste to fcells in a multicellular organism occurs resulting in harm or undesired esthetic results. Cell proliferative disorders include cancers, fibrotic diseases, and blood vessel proliferative diseases.

As used herein, the term "fibrosis" means those disorders or disease states that are caused by the abnormal deposition of scar tissue. Fibrosis includes, but is not limited to, cardiovascular fibrosis such as that associated with left ventricular hypertrophy, myocardial infarctions, and myocarditis. Fibrosis also includes all arteriosclerotic disorders. Fibrosis also includes pulmonary fibrosis, adult respiratory distress syndrome, inflammatory disorders, sclerodermas, cirrhosis, keloids, and hypertrophic scars.

A disease or disorder "associated with a defect in a PDGFR-mediated biological activity, such as proliferation, migration, contraction and extracellular matrix synthesis and secretion" refers generally to a disease or disorder, in which treatment according to the invention is beneficial. It is preferably a disease or disorder which is caused at least in part by an abnormal amount of PDGF or other molecule in the PDGF pathway, in particular an abnormally high amount of PDGF, or a defect in PDGF signaling.

"A therapeutically effective amount" of a compound is an amount which results in therapeutic effect in the subject to whom it was administered.

The term "PDGFR therapeutic" refers to a mutated PDGFR, or nucleic acid encoding such, having therapeutically beneficial effects, e.g., in the treatment or prevention of PVR.

A "delivery complex" shall mean a targeting means (e.g. a molecule that results in higher affinity binding of a gene, protein, polypeptide or peptide to a target cell surface and/or increased cellular or nuclear uptake by a target cell). Examples of targeting means include: sterols (e.g. cholesterol), lipids (e.g. a cationic lipid, virosome or liposome), viruses (e.g. adenovirus, adeno-associated virus, and retrovirus) or target cell specific binding agents (e.g. ligands recognized by target cell specific receptors). Preferred complexes are sufficiently stable in vivo to prevent significant uncoupling prior to internalization by the target cell. However, the complex is cleavable under appropriate conditions within the cell so that the gene, protein, polypeptide or peptide is released in a functional form.

The term "isolated" as used herein with respect to nucleic acids, such as DNA or RNA, refers to molecules separated from other DNAs, or RNAs, respectively, that are present in the natural source of the macromolecule. For example, an isolated nucleic acid encoding one of the subject PDGFR polypeptides preferably includes no more than 10 kilobases (kb) of nucleic acid sequence which naturally immediately flanks the PDGFR gene in genomic DNA, more preferably no more than 5 kb of such naturally occurring flanking sequences, and most preferably less than 1.5 kb of such naturally occurring flanking sequence. The term isolated as used herein also refers to a nucleic acid or peptide that is substantially free of cellular material, viral material, or culture medium when produced by recombinant DNA techniques, or chemical precursors or other chemicals when chemically synthesized. Moreover, an "isolated nucleic acid" is meant to include nucleic acid fragments which are not naturally occurring as fragments and would not be found in the natural state. The term "isolated" is also used herein to refer to polypeptides which are isolated from other cellular proteins and is meant to encompass both purified and recombinant polypeptides.

"Non-human animals" of the invention include mammalians such as rodents, non-human primates, sheep, dog, cow, chickens, amphibians, reptiles, etc. Preferred non-human animals are selected from the rodent family including rat and mouse and most preferably human.

As used herein, the term "nucleic acid" refers to polynucleotides such as deoxyribonucleic acid (DNA), and, where appropriate, ribonucleic acid (RNA). The term should also be understood to include, as equivalents, analogs of either RNA or DNA made from nucleotide analogs, and, as applicable to the embodiment being described, single (sense or antisense) and double-stranded polynucleotides.

As used herein, the term "promoter" means a DNA sequence that regulates expression of a selected DNA sequence operably linked to the promoter, and which effects expression of the selected DNA sequence in cells. The term encompasses "tissue specific" promoters, i.e. promoters, which effect expression of the selected DNA sequence only in specific cells (e.g. cells of a specific tissue). The term also covers so-called "leaky" promoters, which regulate expression of a selected DNA primarily in one tissue, but cause expression in other tissues as well. The term also encompasses non-tissue specific promoters and promoters that constitutively express or that are inducible (i.e. expression levels can be controlled).

The terms "protein", "polypeptide" and "peptide" are used interchangeably herein when referring to a gene product.

The term "recombinant protein" refers to a polypeptide of the present invention which is produced by recombinant DNA techniques, wherein generally, DNA encoding a PDGFR polypeptide is inserted into a suitable expression vector which is in turn used to transform a host cell to produce the heterologous protein. Moreover, the phrase "derived from", with respect to a recombinant PDGFR gene, is meant to include within the meaning of "recombinant protein" those proteins having an amino acid sequence of a native PDGFR polypeptide, or an amino acid sequence similar thereto which is generated by mutations including substitutions and deletions (including truncation) of a naturally occurring form of the polypeptide.

"Small molecule" as used herein, is meant to refer to a composition, which has a molecular weight of less than about 5 kD and most preferably less than about 4 kD. Small molecules can be nucleic acids, peptides, polypeptides, peptidomimetics, carbohydrates, lipids or other organic (carbon containing) or inorganic molecules. Many pharmaceutical companies have extensive libraries of chemical and/or biological mixtures, often fungal, bacterial, or algal extracts, which can be screened with any of the assays of the invention.

"Transcriptional regulatory sequence" is a generic term used throughout the specification to refer to DNA sequences, such as initiation signals, enhancers, and promoters, which induce or control transcription of protein coding sequences with which they are operably linked. In preferred embodiments, transcription of one of the PDGFR genes is under the control of a promoter sequence (or other transcriptional regulatory sequence), which controls the expression of the recombinant gene in a cell-type in which expression is intended. It will also be understood that the recombinant gene can be under the control of transcriptional regulatory sequences which are the same or which are different from those sequences, which control transcription of the naturally-occurring forms of PDGFR polypeptides.

As used herein, the term "transgene" means a nucleic acid sequence (encoding, e.g., one of the mutated PDGFR polypeptides), which has or will be introduced into a cell. A transgene could be partly or entirely heterologous, i.e., foreign, to the transgenic animal or cell into which it is introduced, or, is homologous to an endogenous gene of the transgenic animal or cell into which it is introduced, but which is designed to be inserted, or is inserted, into the animal's genome in such a way as to alter the genome of the cell into which it is inserted (e.g., it is inserted at a location which differs from that of the natural gene or its insertion results in a knockout). A transgene can also be present in a cell in the form of an episome. A transgene can include one or more transcriptional regulatory sequences and any other nucleic acid, such as introns, that may be necessary for optimal expression of a selected nucleic acid.

The term "treating" as used herein is intended to encompass curing as well as ameliorating at least one symptom of the condition or disease.

The term "vector" refers to a nucleic acid molecule capable of transporting another nucleic acid to which it has been linked. One type of preferred vector is an episome, i.e., a nucleic acid capable of extra-chromosomal replication. Preferred vectors are those capable of autonomous replication and/or expression of nucleic acids to which they are linked. Vectors capable of directing the expression of genes to which they are operatively linked are referred to herein as "expression vectors". In general, expression vectors of utility in recombinant DNA techniques are often in the form of "plasmids" which refer generally to circular double stranded DNA loops which, in their vector form are not bound to the chromosome. In the present specification, "plasmid" and "vector" are used interchangeably as the plasmid is the most commonly used form of vector. However, the invention is intended to include such other forms of expression vectors which serve equivalent functions and which become known in the art subsequently hereto.

As used herein, the term "transfection" means the introduction of a nucleic acid, e.g., via an expression vector, into a recipient cell by nucleic acid-mediated gene transfer. "Transformation", as used herein, refers to a process in which a cell's genotype is changed as a result of the cellular uptake of exogenous DNA or RNA.

As used herein, the expressions "cell," "cell line," and "cell culture" are used interchangeably and all such designations include progeny. Thus, the words "transformants" and "transformed cells" include the primary subject cell and cultures derived therefrom without regard for the number of transfers. It is also understood that all progeny may not be precisely identical in DNA content, due to deliberate or inadvertent mutations. Mutant progeny that have the same function or biological activity as screened for in the originally transformed cell are included. Where distinct designations are intended, it will be clear from the context.

A nucleic acid is "operably linked" to another nucleic acid when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous and, in the case of a secretory leader, contiguous and in reading phase. Linking is accomplished by ligation at convenient restriction sites. If such sites do not exist, the synthetic oligonucleotide adaptors or linkers are used in accordance with conventional practice.

As used herein, the twenty conventional amino acids and their abbreviations follow conventional usage (*Immunology—A Synthesis,* 2nd Edition, E. S. Golub and D. R. Gren, Eds., Sinauer Associates, Sunderland, Mass. (1991), which is incorporated herein by reference). Stereoisomers (e.g., D-amino acids) of the twenty conventional amino acids, unnatural amino acids such as, α,α-disubstituted amino acids, N-alkyl amino acids, lactic acid, and other unconventional amino acids may also be suitable components for polypeptides of the present invention. Examples of unconventional amino acids include: 4-hydroxyproline, γ-carboxyglutamate, ε-N,N,N-trimethyllysine, ε-N-acetyllysine, O-phosphoserine, N-acetylserine, N-formylmethionine, 3-methylhistidine, 5-hydroxylysine, ω-N-methylarginine, and other similar amino acids and imino acids (e.g., 4-hydroxyproline). In the polypeptide notation used herein, the lefthand direction is the amino terminal direction and the righthand direction is the carboxy-terminal direction, in accordance with standard usage and convention. Similarly, unless specified otherwise, the lefthand end of single-stranded polynucleotide sequences is the 5' end; the lefthand direction of double-stranded polynucleotide sequences is referred to as the 5' direction. The direction of 5' to 3' addition of nascent RNA transcripts is referred to as the transcription direction; sequence regions on the DNA strand having the same sequence as the RNA and which are 5' to the 5' end of the RNA transcript are referred to as "upstream sequences"; sequence regions on the DNA strand having the same sequence as the RNA and which are 3' to the 3' end of the RNA transcript are referred to as "downstream sequences".

The term "agent" is used herein to denote a chemical compound, a mixture of chemical compounds, a biological macromolecule, or an extract made from biological materials such as bacteria, plants, fungi, or animal (particularly mammalian) cells or tissues.

The term "naturally-occurring" as used herein as applied to an object refers to the fact that an object can be found in nature. For example, a polypeptide or polynucleotide sequence that is present in an organism (including viruses) that can be isolated from a source in nature and which has not been intentionally modified by man in the laboratory is naturally-occurring.

The following terms are used to describe the sequence relationships between two or more polynucleotides: "reference sequence", "comparison window", "sequence identity", "percentage of sequence identity", and "substantial identity". A "reference sequence" is a defined sequence used as a basis for a sequence comparision; a reference sequence may be a subset of a larger sequence, for example, as a segment of a full-length cDNA or gene sequence given in a sequence listing, or may comprise a complete cDNA or gene sequence. Generally, a reference sequence is at least 20 nucleotides in length, frequently at least 25 nucleotides in length, and often at least 50 nucleotides in length. Since two polynucleotides may each (1) comprise a sequence (i.e., a portion of the complete polynucleotide sequence) that is similar between the two polynucleotides, and (2) may further comprise a sequence that is divergent between the two polynucleotides, sequence comparisons between two (or more) polynucleotides are typically performed by comparing sequences of the two polynucleotides over a "comparison window" to identify and compare local regions of sequence similarity. A "comparison window", as used herein, refers to a conceptual segment of at least 20 contiguous nucleotide positions wherein a polynucleotide sequence may be compared to a reference sequence of at least 20 contiguous nucleotides and wherein the portion of the polynucleotide sequence in the comparison window may comprise additions or deletions (i.e., gaps) of 20 percent or less as compared to the reference sequence (which does not comprise additions or deletions) for optimal alignment of the two sequences. Optimal alignment of sequences for aligning a comparison window may be conducted by the local homology algorithm of Smith and Waterman (1981) *Adv. Appl. Math.* 2: 482, by the homology alignment algorithm of Needleman and Wunsch (1970) *J. Mol. Biol.* 48: 443, by the search for similarity method of Pearson and Lipman (1988) *Proc. Natl. Acad. Sci. (U.S.A.)* 85: 2444, by computerized implementations of these algorithms (GAP, BESTFIT, FASTA, and TFASTA in the Wisconsin Genetics Software Package Release 7.0, Genetics Computer Group, 575 Science Dr., Madison, Wis.), or by inspection, and the best alignment (i.e., resulting in the highest percentage of homology over the comparison window) generated by the various methods is selected. The term "sequence identity" means that two polynucleotide sequences are identical (i.e., on a nucleotide-by-nucleotide basis) over the window of comparison. The term "percentage of sequence identity" is calculated by comparing two optimally aligned sequences over the window of comparison, determining the number of positions at which the identical nucleic acid base (e.g., A, T, C, G, U, or I) occurs in both sequences to yield the number of matched positions, dividing the number of matched positions by the total number of positions in the window of comparision (i.e., the window size), and multiplying the result by 100 to yield the percentage of sequence identity. The terms "substantial identity" as used herein denotes a characteristic of a polynucleotide sequence, wherein the polynucleotide comprises a sequence that has at least 85 percent sequence identity, preferably at least 90 to 95 percent sequence identity, more usually at least 99 percent sequence identity as compared to a reference sequence over a comparison window of at least 20 nucleotide positions, frequently over a window of at least 25–50 nucleotides, wherein the percentage of sequence identity is calculated by comparing the reference sequence to the polynucleotide sequence which may include deletions or additions which total 20 percent or less of the reference sequence over the window of comparison.

As applied to polypeptides, the term "substantial identity" means that two peptide sequences, when optimally aligned, such as by the programs GAP or BESTFIT using default gap weights, share at least 80 percent sequence identity, preferably at least 90 percent sequence identity, more preferably at least 95 percent sequence identity or more (e.g., 99 percent sequence identity). Preferably, residue positions which are not identical differ by conservative amino acid substitutions. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, and asparagine-glutamine.

When referring to an amino acid position as being "about amino acid" it is meant that the amino acid could be up to 10 or preferably 5 amino acids upstream or downstream of the enumerated amino acid. When referring to a nucleotide position as being "about nucleotide" it is meant that the nucleotide could be up to 30, preferably 15 nucleotides upstream or downstream of the enumerated amino acid.

As used herein, "substantially pure" means an object species is the predominant species present (i.e., on a molar basis it is more abundant than any other individual species in the composition), and preferably a substantially purified fraction is a composition wherein the object species comprises at least about 50 percent (on a molar basis) of all macromolecular species present. Generally, a substantially pure composition will comprise more than about 80 to 90 percent of all macromolecular species present in the composition. Most preferably, the object species is purified to essential homogeneity (contaminant species cannot be detected in the composition by conventional detection methods) wherein the composition consists essentially of a single macromolecular species.

"ECD", "TM domain" and "ICD" refer to the extracellular domain, transmembrane domain and intracellular domain of a receptor tyrosine kinase, respectively.

The term "homogeneous population of cells" refers to a substantially homogeneous population of cells wherein at least about 80%, and preferably about 90%, of the cells in the population are of the same cell type. Examples of homogenous cell populations include cell lines. A cell line can be a eukaryotic cell line, normally an animal cell line and desirably a mammalian cell line.

Compositions of the Invention

The invention provides nucleic acids encoding mutant PDGFRs and mutant PDGFR polypeptides.

For convenience, a brief description of PDGFRs and their ligands is provided. PDGF is a major mitogen for cells of mesenchymal origin. The protein mitogen is usually a 32 kDa protein heterodimer usually composed of two polypeptide chains, A and B, linked by disulfide bonds. The B chain of the PDGF ligand is identical to the transforming protein of the v-sis oncogene. In addition to the PDGF AB heterodimer, two homodimeric forms of PDGF, denoted AA and BB, have been identified. Ligand binding to the receptor results in dimerization of two receptors generally leading to intermolecular phosphorylation of each receptor, commonly referred to as autophosphorylation or transphosphorylation, and activation of the receptor complex. PDGFRs are receptor protein tyrosine kinases comprising a large, glycosylated, extracellular ligand binding domain (ECD) and an intracellular domain (ICD), which contains a tyrosine kinase catalytic domain. A single hydrophobic transmembrane (TM) domain connects the ECD and ICD. The hPDGF receptor that preferentially binds the AA homodimer is referred to as the A receptor, the α-receptor and, as used herein, the type A receptor (A-hPDGF-R or PDGFRα). The hPDGF receptor that binds the BB homodimer with high affinity has been variously referred as the B receptor, the β-receptor and, as used herein, the type B receptor (B-hPDGF-R or PDGFRβ).

The two receptors have a similar domain organization, with five immunoglobulin-like domains extracellularly and an intracellular split protein tyrosine kinase domain.

The nucleotide sequence of a cDNA sequence encoding PDGFRα is set forth in SEQ ID NO: 1 and encodes a 1089 amino acid full length protein having the amino acid sequence set fort in SEQ ID NO: 2. This receptor is described, e.g., in Kelly et al. (1991) J. Biol. Chem. 266:8987 and in U.S. Pat. No. 5,371,205. The nucleotide and amino acid sequences can also be found under GenBank Accession Nos. PFHUGA; NP_006197; and NM_006206. The signal sequence is from nucleotide 1 to nucleotide 60 or 72 and corresponds to amino acids 1 to 20 or 24, respectively, of SEQ ID NO: 2. The mature receptor is encoded by nucleotide 61 or 73 to nucleotide 3166 and corresponds to amino acids 21 or 25 to 1089 of SEQ ID NO: 2. The coding sequence for the extracellular domain of the mature receptor is from nucleotide 1 through 1471 of SEQ ID NO: 1 and corresponds to amino acids 1 to 490 of SEQ ID NO: 2; the transmembrane region is from nucleotide 1472 through 1546 of SEQ ID NO: 1 and corresponds to amino acids 491 to 515 of SEQ ID NO: 2. Other reports indicate the transmembrane domain as corresponding to amino acids 525 to 548 (Kelly et al., supra). The intracellular region is from nucleotides 1547 through 3166 of SEQ ID NO: 1 and corresponds to amino acids 516 (or 549) to 1055 of SEQ ID NO: 2. The split tyrosine kinase region is encoded by nucleotides 1669–1982 and 2279 to about 2700 of SEQ ID NO: 1, which corresponds to amino acids 556 to 661 and 760 to about 900 of SEQ ID NO: 2. Immunoglobulin-like domains are found at about amino acids 42–102; 143–191; 228–292; 338–399 and 428–503 of SEQ ID NO: 2.

The nucleotide sequence of a cDNA sequence encoding PDGFRβ is set forth in SEQ ID NO: 13 and encodes a full length 1106 amino acid protein having the amino acid sequence set forth in SEQ ID NO: 14. This receptor is described in Gronwald et al. (1988) PNAS 85:3435 and in Matsui et al. (1989) Science 243:800, and the nucleotide and amino acid sequences can be found at GenBank Accession Nos. AAA60049; NP002600; and J03278. The first 32 amino acids encode the signal peptide sequence. The mature receptor corresponds to amino acids 33 to 1106 of SEQ ID NO: 14. The transmembrane sequence corresponds to amino acid residues 532 to 556. Immunoglobulin-like domains can be found at about amino acids 227–298 and 335–398 of SEQ ID NO: 14. The split tyrosine kinase domain corresponds to about amino acids 604–694 and 799–951 of SEQ ID NO: 14. Codon 260 (Met) can also be Ile (Kelly et al., supra).

The intracellular, tyrosine kinase domain of the type A and type B receptors have about 80% identical residues. The extracellular domain of the type A and B receptors have about 34–35% identical residues, an additional 14% of the remaining residues being conservative substitutions. The transmembrane regions of the hPDGF receptors have about 48% identical residues, and of the 52% of residues that differ, 70% are conservative substitutions. As seen in the tables, both receptor sequences have a 107 amino acid insertion interrupting the tyrosine kinase region (encoded by residues 1983–2278 of type A). Both receptors are further described in U.S. Pat. No. 6,110,737.

The binding of PDGF to its receptor at the cell membrane triggers a diverse group of early cellular responses including activation of receptor tyrosine kinase, increased phosphatidylinositol turnover, enhanced expression of a group of genes, activation of phospholipase A2, changes in cell shape, increase in cellular calcium concentration, changes in intracellular pH, and internalization and degradation of bound PDGF. These changes are followed by an increase in the rate of proliferation of the target cells. Both PDGFR chains interact with several signal transduction molecules, in particular Src family members inside cells. Several amino acids mediating such interaction have been identified. For example, in the PDGFRα, the following amino acid have been identified as "functional": Tyr 572 and 574, which are located in the kinase domain are required for binding and activation of Src family kinases to the receptor; Tyr 720, which is located in the kinase domain is required for recruiting of the tyrosine phosphatase SHP-2 to the receptor; Tyr 731 and 742, which are located in the intracellular domain between the split kinase domain, are required for binding of phosphoinositide 3-kinase (PI3K) to the receptor; and Tyr 1018, which is located in the intracellular domain is required for recruiting and activation of phospholipase C-gamma (PLCγ) (see, Examples).

The PDGFRβ contains the following functional amino acids: Tyrosine (Tyr) 759 and 581, which are located in the juxtamembrane domain (JM) of the receptor and are required for Src binding to the receptor; Tyr 740, 751 and 771, which are located in the kinase insert (KI) of the receptor and are responsible for PI3K and RasGAP binding, respectively; and Try 1009 and 1021, which are are located in the Tail of the receptor and which are involved in the binding of SHP-2 and PLCγ, respectively. Montamayeur et al. (1997) *J. Biol. Chem.* 272:32670.

The invention provides nucleic acids encoding mutated PDGFRs. In one embodiment, the mutated PDGFR is a truncated receptor, e.g., a receptor comprising at least a portion of the extracellular domain, the transmembrane domain, and one or more amino acids from the intracellular domain. A preferred truncted receptor does not contain the kinase domain. An exemplary truncated PDGFRα is set forth in the Examples and comprises the extracellular domain, the transmembrane domain and a portion of the intracellular domain, i.e., up to and including about Pro589 of SEQ ID NO: 2. The amino acid sequence of a preferred truncated receptor is set forth as SEQ ID NO: 12, and the nucleotide sequence encoding it is set forth in SEQ ID NO: 11. Any of the three stop codons can be added to the nucleotide sequence of SEQ ID NO: 11. Other preferred truncated receptors can be represented by the formula X-Y-Z, wherein Y consists of a protein of PDGFRα consisting essentially of amino acids 1 to 589 or amino acids 21 to 589 of SEQ ID NO: 2; X and Z consist of at least one amino acid. In a preferred embodiment, if Z is more than one amino acid, Z doe not have the amino acid sequence of human PDGFRα located downstream of amino acid 589.

Similarly, a preferred truncated beta receptor comprises amino acid 1 or 33 to about amino acid 561 of SEQ ID NO: 14. A preferred truncated beta receptor mutant comprises amino acid 1 to amino acid 261 of SEQ ID NO: 14. Accordingly, the last amino acid of this mutant is an arginine. The amino acid sequence of this mutant is set forth in SEQ ID NO: 23 and encoded by a nucleotide sequence set forth in SEQ ID NO: 24. Any stop codon can be used at the end of SEQ ID NO: 24. Another truncated beta receptor mutant comprises amino acids 1 or 33 to amino acid 561, wherein amino acid 561 is substituted with a serine. Other preferred truncated beta receptors can be represented by the formula X-Y-Z, wherein Y consists of a portion of PDGFR-beta consisting essentially of amino acids 1 to 561 or amino acids 21 to 561 or amino acids 33 to 561 of SEQ ID NO: 14; X and Z consist of at least one amino acid. In a preferred embodiment, if Z is more than one amino acid, Z doe not have the amino acid sequence of human PDGFRbeta located downstream of amino acid 561.

Figure 1:
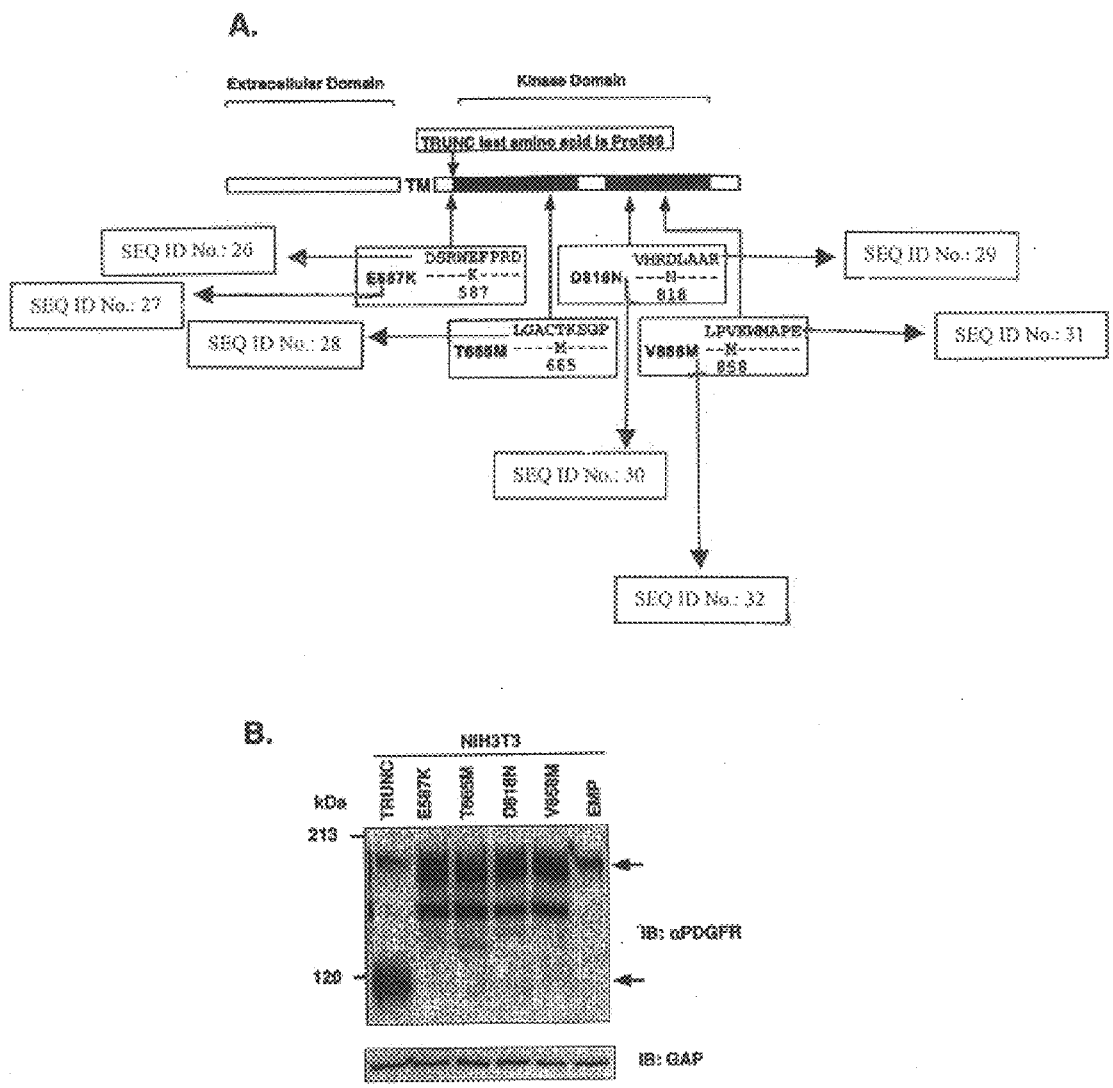
FIG. 1A shows a diagram of the human αPDGFR, indicating the last amino acid of the truncated receptor and the position of each point mutation. A stop codon terminates the truncated receptor such that the cytoplasmic domain encodes only the juxtamembrane domain. For the other mutations the amino acid sequence of the wild type receptor is indicated in the top line, and the amino acid change present in the mutant receptor is shown in the bottom line. The numbers indicate the position of each of the mutations. TM: transmembrane domain; TRUNC: truncated receptor; E587K: glutamic acid at position 587 was changed to lysine; T665M: threonine at position 665 was changed to methionine; D818N: aspartic acid at position 818 was changed to asparagine; V859M: valine of position 859 was changed to methionine.
FIG. 1B shows a Western blot of cell lysates from NIH 3T3 cells infected with a replication-incompetent retrovirus harboring one of the platelet-derived growth factor α receptor (αPDGFR) mutant indicated in FIG. 1B or empty vector (EMP) incubated with antibody against αPDGFR (top panel) or Ras GTP-activating protein (RasGAP; lysate control, bottom panel). Two distinct sizes of αPDGFR were detected at around 190 kDa (full-length receptor, top arrow) and about 120 kDa (truncated receptor, bottom arrow). The point mutants migrated slightly faster than endogenous wild type receptor.

Other preferred PDGFR mutants of the invention consist of at least a portion of a PDGFR comprising one or more mutations in the kinase domain. The mutation can be a deletion or an insertion of an amino acid, however, it is preferably an amino acid substitution. Even more preferred mutations consist in substitutions of one or more amino acids located in the kinase domain. Exemplary amino acids located in the kinase domain of the PDGFRα which can be mutated include Glu587, Thr665, Asp818 and Val859. The location of these residues is shown in FIG. 1A. Preferred substitutions include Glu587Lys; Thr665Met; Asp818Asn; and Val859Met, as shown in FIG. 1A. The full length amino acid sequence of the PDGFRα in which these mutations were introduced are set forth as SEQ ID Nos: 4, 6, 8, and 10, respectively, and nucleotide sequences encoding these are set forth as SEQ ID Nos: 3, 5, 7, and 9, respectively. An alternative nucleic acid sequence encoding a polypeptide having SEQ ID NO: 4 consists of SEQ ID NO: 3, in which codon 587 is "AAA." An alternative nucleic acid sequence encoding a polypeptide having SEQ ID NO: 8 consists of SEQ ID NO: 7, in which codon 818 is "AAC." These particular receptor mutants have been shown to decrease the proliferation of cells, when expressed in cells containing the wild type receptor and contacted with PDGF, as well as to reduce the likelihood of PVR development (see Examples).

The invention provides other mutants in which one or more tyrosine located in the intracellular domain and/or in the kinase domain is substituted with another amino acid. Preferred such mutants of PDGFRα include those in which one or more of amino acids 572, 574, 627, 720, 731, 742, 988, and 1018 are mutated, e.g., substituted with Phe. When substituted with Phe, the mutants are referred to as Tyr572Phe; Tyr574Phe; Tyr720Phe; Tyr731Phe; Tyr742Phe;

Tyr988Phe; and Tyr1018Phe, respectively. These mutations and the effect on the activity of the receptor are listed in Table 1 in the Examples. The Tyr572Phe; Tyr574Phe mutant is described in Gelderloos et al. (1998) *J Biol Chem.* 273:5908. The Tyr720Phe mutant is described in Bazenet et al. (1996) *Mol Cell Biol.* 16:6926. The following mutant receptors are described in Rosenkranz et al. (1999) *J Biol Chem.* 274:28335: the Tyr731Phe;Tyr742Phe mutant; the Tyr1018Phe mutant; the Tyr572Phe; Tyr574Phe; Tyr720Phe; Tyr731Phe; Tyr742Phe; Tyr988Phe; and Tyr1018Phe mutant.

Another preferred mutant of PDGFRα includes the substitution of the Lys at position 627 with an Arg (Lys627Arg). This mutant is further described in Rozenkranz et al., supra.

Similar mutants of PDGFRβ were obtained. Preferred mutants are those in which amino acids 594, 672, 826 or 867 of SEQ ID NO: 14 are mutated. Even more preferred mutants are E594K (i.e., Glu594Lys); T672M (i.e., Thr672Met); D826N (i.e., Asp826Asn); and L867M (i.e., Leu867Met) with reference to SEQ ID NO: 14. The amino acid sequences of each of these mutants is set forth in SEQ ID Nos: 16, 18, 20, and 22, respectively, and are encoded by the nucleic acids set forth in SEQ ID Nos: 15, 17, 19, and 21, respectively. An alternative nucleic acid sequences encoding a polypeptide having SEQ ID NO: 16 consists of SEQ ID NO: 15, in which codon 594 is an "AAA." An alternative nucleic acid sequence encoding a polypeptide having SEQ ID NO: 20 consists of SEQ ID NO: 19, in which codon 826 is "AAT."

For convenience, the identity of the SEQ ID Nos are listed below:

| | |
|---|---|
| SEQ ID NO: 1 | wild-type αPDGFR nucleotide sequence; |
| SEQ ID NO: 2 | wild-type αPDGFR amino acid sequence; |
| SEQ ID NO: 3 | αPDGFR mutant Glu587Lys nucleotide sequence; |
| SEQ ID NO: 4 | αPDGFR mutant Glu587Lys amino acid sequence; |
| SEQ ID NO: 5 | αPDGFR mutant Thr665Met nucleotide sequence; |
| SEQ ID NO: 6 | αPDGFR mutant Thr665Met amino acid sequence; |
| SEQ ID NO: 7 | αPDGFR mutant Asp818Asn nucleotide sequence; |
| SEQ ID NO: 8 | αPDGFR mutant Asp818Asn amino acid sequence; |
| SEQ ID NO: 9 | αPDGFR mutant Val859Met nucleotide sequence; |
| SEQ ID NO: 10 | αPDGFR mutant Val859Met amino acid sequence; |
| SEQ ID NO: 11 | αPDGFR truncated mutant nucleotide sequence; |
| SEQ ID NO: 12 | αPDGFR truncated mutant amino acid sequence; |
| SEQ ID NO: 13 | wild-type βPDGFR nucleotide sequence; |
| SEQ ID NO: 14 | wild-type βPDGFR amino acid sequence; |
| SEQ ID NO: 15 | βPDGFR mutant Glu594Lys nucleotide sequence; |
| SEQ ID NO: 16 | βPDGFR mutant Glu594Lys amino acid sequence; |
| SEQ ID NO: 17 | βPDGFR mutant Thr672Met nucleotide sequence; |
| SEQ ID NO: 18 | βPDGFR mutant Thr672Met amino acid sequence; |
| SEQ ID NO: 19 | βPDGFR mutant Asp826Asn nucleotide sequence; |
| SEQ ID NO: 20 | βPDGFR mutant Asp826Asn amino acid sequence; |
| SEQ ID NO: 21 | βPDGFR mutant Leu867Met nucleotide sequence; |
| SEQ ID NO: 22 | βPDGFR mutant Leu867Met amino acid sequence; |
| SEQ ID NO: 23 | βPDGFR truncated mutant nucleotide sequence; and |
| SEQ ID NO: 24 | βPDGFR truncated mutant amino acid sequence. |

Preferred nucleic acids of the invention can encode polypeptides comprising one or more of the above-referenced single amino acid mutations. These nucleic acids can encode the full length PDGFR chain or a portion thereof. Preferred mutants contain the full length mature form of a PDGFR chain. Other preferred mutants comprise essentially the full length mature form of a receptor chain, i.e., lacking only a few amino acids at the N- and/or C-terminus of the polypeptide, e.g., lacking from 1–5; from 5–10; from 10–20 or from 20–50 amino acids.

In certain embodiments, the mutated PDGFR chain is a chimeric (or fusion) polypeptide, e.g., a chimera between the alpha and the beta chains. For example, a chimera can comprise the extracellular domain of the alpha chain and the intracellular domain of the beta chain. Alternatively, a chimera may have the extracellular and transmembrane domains from one type of chain and the intracellular domain from the other chain. Such chimeras are described e.g., in DeMali et al. (1997) J. Biol. Chem. 272: 9011. In other embodiments, the transmembrane domain of a PDGFR chain is substituted with that of a heterologous transmembrane protein. Other transmembrane proteins include other receptors, e.g., EGF receptor.

In yet other embodiments, the nucleic acid of the invention encodes a mutated PDGFR chain which is fused to a heterologous polypeptide. For example, the polynucleotide of the present invention may also be fused in frame to a marker sequence, also referred to herein as "Tag sequence" encoding a "Tag peptide", which allows for marking and/or purification of the polypeptide of the present invention. In a preferred embodiment, the marker sequence is a hexahistidine tag, e.g., supplied by a PQE-9 vector. Numerous other Tag peptides are available commercially. Other frequently used Tags include myc-epitopes (e.g., see Ellison et al. (1991) *J Biol Chem* 266:21150–21157), which includes a 10-residue sequence from c-myc, the pFLAG system (International Biotechnologies, Inc.), the pEZZ-protein A system (Pharmacia, N.J.), and a 16 amino acid portion of the *Haemophilus influenza* hemagglutinin protein. Furthermore, any polypeptide can be used as a Tag so long as a reagent, e.g., an antibody interacting specifically with the Tag polypeptide is available or can be prepared or identified. Alternatively, the heterologous polypeptide may be added for stabilizing the protein; or for solubilizing it for facilitating its folding.

Other fusion proteins of interest comprise at least a portion of a mutant PDGFR fused to the protein transduction domain from the human immunodeficiency virus TAT protein. It has been shown that fusion of proteins, even proteins as large as beta-galactosidase to such a domain of TAT results in delivery of the fusion polypeptide to all tissues in mice (see, e.g., Schwarze et al. (1999) Science 285:1569).

The nucleic acids of the invention is preferably derived from human nucleic acid, however, it can also be derived from or comprise at least part of mouse or other mammalian PDGFR nucleic acid. Numerous vertebrate, e.g., mammalian PDGFR chain nucleic acids are available, and can be found in the literature and in GenBank. Regardless of species, particularly preferred PDGFR nucleic acids encode polypeptides that are at least 70%, 80%, 90%, or 95% similar or identical to an amino acid sequence of a human or other mammalian PDGFR. Thus, preferred nucleic acids of the invention encode PDGFR mutants which are at least about 70%, 80%, 90% or 95% similar or identical to SEQ ID NO: 2 (PDGFRα) or 14 (or PDGFRβ) and which comprise one or more of the mutated amino acids identified herein. Other preferred nucleic acids of the invention include those which are at least about 70%, 80%, 90%, or 95% similar or identical to an amino acid sequence of a truncated PDGFR, such as set forth in SEQ ID Nos: 12 (truncated PDGFRα) and 44 (truncated PDGFRβ).

Other preferred nucleic acids which are mutated to produce the mutated PDGFRs for use according to the invention are nucleic acids which are at least about 70%, 80%, 90%, 95%, 98% or 99% identical to SEQ ID NO: 2 (PDGFRα) or 14 (or PDGFRβ. Other preferred nucleic acids are those which are at least about 70%, 80%, 90%, 95%, 98% or 99% identical to SEQ ID Nos: 12 (truncated PDGFRα) or 44 (truncated PDGFRβ).

Also within the scope of the invention are nucleic acids encoding mutated PDGFRs which hybridize under stringent conditions to a nucleic acid represented by SEQ ID NOs: 1 or 13 or complement thereof Appropriate stringency conditions which promote DNA hybridization, for example, 6.0× sodium chloride/sodium citrate (SSC) at about 45° C., followed by a wash of 2.0×SSC at 50° C., are known to those skilled in the art or can be found in Current Protocols in Molecular Biology, John Wiley & Sons, N.Y. (1989), 6.3.1–6.3.6. For example, the salt concentration in the wash step can be selected from a low stringency of about 2.0× SSC at 50° C. to a high stringency of about 0.2×SSC at 50° C. In addition, the temperature in the wash step can be increased from low stringency conditions at room temperature, about 22° C., to high stringency conditions at about 65° C. Both temperature and salt may be varied, or temperature of salt concentration may be held constant while the other variable is changed. In a preferred embodiment, a nucleic acid encoding a mutated PDGFR of the present invention will hybridize to one of SEQ ID NOS 1 or 25 or complement thereof under moderately stringent conditions, for example at about 2.0×SSC and about 40° C. In a particularly preferred embodiment, a nucleic acid encoding a mutated PDGFR of the present invention will bind to one of SEQ ID NOs: 1 or 13 or complement thereof under high stringency conditions.

Nucleic acids encoding PDGFRs in which a mutation has been introduced for the purposes of the invention may also be nucleic acids having a sequence that differs from the nucleotide sequences shown in one of SEQ ID NOs: 1 or 13 due to degeneracy in the genetic code. Such nucleic acids encode functionally equivalent peptides but differ in sequence from the sequence shown in the sequence listing due to degeneracy in the genetic code. For example, a number of amino acids are designated by more than one triplet. Codons that specify the same amino acid, or synonyms (for example, CAU and CAC each encode histidine) may result in "silent" mutations, which do not affect the amino acid sequence of a PDGFR polypeptide.

When using mutated PDGFRs of the invention which are not derived from the wild type human PDGFRα or PDGFRβ, but differ from it in several amino acids (other than those made in the polypeptide to mutate the receptor), it is desirable that such changes do not substantially affect any other characteristics of the receptor which is required for its use according to the invention, e.g., for treating a fibrotic disease. Thus, such modifications preferably do not affect the three-dimensional structure of the receptor, its ability to insert into the cytoplasmic membrane, its stability, or its ability to interact with other molecules. The assays further disclosed herein can be used to confirm this.

In other embodiments, nucleic acids encoding mutated PDGFRs may include other appended groups such as peptides (e.g., for targeting host cell receptors in vivo), or agents that facilitate transport across the cell membrane.

Methods for Testing the Efficacy of PDGFR Mutants

As described in the Examples, while the PDGFR mutants differed in their intrinsic kinase activity and their potential to prevent PDGF-dependent signaling, they were all effective at blocking PDGF-mediated cell growth stimulation and the development of PVR in the rabbit model. Accordingly, the preferred test for determining the efficiency of a mutated PDGFR to be useful in treating a proliferative disease, such as a fibrotic disease, e.g., PVR, is to determine the effect of the mutated PDGFR to inhibit PDGF-stimulated cell cycle progression. The antiproliferative effect of a mutant PDGFR can be determined by methods known in the art, such as by a cell count or $^3$H thymidine incorporation, as further described in the Examples.

Other preferred tests for determining the efficiency of PDGFR mutants are is an in vitro or in vivo assay systems for fibrotic or proliferative diseases. For example, the efficiency of PDGFR mutants as therapeutics for fibrotic or proliferative diseases can be tested in the gel contraction assays further described herein (see, Examples). A preferred test for determining the efficiency of PDGFR mutants as therapeutics for PVR is the rabbit animal model that is further described in the Examples. Other animal models can be used for other proliferative diseases.

Under certain circumstances, it will be desirable to use mammalian cells which lack a PDGF receptor where the signal sequence directs the peptide into the cell membrane. Lymphocytes and cardiac myocytes are primary cells which lack a receptor and which can thus be used for that purpose. Also, Chinese hamster ovary cells (CHO), epithelial cells lines and a number of human tumor cell lines lack PDGF receptors.

Administration of the Mutated PDGFR Nucleic Acids or Polypeptides

In one embodiment, a mutated PDGFR polypeptide is first produced in vitro and then administered to a subject in need thereof. In a preferred embodiment, a nucleic acid encoding a mutated PDGFR is administered to a subject in need thereof.

Typically, expression vectors used for expressing, in vivo or in vitro a mutated PDGFR protein contain a nucleic acid encoding a mutated PDGFR polypeptide, operably linked to at least one transcriptional regulatory sequence. Regulatory sequences are art-recognized and are selected to direct expression of the subject proteins in the desired fashion (time and place). Transcriptional regulatory sequences are described in Goeddel; Gene Expression Technology: Methods in Enzymology 185, Academic Press, San Diego, Calif. (1990).

Suitable vectors for the expression of a mutated PDGFR polypeptide include plasmids of the types: pBR322-derived plasmids, pEMBL-derived plasmids, pEX-derived plasmids, pBTac-derived plasmids and pUC-derived plasmids for expression in prokaryotic cells, such as E. coli.

The preferred mammalian expression vectors contain both prokaryotic sequences, to facilitate the propagation of the vector in bacteria, and one or more eukaryotic transcription units that are expressed in eukaryotic cells. The pcDNAI/amp, pcDNAI/neo, pRc/CMV, pSV2gpt, pSV2neo, pSV2-dhfr, pTk2, pRSVneo, pMSG, pSVT7, pko-neo and pHyg derived vectors are examples of mammalian expression vectors suitable for transfection of eukaryotic cells. Some of these vectors are modified with sequences from bacterial plasmids, such as pBR322, to facilitate replication and drug resistance selection in both prokaryotic and eukaryotic cells. Alternatively, derivatives of viruses such as the bovine papillomavirus (BPV-1), or Epstein-Barr virus (pHEBo, pREP-derived and p205) can be used for transient expression of proteins in eukaryotic cells. The various methods employed in the preparation of the plasmids and transformation of host organisms are well known in the art. For other suitable expression systems for both prokaryotic and eukaryotic cells, as well as general recombinant procedures, see Molecular Cloning A Laboratory Manual, 2nd Ed., ed. by Sambrook, Fritsch and Maniatis (Cold Spring Harbor Laboratory Press: 1989) Chapters 16 and 17.

In a preferred embodiment, the promoter is a constitutive promoter, e.g., a strong viral promoter, e.g., CMV promoter. The promoter can also be cell- or tissue-specific, that permits substantial transcription of the DNA only in predetermined cells, e.g., in professional antigen presenting cells, such as a promoter specific for fibroblasts, or smooth muscle cells, retinal cells or RPE cells. A smooth muscle specific promoter is, e.g., the promoter of the smooth muscle cell marker SM22alpha (Akyura et al., (2000) *Mol Med* 6:983. Retinal pigment epithelial cell specific promoter is, e.g., the promoter of the Rpe65 gene (Boulanger et al. (2000) *J Biol Chem* 275:31274). The promoter can also be an inducible promoter, e.g., a metallothionein promoter. Other inducible promoters include those that are controlled by the inducible binding, or activation, of a transcription factor, e.g., as described in U.S. Pat. Nos. 5,869,337 and 5,830,462 by Crabtree et al., describing small molecule inducible gene expression (a genetic switch); International patent applications PCT/US94/01617, PCT/US95/10591, PCT/US96/09948 and the like, as well as in other heterologous transcription systems such as those involving tetracyclin-based regulation reported by Bujard et al., generally referred to as an allosteric "off-switch" described by Gossen and Bujard (Proc. Natl. Acad. Sci. U.S.A. (1992) 89:5547) and in U.S. Pat. Nos. 5,464,758; 5,650,298; and 5,589,362 by Bujard et al. Other inducible transcription systems involve steroid or other hormone-based regulation.

The polynucleotide of the invention together with all necessary transcriptional and translational control sequences is referred to herein as "construct of the invention" or "transgene of the invention." The polynucleotide of the invention may also be introduced into the cell in which it is to be expressed together with another DNA sequence (which may be on the same or a different DNA molecule as the polynucleotide of the invention) coding for another agent. Exemplary agents are further described below. In one embodiment, the DNA encodes a polymerase for transcribing the DNA, and may comprise recognition sites for the polymerase and the injectable preparation may include an initial quantity of the polymerase.

In certain instances, it may be preferred that the polynucleotide is translated for a limited period of time so that the polypeptide delivery is transitory. This can be achieved, e.g., by the use of an inducible promoter.

The polynucleotides used in the present invention may also be produced in part or in total by chemical synthesis, e.g., by the phosphoramidite method described by Beaucage and Carruthers, Tetra. Letts., 22:1859–1862 (1981) or the triester method according to the method described by Matteucci et al., J. Am. Chem. Soc., 103:3185 (1981), and may be performed on commercial automated oligonucleotide synthesizers. A double-stranded fragment may be obtained from the single stranded product of chemical synthesis either by synthesizing the complementary strand and annealing the strand together under appropriate conditions or by adding the complementary strand using DNA polymerase with an appropriate primer sequence.

The polynucleotide of the invention operably linked to all necessary transcriptional and translational regulation elements can be injected as naked DNA into a subject. In a preferred embodiment, the polynucleotide of the invention and necessary regulatory elements are present in a plasmid or vector. Thus, the polynucleotide of the invention may be DNA, which is itself non-replicating, but is inserted into a plasmid, which may further comprise a replicator. The DNA may be a sequence engineered so as not to integrate into the host cell genome.

Preferred vectors for use according to the invention are expression vectors, i.e., vectors that allow expression of a nucleic acid in a cell vectors. Preferred expression vectors are those which contain both prokaryotic sequences, to facilitate the propagation of the vector in bacteria, and one or more eukaryotic transcription units that are expressed in eukaryotic cells. The pcDNAI/amp, pcDNAI/neo, pRc/CMV, pSV2gpt, pSV2neo, pSV2-dhfr, pTk2, pRSVneo, pMSG, pSVT7, pko-neo and pHyg derived vectors are examples of mammalian expression vectors suitable for transfection of eukaryotic cells. Some of these vectors are modified with sequences from bacterial plasmids, such as pBR322, to facilitate replication and drug resistance selection in both prokaryotic and eukaryotic cells. Alternatively, derivatives of viruses such as the bovine papillomavirus (BPV-1), or Epstein-Barr virus (pHEBo, pREP-derived and p205) can be used for transient expression of proteins in eukaryotic cells. The various methods employed in the preparation of the plasmids and transformation of host organisms are well known in the art. For other suitable expression systems for both prokaryotic and eukaryotic cells, as well as general recombinant procedures, see Molecular Cloning A Laboratory Manual, 2nd Ed., ed. by Sambrook, Fritsch and Maniatis (Cold Spring Harbor Laboratory Press: 1989) Chapters 16 and 17.

Any means for the introduction of polynucleotides into mammals, human or non-human, may be adapted to the practice of this invention for the delivery of the various constructs of the invention into the intended recipient. In one embodiment of the invention, the DNA constructs are delivered to cells by transfection, i.e., by delivery of "naked" DNA or in a complex with a colloidal dispersion system. A colloidal system includes macromolecule complexes, nanocapsules, microspheres, beads, and lipid-based systems including oil-in-water emulsions, micelles, mixed micelles, and liposomes. The preferred colloidal system of this invention is a lipid-complexed or liposome-formulated DNA. In the former approach, prior to formulation of DNA, e.g., with lipid, a plasmid containing a transgene bearing the desired DNA constructs may first be experimentally optimized for expression (e.g., inclusion of an intron in the 5' untranslated region and elimination of unnecessary sequences (Felgner, et al., Ann NY Acad Sci 126–139, 1995). Formulation of DNA, e.g. with various lipid or liposome materials, may then be effected using known methods and materials and delivered to the recipient mammal. See, e.g., Canonico et al, Am J Respir Cell Mol Biol 10:24–29, 1994; Tsan et al, Am J Physiol 268; Alton et al., Nat Genet. 5:135–142, 1993 and U.S. Pat. No. 5,679,647 by Carson et al. Colloidal dispersion systems.

The targeting of liposomes can be classified based on anatomical and mechanistic factors. Anatomical classification is based on the level of selectivity, for example, organ-specific, cell-specific, and organelle-specific. Mechanistic targeting can be distinguished based upon whether it is passive or active. Passive targeting utilizes the natural tendency of liposomes to distribute to cells of the reticuloendothelial system (RES) in organs, which contain sinusoidal capillaries. Active targeting, on the other hand, involves alteration of the liposome by coupling the liposome to a specific ligand such as a monoclonal antibody, sugar, glycolipid, or protein, or by changing the composition or size of the liposome in order to achieve targeting to organs and cell types other than the naturally occurring sites of localization.

The surface of the targeted delivery system may be modified in a variety of ways. In the case of a liposomal targeted delivery system, lipid groups can be incorporated into the lipid bilayer of the liposome in order to maintain the targeting ligand in stable association with the liposomal bilayer. Various linking groups can be used for joining the lipid chains to the targeting ligand. Naked DNA or DNA associated with a delivery vehicle, e.g., liposomes, can be administered to several sites in a subject (see below).

For example, smooth muscle cells can be targeted with an antibody binding specifically to SM22α, a smooth muscle cell marker. Retinal cells and RPE cells can similarly be targeted.

In a preferred method of the invention, the DNA constructs are delivered using viral vectors. The transgene may be incorporated into any of a variety of viral vectors useful in gene therapy, such as recombinant retroviruses, adenovirus, adeno-associated virus (AAV), and herpes simplex virus-1, or recombinant bacterial or eukaryotic plasmids. While various viral vectors may be used in the practice of this invention, AAV- and adenovirus-based approaches are of particular interest. Such vectors are generally understood to be the recombinant gene delivery system of choice for the transfer of exogenous genes in vivo, particularly into humans. The following additional guidance on the choice and use of viral vectors may be helpful to the practitioner. As described in greater detail below, such embodiments of the subject expression constructs are specifically contemplated for use in various in vivo and ex vivo gene therapy protocols.

A. Adenoviral Vectors

A viral gene delivery system useful in the present invention utilizes adenovirus-derived vectors. Knowledge of the genetic organization of adenovirus, a 36 kB, linear and double-stranded DNA virus, allows substitution of a large piece of adenoviral DNA with foreign sequences up to 8 kB. In contrast to retrovirus, the infection of adenoviral DNA into host cells does not result in chromosomal integration because adenoviral DNA can replicate in an episomal manner without potential genotoxicity. Also, adenoviruses are structurally stable, and no genome rearrangement has been detected after extensive amplification. Adenovirus can infect virtually all epithelial cells regardless of their cell cycle stage. So far, adenoviral infection appears to be linked only to mild disease such as acute respiratory disease in the human.

Adenoviruses have been shown in particular to be efficient in gene delivery to the RPE cells. For example, Baffi et al. describe the delivery of an adenovirus encoding vascular endothelial growth factor to the subretinal space in the rat, resulting in the expression of VEGF in the RPE cells of the rat (Baffi et al. (2000) *Invest Ophthalmol Vis Sci* 41:3582). Another reference describes that laser photocoagulation further increases the susceptibility of proliferating RPE cells to adenovirus-mediated gene delivery (Lai et al. (1999) *Curr Eye Res* 19:411). Sakamoto et al. describe that a vitrectomy also improves adenovirus-mediated gene delivery to the retina (Sakamoto et al. (1998) Gene Ther. 5: 1088). Ali et al. report that co-injection of adenovirus expressing CTLA4-Ig prolongs adenovirally mediated gene expression in the mouse retina, by blocking T cell activation (Ali et al. (1998) Gene Ther. 5:1561). Other references decribing expression of a transgene in retinal cells and RPE cells, upon injection of an adenoviral vector comprising the transgene in the vitreous cavity of eyes of non-human animals include Lai et al. (2000): *Invest Ophthalmol Vis Sci* 41:580; Yu et al. (2000) *Growth Factors* 17:301; and Rackoczy et al. (1998) *Aust N Z J Ophthalmol* 26 Suppl 1:S56.

Adenovirus is particularly suitable for use as a gene transfer vector because of its mid-sized genome, ease of manipulation, high titer, wide target-cell range, and high infectivity. Both ends of the viral genome contain 100–200 base pair (bp) inverted terminal repeats (ITR), which are cis elements necessary for viral DNA replication and packaging. The early (E) and late (L) regions of the genome contain different transcription units that are divided by the onset of viral DNA replication. The E1 region (E1A and E1B) encodes proteins responsible for the regulation of transcription of the viral genome and a few cellular genes. The expression of the E2 region (E2A and E2B) results in the synthesis of the proteins for viral DNA replication. These proteins are involved in DNA replication, late gene expression, and host cell shut off (Renan (1990) Radiotherap. Oncol. 19:197). The products of the late genes, including the majority of the viral capsid proteins, are expressed only after significant processing of a single primary transcript issued by the major late promoter (MLP). The MLP (located at 16.8 m.u.) is particularly efficient during the late phase of infection, and all the mRNAs issued from this promoter possess a 5' tripartite leader (TL) sequence which makes them preferred mRNAs for translation.

The genome of an adenovirus can be manipulated such that it encodes a gene product of interest, but is inactivated in terms of its ability to replicate in a normal lytic viral life cycle (see, for example, Berkner et al., (1988) BioTechniques 6:616; Rosenfeld et al., (1991) Science 252:431–434; and Rosenfeld et al., (1992) Cell 68:143–155). Suitable adenoviral vectors derived from the adenovirus strain Ad type 5 d1324 or other strains of adenovirus (e.g., Ad2, Ad3, Ad7 etc.) are well known to those skilled in the art. Recombinant adenoviruses can be advantageous in certain circumstances in that they are not capable of infecting nondividing cells and can be used to infect a wide variety of cell types, including airway epithelium (Rosenfeld et al., (1992) cited supra), endothelial cells (Lemarchand et al., (1992) PNAS USA 89:6482–6486), hepatocytes (Herz and Gerard, (1993) PNAS USA 90:2812–2816) and muscle cells (Quantin et al., (1992) PNAS USA 89:2581–2584).

Adenovirus vectors have also been used in vaccine development (Grunhaus and Horwitz (1992) Siminar in Virology 3:237; Graham and Prevec (1992) Biotechnology 20:363). Experiments in administering recombinant adenovirus to different tissues include trachea instillation (Rosenfeld et al. (1991); Rosenfeld et al. (1992) Cell 68:143), muscle injection (Ragot et al. (1993) Nature 361:647), peripheral intravenous injection (Herz and Gerard (1993) Proc. Natl. Acad. Sci. U.S.A. 90:2812), and stereotactic inoculation into the brain (Le Gal La Salle et al. (1993) Science 254:988).

Furthermore, the virus particle is relatively stable and amenable to purification and concentration, and as above, can be modified so as to affect the spectrum of infectivity. Additionally, adenovirus is easy to grow and manipulate and exhibits broad host range in vitro and in vivo. This group of viruses can be obtained in high titers, e.g., $10^9$–$10^{11}$ plaque-forming unit (PFU)/ml, and they are highly infective. The life cycle of adenovirus does not require integration into the host cell genome. The foreign genes delivered by adenovirus vectors are episomal, and therefore, have low genotoxicity to host cells. No side effects have been reported in studies of vaccination with wild-type adenovirus (Couch et al., 1963; Top et al., 1971), demonstrating their safety and therapeutic potential as in vivo gene transfer vectors. Moreover, the carrying capacity of the adenoviral genome for foreign DNA is large (up to 8 kilobases) relative to other gene delivery vectors (Berkner et al., supra; Haj-Ahmand and Graham (1986) J. Virol. 57:267). Most replication-defective adenoviral vectors currently in use and therefore favored by the present invention are deleted for all or parts of the viral E1 and E3 genes but retain as much as 80% of the adenoviral genetic material (see, e.g., Jones et al., (1979) Cell 16:683; Berkner et al., supra; and Graham et al., in Methods in Molecular Biology, E. J. Murray, Ed. (Humana, Clifton, N.J., 1991) vol. 7. pp. 109–127). Expression of the inserted polynucleotide of the invention can be under control of, for example, the E1A promoter, the major late promoter (MLP) and associated leader sequences, the viral E3 promoter, or exogenously added promoter sequences.

Other than the requirement that the adenovirus vector be replication defective, or at least conditionally defective, the nature of the adenovirus vector is not believed to be crucial to the successful practice of the invention. The adenovirus may be of any of the 42 different known serotypes or subgroups A–F. Adenovirus type 5 of subgroup C is the preferred starting material in order to obtain the conditional replication-defective adenovirus vector for use in the method of the present invention. This is because Adenovirus type 5 is a human adenovirus about which a great deal of biochemical and genetic information is known, and it has historically been used for most constructions employing adenovirus as a vector. As stated above, the typical vector according to the present invention is replication defective and will not have an adenovirus E1 region. Thus, it will be most convenient to introduce the nucleic acid of interest at the position from which the E1 coding sequences have been removed. However, the position of insertion of the polynucleotide or construct on the invention (also referred to as "nucleic acid of interest") in a region within the adenovirus sequences is not critical to the present invention. For example, it may also be inserted in lieu of the deleted E3 region in E3 replacement vectors as described previously by Karlsson et. al. (1986) or in the E4 region where a helper cell line or helper virus complements the E4 defect.

A preferred helper cell line is 293 (ATCC Accession No. CRL1573). This helper cell line, also termed a "packaging cell line" was developed by Frank Graham (Graham et al. (1987) J. Gen. Virol. 36:59–72 and Graham (1977) J.General Virology 68:937–940) and provides E1A and E1B in trans. However, helper cell lines may also be derived from human cells such as human embryonic kidney cells, muscle cells, hematopoietic cells or other human embryonic mesenchymal or epithelial cells. Alternatively, the helper cells may be derived from the cells of other mammalian species that are permissive for human adenovirus. Such cells include, e.g., Vero cells or other monkey embryonic mesenchymal or epithelial cells.

Adenoviruses can also be cell type specific, i.e., infect only restricted types of cells and/or express a transgene only in restricted types of cells. For example, the viruses comprise a gene under the transcriptional control of a transcription initiation region specifically regulated by target host cells, as described e.g., in U.S. Pat. No. 5,698,443, by Henderson and Schuur, issued Dec. 16, 1997. Thus, replication competent adenoviruses can be restricted to certain cells by, e.g., inserting a cell specific response element to regulate a synthesis of a protein necessary for replication, e.g., E1A or E1B.

DNA sequences of a number of adenovirus types are available from Genbank. For example, human adenovirus type 5 has GenBank Accession No.M73260. The adenovirus DNA sequences may be obtained from any of the 42 human adenovirus types currently identified. Various adenovirus strains are available from the American Type Culture Collection, Rockville, Md., or by request from a number of commercial and academic sources. A transgene as described herein may be incorporated into any adenoviral vector and delivery protocol, by restriction digest, linker ligation or filling in of ends, and ligation.

Adenovirus producer cell lines can include one or more of the adenoviral genes E1, E2a, and E4 DNA sequence, for packaging adenovirus vectors in which one or more of these genes have been mutated or deleted are described, e.g., in PCT/US95/15947 (WO 96/18418) by Kadan et al.; PCT/US95/07341 (WO 95/346671) by Kovesdi et al.; PCT/FR94/00624 (WO94/28152) by Imler et al.; PCT/FR94/00851 (WO 95/02697) by Perrocaudet et al., PCT/US95/14793 (WO96/14061) by Wang et al.

B. AAV Vectors

Yet another viral vector system useful for delivery of the subject polynucleotides is the adeno-associated virus (AAV). Adeno-associated virus is a naturally occurring defective virus that requires another virus, such as an adenovirus or a herpes virus, as a helper virus for efficient replication and a productive life cycle. (For a review, see Muzyczka et al., Curr. Topics in Micro. and Immunol. (1992) 158:97–129).

AAV has not been associated with the cause of any disease. AAV is not a transforming or oncogenic virus. AAV integration into chromosomes of human cell lines does not cause any significant alteration in the growth properties or morphological characteristics of the cells. These properties of AAV also recommend it as a potentially useful human gene therapy vector.

AAV is also one of the few viruses that may integrate its DNA into non-dividing cells, e.g., pulmonary epithelial cells, and exhibits a high frequency of stable integration (see for example Flotte et al., (1992) Am. J. Respir. Cell. Mol. Biol. 7:349–356; Samulski et al., (1989) J. Virol. 63:3822–3828; and McLaughlin et al., (1989) J. Virol. 62:1963–1973). Vectors containing as little as 300 base pairs of AAV can be packaged and can integrate. Space for exogenous DNA is limited to about 4.5 kb. An AAV vector such as that described in Tratschin et al., (1985) Mol. Cell. Biol. 5:3251–3260 can be used to introduce DNA into cells. A variety of nucleic acids have been introduced into different cell types using AAV vectors (see for example Hermonat et al., (1984) PNAS USA 81:6466–6470; Tratschin et al., (1985) Mol. Cell. Biol. 4:2072–2081; Wondisford et al., (1988) Mol. Endocrinol. 2:32–39; Tratschin et al., (1984) J. Virol. 51:611–619; and Flotte et al., (1993) J. Biol. Chem. 268:3781–3790).

AAV has been used successfully to introduce gene constructs into retinal cells in animals, including non-human primates. For example, an AAV virus containing a gene encoding FGF-2 was administered by subretinal injection into a transgenic rat model for retinitis pigmentosa, which resulted in reduction of the rate of photoreceptor degeneration (Lau et al. (2000) Invest. Ophthalmol. Vis. Csci. 41:3622). AAV has been used for gene transduction in photoreceptor cells in non-human animals (see, e.g., Flannery et al. (1997) PNAS 94:6916; Bennett et al. (2000) PNAS 96:9920). RPE cells have also been transduced efficiently by subretinal injection of an AAV (Bennett et al. (1997) Invest. Ophthalmol. Visual Sci. 38:2857). Grant et al. also describe that a recombinant AAV injected into the vitreous body or the subretinal space of mouse eyes results in the transduction of cells of the retinal pigment epithelium (RPE), ganglion cells and photoreceptor cells for up to three months, i.e., for as long as the experiment was conducted (Grant et al. (1997) Curr. Eye Res. 16, 949). Efficient transduction of RPE cells in non-human animals is also described in Rollins et al. (2000) Clin Experiment Ophthalmol 28:382–6; Ali et al. (1998) Hum Gene Ther 9:81; and Ali et al. (1996) Hum Mol Genet. 5:591.

The AAV-based expression vector to be used typically includes the 145 nucleotide AAV inverted terminal repeats (ITRs) flanking a restriction site that can be used for subcloning of the transgene, either directly using the restriction site available, or by excision of the transgene with restriction enzymes followed by blunting of the ends, ligation of appropriate DNA linkers, restriction digestion, and ligation into the site between the ITRs. The capacity of AAV vectors is about 4.4 kb. The following proteins have been expressed using various AAV-based vectors, and a variety of promoter/enhancers: neomycin phosphotransferase, chloramphenicol acetyl transferase, Fanconi's anemia gene, cystic fibrosis transmembrane conductance regulator, and granulocyte macrophage colony-stimulating factor (Kotin, R. M., Human Gene Therapy 5:793–801, 1994, Table I). A transgene incorporating the various DNA constructs of this invention can similarly be included in an AAV-based vector. As an alternative to inclusion of a constitutive promoter such as CMV to drive expression of the polynucleotide of interest, an AAV promoter can be used (ITR itself or AAV p5 (Flotte, et al. J. Biol.Chem. 268:3781–3790, 1993)).

Such a vector can be packaged into AAV virions by reported methods. For example, a human cell line such as 293 can be co-transfected with the AAV-based expression vector and another plasmid containing open reading frames encoding AAV rep and cap (which are obligatory for replication and packaging of the recombinant viral construct) under the control of endogenous AAV promoters or a heterologous promoter. In the absence of helper virus, the rep proteins Rep68 and Rep78 prevent accumulation of the replicative form, but upon superinfection with adenovirus or herpes virus, these proteins permit replication from the ITRs (present only in the construct containing the transgene) and expression of the viral capsid proteins. This system results in packaging of the transgene DNA into AAV virions (Carter, B. J., Current Opinion in Biotechnology 3:533–539, 1992; Kotin, R. M, Human Gene Therapy 5:793–801, 1994)). Typically, three days after transfection, recombinant AAV is harvested from the cells along with adenovirus and the contaminating adenovirus is then inactivated by heat treatment.

Methods to improve the titer of AAV can also be used to express the polynucleotide of the invention in an AAV virion. Such strategies include, but are not limited to: stable expression of the ITR-flanked transgene in a cell line followed by transfection with a second plasmid to direct viral packaging; use of a cell line that expresses AAV proteins inducibly, such as temperature-sensitive inducible expression or pharmacologically inducible expression. Alternatively, a cell can be transformed with a first AAV vector including a 5' ITR, a 3' ITR flanking a heterologous gene, and a second AAV vector which includes an inducible origin of replication, e.g., SV40 origin of replication, which is capable of being induced by an agent, such as the SV40 T antigen and which includes DNA sequences encoding the AAV rep and cap proteins. Upon induction by an agent, the second AAV vector may replicate to a high copy number, and thereby increased numbers of infectious AAV particles may be generated (see, e.g., U.S. Pat. No. 5,693,531 by Chiorini et al., issued Dec. 2, 1997). In yet another method for producing large amounts of recombinant AAV, a chimeric plasmid is used which incorporate the Epstein Barr Nuclear Antigen (EBNA) gene, the latent origin of replication of Epstein Barr virus (orip) and an AAV genome. These plasmids are maintained as a multicopy extra-chromosomal elements in cells, such as in 293 cells. Upon addition of wild-type helper functions, these cells will produce high amounts of recombinant AAV (U.S. Pat. No. 5,691,176 by Lebkowski et al., issued Nov. 25, 1997). In another system, an AAV packaging plasmid is provided that allows expression of the rep gene, wherein the p5 promoter, which normally controls rep expression, is replaced with a heterologous promoter (U.S. Pat. No. 5,658,776, by Flotte et al., issued Aug. 19, 1997). Additionally, one may increase the efficiency of AAV transduction by treating the cells with an agent that facilitates the conversion of the single stranded form to the double stranded form, as described in Wilson et al., WO96/39530.

AAV stocks can be produced as described in Hermonat and Muzyczka (1984) PNAS 81:6466, modified by using the pAAV/Ad described by Samulski et al. (1989) J. Virol. 63:3822. Concentration and purification of the virus can be achieved by reported methods such as banding in cesium chloride gradients, as was used for the initial report of AAV vector expression in vivo (Flotte, et al. J.Biol. Chem. 268:3781–3790, 1993) or chromatographic purification, as described in O'Riordan et al., WO97/08298.

Methods for in vitro packaging AAV vectors are also available and have the advantage that there is no size limitation of the DNA packaged into the particles (see, U.S. Pat No. 5,688,676, by Zhou et al., issued Nov. 18, 1997). This procedure involves the preparation of cell free packaging extracts.

For additional detailed guidance on AAV technology which may be useful in the practice of the subject invention, including methods and materials for the incorporation of a transgene, the propagation and purification of the recombinant AAV vector containing the transgene, and its use in transfecting cells and mammals, see e.g. Carter et al, U.S. Pat. No. 4,797,368 (Jan. 10, 1989); Muzyczka et al, U.S. Pat. No. 5,139,941 (Aug. 18, 1992); Lebkowski et al, U.S. Pat. No. 5,173,414 (Dec. 22, 1992); Srivastava, U.S. Pat. No. 5,252,479 (Oct. 12, 1993); Lebkowski et al, U.S. Pat. No. 5,354,678 (Oct. 11, 1994); Shenk et al, U.S. Pat. No. 5,436,146(Jul. 25, 1995); Chatterjee et al, U.S. Pat. No. 5,454,935 (Dec. 12, 995), Carter et al WO 93/24641 (published Dec. 9, 1993), and Natsoulis, U.S. Pat. No. 5,622,856 (Apr. 22, 1997). Further information regarding AAVs and the adenovirus or herpes helper functions required can be found in the following articles: Berns and Bohensky (1987), "Adeno-Associated Viruses: An Update", Advanced in Virus Research, Academic Press, 33:243–306. The genome of AAV is described in Laughlin et al. (1983) "Cloning of infectious adeno-associated virus genomes in bacterial plasmids", Gene, 23: 65–73. Expression of AAV is described in Beaton et al. (1989) "Expression from the Adeno-associated virus p5 and p19 promoters is negatively regulated in trans by the rep protein", J. Virol., 63:4450–4454. Construction of rAAV is described in a number of publications: Tratschin et al. (1984) "Adeno-associated virus vector for high frequency integration, expression and rescue of genes in mammalian cells", Mol. Cell. Biol., 4:2072–2081; Hermonat and Muzyczka (1984) "Use of adeno-associated virus as a mammalian DNA cloning vector: Transduction of neomycin resistance into mammalian tissue culture cells", Proc. Natl. Acad. Sci. USA, 81:6466–6470; McLaughlin et al. (1988) "Adeno-associated virus general transduction vectors: Analysis of Proviral Structures", J. Virol., 62:1963–1973; and Samulski et al.

(1989) "Helper-free stocks of recombinant adeno-associated viruses: normal integration does not require viral gene expression", J. Virol., 63:3822–3828. Cell lines that can be transformed by rAAV are those described in Lebkowski et al. (1988) "Adeno-associated virus: a vector system for efficient introduction and integration of DNA into a variety of mammalian cell types", Mol. Cell. Biol., 8:3988–3996. "Producer" or "packaging" cell lines used in manufacturing recombinant retroviruses are described in Dougherty et al. (1989) J. Virol., 63:3209–3212; and Markowitz et al. (1988) J. Virol., 62:1120–1124.

C. Hybrid Adenovirus-AAV Vectors

Hybrid Adenovirus-AAV vectors represented by an adenovirus capsid containing a nucleic acid comprising a portion of an adenovirus, and 5' and 3' ITR sequences from an AAV which flank a selected transgene under the control of a promoter. See e.g. Wilson et al, International Patent Application Publication No. WO 96/13598. This hybrid vector is characterized by high titer transgene delivery to a host cell and the ability to stably integrate the transgene into the host cell chromosome in the presence of the rep gene. This virus is capable of infecting virtually all cell types (conferred by its adenovirus sequences) and stable long term transgene integration into the host cell genome (conferred by its AAV sequences).

The adenovirus nucleic acid sequences employed in this vector can range from a minimum sequence amount, which requires the use of a helper virus to produce the hybrid virus particle, to only selected deletions of adenovirus genes, which deleted gene products can be supplied in the hybrid viral process by a packaging cell. For example, a hybrid virus can comprise the 5' and 3' inverted terminal repeat (ITR) sequences of an adenovirus (which function as origins of replication). The left terminal sequence (5') sequence of the Ad5 genome that can be used spans bp 1 to about 360 of the conventional adenovirus genome (also referred to as map units 0–1) and includes the 5' ITR and the packaging/enhancer domain. The 3' adenovirus sequences of the hybrid virus include the right terminal 3' ITR sequence which is about 580 nucleotides (about bp 35,353-end of the adenovirus, referred to as about map units 98.4–100).

The AAV sequences useful in the hybrid vector are viral sequences from which the rep and cap polypeptide encoding sequences are deleted and are usually the cis acting 5' and 3' ITR sequences. Thus, the AAV ITR sequences are flanked by the selected adenovirus sequences and the AAV ITR sequences themselves flank a selected transgene. The preparation of the hybrid vector is further described in detail in published PCT application entitled "Hybrid Adenovirus-AAV Virus and Method of Use Thereof, WO 96/13598 by Wilson et al.

For additional detailed guidance on adenovirus and hybrid adenovirus-AAV technology which may be useful in the practice of the subject invention, including methods and materials for the incorporation of a transgene, the propagation and purification of recombinant virus containing the transgene, and its use in transfecting cells and mammals, see also Wilson et al, WO 94/28938, WO 96/13597 and WO 96/26285, and references cited therein.

D. Retroviruses

The retroviruses are a group of single-stranded RNA viruses characterized by an ability to convert their RNA to double-stranded DNA in infected cells by a process of reverse-transcription (Coffin (1990) Retroviridae and their Replication" In Fields, Knipe ed. Virology. New York: Raven Press). The resulting DNA then stably integrates into cellular chromosomes as a provirus and directs synthesis of viral proteins. The integration results in the retention of the viral gene sequences in the recipient cell and its descendants. The retroviral genome contains three genes, gag, pol, and env that code for capsial proteins, polymerase enzyme, and envelope components, respectively. A sequence found upstream from the gag gene, termed psi, functions as a signal for packaging of the genome into virions. Two long terminal repeat (LTR) sequences are present at the 5' and 3' ends of the viral genome. These contain strong promoter and enhancer sequences and are also required for integration in the host cell genome (Coffin (1990), supra).

In order to construct a retroviral vector, a nucleic acid of interest is inserted into the viral genome in the place of certain viral sequences to produce a virus that is replication-defective. In order to produce virions, a packaging cell line containing the gag, pol, and env genes but without the LTR and psi components is constructed (Mann et al. (1983) Cell 33:153). When a recombinant plasmid containing a human cDNA, together with the retroviral LTR and psi sequences is introduced into this cell line (by calcium phosphate precipitation for example), the psi sequence allows the RNA transcript of the recombinant plasmid to be packaged into viral particles, which are then secreted into the culture media (Nicolas and Rubenstein (1988) "Retroviral Vectors", In: Rodriguez and Denhardt ed. Vectors: A Survey of Molecular Cloning Vectors and their Uses. Stoneham:Butterworth; Temin, (1986) "Retrovirus Vectors for Gene Transfer: Efficient Integration into and Expression of Exogenous DNA in Vertebrate Cell Genome", In: Kucherlapati ed. Gene Transfer. New York: Plenum Press; Mann et al., 1983, supra). The media containing the recombinant retroviruses is then collected, optionally concentrated, and used for gene transfer. Retroviral vectors are able to infect a broad variety of cell types. Integration and stable expression require the division of host cells (Paskind et al. (1975) Virology 67:242). This aspect is particularly relevant for the treatment of PVR, since these vectors allow selective targeting of cells which proliferate, i.e., selective targeting of the cells in the epiretinal membrane, since these are the only ones proliferating in eyes of PVR subjects.

A major prerequisite for the use of retroviruses is to ensure the safety of their use, particularly with regard to the possibility of the spread of wild-type virus in the cell population. The development of specialized cell lines (termed "packaging cells") which produce only replication-defective retroviruses has increased the utility of retroviruses for gene therapy, and defective retroviruses are well characterized for use in gene transfer for gene therapy purposes (for a review see Miller, A. D. (1990) Blood 76:271). Thus, recombinant retrovirus can be constructed in which part of the retroviral coding sequence (gag, pol, env) has been replaced by nucleic acid encoding a protein of the present invention, e.g., a transcriptional activator, rendering the retrovirus replication defective. The replication defective retrovirus is then packaged into virions which can be used to infect a target cell through the use of a helper virus by standard techniques. Protocols for producing recombinant retroviruses and for infecting cells in vitro or in vivo with such viruses can be found in Current Protocols in Molecular Biology, Ausubel, F. M. et al., (eds.) Greene Publishing Associates, (1989), Sections 9.10–9.14 and other standard laboratory manuals. Examples of suitable retroviruses include pLJ, pZIP, pWE and pEM which are well known to those skilled in the art. A preferred retroviral vector is a pSR MSVtkNeo (Muller et al. (1991) Mol. Cell Biol. 11:1785 and pSR MSV(XbaI) (Sawyers et al. (1995) J. Exp. Med. 181:307) and derivatives thereof. For example, the unique BamHI sites in both of these vectors can be removed by digesting the vectors with BamHI, filling in with Klenow and religating to produce pSMTN2 and pSMTX2, respectively, as described in PCT/US96/09948 by Clackson et al. Examples of suitable packaging virus lines for preparing both ecotropic and amphotropic retroviral systems include Crip, Cre, 2 and Am.

Retroviruses, including lentiviruses, have been used to introduce a variety of genes into many different cell types, including neural cells, epithelial cells, retinal cells, endothelial cells, lymphocytes, myoblasts, hepatocytes, bone marrow cells, in vitro and/or in vivo (see for example, review by Federico (1999) Curr. Opin. Biotechnol. 10:448; Eglitis et al., (1985) Science 230:1395–1398; Danos and Mulligan, (1988) PNAS USA 85:6460–6464; Wilson et al., (1988) PNAS USA 85:3014–3018; Armentano et al., (1990) PNAS USA 87:6141–6145; Huber et al., (1991) PNAS USA 88:8039–8043; Ferry et al., (1991) PNAS USA 88:8377–8381; Chowdhury et al., (1991) Science 254:1802–1805; van Beusechem et al., (1992) PNAS USA 89:7640–7644; Kay et al., (1992) Human Gene Therapy 3:641–647; Dai et al., (1992) PNAS USA 89:10892–10895; Hwu et al., (1993) J. Immunol. 150:4104–4115; U.S. Pat. No. 4,868,116; U.S. Pat. No. 4,980,286; PCT Application WO 89/07136; PCT Application WO 89/02468; PCT Application WO 89/05345; and PCT Application WO 92/07573).

Furthermore, it has been shown that it is possible to limit the infection spectrum of retroviruses and consequently of retroviral-based vectors, by modifying the viral packaging proteins on the surface of the viral particle (see, for example PCT publications WO93/25234, WO94/06920, and WO94/11524). For instance, strategies for the modification of the infection spectrum of retroviral vectors include: coupling antibodies specific for cell surface antigens to the viral env protein (Roux et al., (1989) PNAS USA 86:9079–9083; Julan et al., (1992) J. Gen Virol 73:3251–3255; and Goud et al., (1983) Virology 163:251–254); or coupling cell surface ligands to the viral env proteins (Neda et al., (1991) J. Biol. Chem. 266:14143–14146). Coupling can be in the form of the chemical cross-linking with a protein or other variety (e.g. lactose to convert the env protein to an asialoglycoprotein), as well as by generating fusion proteins (e.g. single-chain antibody/env fusion proteins). This technique, while useful to limit or otherwise direct the infection to certain tissue types, and can also be used to convert an ecotropic vector in to an amphotropic vector.

E. Other Viral Systems

Other viral vector systems that can be used to deliver a polynucleotide of the invention have been derived from herpes virus, e.g., Herpes Simplex Virus (U.S. Pat. No. 5,631,236 by Woo et al., issued May 20, 1997 and WO 00/08191 by Neurovex), vaccinia virus (Ridgeway (1988) Ridgeway, "Mammalian expression vectors," In: Rodriguez R L, Denhardt D T, ed. Vectors: A survey of molecular cloning vectors and their uses. Stoneham: Butterworth,; Baichwal and Sugden (1986) "Vectors for gene transfer derived from animal DNA viruses: Transient and stable expression of transferred genes," In: Kucherlapati R, ed. Gene transfer. New York: Plenum Press; Coupar et al. (1988) Gene, 68:1–10), and several RNA viruses. Preferred viruses include an alphavirus, a poxivirus, an arena virus, a vaccinia virus, a polio virus, and the like. They offer several attractive features for various mammalian cells (Friedmann (1989) Science, 244:1275–1281; Ridgeway, 1988, supra; Baichwal and Sugden, 1986, supra; Coupar et al., 1988; Horwich et al.(1990) J. Virol., 64:642–650).

With the recent recognition of defective hepatitis B viruses, new insight was gained into the structure-function relationship of different viral sequences. In vitro studies showed that the virus could retain the ability for helper-dependent packaging and reverse transcription despite the deletion of up to 80% of its genome (Horwich et al., 1990, supra). This suggested that large portions of the genome could be replaced with foreign genetic material. The hepatotropism and persistence (integration) were particularly attractive properties for liver-directed gene transfer. Chang et al. recently introduced the chloramphenicol acetyltransferase (CAT) gene into duck hepatitis B virus genome in the place of the polymerase, surface, and pre-surface coding sequences. It was cotransfected with wild-type virus into an avian hepatoma cell line. Culture media containing high titers of the recombinant virus were used to infect primary duckling hepatocytes. Stable CAT gene expression was detected for at least 24 days after transfection (Chang et al. (1991) Hepatology, 14:124A).

Since in certain embodiments, the compositions of the invention will be administered via a specific device, e.g., by injection using a syringe, the invention also provides devices, e.g., syringes, comprising a composition of the invention.

Diseases and Conditions that Can be Treated According to the Methods of the Invention Generally, the invention provides methods for normalizing PDGF-mediated cellular responses, such as cell migration, cell proliferation, contraction, and/or extracellular matrix synthesis or secretion. In a preferred embodiment, the invention provides methods for treating or preventing fibrotic diseases or disorders. Such diseases or disorders generally arise from an excessive or unregulated deposition of new cells and extracellular matrix at a particular site, such as at a site of wound healing. This extra material can cause a disease or disorder by interfering with normal tissue functions. The extra material can also be unsightly. The newly deposited cells and extracellular matrix are generally referred to as scar tissue. In most fibrotic diseases the scar tissue contracts, thereby leading to additional undesirable consequences. Exemplary fibrotic diseases include pulmonary fibrosis (fibrotic disease of the lung), glomerulonephritis (fibrotic disease of the kidney), cirrhosis of the liver (fibrotic disease of the liver), epithelium or skin wound healing, atherosclerosis, and proliferative vitreoretinopathy (PVR). Fibrotic diseases also include repair of tendon damage, the healing of crash injuries, the healing of central nervous system (CNS) injuries, conditions, which result in the formation of scar tissue in the CNS, scar tissue formation resulting from strokes, and tissue adhesion, e.g., as a result of injury or surgery. Thus, the methods of the invention allow healing of wounds or fibrotic diseases with reduced scarring.

The involvement of PDGF in fibrotic diseases has been described in the literature. For example, PDGF and PDGF-R has recently been implicated in fibrotic diseases of the lung (Antoniades, H. N.; et al. J. Clin. Invest. 1990, 86, 1055), kidney and liver (Peterson, T. C. Hepatology, 1993, 17, 486). The involvement of PDGF in PVR has been suggested in Andrews et al. (1999) Invest. Opthalmol. & Vis. Sci. 40:2683.

Wound healing, after a tissue injury, is a process, which can be divided into three phases: inflammation; proliferation; and modulation of the scar. The first phase is caused by breakage of the blood-ocular barrier immediately after the injury and the occurance of an initial inflammatory response. During this stage, platelets are believed to migrate to the site of the lesion and release growth factors, such as PDGF, TGF-β, and EGF. These factors then attract polymorphonuclear cells, which arrive a few hours after the injury, and which release additional factors that attract circulating blood monocytes, which can become macrophages, cells which secrete additional growth factors, e.g., fibroblast growth factor (FGF). In the second stage of the wound healing process, macrophages stimulate the proliferation and accumulation of connective tissue cells that give rise to granulation tissue. The third phase of the wound healing process consists in the reorganization of the cells and extracellular matrix, i.e., the modulation of the tissue previously formed. The fibroblasts then contract and the granulation becomes a mature scar (Pastor J. C. (1998) Survey of Ophthalmology 43:3).

In one embodiment, the method of the invention comprises contacting the site of wound healing or fibrosis with a vector containing a transgene encoding a mutated PDGFR, such that the vector delivers the transgene to cells whose proliferation is undesired, e.g., the connective tissue cells or fibroblasts or other cells which are attracted to the injury site. Expression of the transgene results then in the expression of a mutant PDGFR, which decreases or inhibits the action of PDGF on these cells, as demonstrated in the Examples. As shown in the Examples, it is not necessary to express high levels of the mutant receptor, even if wild type receptor is expressed in the cells. Of course, instead of contacting the site of injury with a vector containing a transgene, it is also possible to deliver the mutated receptor protein directly to the cell in a manner allowing for the mutant receptor protein to be taken up by the cells, e.g., by using a fusion protein of a mutant PDGFR fused to a TAT transduction domain (see, supra). Methods for administering vectors and polypeptides to target cells are further described herein. To achieve targeting of the desired cells, vectors or delivery vehicles that specifically target the desired cells can be used. Alternatively, or in conjunction with such vectors or delivery vehicles, when a vector is delivered to a site of injury, a tissue- or cell-specific promoter can be used to direct expression of the transgene specifically in the desired cell. These methods are also further described herein.

A preferred fibrotic disease that can be treated according to the methods of the invention is PVR. As described in the Background of the Invention, PVR is a major cause for failed retinal detachment surgery. PVR can also be caused by rehgmatogenous retinal detachments, in particular, if associated with other risk factors, such as viterous hemorrhages, aphakia, long-standing retinal detachment, and surgical failures (Pastor J. C., supra). PVR is characterized by the growth and contraction of cellular membranes within the hyaloid and the retinal on both retinal surfaces. It is the traction exerted by these membranes that causes traction retinal detachment that reopens otherwise successfully treated retinal breaks, and may create new retinal breaks. PVR may result in blindness.

PVR is now considered to be result from a scarring process amplified by inflammation (Pastor J. C. (1998) Survey of Ophthalmology 43:3). The development of PVR essentially goes through the same three stages as the general wound healing process described above: inflammation; proliferation; and modulation of the scar. Briefly, a retinal tear causes an inflammatory response and the breakage of the blood-ocular barrier, allowing platelets to migrate to the lesion and release growth factors, e.g., PDGF. An extracellular matrix containing fibrin and fibronectin is produced, which stimulates cell migration by acting as chemotactic elements. Monocytes, as well as glial and retinal pigment epithelial (RPE) cells are attracted to the site of injury and form either together or separately an epiretinal membrane. More growth factors are then secreted by the cells present at the site of injury, and these factors contribute to the second stage, i.e., that of proliferation. The third stage consists of membrane contraction, which results in traction retinal detachments (Pastor J. C., supra), causing loss of visual accuity and potentially blindness.

Various treatments for PVR are described in Pastor J. C., supra, including the use of tamponade agents, such as silicone oil. Some antiproliferative agents have also been administered to patients, e.g., by direct injection into the vitreous. Some drugs are also currently in clinical testing (Pastor J. C., supra).

In one embodiment of the invention, PVR in a subject is treated by administering to the site of the retinal lesion a vector containing a transgene encoding a mutated PDGFR, in a form permitting the vector to be taken up by cells, and expressed in cells. Alternatively, a mutated PDGFR protein is administered to the site of the retinal lesion. The target cells, i.e., the cells in which expression of the mutated PDGFR is desired are the cells in the epiretinal membrane, such as RPE cells, glial cells or potentially fibroblasts and macrophages. Accordingly, in one embodiment, a vector or a mutant PDGFR protein is injected into the vitreous of the eyes of a subject in need thereof The injection can be targeted to the site of the vitreous in which the epiretinal membrane is located, as determined according to methods known in the art. As further described herein, viral vectors have successfully been used for gene delivery to RPE cells. In addition, preferred vectors are those which infect selectively cells that are proliferating. In fact, in PVR, the only proliferating cells in the eye of a subject with PVR are the cells of the epiretinal membrane. Thus, the use of a vector, e.g., retroviral vector, which selectively targets proliferating cells allows for selective targeting of the cells of the epiretinal membrane. Methods for administering vectors and proteins to the vitreous are further described herein.

In one embodiment, PVR can be treated by administering a composition of the invention, and a composition that is cytotoxic to the epiretinal membranes.

The compounds of the invention (e.g., vectors comprising a transgene encoding a mutated PDGFR or a mutated PDGFR protein) can also be used to treat other diseases or disorders. Indeed, PDGF is known to be a powerful cell growth factor related to the control of cell growth and division (Cell 46, 155 (1986)), and its presence in abnormal amounts is known to result in aberrant cell growth. Since it has been shown herein that the mutant PDGFR described herein inhibit PDGF-induced cell growth, these mutants can be used to inhibit the PDGF induced growth of any cells, both in normal situations and in diseases associated with an abnormal PDGF or PDGFR level or protein. Thus, generally the mutant PDGFRs of the invention can be used for treating proliferative diseases. Examples of diseases characterized by an abnormal production of PDGF or PDGFR include leukemias, cancers, psoriasis, glomerular nephritis, organofibrosis, atherosclerosis, restenosis after percutaneous coronary angioplasty or bypass surgery and rheumatoid arthritis. Examples of specific tumor cell types, which overexpress either the PDGF protein or receptor thus leading to the uncontrolled growth of cancer cells via an autocrine or paracrine mechanism include glioblastoma and Kaposi's sarcoma (see Silver, B. J., BioFactors, 1992, 3, 217). Accordingly, the mutant PDGFRs of the invention can be used for treatment of such diseases. Treatment can be undertaken by administering, such as by injection, a vector comprising a transgene encoding a mutated PDGFR or a mutated PDGFR protein to the site of the abnormal cell proliferation, such that the mutated PDGFR is expressed in cells in which one desires to limit growth. It was reported in one clinical trial that abnormal cell growth in is a disease was suppressed by administration of an anti-PDGF antibody (J. Exp. Med. 175, 1413 (1992)).

It has been reported by Thornton, S. C.; et al. (Clin. Exp. Immun. 1991, 86, 79) that TNF-alpha and PDGF (obtained from human rheumatoid arthritis patients) are the major cytokines involved in proliferation of synovial cells. Accordingly, the methods of the invention are believed to be also useful for treating rheumatoid arthritis, characterized by abnormal proliferation of synovial cells.

PDGF is a potent growth factor for mesenchymal and neuroectodermal cells. Endothelial cells have been considered nonresponsive to PDGF, but a recent study has shown that PDGF may have a role in angiogenesis during placenta development. In addition, it has been demonstrated, that PDGFR-b is expressed in endothelial cells in inflammatory tissue and glial tumors (Plate et al., Laboratory Investigation 4:529, 1992). This suggests, that PDGF may play a role in vascular functions in pathological conditions, and thus suggests that the mutant PDGFRs of the invention are useful for treating diseases pertaining characterized by abnormal growth of these cells.

PDGF is considered to be a principal growth-regulatory molecule responsible for smooth muscle cell proliferation. One smooth muscle disorder is atherosclerosis, which is a disease characterized by focal thickening of the inner portion of the artery wall, predisposing an individual to myocardial infarction (heart attack), cerebral infarction (stroke), hypertension (high blood pressure) and gangrene of the extremities. In addition to consisting primarily of proliferated smooth muscle cells, lesions of atherosclerosis are surrounded by large amounts of lipid-laden macrophages, varying numbers of lymphocytes and large amounts of connective tissue. PDGF has been found in numerous cells in such lesions, and it is believed that PDGF plays a critical role in the atherosclerosis disease process.

Another smooth muscle cell disease that can be treated according to the methods of the invention is restenosis. This disease is characterized by the regrowth of smooth muscle cells into the lumen of blood vessels following angioplasty or other arterial damage, is a frequent and recurring problem in the long term success of angioplasty. The failure rates of angioplasty as a result of restenosis within six months are reported to be between 25–50% (Leimgruber et al., 1986; Gruentzieg et al., 1987; Nobuyoshi et al., 1988; Serruys et al., 1988). Restenosis also occurs after arterial reconstructions, atherectomy, stent implantation, and laser angioplasty. Injury to arteries during angioplasty results in the activation of medial smooth muscle cells, which begin to migrate and proliferate into the lumen of the artery to form a neointima, or a new layer of cells. It is believed that expansion of this neointima as a result of the new layer of smooth muscle cells, extracellular matrix, and recruited inflammatory cells, is the cause of the eventual reduction of blood flow through the artery and recurrence of ischemic symptoms. The composition of the instant invention is also useful in the prevention of restenosis after percutaneous transluminal coronary angioplasty by inhibiting neointimal formation (C. Indolfi et al. Nature medicine, 1:541–545 (1995). Such diseases are expected to be treatable with the compounds of the invention.

Administration of the Compounds of the Invention to a Subject

Methods for treating a subject having a disorder relating to a biological activity mediated by PDGF, such as cell proliferation, migration, synthesis and secretion of extracellular matrix and cell contraction can be treated by administration to the subject of a pharmaceutically effective amount of a compound of the invention. A compound of the invention refers to a nucleic acid encoding a mutated PDGFR, to a mutated PDGFR protein, or a compound identified in the gel contraction assay described herein. A nucleic acid is generally administered in the form of a vector, such as a viral vector comprising all transcriptional regulatory elements necessary for appropriate expression in a target cell.

Depending on the type of disease, different methods of administration of the compounds of the invention can be used. For example, a skin disease can be treated by applying a compound of the invention together with an appropriate delivery vehicle to the skin. For treating a lung disease, the compound can be inhaled. Alternatively, for treating a tissue that is inside a human body, a compound of the invention may have to be injected to the desired site. Set forth below are general guidelines for administration of compounds. Specific methods for administration of compounds for treating ocular diseases, such as PVR are described after the general methods.

The therapeutic methods of the invention generally comprises administering to a subject in need thereof, a pharmaceutically effective amount of a compound. The compounds of the invention can be administered in a "growth inhibitory amount," i.e., an amount of the compound which is pharmaceutically effective to inhibit or decrease proliferation of target cells. The compounds of this invention may be administered to mammals, preferably humans, either alone or, preferably, in combination with pharmaceutically acceptable carriers, excipients or diluents, in a pharmaceutical composition, according to standard pharmaceutical practice. The compounds can be administered orally or parenterally, including the intravenous, intramuscular, intraperitoneal, subcutaneous, rectal and topical routes of administration.

Toxicity and therapeutic efficacy of the compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Reagents which exhibit large therapeutic indices are preferred. While reagents that exhibit toxic side effects may be used, care should be taken to design a delivery system that targets such reagents to the site of affected tissue in order to minimize potential damage to uninfected cells and, thereby, reduce side effects.

The data obtained from cell culture assays and animal studies can be used in formulating a range of dosage for use in humans. The dosage of such reagents lies preferably within a range of circulating concentrations that include the $ED_{50}$ with little or no toxicity. The dosage may vary within this range depending upon the dosage form employed and the route of administration utilized. For any reagent used in the method of the invention, the therapeutically effective dose can be estimated initially from cell culture assays. A dose may be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, microcrystalline cellulose, sodium crosscarmellose, corn starch, or alginic acid; binding agents, for example starch, gelatin, polyvinyl-pyrrolidone or acacia, and lubricating agents, for example, magnesium stearate, stearic acid or talc. The tablets may be uncoated or they may be coated by known techniques to mask the unpleasant taste of the drug or delay disintegration and absorption in the gastrointestinal tract and thereby provide a sustained action over a longer period. For example, a water soluble taste masking material such as hydroxypropylmethyl-cellulose or hydroxypropylcellulose, or a time delay material such as ethyl cellulose, cellulose acetate buryrate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water soluble carrier such as polyethyleneglycol or an oil medium, for example peanut oil, liquid paraffin, or olive oil.

Aqueous suspensions contain the active material in admixture with excipients suitable for the manufacture of aqueous suspensions. Such excipients are suspending agents, for example sodium carboxymethylcellulose, methylcellulose, hydroxypropylmethyl-cellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethylene-oxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose, saccharin or aspartame.

Oily suspensions may be formulated by suspending the active ingredient in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as butylated hydroxyanisol or alpha-tocopherol.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present. These compositions may be preserved by the addition of an anti-oxidant such as ascorbic acid.

The pharmaceutical compositions of the invention may also be in the form of an oil-in-water emulsions. The oily phase may be a vegetable oil, for example olive oil or arachis oil, or a mineral oil, for example liquid paraffin or mixtures of these. Suitable emulsifying agents may be naturally-occurring phosphatides, for example soy bean lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening, flavouring agents, preservatives and antioxidants.

Syrups and elixirs may be formulated with sweetening agents, for example glycerol, propylene glycol, sorbitol or sucrose. Such formulations may also contain a demulcent, a preservative, flavoring and coloring agents and antioxidant.

The pharmaceutical compositions may be in the form of a sterile injectable aqueous solutions. Among the acceptable vehicles and solvents that may be employed are water, Ringer's solution and isotonic sodium chloride solution.

The sterile injectable preparation may also be a sterile injectable oil-in-water microemulsion where the active ingredient is dissolved in the oily phase. For example, the active ingredient may be first dissolved in a mixture of soybean oil and lecithin. The oil solution then introduced into a water and glycerol mixture and processed to form a microemulation.

The injectable solutions or microemulsions may be introduced into a patient's blood-stream by local bolus injection. Alternatively, it may be advantageous to administer the solution or microemulsion in such a way as to maintain a constant circulating concentration of the instant compound. In order to maintain such a constant concentration, a continuous intravenous delivery device may be utilized. An example of such a device is the Deltec CADD-PLUS.TM. model 5400 intravenous pump.

The pharmaceutical compositions may be in the form of a sterile injectable aqueous or oleagenous suspension for intramuscular and subcutaneous administration. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Compounds of the invention may also be administered in the form of a suppositories for rectal administration of the drug. These compositions can be prepared by mixing the drug with a suitable nonirritating excipient which is solid at ordinary temperatures but liquid at the rectal temperature and will therefore melt in the rectum to release the drug.

Such materials include cocoa butter, glycerinated gelatin, hydrogenated vegetable oils, mixtures of polyethylene glycols of various molecular weights and fatty acid esters of polyethylene glycol.

For topical use, creams, ointments, jellies, solutions or suspensions, etc., containing the compound of the invention are employed. For purposes of this application, topical application shall include mouth washes and gargles.

The compounds for the present invention can be administered in intranasal form via topical use of suitable intranasal vehicles and delivery devices, or via transdermal routes, using those forms of transdermal skin patches well known to those of ordinary skill in the art. To be administered in the form of a transdermal delivery system, the dosage administration will, of course, be continuous rather than intermittent throughout the dosage regimen.

As used herein, the term "composition" is intended to encompass a product comprising the specified ingredients in the specific amounts, as well as any product which results, directly or indirectly, from combination of the specific ingredients in the specified amounts.

The compounds identified by the instant method may also be co-administered with other well known therapeutic agents that are selected for their particular usefulness against the condition that is being treated.

When a composition according to this invention is administered into a human subject, the daily dosage will normally be determined by the prescribing physician with the dosage generally varying according to the age, weight, and response of the individual patient, as well as the severity of the patient's symptoms.

In a preferred embodiment for treating PVR, the compound of the invention is introduced into the vitreous cavity of an eye of a subject, e.g., by injection. The injection can be preformed according to procedures standard in the art.

The compound will be suspended in an opthalmologically acceptable carrier for introduction into the eye of a subject. The term "carrier" denotes an organic or inorganic ingredient, natural or synthetic, with which the active ingredient is combined to facilitate the application. An opthalmologically acceptable carrier is a substance which is non-toxic to the subject given the treatment and which also does not inhibit or degrade the activity of the compound of the invention. An opthalmologically acceptable carrier is preferably a sterile diluent having a pH and osmolarity compatible with normal human vitreous. Examples of opthalmologically acceptable carriers include phosphate buffered saline and lactated Ringer's solution. A particularly preferred opthalmologically acceptable carrier for suspension of the compound of the invention is $Ca^{2+}$- and $Mg^{2+}$-free phosphate buffered saline (PBS) of pH 7.4 and 298 milliosmoles. Other opthalmologically acceptable carriers are well known in the art and can be found in standard reference texts such as Remington's Pharmaceutical Sciences (Mack Publishing Company, Easton, Pa.). Ophthalmologically acceptable compositions can routinely contain salts, buffering agents, preservatives, compatible carriers, and optionally other therapeutic ingredients. When used in ophthalmology, the salts should be ophthalmologically acceptable, but nonophthalmologically acceptable salts can be conveniently used to prepare ophthalmologically acceptable salts thereof and are not excluded from the scope of the invention. Such opthamologically acceptable salts include, but are not limited to those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, maleic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, formic, malonic, naphthalene-2-sulfonic, benzenesulfonic and the like. Also, ophthalmologically acceptable salts can be prepared as alkaline metal or alkaline earth salts, such as sodium, potassium or calcium salts of the carboxylic acid group. The components of the ophthalmological compositions are also capable of being comingled with the molecules of the present invention, and with each other in a manner such that there is no interaction which would substantially impair the desired pharmaceutical affect.

It may also be advantageous to administer the compound of the invention utililizing a method of a slow release, for instance, by inbraveitreal injection of the dose of the compound encapsulated in a microvesicle, such as a liposome, from which the compound is released over the course of several days, e.g., between 3 to 20 days. The compound can be formulated for slow release, such as incorporation into a slow release polymer from which the dosage of drug is slowly released over the course of several days, e.g., 2 to 30 days (see, e.g., Berger et al. (1996) Invest. Ophtahlamol Vis Sci 37:2318).

The compound useful for treating or preventing PVP is introduced into the eye in amounts sufficient to inhibit proliferation, migration, contraction, and/or extracellular matrix secretion from cells forming epiretinal membranes, e.g., RPE cells. The amount of the compound that is introduced can vary according to the condition of the subject being treated, the pH of the intraocular fluid, the severity of the condition, the time available for treatment, and the like. The total amount of compound used in the invention can vary with, in addition to the concentration noted above, the volume introduced into the vitreous cavity of the subject's eye. The volume of compound introduced can be a function of the size of the eye, the age of the subject, the severity of the condition and the like. Administration of the same total amount of compound can be accomplished using a greater volume of a lower concentration dispase solution or a smaller volume of a higher concentration compound solution, according to the needs of the subject or preferences of the practitioner. The volume of the vitreous cavity is limited, however, so that in general between 100 microliters and 500 microliters can be injected into the eye of a subject.

As used herein, an effective amount of a compound of the invention, e.g., a construct encoding a PDGFR mutant or a compound as identified by a gel contraction assay described herein, is a dosage large enough to reduce the development of an epiretinal membrane in the vitreous of a subject, e.g., by inhibiting proliferation and/or contraction and/or extracellular matrix secretion and/or migration of cells in or to the epiretinal membrane. An effective amount is not, however, a dosage so large as to cause adverse side affects. Generally, an effective amount can vary with the subject's age and condition, as well as the extent of the condition being treated, and can be determined by one of skilled in the art. The dosage can be adjusted by the individual practitioner in the event of any complication.

Although injection of the compounds of the invention into the vitrous cavity is a preferred mode of administration of the therapeutic, a variety of other administration routes for the compound of the invention are available. The particular mode selected will depend of course, upon the particular subject, the severity of the condition being treated and the dosage required for therapeutic efficacy. The methods of this invention, generally speaking, can be practiced using any mode of administration that is ophthalmologically acceptable, meaning any mode that produces effective levels of the active compounds without causing clinically unacceptable adverse affects.

The invention permits use of a compound of the invention, e.g., a construct encoding a PDGFR mutant, in connection with any intraocular surgery, which may result in PVR. As used herein, "intraocular surgery" means surgery within the eye and encompasses surgeries for many different conditions. Intraocular surgeries in which the invention can be used include vitrectomy for macular hole surgery, vitrectomy for proliferative vascular retinopathies, repair of a retinal detachment, prevention of a retinal detachment, subretinal surgery, submacular surgery and retinal transplantation. Other intraocular surgeries to which the invention is applicable will be known to those of skill in the art.

The invention can also be used for non-surgical treatment of blinding complications associated with certain conditions of the eye. Conditions treatable by the invention include those conditions in which a retinal tear or a partial or complete retinal detachment can occur if left untreated. Such conditions include diabetic retinopathy, central vein occlusion, proliferative vitreal retinopathy and proliferative vascular retinopathy.

The compound of the invention may be injected into the anterior vitreous cavity using topical or retrobulbar anesthesia. The compound can also be introduced intravitreally using a drug delivery vehicle. For example, the compound can be issolved in a biologically inert fluid that is also useful as a mechanical tamponade to help keep the retina in place, preferably an oil such as silicone oil. It has been reported that silicone oil also serves as a delivery vehicle system in the eyes, thereby serving two purposes at the same time (Pastor C. P., supra).

Cell Contraction Assay for Identifying Compounds for Treating PDGF-related Diseases The invention further provides assays for identifying compounds, e.g., small molecules, which can be used for treating fibrotic diseases. The assay generally comprises determining the effect of a test compound on the contraction of a cell population present in essentially a monolayer in a cell culture dish. In an even more preferred embodiment, the cells are plated in a gel, such as a collagen gel. A preferred collagen gel is a collagen type I gel. The cells can be plated on top of the gel, or alternatively within the gel. A preferred contraction assay is set forth in the Examples. Briefly, the cells are suspended in a gel, e.g., a collagen gel and plated in a dish, and culture medium is added to the dish. The diameter of gel is then measured (control diameter). The cells are incubated with a test substance for an appropriate time, and the diameter is then measured again to determine whether any contraction occurred. In a situation in which one desires to determine the effect of a test substance on stimulation of contraction by a certain agent, e.g., PDGF, the cells are incubated with the test substance and the agent, e.g. PDGF, and the effect of the substance on the PDGF-induced contraction is determined. In the embodiment in which one desires to isolated therapeutics for treating PVR, one can incubate the cells with vitreous or TNF-beta or PDGF and with the test substance, compare contraction of cells incubated with vitreous or TNF-beta or PDGF together or not with the test substance. Thus, a decrease of the contraction induced by vitreous or TNF-beta or PDGF in the presence of the test substance relative to the absence of the test substance indicates that the test substances prevents contraction of the cells, and that, thus, the test substances would be efficient for treating diseases or disorders resulting at least in part from cell contraction, e.g., excessive scarring.

Thus, generally, the invention provides a method for identifying an agent effective in treating a fibrotic disease in a subject, comprising contacting the agent with cells and a stimulus, under conditions in which the cells contract in the presence of the stimulus, and wherein a reduction in the contraction of the cells in the presence of the agent relative to their contraction in the absence of the agent indicates that the agent is effective in treating a fibrotic disease in a subject. The cells may be suspended in a collagen matrix having a defined size, and the method comprises comparing the size of the collagen matrix in the presence relative to the absence of the agent.

Although the cells used in the assay can be primary cultures, the cells are preferably from established cell lines. Indeed, it is more convenient to use cell lines, rather to have to isolate fresh cells and establish a culture of the fresh cells. A cell line can also be established from primary cultures according to method known in the art, such as by infection with SV40. Even more preferred cells are epithelial cells or fibrobast cells. The cells can be mammalian cells, such as human, mouse, rat, canine, ovine, bovine or chicken cells. In a preferred embodiment, the cells are immortalized mouse embryo fibroblasts.

Although certain types of gel contraction assays are known in the art, it has been discovered (as described in the Examples) that cell lines, e.g., immortalized cells, as opposed to primary cell cultures, can be used in a gel contraction assay to predict the effect of a drug in treating a disease associated with cell and/or matrix contraction. The use of cell lines is much more convenient, since it avoids having to isolate fresh cells everytime one desires to conduct an assay. It also allows for a better reproducibility, since the assay would be based on the same cells, rather than on fresh cells obtained from different subjects or animals. It has been shown herein that there is a strong correlation between the effect on contraction of a substance (a mutated receptor) and its ability to prevent development of PVR in an animal model.

The preferred assays of the invention further differ from the collagen contraction assays described in that the cells can be imbedded within the gel. This allows to save time in that it avoids having to first plate the gel in a dish and then the cells. Rather the cells are mixed with the gel and the mixture is then plated in the dish.

Gel contraction assays can easily be carried in the form of high throughput assays for testing millions of compounds simultaneously.

The contraction assays can be used for identifying compounds for treating various types of diseases in which cell and/or matrix contraction is involved, e.g., fibrotic diseases. For identifying compounds for identifying one or another fibrotic disease, the cell used in the assay can be chose such as to ressemble the cells that contract in the particular fibrotic disease and the particular stimulus in the disease that causes cell contraction. Thus, for example, for identifying compounds which prevent excessive scarring in skin wound healing, the cells used in the assay can be epithelial cells, e.g., from an epithelial cell line, and the simulus can be PDGR.

Kits of the Invention

The invention provides kits for treating and/or preventing diseases or disorders associated with a defect in PDGFR-mediated biological activity, such as cell proliferation, cell migration, synthesis and secretion of extracellular matrix, and cell contraction, e.g., fibrotic diseases. In preferred embodiments, the invention provides kits for treating abnormal wound healing processes, e.g., PVR. Certain kits include a container containing an amount of a compound of the invention, e.g., a nucleic acid or viral particle encoding a PDGFR mutant, in an ophthalmologically acceptable carrier effective to treat or prevent a disease, e.g., abnormal wound healing processes. Kits may also contain other compositions and devices useful for administration of the compound of the invention to the subject, e.g., a syringe. Kits may also contain instructions for use.

The kits may be enclosed in a package, such as a box, blister pack or similar packing vehicle used conventionally to hold containers of liquid. The package can be coated with an impervious cover to assist in protecting the sterility of the contents during transport and storage. The containers preferably are glass bottles, but can be formed of any inert material such as a rigid or flexible plastic in the form of bottles or bags that allow transport and storage of liquid without loss of fluid or contamination of the contents.

Other kits of the invention comprise the components of the gel contraction assay described herein. For example, a kit may comprise a cells for use in the assay, e.g., a cell line; the gel, e.g., collagen type I; cell growth medium; a simulus, e.g., PDGF; and control reagents.

The present invention is further illustrated by the following examples, which should not be construed as limiting in any way. The contents of all cited references (including literature references, issued patents, published patent applications as cited throughout this application) are hereby expressly incorporated by reference.

The practice of the present invention will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, Molecular Cloning A Laboratory Manual, $_2$nd Ed., ed. by Sambrook, Fritsch and Maniatis (Cold Spring Harbor Laboratory Press: 1989); DNA Cloning, Volumes I and II (D. N. Glover ed., 1985); Oligonucleotide Synthesis (M. J. Gait ed., 1984); Mullis et al. U.S. Pat. No. 4,683,195; Nucleic Acid Hybridization (B. D. Hames & S. J. Higgins eds. 1984); Transcription And Translation (B. D. Hames & S. J. Higgins eds. 1984); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the treatise, Methods In Enzymology (Academic Press, Inc., N.Y.); Gene Transfer Vectors For Mammalian Cells (J. H. Miller and M. P. Calos eds., 1987, Cold Spring Harbor Laboratory); Methods In Enzymology, Vols. 154 and 155 (Wu et al. eds.), Immunochemical Methods In Cell And Molecular Biology (Mayer and Walker, eds., Academic Press, London, 1987); Handbook Of Experimental Immunology, Volumes I–IV (D. M. Weir and C. C. Blackwell, eds., 1986); Manipulating the Mouse Embryo, (Cold Spring Harbor Laboratory Press, Cold Spring Harbor, N.Y., 1986).

EXAMPLES

Example 1

Expression of αPDGFR Mutants

This example describes the construction of αPDGFR mutants capable of inhibiting or reducing the activity of the wildtype (WT) αPDGFR.

Five αPDGFR mutants including one dominant negative αPDGFR mutant, shown in FIG. 1A., were created based on the homology of the αPDGFR with the c-kit receptor. The c-kit receptor belongs to the same family of tyrosine receptor kinase as the αPDGFR, and like the αPDGFR it has an extracellular domain, transmembrane domain, juxtamembrane domain, and tyrosine kinase that is interrupted by a kinase insert. Qiu, F. H. et al. (1988) *Embo. J.* 7:1003; Majumder, S. et al. (1988) *Mol. Cell. Biol.* 8:4896; Yarden, Y. et al. (1986) *Nature* 323:226. Single point mutations in c-kit are responsible for the deficits of $W^{37}$, $W^v$, $W^{42}$, and $W^{41}$ strains of mice. The abnormalities include white spotting on the skin, infertility, stem cell deficiency and anemia. $W^{37}$ has a substitution of Glu to Lys at position 582 juxtamembrane domain); $W^v$ has Met instead of Thr at 660 (first half of the kinase domain); Asp replaces Asn at 790 (second half of the kinase domain) in $W^{42}$; and $W^{41}$ has a Val to Met substitution at 831 (second half of the kinase domain). Nocka, K. et al. (1990) *Embo. J.* 9:1805; Tan, J. C. et al. (1990) *Science* 247:209. The affected mice were heterozygous for the mutations suggesting that the mutant form of c-kit was dominant to the normal copy of c-kit, which was also expressed. In fact, all the c-kit receptor mutants have been shown to function as dominant negatives in a mast cell proliferation assay. Nocka, K. et al (1990) *Embo. J.* 9:1805. Mice do not survive when both c-kit alleles harbor either the $W^{37}$ or $W^{42}$ point mutant. Geissler, E. N. et al. (1981) *Genetics* 97:337.

The point mutants in c-kit lie in regions of the intracellular domain that are highly conserved within this class of receptor tyrosine kinases. When the single amino acid substitution correspodingly to $W^{37}$ was introduced into Xenopus αPDGFR, the resulting mutant blocked αPDGFR-dependent events during development. Furthermore, this mutant prevented PDGF-dependent tyrosine phosphorylation of the wild type (WT) αPDGFR when the mutant and WT receptor were co-expressed. Ataliotis, P. et al. (1995) *Development* 121:3099.

Four αPDGFR mutants were created by introducing into the WT αPDGFR each of the W mutations of the c-kit receptor, i.e., a single amino acid substitution, which corresponds to the $W^{37}$, $W^v$, $W^{42}$, or $W^{41}$ c-kit mutants. Another αPDGFR mutant was created by truncation of the WT receptor to eliminate the kinase domain and carboxyterminus. Such a truncated receptor heterodimerizes with a WT receptor and prevents activation of the WT receptor.

The truncated receptor was generated as follows. The 4.3 kb Not I/Xba I cDNA fragment containing the α/β chimeric receptor DeMali, K. A. et al. (1997) *J. Biol. Chem.* 272:9011, was subcloned into pBlueScript SK (Stratagene, La Jolla, Calif.). This construct was cut with Sac II and Xba I, and the liberated cDNA fragment (which contains all of the βPDGFR sequence) was discarded. The remaining fragment was treated with Klenow to blunt-end the DNA, and then religated. The 2.0 kb Not I/Sal I αPDGFR fragment was subcloned into pLXSN$^2$, DeMali, K. A. et al. (1997) *J. Biol. Chem.* 272:9011, that had also been cut with this enzyme pair. The protein encoded by this portion of the αPDGFR cDNA includes all of the extracellular, transmembrane, and juxtamembrane domains, and has a stop codon at nucleotide 1972, with no change in the predicted amino acid sequence. The last amino acid of the truncated receptor is proline 589, in the sequence "DSRWEFP" (SEQ ID NO: 25), and is near or at the juxtamembrane/kinase domain junction. The nucleotide and amino acid sequences of the truncated αPDGFR are set forth in SEQ ID Nos: 11 and 12, respectively.

Because the protein sequence surrounding the mutated amino acid in the $W^{37}$, $W^v$, $W^{42}$, and $W^{41}$ in c-kit receptors were highly conserved, corresponding substitution in the αPDGFR could be made. Accordingly, the following mutations were introduced into the human αPDGFR cDNA: Glu to Lys at the position 587 for $W^{37}$ (SEQ ID NO: 3 encoding amino acid sequence SEQ ID NO: 4); Thr to Met at 665 for $W_y$ (SEQ ID NO: 5 encoding amino acid sequence SEQ ID NO: 6); Asp to Asn at 818 for $W^{42}$ (SEQ ID NO: 7 encoding amino acid sequence SEQ ID NO: 6); and Val to Met at 859 for $W^{41}$ (SEQ ID NO: 9 encoding amino acid sequence SEQ ID NO: 8) (FIG. 1A). The mutants were generated using polymerase chain reaction (PCR), and the template was 18G generated from 18F. The 18F was made by subcloning the 3.5 kb wild type human αPDGFR cDNA (SEQ ID NO: 1; Bazenet, C. E. et al. (1996) Mol. Cell. Biol. 16:6926) into pBlueScript II SK+ (Stratagene, La Jolla, Calif.) using Not I/Bam HI site. We generated 18G from 18F by introducing Sac II site at 1975, which is an unique site for this construct. DeMali, K. A. et al. (1997) J. Biol. Chem. 272:9011. The PCR-generated mutants were subcloned into 18G as an Nco I/Sac II fragment (E587K), as a Sac II/Stu I fragment (T665M), or as a Stu I/Sph I fragment (D818N and V859M). The sequences of the point mutants and that of the truncated receptor were confirmed by sequencing the DNA.

βPDGFR mutants having point mutations corresponding to those introduced into the αPDGFR were also prepared. The wildtype αPDGFR nucleotide and amino acid sequences are set forth as SEQ ID Nos: 11 and 12, and the mutant αPDGFR nucleotide and amino acid sequences are set forth as SEQ ID Nos: 13–42, respectively.

The mutant PDGFR constructs were subcloned into pLH-DCX$^2$ retroviral vector using the Not I/Sal I site. This vector has a modified multiple cloning site containing Not I-Bgl II-Sal I-Hind III driven by cytomegalovirus (CMV) promoter. The vector also encodes a histidinol resistant gene, which is driven by the long terminal repeat (LTR) promoter. Purified DNA (25 μg) was transfected into 293 GPG replication-incompetent retrovirus-producing cells, Ory, D. S. et al. (1996) Proc. Natl. Acad. Sci. USA 93:11400, using lipofectamine (Gibco BRL) according to the manufacture's instruction, and virus in the supernatant was collected from day 3 through 8. The virus was concentrated by centrifugation at 30,000 g at 4° C. for 90 minutes, and resuspended in TNE solution (50 mM Tris-HCl pH 7.8, 130 mM NaCl, 1 mM EDTA), and it was stored at −70° C. until use.

The mutant receptors were then expressed in NIH 3T3 and rabbit conjunctival fibroblast (RCF) cells. NIH 3T3 cells were cultured and maintained in Dulbecco's Modified Essential Media (DMEM; Gibco BRL, Grand Island, N.Y.) with 10% fetal bovine serum (FBS; Gemini Bio Products, Calabasas, Calif.) supplemented with antibiotics. Primary RCFs were isolated from rabbit conjunctiva and maintained as previously described, Nakagawa, M. et al. (1995) Invest. Ophthalmol. Vis. Sci. 36:2388, except that instead of amphotericin B and gentamycin, 500 U/ml of penicillin-G and 500 μg/ml of streptomycin were used as antibiotic supplements.

To express the mutant receptors, NIH 3T3 cells were incubated overnight with the virus harbouring mutated αPDGFR or empty vector in the presence of 4 μg/ml of polybrene in DMEM with 10% FBS. The infected cells were passaged into new dishes and cultured in DMEM with 10% FBS supplemented with 5 mM histidinol (Sigma, St. Louis. Mo.). Mass populations of drug resistant cells (i.e., population of cells that does not derive from one single transfected cell, but rather from multiple transfected cells) were in the experiments.

NIH 3T3 cells were chosen in this example because it is a well characterized cell line that responds mitogenically to PDGF-AA (see FIG. 4 below). The level of expression of the wiltype and mutated receptors in the cells was deteremined by immunoprecipitation and Western Blotting, as follows. NIH 3T3 cells were grown to 80% confluency and then incubated for 20 hours in DMEM containing 0.1% FBS and 0.4 mg/ml bovine serum albumin (BSA) to obtain serum starved cells. Cells were exposed at 37° C. for 5 minutes to either 50 ng/ml of PDGF-AA or left unstimulated with buffer. Cells were washed with H/S (20 mM Hepes, pH 7.4, 150 mM NaCl) twice and then lysed in EB (10 mM Tris-HCl, pH 7.4, 5 mM EDTA, 50 mM NaCl, 50 mM NaF, 1% Triton-X 100, 0.1% BSA, 20 μg/ml aprotinin, 2 mM Na$_3$VO$_4$, 1 mM phenylmethylsulfonyl floride; PMSF) or RIPA buffer (150 mM NaCl, 10 mM NaPO$_4$, 2 mM EDTA, 1% DOC, 1% NP40, 0.1% SDS, 20 μg/ml aprotinin). Kazlauskas, A et al. (1988) J. Cell Biol. 106:1395. Lysates were centrifuged for 15 minutes at 13,000 g, and the pellet was discarded and the soluble fraction was used as the total cell lysate. The protein concentration was measured using protein assay kit (Pierce, Rockfield, Ill.) following the manufacture's instruction.

For Western blotting, total cell lysates containing 20 μg of protein from NIH 3T3 cells transfected with each of the αPDGFR point or truncated mutants or empty vector were resolved in 7.5% SDS-PAGE gel under reduced conditions. Proteins were transferred onto Immobilon (Millipore, Bedford Mass.). Membranes were blocked using Block (10 mg/ml BSA, 10 mg/ml ovalbumin, 0.05% Tween 20, dissolved in Western Rinse; 1 mM Tris-HCl, pH 7.5, 150 mM NaCl) for anti-phosphotyrosine blotting. The membranes were blocked in Blotto (10 mg/ml non fat dry milk, 0.05% Tween 20 in Western Rinse Solution) for other blotting. Membranes were incubated with primary antibodies (27P and 80.8 antibodies against αPDGFR in a 1:1 ratio and a dilution of 1:1000 or Ras GTP-activating protein (RasGAP) antibody 69.3 at a dilution of 1:4000) for 1 hour at room temperature, and washed 5 times with Western Rinse solution (150 mM NaCl, 10 mM Tris-HCl pH 7.5, 1.5 mM Tris base). The blots were then incubated with secondary antibody for 1 hour at room temperature and washed 5 times by Western Rinse solution as well. Secondary antibodies were horseradish peroxidase conjugated goat anti-rabbit or anti-mouse antibodies (Amersham Pharmacia Biotech) diluted 1:5000. Finally all blots were visualized using ECL (Amersham Pharmacia Biotech, Piscataway, N.J.).

The 27P antibody is crude polyclonal rabbit antibody raised against a glutathione S-transferase (GST-) fusion protein including the human PDGFR carboxyl terminus (amino acids 951–1089), which available from Pharmingen. The 80.8 antibody was raised against a GST-fusion protein including a portion of the first immunoglobulin domain (amino acids 52–94) of human αPDGFR. Both of these antibodies recognize the human and mouse αPDGFR and thus recognize both the endogenous and the introduced receptor. The Ras GTP-activating protein (RasGAP) antibody is a crude rabbit antisera against the SH2-SH3-SH2 of the human RasGAP (69.3), which serves as an internal control for the amount of protein loaded on the gel.

The results of the Western blot, which are shown in FIG. 1B, indicate that each of the mutants (which migrate slightly faster than the endogenous receptor, were expressed 2–4 fold above the level of the endogenous, WT, αPDGFR (FIG. 1B). The truncated receptor migrates faster due to its smaller size since it lacks the kinase domain and carboxy-terminus. Since only one of the antibodies recognizes the truncated receptor (it lacks the 27P epitope) the level of expression of this receptor may be underestimated. The results indicate that all 5 of the mutant α-receptors were successfully constructed and stably expressed.

Mutants of the human beta PDGFR were similarly constructed and their stable expression verified. These receptors were the following: a truncated mutant, lacking essentially all of the cytoplasmic doamin, in which the last residue is amino acid 561 of SEQ ID NO: 14. The amino acid sequence of this receptor is set forth in SEQ ID NO: 24, and encoded by the nucleotide sequence is SEQ ID NO: 23. Four point mutation receptors were generated: E594K; T672M; D826N; and L867M, the amino acid sequence of each of which is set forth in SEQ ID Nos: 16, 18, 20 and 22, respectively, and the nucleotide sequence is set forth in SEQ ID Nos: 15, 17, 19, and 21, respectively.

Example 2

The Wild-type Receptor is Poorly Phosphorylated in Cells Expressing the Truncated αPDGFR This example describes the measurement of PDGF-dependent tyrosine phosphorylation of the αPDGFR, which is an early required event in the signaling cascade.

Figure 2:
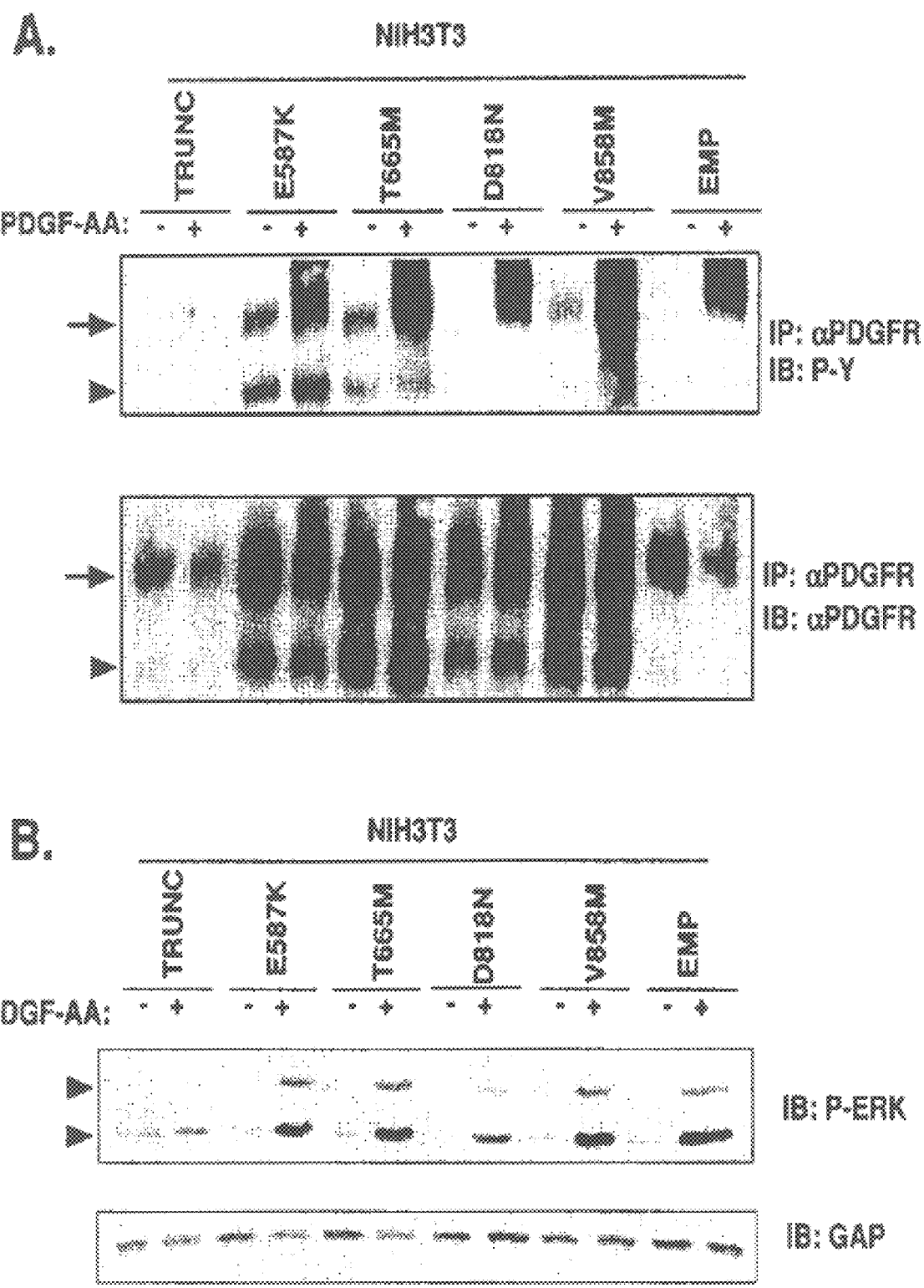
FIG. 2A shows Western blots of anti-αPDGFR antibody (27P) immunoprecipitated protein from NIH 3T3 cells expressing a mutant receptor or the empty expression vector (EMP), which were serum starved overnight, and exposed to either buffer (−) or 50 ng/ml of PDGF-AA (+) for 5 minutes, and incubated with an anti-phosphotyrosine (P-Y) antibody (top panel), or with an anti-αPDGFR antibody (bottom panel) after stripping of the anti-phosphotyrosine antibody. In both panels, the arrow indicates the mature αPDGFR, while the arrowhead points to the immature form of the receptor. IP: immunoprecipitation; IB: immunoblot (western); the abbreviations for the receptor mutants are detailed in the legend of FIG. 1.
FIG. 2B shows a Western blot of lysates from cells that were stimulated as described in FIG. 2A, incubated with anti-phospho-Erk (P-Erk, top panel) or anti-Ras GTP-activating protein (RasGAP; lysate control, bottom panel) antibody. The arrowheads point to the p44 and p42 forms of Erk, both of which are activated by growth factors such as PDGF.

NIH 3T3 cells expressing a mutant receptor or the empty expression vector (EMP) were serum starved overnight, as described above, and exposed to either buffer (−) or 50 ng/ml of PDGF-AA (+) for 5 minutes. The cells were lysed, and immunoprecipitated with the 27P antibody, which recognizes both the endogenous mouse and introduced human PDGF α receptor (αPDGFR) mutant. Immune complex was bound to formalin-fixed membranes of *Staphylococcus aureus*, spun through an EB sucrose gradient, and washed twice with EB, then with PAN (10 mM Pipes, pH 7.0, 100 mM NaCl, 1% aprotinin) +0.5% Nonidet P-40 (NP-40), and finally with PAN. The samples were resuspended in PAN before using for Western blotting. Immunoprecipitates representing approximately $1 \times 10^6$ cells were subjected to an anti-phosphotyrosine western blot (FIG. 2A, top panel). The anti-phosphotyrosine antibody consisted actually of a mixture of 4G10 and PY20 at a ratio of 1:1 used at a dilution of 1:5000. 4G10 and PY20 are mouse monoclonal anti-phosphotyrosine antibodies, which were purchased from Upstate biotechnology Inc (Lake Placid, N.Y.) or Transduction Laboratories (San Diego, Calif.). The secondary antibody was as described above.

The anti-phosphotyrosine antibodies were stripped from the Western blot and the later was then incubated with an anti-αPDGFR antibody (27P and 80.8) (FIG. 2A, bottom panel). Three independent experiments showed similar results.

Figure 3:
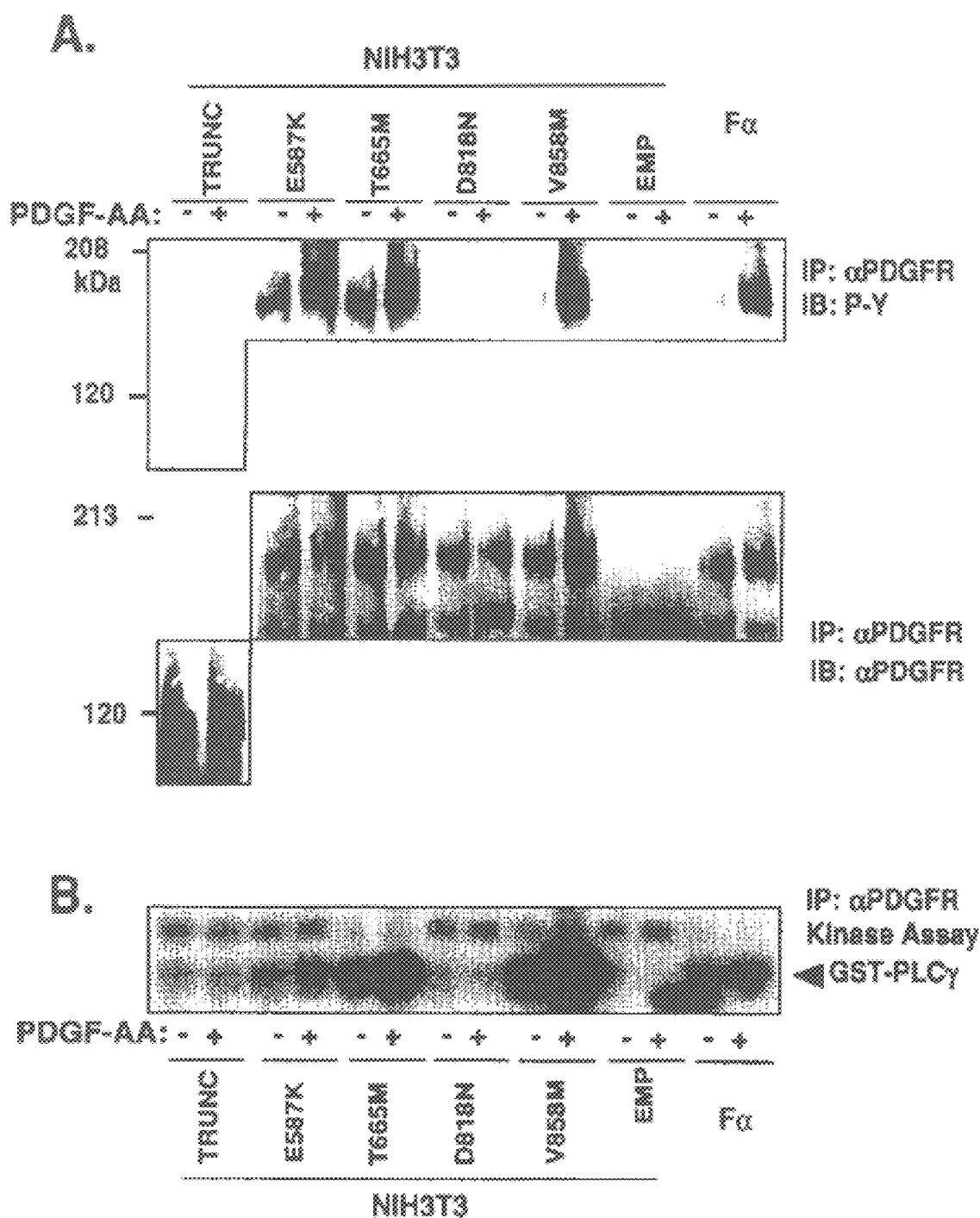
FIG. 3A shows a Western blot of anti-αPDGFR antibody 292 immunoprecipitated proteins from lysates from NIH 3T3 cells expressing an empty vector (EMP) or the indicated mutant receptors, which were serum starved, and exposed to either buffer (−) or 50 ng/ml of PDGF-AA (+) for 5 minutes, or from Fα cells (positive control), incubated with anti-phosphotyrosine (P-Y) antibody (top panel), or an anti-αPDGFR antibody (bottom panel) after stripping of the anti-phosphotyrosine antibody. IP: immunoprecipitation; IB: immunoblot (western); the abbreviations for the receptor mutants are detailed in the legend of FIG. 1.
FIG. 3B shows an autoradiography of an SDS-PAGE gel containing in vitro kinase reaction assays of mutant αPDGFRs, immunoprecipitated from NIH3T3 cells treated as described in FIG. 3A, with the 292 antibody and incubated with Glutathione S-transferase fusion phospholipase C-gamma (GST-PLCγ), an exogenous substrate, and [$^{32}$P]-γ ATP. The arrowhead indicates the position of GST-PLCγ.

The results are set forth in FIG. 2A. Anti-phosphotyrosine western blot analysis of these samples indicated that PDGF triggered the expected increase in phosphorylation content of the WT receptor (FIG. 2A, lanes "EMP"). In contrast, the WT receptor was poorly phosphorylated in cells expressing the truncated receptor, even though there were comparable amounts of WT receptor recovered in the "TRUNC" and "EMP" samples (FIG. 2A). The phosphotyrosine signal of the immunoprecipitated receptor was not inhibited in any of the other cells. This is probably at least in part because some of these mutants retain kinase activity (see below, FIG. 3), and were immunoprecipitated with the 27P antibody.

Example 3

The Truncated αPDGFR Efficiently Blocks PDGF-dependent Signaling Events

This Example describes that PDGF-dependent activation of Erk is inhibited by the truncated αPDGFR.

Erk is a member of the mitogen-activated protein (MAP) kinase pathway that is activated by the αPDGFR, as well as many other receptors. Thus, the level of Erk phosphorylation following PDGF treatment of cells is an indication of PDGF-dependent signaling events.

Cells were stimulated as described in Example 2 and 20 μg of total cell lysate was subjected to western blotting analysis using anti-phospho-Erk or anti-Ras GTP-activating protein antibody as an internal control for the amount of protein. The phospho-extracellular signal related kinase (Erk) rabbit polyclonal antibody was purchased from New England Biolabs (Beverly, Mass.) and used at a dilution of 1:1000.

The results, which are shown in FIG. 2B, indicate that stimulation of the control cells (EMP) resulted in enhanced phosphorylation of Erk. Both the p44 and p42 forms of Erk, which are usually activated by growth factors such as PDGF, are phosphorylated. The results further show that, similar to the effect on tyrosine phosphorylation of the receptor, expression of the truncated receptor greatly diminished PDGF-dependent activation of Erk (FIG. 2B). Cells expressing the D818N mutant also failed to fully activated Erk in response to PDGF, whereas Erk activation in cells expressing the other point mutants was unaffected, or even enhanced in some experiments (FIG. 2B and data not shown). Thus, the truncated receptor efficiently blocks PDGF-dependent signaling events, whereas the point mutants either had no effect, or only partially inhibited.

Example 4

The Truncated and D818N αPDGFR Receptor Mutants Block Their PDGF-stimulated Tyrosine Phosphorylation To characterize the kinase activity of the point mutants, these were immunoprecipitated using the 292 monoclonal antibody, which selectively recognizes an extracellular epitope of the introduced receptor and recognizes all of the mutants used in this study. While PDGF-stimulation is expected to dimerize mutant and wild type receptors, lysing cells in RIPA buffer breaks receptor dimers. Kelly, J. D. et al. (1991) *J. Biol. Chem.* 266:8987. Consequently, 292 immunoprecipitates are not expected to contain co-immunoprecipitating WT receptor. NIH 3T3 cells expressing the empty vector or receptor mutants were left resting, or stimulated with 50 ng/ml of PDGF-AA for 5 minutes, the cells were lysed in RIPA buffer and the resulting samples were subjected to anti-phosphotyrosine and anti-αPDGFR western blot analysis. In this series of experiments, we included the previously described Fα cell line, which is an NIH 3T3-like cell line that express the introduced human αPDGFR. Andrews, A. et al (1999) *Invest. Ophthalmol. Vis. Sci.* 40:2683. This cell line was included as a positive control, since the WT receptor in NIH 3T3 cells is mouse, and not recognized by the 292 antibody. As expected, the αPDGFR was immunoprecipitated from the Fα cells, but not the NIH 3T3 cells expressing the empty vector, and PDGF stimulation increased the phosphotyrosine content of the receptor (FIG. 3A). PDGF promoted tyrosine phosphorylation of three out of the four point mutants. There was no detectable basal or PDGF-stimulated tyrosine phosphorylation of the truncated and D818N αPDGFR receptor mutant.

Example 5

Kinase Activity of the Mutant αPDGFR Receptors

This examples demonstrates that certain of the αPDGFR mutants have a decreased kinase activity towards an exogenous substrate, whereas other mutants have a similar or even higher kinase activity.

Mutant αPDGFRs were selectively immunoprecipitated with the 292 antibody, and samples representing $2\times10^5$ cells from 292 antibodies were subjected to an in vitro kinase assay. Immunoprecipitates were preincubated with 2 μg of GST protein for 10 min at 0° C., then 2 μg of Glutathione S-transferase fusion phospholipase C-gamma (GST-PLCγ, an exogenous substrate, 10 μCi of γ-[$^{32}$P] ATP (DuPont NEN Research Products, Boston, Mass.), and universal kinase buffer (UKB; 20 mM Pipes, pH 7.0, 10 mM $MnCl_2$, 20 μg/ml aprotinin) were added. The samples were incubated at 30° C. for 5 min. The proteins were separated by 7.5% sodium dodecyl sulfate-polyacrylamide gel electrophoresis (SDS-PAGE), the gel was dried, and the radiolabeled protein was detected by autoradiography.

The results, which are shown in FIG. 3B, indicate that, as expected, the WT αPDGFR phosphorylated the exogenous substrate, and there was a modest enhancement of this activity when the receptor was immunoprecipitated from PDGF-stimulated cells. In contrast, the substrate was not phosphorylated by the truncated or D818N receptors. The kinase activity of the E587K mutant was comparable to the WT receptor, whereas the T665M and V859M mutants were more active than the WT receptor.

Thus, the truncated and D818N mutants appear to have essentially no kinase activity; the kinase activity of the E587K mutant is comparable to that of the WT receptor; and the T665M and V859M mutants have a stronger kinase activity that the WT receptor. The behavior of these αPDGFR mutants are similar, although not identical, to the analogous c-kit receptor mutants, in which kinase activity was lowest in $W^{42}$ (corresponds to D818N) and $W^{37}$ (E587K), $W^v$ (T665M) was intermediate, and $W^{41}$ (V859M) was the best, although still below the WT levels. Nocka, K. et al. (1990) *Embo. J.* 9:1805.

Example 6

The PDGFR Mutants Inhibit PDGF-AA Dependent Entry into S Phase

This Example demonstrates that the presence of αPDGFR or βPDGFR mutants inhibit PDGF-dependent biological responses, in particular, cell cycle progression, even in the presence of the WT receptor.

NIH 3T3 cells expressing either empty vector (EMP) or one of the αPDGFR mutants were trypsinized, resuspended in DMEM with 10% FBS, and plated at a density of $5\times10^5$ cells/well in 24-well tissue culture plates and cultured overnight. The cells were rinsed twice with phosphate buffered saline (PBS), and serum starved by incubation in 0.5 ml of DMEM with 0.1% FBS and 0.4 mg/ml of bovine serum albumin (BSA; Sigma) for 48 hours. The cells were then exposed to 50 ng/ml of PDGF-AA, 10% Fetal bovine serum (FBS) (v/v), or buffer for 22 hours. The cells were then pulsed for 4 hours in DMEM with 10% FBS containing 0.8 μCi/ml of [$^3$H]-thymidine (DuPont NEN Research Products). Finally, the cells were washed twice with PBS, and once with 5% trichloro acetic acid, and lysed in 250 μl of 0.25 N NaOH. The lysates were transferred into scintillation tubes containing 50 μl of 6 N HCl, and then 3 ml of scintillation fluid (ICN) was added. The incorporated radioactivity of [$^3$H]-thymidine uptake was quantitated in a scintillation counter (Packard, Meriden Conn.). The data were expressed as fold induction, which was calculated by dividing stimulated samples by the buffer control. Each condition was assayed triplicate, and the mean±standard deviation (SD) was obtained.

In at least three experiments, we consistently found that the PDGF-dependent response was greatly reduced or completely eliminated in cells expressing any of the mutant receptors. The abbreviations for the receptor mutants are detailed in the legend of FIG. 1.

Figure 4:
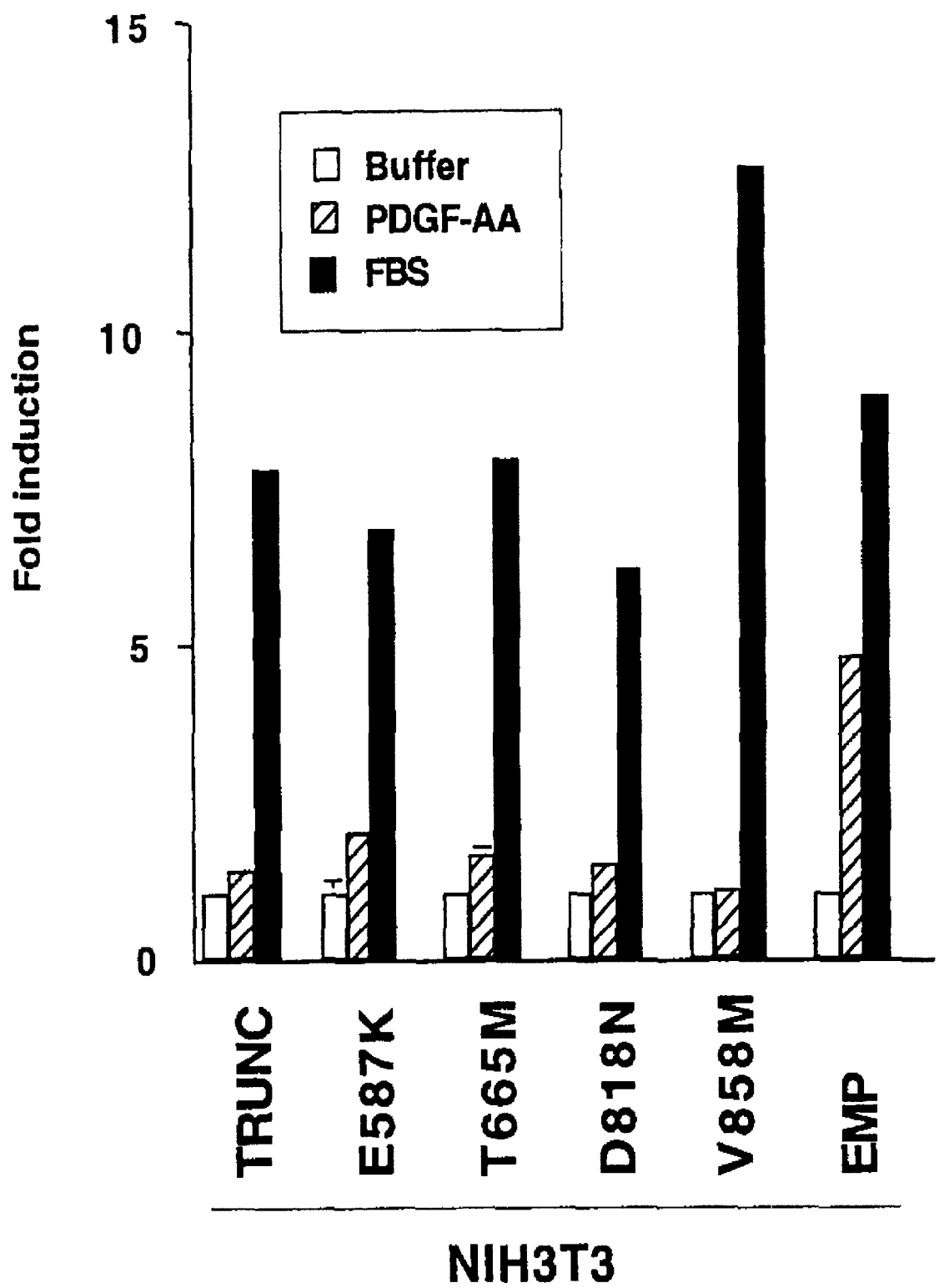
FIG. 4 is a histogram showing the amount of fold induction of [$^3$H]-thymidine incorporated in NIH 3T3 cells expressing either empty vector (EMP) or the indicated mutant, that were serum starved for 48 hours, then incubated with platelet-derived growth factor (PDGF)-AA (50 ng/ml); Fetal bovine serum (FBS;10%); or buffer for 22 hours, relative to unstimulated samples.

The results, which are shown in FIG. 4, indicate that cells expressing an empty vector responded to PDGF-AA, and that the magnitude of the response was typically at least 50% of the response seen when cells were stimulated with 10% FBS. In all of the other cell lines PDGF-AA failed to induce a robust response, whereas each of the cell lines did respond normally to serum. The somewhat elevated response to serum in the V859M cells was not routinely observed.

The same results were obtained with all five βPDGFR mutants, i.e., the truncated as well as the four point mutants. All of these mutants similarly prevented cell proliferation in response to PDGF-AA.

Thus, expression of the mutant receptors selectively blocks PDGF dependent cell cycle progression, whereas it has little effect on the response of these cells to serum. Since this effect was observed in cells, which naturally express αPDGFR, these results demonstrate that the αPDGFR and βPDGFR mutants have a dominant effect over the WT receptor in blocking PDGF-dependent entry into S phase.

Example 7

Attenuation of Experimental PVR in Rabbits with the PDGFR Mutants

This Example demonstrates that expression of the αPDGFR mutants in rabbit conjunctival fibroblast (RCF) prevents development of PVR.

The effect of the αPDGFR mutants on development of PVR was tested in a rabbit model, in which PVR is induced in the rabbit eye by co-injection of rabbit conjunctival fibroblasts (RCFs) and platelet-rich plasma (PRP). Nakagawa, M. et al (1995) *Invest. Ophthalmol. Vis. Sci.* 36:2388. The mutants were transfected and expressed in RCFs, injected into rabbit eyes, and the development of PVR was measured. RCF cells were used in this model to avoid species variables, which would occur if NIH 3T3 cells were used.

Figure 5:
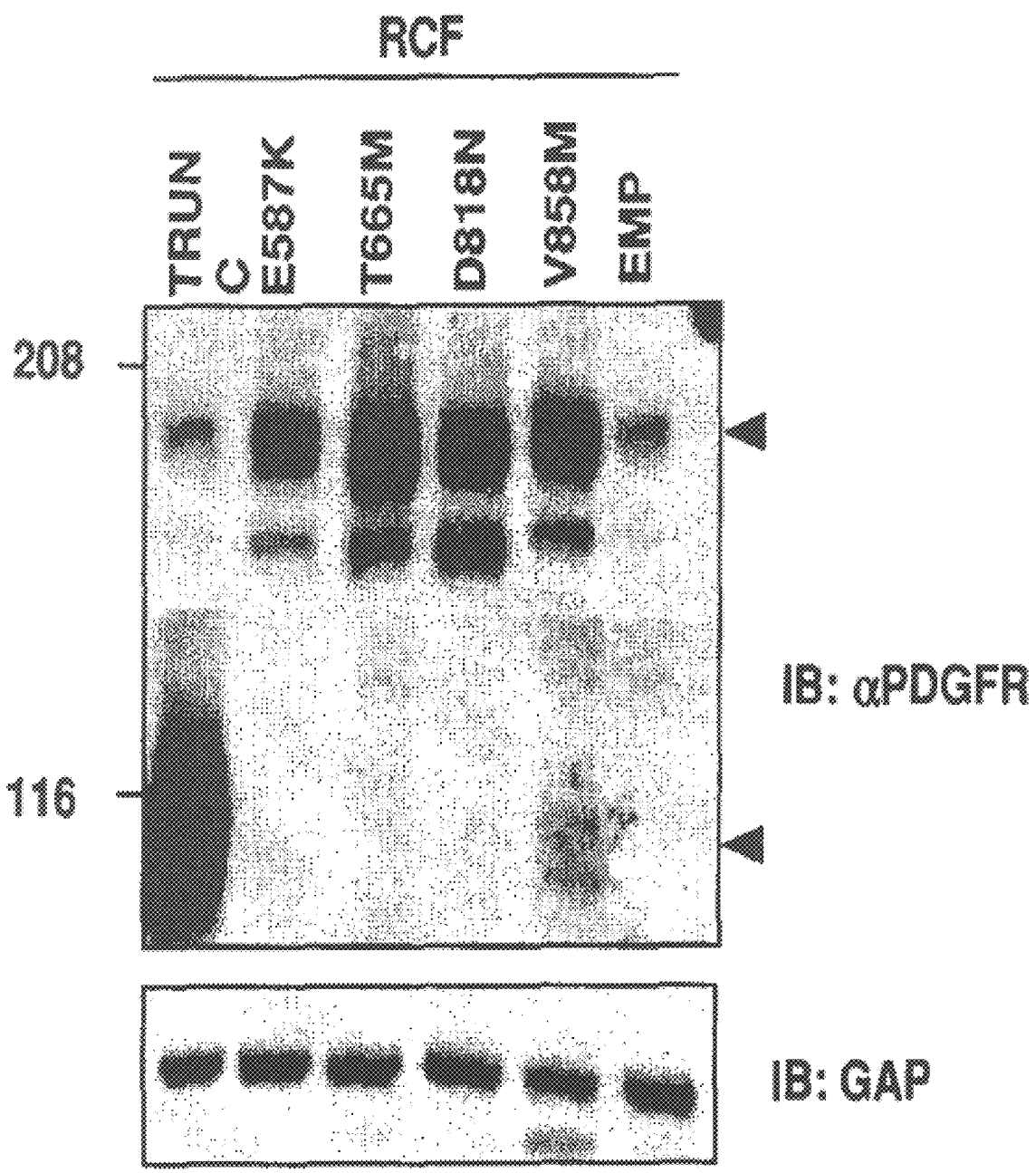
FIG. 5 is a Western blot of cell lysates from primary rabbit conjunctival fibroblasts (RCFs) transfected with the empty expression vector (EMP) or the indicated receptor mutant, incubated with anti-αPDGFR antibody (upper panel) or anti-Ras GTP-activating protein (RasGAP; lower panel). The arrowheads point to the mature and the truncated receptors. IB: immunoblot (western); the abbreviations for the receptor mutants are detailed in the legend of FIG. 1.

An empty vector or each of the αPDGFR mutants was introduced into fourth passage RCFs, and mass populations of drug-resistant cells were obtained. The level of expression of the mutant receptors was determined by performing Western blot analysis. For this, the transfected cells were serum-starved overnight, lysed and 20 μg of protein was subjected to electrophoresis, transferred to a Western blot and incubated with an anti-αPDGFR or anti-Ras GTP-activating protein (RasGAP) antibody, washed, and subjected to autoradiography, as described above. The results of the Western blot, which are shown in FIG. 5, indicate that the resulting cell lines do indeed express endogenous αPDGFR, and that the introduced receptor was expressed at a 6–10 fold higher level relative to the WT receptor (EMP lane). The truncated receptor was expressed at least 30 fold over the endogenous receptor. The heterogenicity of the population with respect to receptor expression was determined by FACS analysis, using the 292 monoclonal antibody. This analysis indicated that there was a single population of receptor-expressing cells for all of the transfected cell populations, except for the truncated receptor. In the case of the truncated receptor, two populations of cells were obtained. The cells were sorted to obtain a single population of high expressors, which were used in the animal model of PVR.

PVR was induced in the rabbit eyes as previously described (Andrews, A. et al. (1999) Invest. Ophthalmol. Vis. Sci. 40:2683 and Nakagawa, M. et al. (1995) Invest. Ophthalmol. Vis. Sci. 36:2388). Briefly, gas vitrectomy was performed by injecting 0.4 ml of expanding perfluoropropane gas ($C_3F_8$) into the vitreous cavity 4 mm posterior to the corneal limbus under anesthetical condition. Three days later, the rabbits were anesthetized and the pupils were dilated. 0.1 ml DMEM containing $1\times10^5$ of RCFs expressing empty vector or αPDGFR mutant were injected into the vitreous cavity together with 0.1 ml of PRP using 30 G needle. Ten rabbits underwent surgery for each cell population expressing the empty vector or the truncated, E587K, T665M, D818N, or V859M αPDGFR mutants. One rabbit in the D818N group died just after the surgery, therefore the total number is 9 for this group. The retinal status was evaluated with an indirect ophthalmoscope fitted with a +30 D fundus lens at 1, 4, 7, 14, 21, and 28 days after the surgery. The PVR was graded from 0 through 5 according to the Fastenberg score. Fastenberg, D. M. et al. (1982) Am. J. Ophthalmol. 93:565. The grading is as follows: 0; no abnormality, 1; vitreous strand, 2; traction of the retina, 3; partial retinal detachment (less than 2 quadrant), 4; extended (more than 2 quadrant) but not total retinal detachment, 5; total retinal detachment. All surgeries were performed under aseptic conditions and pursuant to the regulation of the ARVO Statement for the Use of Animals in Ophthalmic and Vision Research. Only the left eye of each rabbit was used for the experiments.

To determine whether the differences among groups of rabbits were statistically significant, the Mann-Whitney U test for non-parametric ordinal data was performed. The response of rabbits injected with empty vector-expressing cells was compared with the response of those injected with mutant receptor-expressing cells. In all cases, $P<0.05$ was considered significant.

Figure 6A:
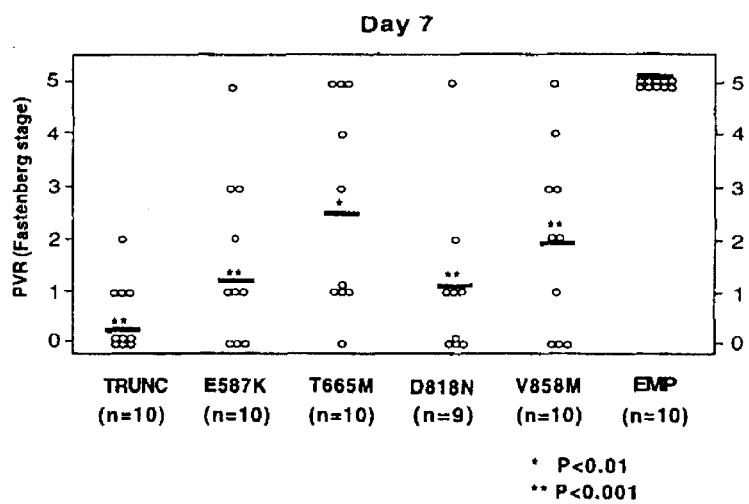
FIG. 6A is a diagram showing the Fastenberg stage of PVR at day 7 after surgery in eyes of rabbits in which RCFs containing the empty vector (EMP) or a αPDGFR mutant were injected (day 0). Each circle represents an individual (there were 9 or 10 in each group) and the horizontal bar indicates the mean of the group. The abbreviations for the receptor mutants are detailed in the legend of FIG. 1.
Figure 6B:
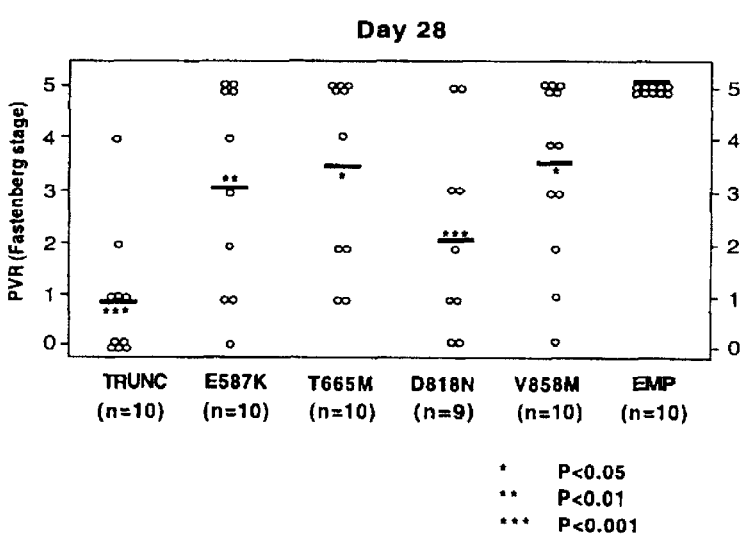
FIG. 6B is a diagram showing the Fastenberg stage of PVR at day 28 after surgery in eyes of rabbits in which RCFs containing the empty vector (EMP) or a αPDGFR mutant were injected (day 0).

The results, which are shown in FIG. 6 for days 7 (FIG. 6A) and 28 (FIG. 6B) after the surgery, show that under these experimental conditions PVR is induced rapidly, such that 30% of the rabbits injected with cells expressing the empty vector underwent total retinal detachment (stage 5) by day 4. By day 7, 100% of the rabbits in the control group had reached the most severe form of the disease. In contrast, PVR was less severe in all of the experimental groups at day 7. At this time point the truncated receptor appeared to be the best in preventing PVR. The experiment was extended for three more weeks, during which time PVR worsened in all of experimental groups. However, in all cases there was a statistically significant difference in severity of the disease between the animals injected with cells expressing αPDGFR mutants versus the control group. As with the earlier time point, the truncated receptor was the best in preventing PVR. None of the rabbits in this group achieved stage 5, and 80% remained at stage 1 or below. Thus, the mutant αPDGFRs significantly attenuate experimental PVR.

One reason why the truncated receptor was more effective in blocking PVR might be because it was expressed to a higher level than the other receptors. To investigate this possibility PDGF-dependent signaling was compared in cells expressing high or low levels of the point mutants. The results indicated, however, that increasing the expression level of the point mutants did not further block PDGF-dependent responses. Thus, the amount of PDGFR mutant is not crucial.

These results also indicate a positive correlation between activation of Erk signals (FIG. 2) and PVR scores at 7 days (FIG. 6; $P=0.035$, by Spearman Rank Correlation test).

The showing that inhibition of αPDGFR can reduce the PVR score incidates that αPDGFR is a critical contributor to PVR. Thus, although the cells used (RCFs) are likely to have receptors for many growth factors, inhibiting αPDGFR resulted in reducing PVR.

Thus, while the mutants differed in their intrinsic kinase activity and potential to prevent PDGF-dependent signaling, they were all effective in blocking PDGF-stimulated cell cycle progression. Furthermore, these receptor mutants were able to prevent PVR, and the truncated receptor was the most effective. Thus, inhibition of PDGF-stimulated cell proliferation seems to be a requirement for a compound, e.g., a mutant PDGFR to be effective in reducing PVR.

Given that a key step in activation of the WT receptor is engaging its kinase activity, it may appear surprising that a kinase active receptor could have a negative influence on the overall response of a cell to the growth factor. However, other investigators have also shown that kinase active receptor tyrosine kinase mutants can be dominant negative mutants. The Y845F mutant of epidermal growth factor receptor (EGFR) has full kinase activation, but inhibits EGF- and serum-dependent mitogenesis. Tice, D. A. et al. (1999) Proc. Natl. Acad. Sci. USA 96:1415. Another example is the thanatophoric dysplasia (TD) II mutant of fibroblast growth factor receptor (FGFR). The TDII mutant is constitutively active, and it causes cell cycle arrest by activating Stat 1 and consequent upregulation of cell cycle inhibitor $p21^{waf1/cip1}$. Su, W. C. et al. (1997) Nature 386:288. The T665M and V859M αPDGFR mutants, which have elevated kinase activity (FIG. 3), may be mimicking these ways to inhibit the endogenous αPDGFR dependent cell cycle progression.

Example 8

Contraction of Cells Triggered by Vitreous is Dependent on TGFβ in the Vitreous

This Example demonstrates that the vitreous enhances fibroblast contraction and that TGFβ is involved in this enhancement. Contraction and the resulting tractional force is an important component of fibrotic diseases such as PVR.

In this Example experiments Fα cells were used. These cells were derived from F cells by introduction of the WT αPDGFR and induce PVR in a rabbit model of the disease (Andrews, A. et al. (1999) Invest. Ophthalmol. Vis. Sci. 40:2683). F cells are an SV-40 immortalized line of mouse embryo fibroblasts derived from mice nullizygous for both the a and βPDGFRs (M. Tallquist and P. Soriano, Fred Hutchinson Cancer Research Center, Seattle, Wash.). The generation, characterization and maintenance of these cell lines were previously described. Andrews, A., E. et al. (1999) Invest. Ophthalmol. Vis. Sci. 40:2683. Normal growth conditions were Dulbecco's Modified Eagles medium (DMEM)+10% fetal bovine serum; the serum concentration was reduced to 1% when the cells were "serum starved".

The effect of rabbit vitrous on the contraction of Fα cells was determined using a gel contraction assay as follows. Vitreous was collected from freshly isolated normal rabbit eyes by first removing the anterior segment (cornea, iris, and lens), and then the vitreous was squeezed out of the remaining posterior portion of the eye. The extracted vitreous was resuspended in PBS containing 5 mg/ml BSA. The samples were centrifuged at 2500×g for 10 minutes at 4° C., and the resulting supernatant was aliquoted and frozen at −70° C. until use.

The contraction assay was based on a previously described reference, Skuta, G. et al. (1999) *J. Biol. Chem.* 274:30163, with the following modifications. Fα cells were suspended in 1.5 mg/ml of neutralized collagen I (Cohesion vitrogen 100, Palo Alto, Calif.) at a density of $10^6$ cells/ml, and were transferred into the 24-well plate (Falcon, Franklyn Lakes, N.J.) that had been preincubated with phosphate-buffer saline (PBS) with 5 mg/ml of bovine serum albumin (BSA) overnight. The gel was solidified by incubating at 37° C. for 90 minutes, and then the well was flooded with DMEM+5 mg/ml of BSA supplemented with an amount of vitreous such that the final concentration of vitreous in the culture medium was 1, 5 or 20%. The gels were incubated at 37° C. with 5% $CO_2$. The initial gel diameter was 15 mm. The media was replaced every 24 hours and the gel diameter was measured after 48 hours. The extent of contraction was calculated by subtracting the diameter of the well at 48 hours from the initial diameter (15 mm). Each experimental condition was assayed in triplicate, and at least three independent experiments were performed. Unpaired t-test was performed to detect statistic difference in contraction assay.

Figure 7A:
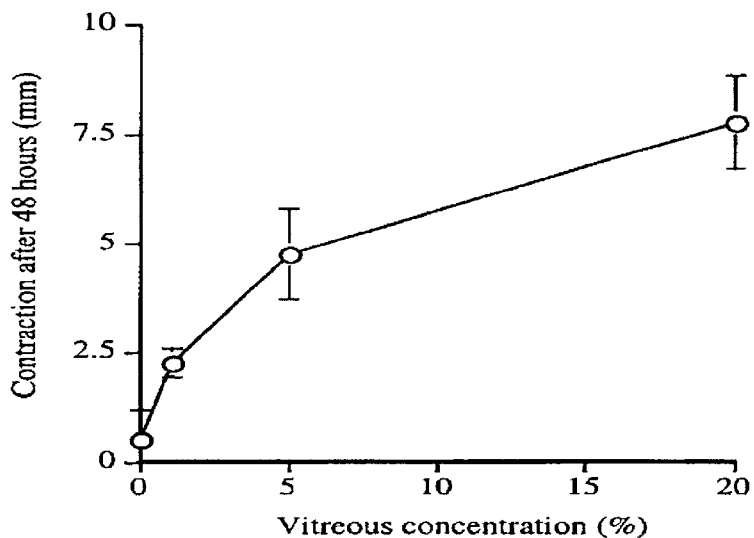
FIG. 7A shows the level of contraction of Fα cells plated in a collagen type I gel in DMEM supplemented with 5 mg/ml BSA and the indicated amount of rabbit vitreous. The gel diameter was measured at the start of the experiment and after 48 hours, and the extent of contraction was calculated by subtracting these two values.

As shown in FIG. 7A, the vitreous promoted contraction in a dose-dependent manner.

The role of TGFβ in vitreous-induced contraction was demonstrated by pre-treating the vitreous with 100 μg/ml of neutralizing TGFβ antibody. Anti-TGFβ or control IgG (100 μg/ml) was added to DMEM supplemented with vitreous (20%) or TGFβ1 (10 ng/ml) and the collagen gel contraction assay was performed. The data are representative data of three independent experiments.

Recombinant human TGFβ1 and PDGF-BB were purchased from R & D systems (Minneapolis, Minn.). Neutralizing anti-pan TGFβ or anti-PDGF antibodies, or control affinity purified goat or rabbit IgG were also purchased from R & D systems. Anti-TGFβ antibody neutralizes TGFβ1, β2, β3, and β5, and anti-PDGF antibody neutralizes PDGF-AA, AB, and BB.

Figure 7B:
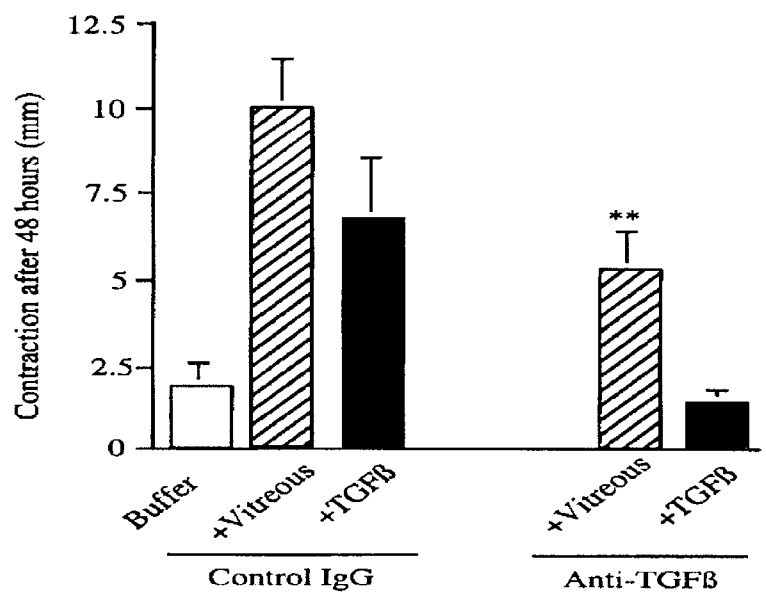
FIG. 7B shows the effect of anti-TGFβ or control IgG (100 μg/ml) on contraction of Fα cells plated in a collagen type I gel in DMEM supplemented with vitreous (20%) or TGFβ1 (10 ng/ml). Double asterisks (**) indicates P<0.01, by t-test compared to the control (control IgG+20% vitreous). The gel diameter was measured at the start of the experiment and after 48 hours, and the extent of contraction was calculated by subtracting these two values.

As shown in FIG. 7B, approximately 60% of the contraction activity disappeared. In contrast, the same amount of neutralizing PDGF antibody or a control IgG had no effect on contraction stimulated by the vitreous (FIG. 7B). Control experiments showed that 10 μg/ml of anti-PDGF antibody, or 100 μg/ml of anti-TGFβ antibody completely blocked the contraction resulting from incubation with 10 ng/ml PDGF-AA, BB, or TGFβ-induced contraction, respectively, demonstrating the effectiveness of these antibodies (FIG. 7B). These findings indicate that TGFβ constitutes greater than half of the contraction activity of the rabbit vitreous, whereas PDGF does not appear to be making a detectable contribution.

Example 9

Contraction of Cells Triggered by Vitreous is Dependent on Expression of the αPDGFR on the Target Cells This Example demonstrates the importance of the αPDGFR in mediating the effect of TGFβ on the contraction of target cells.

Figure 7C:
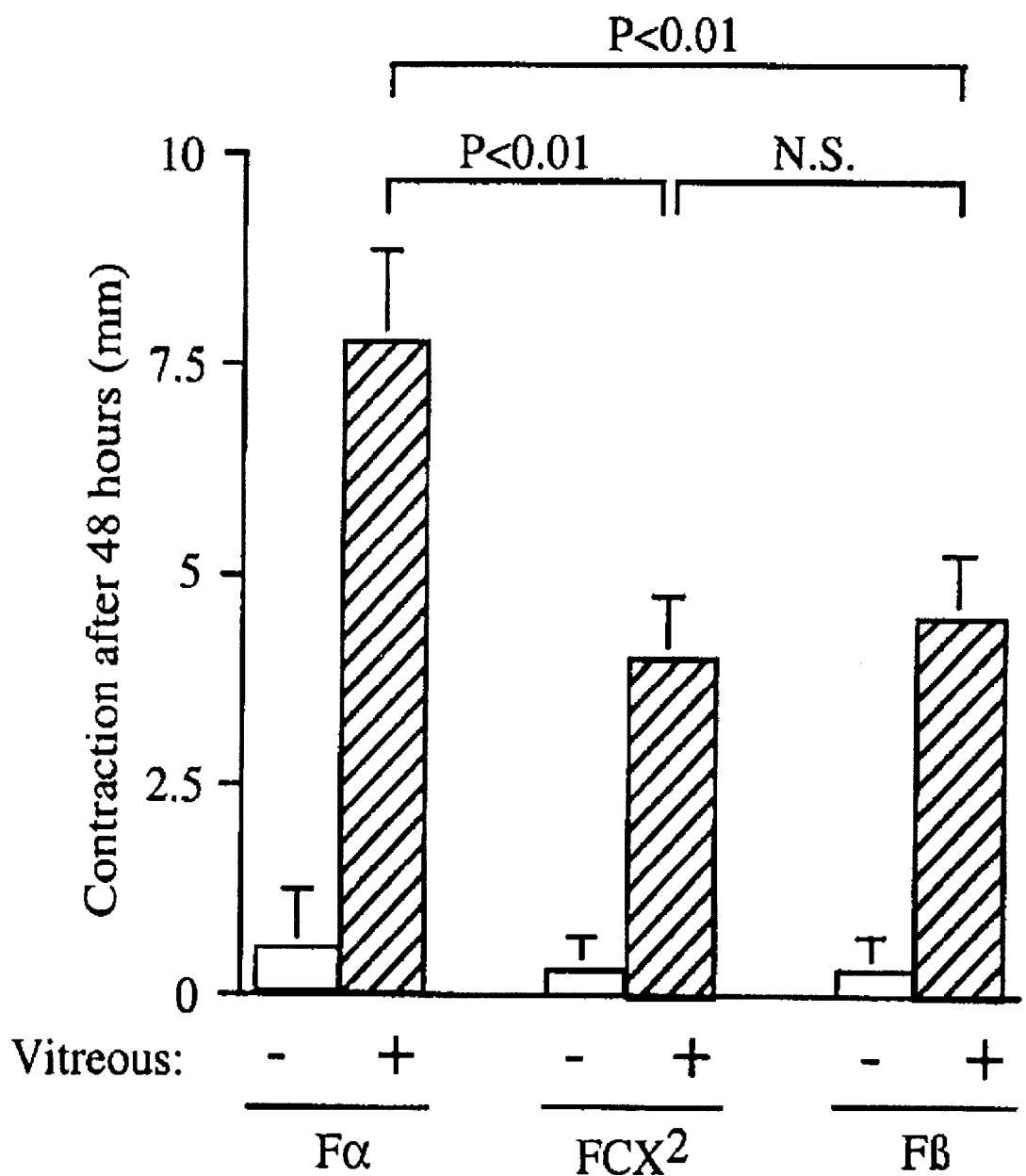
FIG. 7C shows the contraction of F cells devoid of PDGFRs (FCX$^2$) or expressing the βPDGFR (Fβ) or αPDGFR (Fα) plated in a collagen type I gel in DMEM supplemented with buffer (−) or vitreous (+) to a final concentration of 20% and added to the indicated cell lines. Contraction was scored at the 48 hours time point. Fα cells responded significantly better than either FCX$^2$ (P<0.01, by t-test) or Fβ cells (P<0.01, by t-test). N.S.=no significance.

The experiments described in Example 9 (FIG. 7B) were repeated with cells that express the βPDGFR (Fβ) instead of the αPDGFR, or no PDGFRs ($FCX^2$). Contraction was scored at the 48 hours time point. The results set forth in FIG. 7C indicate that Fα cells responded significantly better than either $FCX^2$ (P<0.01, by t-test) or Fβ cells (P<0.01, by t-test). Fβ responded slightly better than $FCX^2$, but this was not significant different. In the absence of αPDGFRs the vitreous was impaired in its ability to promote contraction (FIG. 7C). This observation indicates that expression of the αPDGFR potentiated the contraction activity of the vitreous.

To more directly test whether TGFβ could moderate contraction of fibroblasts via the αPDGFR, the response of the three cell lines to purified TGFβ was examined. Cells expressing no PDGFRs ($FCX^2$), the αPDGFR (Fα), or the βPDGFR (Fβ) were subjected to the collagen gel contraction assay described in Example 8 in the presence of buffer, 10% FBS (B), 50 ng/ml PDGF-BB, or 1 ng/ml TGFβ1. The gel diameter was measured after 24, 48, or 72 hours, and the media was replaced every day.

Figure 8:
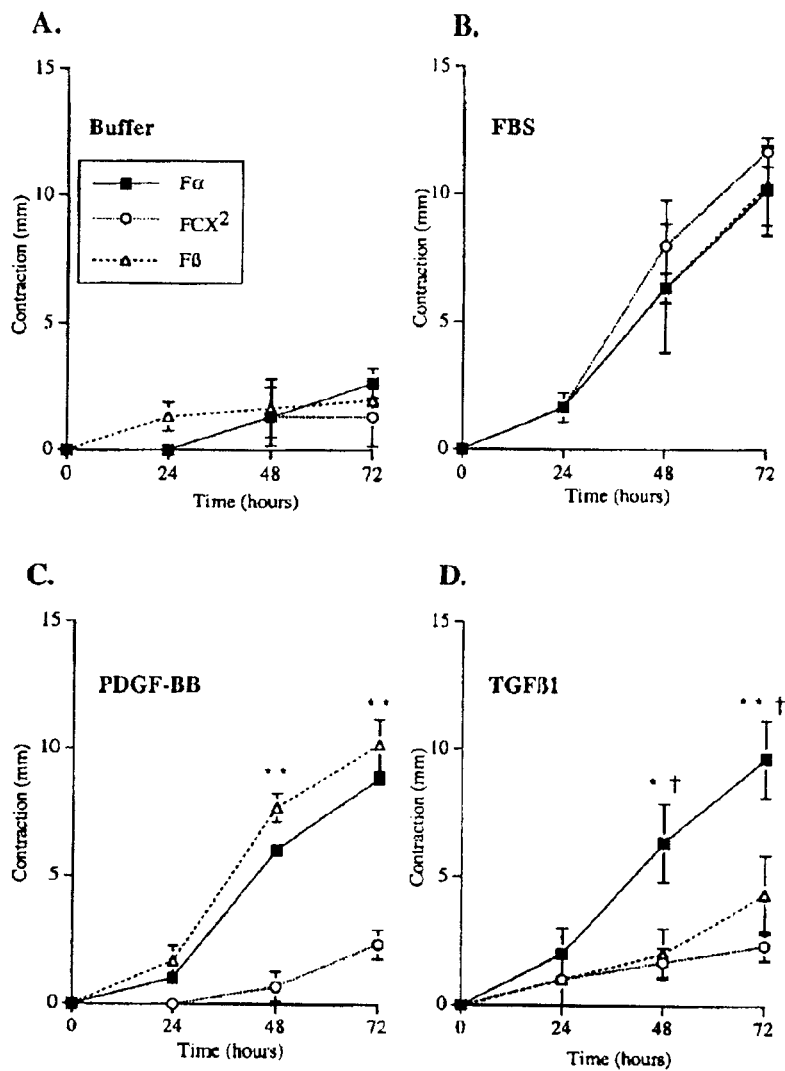
FIG. 8A shows the contraction of cells expressing no PDGFRs (FCX$^2$), the αPDGFR (Fα), or the βPDGFR (Fβ) plated in a collagen type I gel in the presence of buffer. The gel diameter was measured after 24, 48, or 72 hours. The data shown are the mean±standard deviation. Single asterisk (*) indicates P<0.05 and double asterisks (**) indicate P<0.01 compared to FCX$^2$ cells.
FIG. 8B shows the contraction of cells expressing no PDGFRs (FCX$^2$), the αPDGFR (Fα), or the βPDGFR (Fβ) plated in a collagen type I gel in the presence of 10% FBS. The gel diameter was measured after 24, 48, or 72 hours. The data shown are the mean±standard deviation. Single asterisk (*) indicates P<0.05 and double asterisks (**) indicate P<0.01 compared to FCX$^2$ cells.
FIG. 8C shows the contraction of cells expressing no PDGFRs (FCX$^2$), the αPDGFR (Fα), or the βPDGFR (Fβ) plated in a collagen type I gel in the presence of 50 ng/ml PDGF-BB. The gel diameter was measured after 24, 48, or 72 hours. The data shown are the mean±standard deviation. Single asterisk (*) indicates P<0.05 and double asterisks (**) indicate P<0.01 compared to FCX$^2$ cells.
FIG. 8D shows the contraction of cells expressing no PDGFRs (FCX$^2$), the αPDGFR (Fα), or the βPDGFR (Fβ) plated in a collagen type I gel in the presence of 1 ng/ml TGFβ1. The gel diameter was measured after 24, 48, or 72 hours. The data shown are the mean±standard deviation. Single asterisk (*) indicates P<0.05 and double asterisks (**) indicate P<0.01 compared to FCX$^2$ cells. The cross (†) indicates P<0.05 compared to the FβWT cells.

As seen in FIG. 8, serum promoted a similar contraction response in all three cell lines, indicating that they all had a comparable potential to contract. In addition, PDGF triggered the same extent of contraction of the Fα and Fβ cells, demonstrating that the two receptors were equally able to drive this response. Similar to the action of the vitreous, purified TGFβ induced contraction of the Fα cells to a much greater extent than either the Fβ cells or the cells that do not express any PDGFR. Cells expressing the βPDGFR or no PDGFRs responded poorly to TGFβ1, whereas those expressing the αPDGFR contracted robustly.

Thus, TGFβ-dependent contraction is dependent on expression of the αPDGFR.

Example 10

TGFβ Activates αPDGFR but not βPDGFR

This Example demonstrates that TGFβ induces tyrosine phosphorylation of the αPDGFR but not the βPDGFR, thereby activating the αPDGFR but not βPDGFR.

To show the effect of TGFβ on αPDGFR, the tyrosine phosphorylation state of the αPDGFR was assayed in TGFβ-treated cells. The F cells with or without PDGFR were grown to 80% confluent and then starved with DMEM containing 1% FBS for 20 hours. Cells were exposed at 37° C. for 5 minutes to either 50 ng/ml of PDGF-BB; with 1 ng/ml of TGFβ1 for 5 minutes, 1 hour, 2 hours, 4 hours, 6 hours or 8 hours; or were left unstimulated. After treatment the cells were washed twice with H/S (20 mM Hepes, pH 7.4, 150 mM NaCl) and then lysed in EB (10 mM Tris-HCl, pH 7.4, 5 mM EDTA, 50 mM NaCl, 50 mM NaF, 1% Triton-X 100, 0.1% BSA, 20 μg/ml aprotinin, 2 mM $Na_3VO_4$, 1 mM phenylmethylsulfonyl fluoride; PMSF). Lysates were centrifuged for 15 minutes at 13,000×g, the pellet was discarded and the soluble fraction was used as the total cell lysate. The protein concentration was measured using protein assay kit (Pierce, Rockfield, Ill.) following the manufacture's instructions.

Receptors were immunoprecipitated from the soluble fraction with the 27P antibody (described above). Immune complex was bound to formalin-fixed membranes of *Staphylococcus aureus*, spun through an EB sucrose gradient, and washed twice with EB, then with PAN (10 mM Pipes, pH 7.0, 100 mM NaCl, 1% aprotinin)+0.5% Nonidet P-40 (NP-40), and finally with PAN. The samples were resuspended in PAN before using for kinase assay or western blotting.

Total cell lysates containing 20 μg of protein or receptor immunoprecipitates from $1.0×10^6$ cells were resolved in 7.5% SDS-PAGE gel under reducing conditions. Proteins were transferred onto Immobilon (Millipore, Bedford Mass.). Membranes were blocked using "BLOCK" (10 mM Tris-HCl, pH 7.5, 1.5 M Tris base, 150 mM NaCl, 10 mg/ml BSA, 10 mg/ml ovalbumin, 0.05% Tween 20) for anti-phosphotyrosine blotting. The membranes were blocked in "BLOTTO" (10 mM Tris-HCl, pH 7.5, 1.5 M Tris base, 150 mM NaCl, 10 mg/ml non fat dry milk, 0.05% Tween 20) for other antibodies. Membranes were incubated with antiphosphotyrosine primary antibodies (4G10:PY20 (1:1): 1:5000). Afterwards the blots were incubated with secondary antibody (horseradish peroxidase conjugated goat anti-rabbit or anti-mouse antibodies (Amersham Pharmacia Biotech) diluted 1:5000) for 1 hour at room temperature and washed 5 times with Western Rinse and visualized using ECL (Amersham Pharmacia Biotech, Piscataway, N.J.).

The membranes were then stripped and reprobed with an anti-αPDGFR antibody or an anti-βPDGFR antibody (anti-αPDGFR, a 1:1 mixture of the 27P and 80.8 antibodies, and antibody 30A for the for βPDGFR (similar antibodies can be obtained from Pharmingen) 1 hour at room temperature, and washed 5 times with Western Rinse solution (150 mM NaCl, 10 mM Tris-HCl pH 7.5, 1.5 mM Tris base), incubated with secondary antibody and autoradiographed as described above. The 27P (anti-αPDGFR), 80.8 (anti-αPDGFR), and 69.3 (anti-Ras GTP activating protein; RasGAP) are rabbit crude antisera, and were characterized previously (Valius, M. et al. (1993) Mol. Cell Biol. 13:133; Bazenet, C. E. et al. (1994) Oncogene 9:517).

Figure 9:
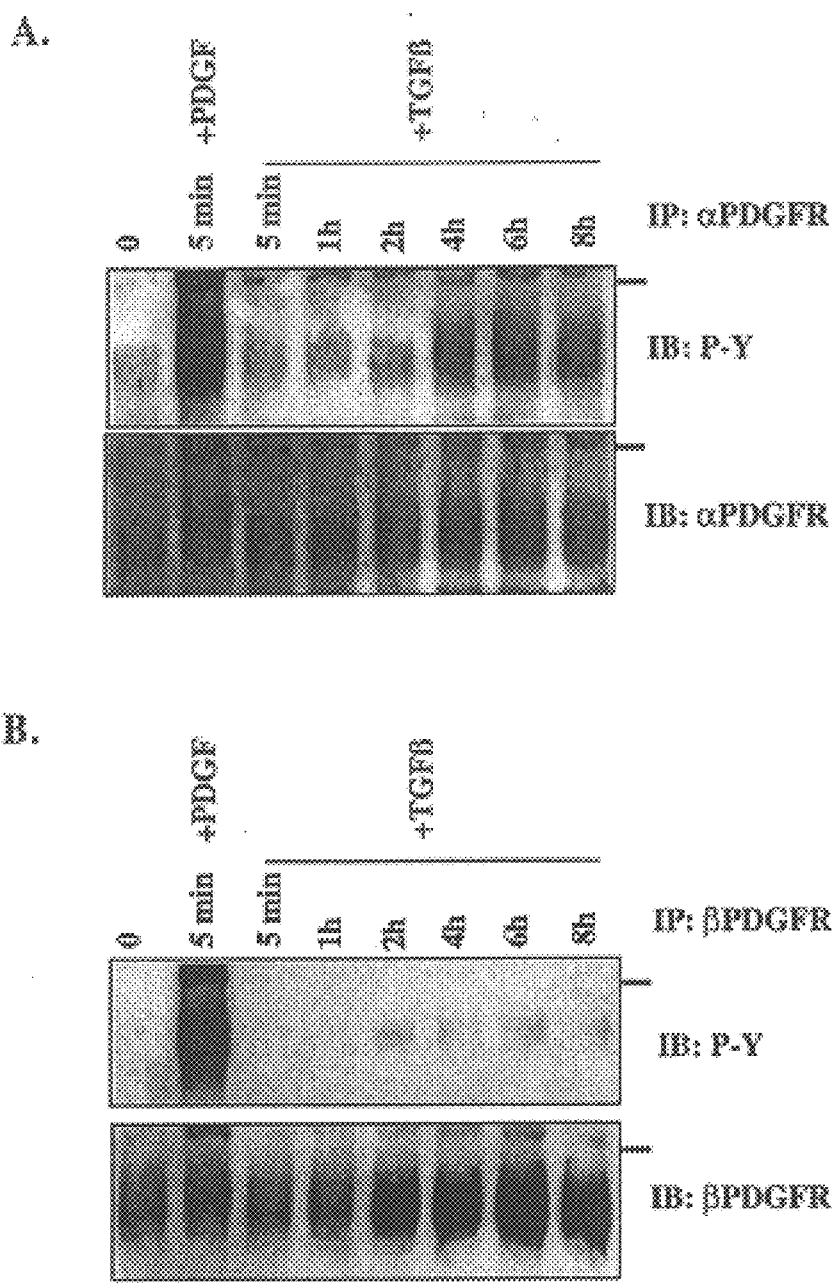
FIG. 9A is a Western blot of anti-αPDGFR antibody precipitated proteins from F cells expressing the α-PDGFR, which were serum starved overnight, and then left unstimulated (0), or stimulated with 50 ng/ml of PDGF-BB or 1 ng/ml of TGFβ1 for the time indicated, incubated with anti-phosphotyrosine antibody (top panel) or with an anti-αPDGFR antibody (bottom panel) after stripping of the anti-phosphotyrosine antibody.
FIG. 9B is Western blot of anti-βPDGFR antibody precipitated proteins from F cells expressing the β-PDGFR, which were serum starved overnight, and then left unstimulated (0), or stimulated with 50 ng/ml of PDGF-BB or 1 ng/ml of TGFβ1 for the time indicated, incubated with anti-phosphotyrosine antibody (top panel) or with an anti-βPDGFR antibody (bottom panel) after stripping of the anti-phosphotyrosine antibody.

The results, shown in FIG. 9 show that in resting cells, the αPDGFR contained barely detectable levels of phosphotyrosine, and exposure to PDGF greatly increased the receptor's phosphotyrosine content (FIG. 9A). TGFβ also increased phosphorylation of the αPDGFR, although the kinetics were slower, and the receptor was not as intensely phosphorylated as in the case of PDGF stimulation (FIG. 9A). In contrast, TGFβ triggered very modest or undetectable tyrosine phosphorylation of the βPDGFR (FIG. 9B). Hence TGFβ activates the αPDGFR, much better than the βPDGFR. This observation offers a potential explanation for why TGFβ was better at triggering contraction using cells expressing the αPDGFR as compared with βPDGFR-expressing cells (FIG. 8).

There are two possibilities regarding the mechanism of activation of αPDGFR by TGFβ: one is ligand dependent, and the other is ligand independent such as cross talk inside the cell. To distinguish between the two scenario, TGFβ-dependent tyrosine phosphorylation of the αPDGFR lacking the majority of the extracellular domain was examined. This mutant was engineered by excising EcoRI/NcoI fragment from the human αPDGFR cDNA, and religating the remainder of the cDNA with an EcoRI/NcoI double-stranded oligo. This internally deleted cDNA encodes a protein that lacks Ig domain 1 to 4, and hence is unable to bind PDGF. The αPDGFR mutant was expressed in F cells as previously described (Rosenkranz, S. et al. (1999) J. Biol. Chem. 274:28335). Briefly, the mutated PDGFR cDNA was subcloned into either of the retroviral pLNCX[2] or pLXSH vectors (Andrews, A. et al. (1999) Invest. Ophthalmol. Vis. Sci. 40:2683; Gelderloos, J. A. et al. (1998) J. Biol. Chem. 273:5908). The cDNA constructs were transfected into the virus-producing 293 GPG cell line (Ory, D. S. et al. (1996) Proc. Natl. Acad. Sci. USA. 93:11400) using lipofectamine. The virus-containing supernatant was collected for 5 days, then concentrated by centrifugation by 25000×g at 4° C. for 90 minutes. The virus was resuspended in a small volume overnight and frozen at −70° C. until use. F cells were infected with the appropriate retrovirus in the presence of 4 µg/ml of polybrene over night, followed by drug selection, as previously described (Rosenkranz, S. et al. (2000) J. Biol. Chem. 275:9620). In all cases mass populations of drug-resistant cells were used.

The level of truncated receptor expression was found to be comparable to the wild type αPDGFR in F cells. Unlike the wild type receptor, the truncated receptor was not phosphorylated after 6 and 8 hous of 1 ng/ml TGFβ stimulation, and also the cells with truncated receptor did not cause contraction in the presence of 1 ng/ml of TGFβ. These data indicate that TGFβ engages the αPDGFR in a PDGF-dependent manner, which is consistent with numerous reports showing the TGFβ stimulates secretion of PDGF-A (Makela, T. P. et al. (1987) Mol. Cell Biol. 7:3656; Majack, R. A. et al. (1990) J. Cell Biol. 111:239; Battegay, E. J. et al. (1990) Cell 63:515).

Example 11

Preparation of αPDGFR Mutants that Fail to Associate with Signaling Enzymes

To identify the signaling pathways downstream of the αPDGFR that are required for mediating TGFβ-contraction, a panel of αPDGFR mutants that selectively fail to associate with signaling enzymes were prepared. These are listed in Table 1.

TABLE 1

Properties of αPDGFR mutants

| Name | Mutation | Properties |
| --- | --- | --- |
| F72/74 | Tyr to Phe substitution at 572 and 574 | Fails to recruit or activate Src family kinases |
| F720 | Tyr to Phe substitution at 720 | Fails to recruit SHP-2 |
| F31/42 | Tyr to Phe substitution at 731 and 742 | Fails to recruit PI3K |
| F1018 | Tyr to Phe substitution at 1018 | Fails to recruit or activate PLCγ |
| F7 | Tyr to Phe substitution at 572, 574, 720, 731, 742, 988, and 1018 | Fails to recruit Src family kinases, SHP-2, PI3K, and PLCγ |
| R627 | Lys to Arg substitution at 627 | Kinase inactive |

Tyr = tyrosine residue;
Phe = phenylalanine residue;
SHP-2 = tyrosine phosphatase SHP-2;
PI3K = phosphoinositide 3-kinase;
PLCγ = phospholipase C-gamma;
Lys = Lysine residue;
Arg = Arginine residue.
The amino acid residue number are with respect to SEQ ID NO: 2.

The αPDGFR mutants were generated using a PCR-based site-directed mutagenesis strategy, as previously described (Rosenkranz, S. et al. (1999) J. Biol. Chem. 274:28335). The αPDGFRs were expressed in F cells as previously described (Rosenkranz, S. et al. (1999) J. Biol. Chem. 274:28335). Briefly, a wild type or mutated PDGFR cDNA was subcloned into either of the retroviral pLNCX[2] or pLXSH vectors (Andrews, A. et al. (1999) Invest. Ophthalmol. Vis. Sci. 40:2683; Gelderloos, J. A. et al. (1998) J. Biol. Chem. 273:5908). The cDNA constructs were transfected into the virus-producing 293 GPG cell line, Ory, D. S. et al. (1996) Proc. Natl. Acad. Sci. U.S.A. 93:11400, using lipofectamine. The virus-containing supernatant was collected for 5 days, then concentrated by centrifugation by 25000×g at 4° C. for 90 minutes. The virus was resuspended in a small volume overnight and frozen at −70° C. until use. F cells were infected with the appropriate retrovirus in the presence of 4 µg/ml of polybrene over night, followed by drug selection, as previously described (Rosenkranz, S. et al. (2000) *J. Biol. Chem.* 275:9620). In all cases mass populations of drug-resistant cells were used.

Figure 10:
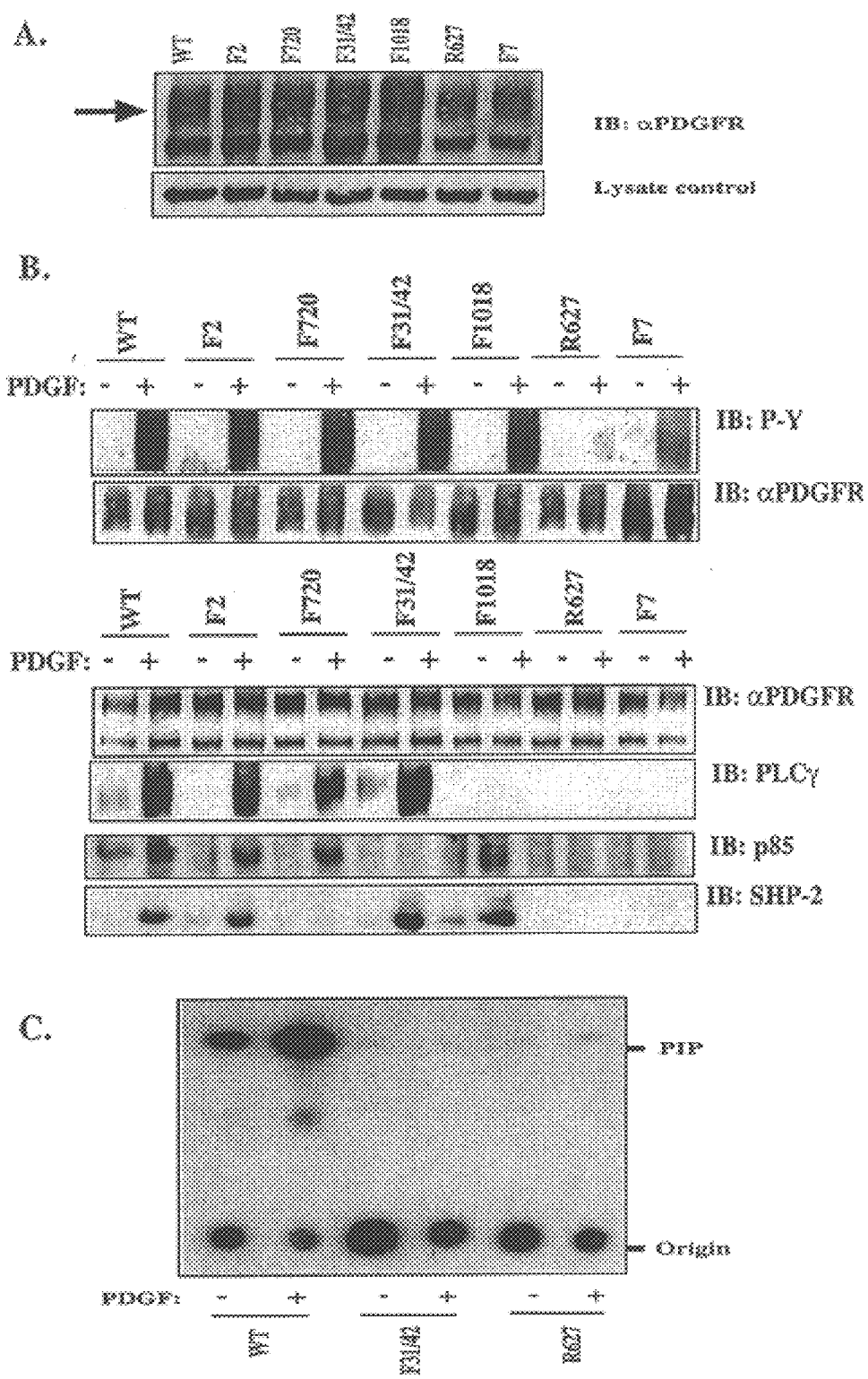
FIG. 10A is a Western blot of lysates from cells transfected with the indicated αPDGFR mutants or the WT αPDGFR, incubated with an antibody specific for either αPDGFR (upper panel) or Ras-GTP activating protein (lower panel). The arrow points to the glycosylated mature form of the receptor (180 kDa), whereas the 160 kDa species is the immature form of the receptor.
FIG. 10B shows Western blots of anti-αPDGFR antibody immunoprecipitated proteins from lysates of F cells expressing various αPDGFR mutants or the WT receptor, which were either left resting (−) or stimulated with 50 ng/ml PDGF-BB (+) for 5 minutes, and incubated with anti-phosphotyrosine antibodies (P-Y) or with anti-αPDGFR antibody. Portions of the membrane that contained the proteins of the appropriate molecular mass were immunoblotted for PLCγ, the regulatory subunit of PI3K (p85), or SHP-2.
FIG. 10C shows a chromatogram exposed to X-ray film showing radioactive phosphatidylinositol phosphate (PIP) of a PI3K activity assay using aliquots of the immunoprecipitates used in FIG. 10B, thereby detecting PI3K that has co-precipitated with the αPDGFR.

To determine the level of expression of the mutant receptors in the transfected F cells, the cells were grown to 80% confluence, serum-starved overnight and then lysed. Twenty µg of protein was subjected to western blotting using an antibody specific for either αPDGFR or Ras-GTP activating protein. The Western blot method and antibodies were as described in the previous Examples. As shown in FIG. 10A, showing the Western blot, and as measured by densitometric analysis, the receptor levels were all within two fold of the level seen in cells expressing the WT receptor.

In FIGS. 10–13 the cells labelled "WT" express the wild type αPDGFR, and are the same as the Fα cells used in FIGS. 7–10. All other cells lines used in FIGS. 10–13 express a mutant αPDGFR, and the name indicates the nature of the mutation.

The ability of the αPDGFR mutants to undergo ligand dependent tyrosine phosphorylation and to associate with signaling enzymes was then tested. F cells expressing various αPDGFR mutants were grown to subconfluence and serum starved overnight. Cells were either left resting (−) or stimulated with 50 ng/ml PDGF-BB (+) for 5 minutes, and lysed. The αPDGFR was immunoprecipitated with αPDGFR antibody, as described above, and the resulting immunoprecipitates were resolved by 7.5% SDS-PAGE and transferred onto Immobilon. The segment of the blot containing the αPDGFR was first blotted with anti-phosphotyrosine antibodies, then stripped and reprobed with an anti-αPDGFR antibody. Portions of the membrane that contained the proteins of the appropriate molecular mass were immunoblotted for PLCγ, the regulatory subunit of PI3K (p85), or SHP-2. Crude rabbit anti-p85 antibody is from Dr. A. Toker (Beth Israel Hospital/Harvard Medical School, Boston, Mass.). The monoclonal antibodies against PLCγ and SHP-2 were purchased from Upstate Biotechnology Inc.

The results, which are presented in FIG. 10B, show that all of the receptors, with the exception of the kinase inactive mutant (R627) were tyrosine phosphorylated following exposure of the cell to PDGF. Seven tyrosine phosphorylation sites are missing in the F7 receptor, and this is probably why this receptor is less phosphorylated. The WT αPDGFR coprecipitated with PLCγ, p85 and SHP-2, whereas the F7 and R627 receptors failed to recruit any of these signaling enzymes. The F720, F31/42 and F1018 receptors displayed a more selectively defect, such that they failed to efficiently associate with SHP-2, p85 or PLCγ, respectively. Thus, the WT and F72/74 receptors bind all of these signaling enzymes, while F720, F31/42 and F1018 are deficient in recruiting SHP-2, p85, PLCγ respectively. The kinase inactive mutant (R627) is not phosphorylated in response to PDGF and does not recruit any of the signaling enzymes. The F7 receptor is kinase active, and undergoes modest tyrosine phosphorylation, however this mutant lacks the tyrosine residues needed for stable association of the signaling enzymes.

To measure the PI3K activity that coprecipitated with the PDGFRs, the receptor immunoprecipitates were subjected to an in vitro PI3K kinase assay. Aliquots of the immunoprecipitates used in FIG. 10B were subjected to a PI3K activity assay. This assay detects PI3K that has co-precipitated with the αPDGFR. The PI3K assay was performed as previously described. Kazlauskas, A. et al. (1990) *Embo. J.* 9:3279. Briefly, immunoprecipitated αPDGFR from approximately $5 \times 10^5$ cells were incubated with phosphatidyl inositol in the presence of [$^{32}$P]-γATP. The reactions were terminated and the phospholipids were extracted and purified by chromatography. The radioactive product of the reaction (phosphoinositide 3 phosphate) was detected by autoradiography.

The results, which are shown in FIG. 10C, indicate that, consistent with the findings of the p85 Western blot (FIG. 10B), PI3K activity coprecipitated with the WT receptor and the amount of activity was greatly enhanced by PDGF stimulation (FIG. 10C). In contrast, PI3K activity did not detectably coprecipitate with the F31/42 receptor (FIG. 10C). The F72/74 receptor expressed in these cells was previously shown to selectively fails to associate with Src family kinases (Gelderloos, J. A. et al. (1998) *J. Biol. Chem.* 273:5908). Finally, the behavior of the αPDGFR mutants in F cells is very similar to what we have previously observed when the receptor was expressed in Ph cells (Rosenkranz, S. et al. (1999) *J. Biol. Chem.* 274:28335).

In summary, this panel of αPDGFR mutants is suitable, in particular, to assess the importance of several parameters of receptor function. These include kinase activity, global ability to recruit signaling enzymes, and the importance of specific signaling pathways that are initiated by PI3K, or PLCγ, or SHP-2 or Src family kinases.

Example 12

The PI3K and PLCγ Pathways are Involved in PDGF- and TGFβ-dependent Contraction

To determine the signaling pathways that drive contraction, cells expressing the αPDGFR mutants were subjected to the collagen gel contraction assay described above. Accordingly, F cells expressing the indicated αPDGFRs were subjected to the collagen gel assay in the presence of buffer, PDGF-BB (50 ng/ml), TGFβ1 (1 ng/ml), or FBS (10%). The data presented are the mean±standard deviation measured at the 48 hours time point. Each experimental condition was assayed in triplicate, and at least 3 independent experiments were performed.

The results, which are shown in FIG. 11C indicate that cells expressing the WT receptor contracted when PDGF was added to the medium, whereas no contraction was seen in cells expressing the kinase inactive (R627) receptor, or the receptor unable to recruit signaling enzymes (F7). The response of all three cell types was comparable under the negative (buffer) and positive (10% FBS) control conditions (FIGS. 11A and B). These findings indicate that activation of the receptor's kinase activity was required for the contraction response, however this was not sufficient, as the F7 receptor is kinase active. The inability of the F7 receptor to mediate contraction indicated that some of the signaling enzymes recruited to the αPDGFR are required to mediate contraction. Cells expressing the receptor which does not engage PI3K (F31/42) did not respond; and failure to engage PLCγ (in the case of the F1018 receptor) severely compromised contraction (FIG. 11C). In contrast, eliminating the contribution of PDGF-driven activation of the Src family kinases (F72/74 receptor) had no effect on contraction (FIG. 11C). The cells expressing the receptor that does not recruit SHP-2 (F720) displayed a somewhat reduced response (FIG. 11C), but this was not routinely observed.

Thus, PDGF-dependent contraction requires that the αPDGFR is kinase active, and be able to recruit signaling enzymes. In addition, PI3K and PLCγ were identified as the primary effectors of the αPDGFR.

In light of the finding that TGFβ-stimulated contraction is dependent on the αPDGFR, we also tested TGFβ-triggered contraction with cells expressing all of the αPDGFR mutants. Like PDGF-dependent contraction, the TGFβ-mediated event was either completely or severely compromised in cells expressing PDGFR mutants that failed to associate with PI3K or PLCγ, respectively (FIG. 11D). The response to TGFβ was similar to that seen with PDGF in all the other cell lines as well, although there were subtle differences consistently observed (FIG. 11C and D). We conclude that the signaling enzymes for αPDGFR-dependent contraction in response to TGFβ are the same as those required in response to PDGF. This observation further supports the idea that TGFβ is acting through the αPDGFR to stimulate contraction.

Thus, these Examples show that the αPDGFR is a critical mediator of TGFβ-dependent contraction, as TGFβ promotes tyrosine phosphorylation of the αPDGFR (FIG. 10), and expression of the αPDGFR greatly promotes TGFβ-dependent contraction (FIG. 8). The TGFβ-dependent αPDGFR activation appears to involve PDGF, as receptors unable to bind were insensitive to TGFβ. This idea is consistent with the previous finding that TGFβ up-regulates PDGF-A secretion in the fibroblasts. Makela, T. P. et al. (1987) *Mol. Cell Biol.* 7:3656; Majack, R. A. et al (1990) *J. Cell Biol.* 111:239; Battegay, E. J. et al. (1990) *Cell* 63:515.

Example 13

The PI3K and PLCγ Pathways are also Involved in Experimental PVR

An important component of PVR is the traction force that is generated when cells of the epiretinal membrane contract. To test if the signaling enzymes that are required for contraction in the in vitro assays also participate in PVR, the cells expressing the various αPDGFR mutants, described in the previous Examples, were assayed in a rabbit PVR model, described above. In this model, rabbits first undergo gas vitrectomy, and then cells are coinjected with platelet poor plasma. The formation of an epiretinal membrane and retinal detachment is observed in living animals over 28 days.

Briefly, PVR was induced by introducing F cells expressing the indicated αPDGFR into the vitreous of the rabbit eyes. The PVR score was evaluated up to 28 days after the surgery according to the classification described above. The mean value and standard error of the scores in a group were indicated. Each group contained 9 or 10 rabbits; the response to parental F cells was previously reported (Andrews et al., supra), and was included here for comparison purposes.

As shown in FIG. 12A, injection of F cells expressing the WT αPDGFR resulted in PVR within 2–3 weeks, whereas the cells expressing the kinase inactive receptor (R627), or the one that does not recruit signaling enzymes (F7) are dramatically less able to cause the disease. The extent of PVR observed in animals injected with these cells was comparable to the very mild response when cells expressing no PDGFRs were injected (FIG. 12A and Andrews, A. et al. (1999) *Invest. Ophthalmol. Vis. Sci.* 40:2683). These findings indicate that the kinase activity of the αPDGFR, as well as its potential to recruit signaling enzymes is essential for PVR.

To address which of the signaling enzymes contribute to PVR, the PVR potential of the cells expressing the other αPDGFR mutants were assayed in the rabbit model. The results, set forth in FIG. 12B, indicate that while the F720 receptor-expressing cells induced PVR similarly to the WT receptor-expressing cells, the PVR potential was significantly reduced in cells expressing the receptor that did not associate with PLCγ (F1018). Furthermore, the capacity to induce PVR was completely eliminated when receptor mutants were used that failed to engage PI3K (FIG. 12B). It was previously found that cells expressing the F72/74 αPDGFR induced PVR with slightly accelerated kinetics (Rosenkranz, S. et al. (2000) *J. Biol. Chem.* 275:9620).

Figure 12:
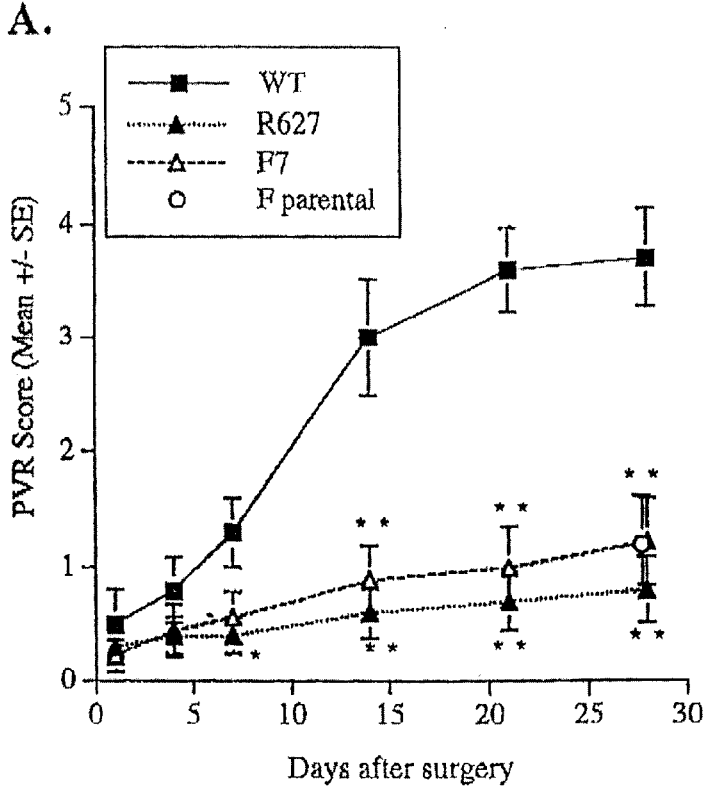
FIG. 12A shows the PVR score of PVR induced by introducing F cells expressing the indicated αPDGFR into the vitreous of the rabbit eyes at 28 days after the surgery. The mean value and standard error of the scores in a group were indicated. The asterisk (*) in the graph indicates significant difference (P<0.05 by Mann-Whitney U test) compared to the FαWT cells, and the double-asterisk (**) indicates P<0.01.
FIG. 12B shows the PVR score of PVR induced by introducing F cells expressing the indicated αPDGFR into the vitreous of the rabbit eyes at 28 days after the surgery. The mean value and standard error of the scores in a group were indicated. The asterisk (*) in the graph indicates significant difference (P<0.05 by Mann-Whitney U test) compared to the FαWT cells, and the double-asterisk (**) indicates P<0.01.
Figure 12:
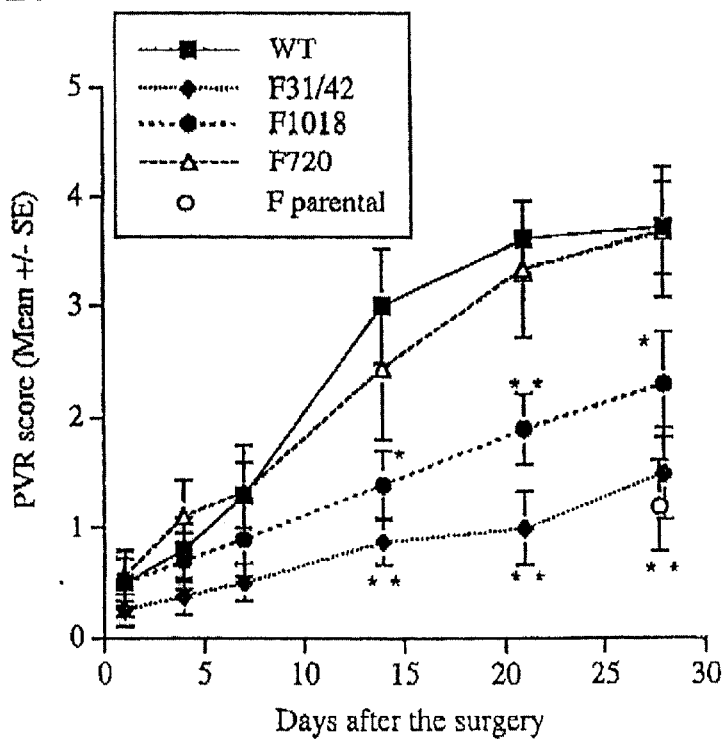
Figure 13:
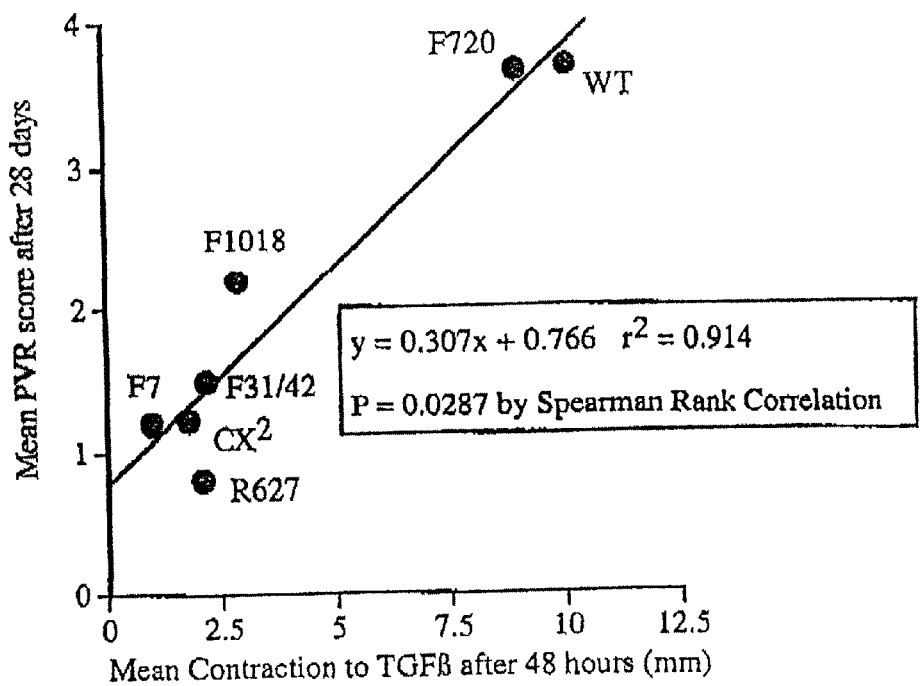
FIG. 13A shows the correlation of the mean PVR score after 28 days and the mean contraction activity (from FIG. 11) in response to TGFβ. TGFβ-dependent contraction activity of each αPDGFR mutant significantly correlates with the PVR score (P=0.0287, by Spearman's Rank correlation).
FIG. 13B shows the correlation of the mean PVR score after 28 days and the mean contraction activity (from FIG.
Figure 13:
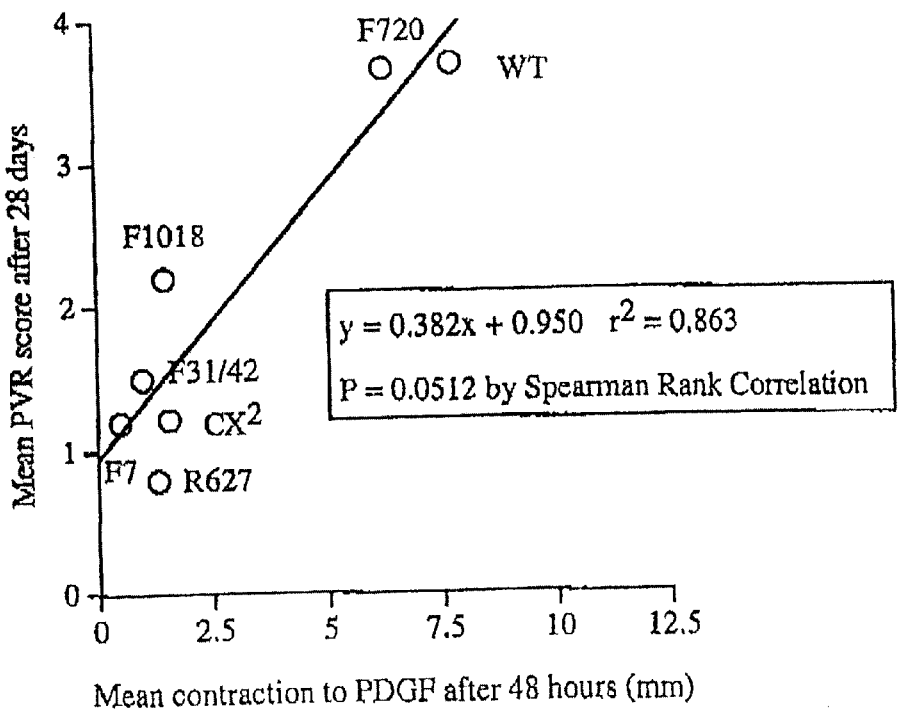

Thus, the data in FIG. 12 indicate that the kinase activity of the αPDGFR, as well as its ability to engage signaling pathways such as PI3K and PLCγ are critical components of the signaling cascades that drive PVR.

Our observation that PI3K is critical in PDGF-dependent contraction in fibroblasts is consistent with reports with other systems. Skuta, G. et al. (1999) *J. Biol Chem.* 274:30163; Ahlen, K. et al. (1998) *Cell Adhes. Commun.* 5:461. Then, how does PI3K mediate the contraction in type I collagen gel? One possibility is that PI3K and PLC activate/potentiate the integrins so that they are able to engage the extracellular matrix in which the cells have been seeded. In addition, it is possible that these signaling enzymes elevate expression of the integrins that interact with the extracellular matrix. For instance, PDGF induces synthesis of 2β1 integrin, Ahlen, K. et al. (1994) *Exp. Cell Res.* 215:347, which is important for collagen type I contraction, Schiro, J. A. et al. (1991) *Cell* 67:403, as well as vitreal remodelling and contraction. Kupper, T. S. et al. (1993) *Faseb J.* 7:1401. Furthermore, PDGF-dependent 2β1 integrin upregulation requires protein kinase C , a ser/thr kinase that has been shown to be a downstream of PI3K. Xu, J. et al. (1996) *J. Cell Biol.* 134:1301; Chou, M. M. et al. (1998) *Curr. Biol.* 8:1069. These lines of evidence indicate that PI3K mediates contraction in fibroblasts by regulating integrin expression. However, PI3K also regulates actin cytoskeleton, Keely, P. J. et al. (1997) *Nature* 390:632, which is important for contraction of collagen gels. Thus, multiple signaling enzymes may be involved in PI3K-dependent collagen gel contraction.

Example 14

Figure 11:
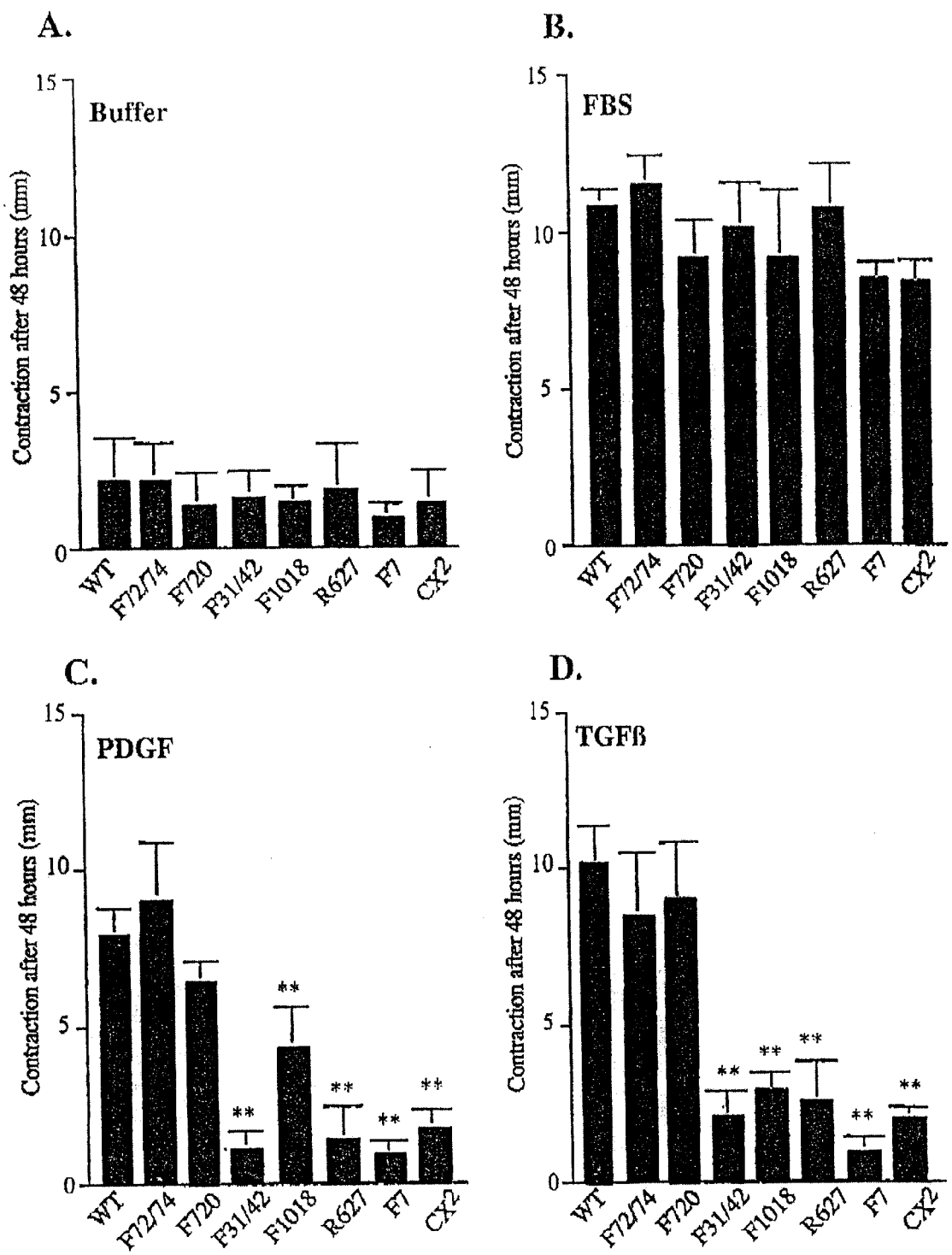
FIG. 11B is a histogram showing the contraction of cells expressing the indicated αPDGFRs plated in a collagen type I gel in the presence of FBS (10%).
FIG. 11A is a histogram showing the contraction of cells expressing the indicated αPDGFRs plated in a collagen type I gel in the presence of buffer.
FIG. 11C is a histogram showing the contraction of cells expressing the indicated αPDGFRs plated in a collagen type I gel in the presence of PDGF-BB (50 ng/ml). The double-asterisk (**) in the graph indicates significant difference (P<0.01 by Unpaired t-test) compared to the FαWT cells.
FIG. 11D is a histogram showing the contraction of cells expressing the indicated αPDGFRs plated in a collagen type I gel in the presence of TGFβ1 (1 ng/ml). The double-asterisk (**) in the graph indicates significant difference (P<0.01 by Unpaired t-test) compared to the FαWT cells.

Correlation Between in vitro Contraction and the Potential to Induce PVR in vivo FIGS. 11 and 12 show that the panel of cells expressing αPDGFR mutants behave similarly in the in vitro contraction assay and the in vivo PVR model. To assess whether there was a statistically significant relationship between these two outcomes the results of the PVR score (mean value at day 28) were plotted against the PDGF- or TGFβ3-induced contraction, and a Spearman's Rank Correlation test was performed. In all cases, P<0.05 was considered significant. As shown in FIG. 13A the contractile activity induced by TGFβ was significantly correlated with mean PVR score in vivo (P=0.0287, by Spearman's Rank Correlation test). In the case of PDGF, shown in FIG. 13B, there is borderline significance (P=0.0512). Thus, both PDGF- and TGFβ-dependent contraction is a predictive factor for PVR. A model for the relationship between TGFβ and αPDGFR-driven PVR is set forth in FIG. 14. Accordingly, TGFβ in the vitreous activates TGFβ receptor, and consequently the αPDGFR, probably by way of ligand such as PDGF-A. The activated αPDGFR engages signaling enzymes such as PI3K, and PLCγ, both of which are required to induce contraction. These cascades lead to contraction of pre- and subretinal cellular membrane and generate the tractional force that results in retinal detachment seen in PVR.

Thus, PDGF- and TGFβ-dependent contraction of fibroblasts is mediated by the PDGF α receptor and is predictive of retinal fibrotic disease. This indicates that the ability of cells to contract is an important component of the disease. A large fraction of the epiretinal membrane is ECM, which is a very likely contributor to the contraction response. Casaroli Marano, R. P. et al. (1994) *Invest. Ophthalmol. Vis. Sci.* 35:2791.

Equivalents

Those skilled in the art will recognize, or be able to ascertain using no more than routine experimentation, many equivalents of the specific embodiments of the invention described herein. Such equivalents are intended to be encompassed by the following claims.

What is claimed is:

1. An isolated nucleic acid encoding a polypeptide comprising an amino acid sequence having the general structure X-Y-Z, wherein Y consists of a portion of platelet derived growth factor-alpha receptor (PDGFαR) consisting essentially of amino acids 1 to 589 or amino acids 21 to 589 of SEQ ID NO: 2 and comprising Tyr572 and/or Tyr574; X and Z consist of zero or at least one amino acid, wherein, if Z is more than one amino acid, Z does not have the amino acid sequence of human PDGFαR located downstream of amino acid 589.

2. The nucleic acid of claim 1, encoding a polypeptide wherein X consists of zero amino acids.

3. The nucleic acid of claim 1, encoding a polypeptide wherein Z consists of zero amino acids.

4. The nucleic acid of claim 1, encoding a polypeptide wherein X and Z consist of zero amino acids.

5. The nucleic acid of claim 1, encoding a polypeptide comprising the amino acid sequence set forth in SEQ ID NO: 12.

6. The nucleic acid of claim 5, operably linked to at least one transcriptional regulatory element.

7. A vector comprising the nucleic acid of claim 6.

8. The nucleic acid of claim 5, encoding a polypeptide consisting of the amino acid sequence set forth in SEQ ID NO: 12.

9. The nucleic acid of claim 1, operably linked to at least one transcriptional regulatory element.

10. A vector comprising the nucleic acid of claim 9.

11. An isolated nucleic acid encoding a polypeptide comprising an amino acid sequence having the general structure X-Y-Z, wherein Y consists of a portion of platelet derived growth factor-alpha receptor (PDGFαR) consisting essentially of an amino acid sequence at least 95% identical to amino acids 1 to 589 or amino acids 21 to 589 of SEQ ID NO: 2 and comprising Tyr572 and/or Tyr574; X and Z consist of zero or at least one amino acid, wherein, if Z is more than one amino acid, Z does not have the amino acid sequence of human PDGFαR located downstream of amino acid 589, wherein the polypeptide is capable of binding A or B PDGF or homo/heterodimers thereof.

12. The nucleic acid of claim 11, wherein Y consists of an amino acid sequence that is at least about 98% identical to amino acids 1 to 589 or amino acids 21 to 589 of SEQ ID NO:2.

13. The nucleic acid of claim 12, encoding a polypeptide wherein X consists of zero amino acids.

14. The nucleic acid of claim 12, encoding a polypeptide wherein Z consists of zero amino acids.

15. The nucleic acid of claim 12, encoding a polypeptide wherein X and Z consist of zero amino acids.

16. The nucleic acid of claim 15, operably linked to at least one transcriptional regulatory element.

17. A vector comprising the nucleic acid of claim 16.

18. The nucleic acid of claim 12, operably linked to at least one transcriptional regulatory element.

19. A vector comprising the nucleic acid of claim 18.

20. The nucleic acid of claim 11, wherein Y consists of an amino acid sequence that is at least about 99% identical to a sequence from about amino acid 1 to from about amino acid 589 or about amino acid 21 to about amino acid 589 of SEQ ID NO: 2.

21. The nucleic acid of claim 20, encoding a polypeptide wherein X consists of zero amino acids.

22. The nucleic acid of claim 20, encoding a polypeptide wherein Z consists of zero amino acids.

23. The nucleic acid of claim 20, encoding a polypeptide wherein X and Z consist of zero amino acids.

24. The nucleic acid of claim 23, operably linked to at least one transcriptional regulatory element.

25. The nucleic acid of claim 20, operably linked to at least one transcriptional regulatory element.

26. A vector comprising the nucleic acid of claim 25.

27. The nucleic acid of claim 11, operably linked to at least one transcriptional regulatory element.

28. A vector comprising the nucleic acid of claim 27.

29. The nucleic acid of claim 11, encoding a polypeptide wherein X consists of zero amino acids.

30. The nucleic acid of claim 11, encoding a polypeptide wherein Z consists of zero amino acids.

31. The nucleic acid of claim 11, encoding a polypeptide wherein X and Z consist of zero amino acids.

32. The nucleic acid of claim 31, operably linked to at least one transcriptional regulatory element.

33. The vector comprising the nucleic acid of claim 32.

34. The nucleic acid of claim 11, comprising the nucleotide sequence set forth in SEQ ID NO: 11.

35. The nucleic acid of claim 34, consisting of the nucleotide sequence set forth in SEQ ID NO: 11.

36. The nucleic acid of claim 35, operably linked to at least one transcriptional regulatory element.

37. A vector comprising the nucleic acid of claim 36.

38. An isolated nucleic acid encoding a polypeptide comprising an amino acid sequence having the general structure X-Y-Z, wherein Y consists of a portion of platelet derived growth factor-alpha receptor (PDGFαR) consisting of about amino acid 1 to about amino acid 589 or about amino acid 21 to about amino acid 589 of SEQ ID NO: 2; X and Z consist of zero or at least one amino acid, wherein, if Z is more than one amino acid, Z does not have the amino acid sequence of human PDGFαR located downstream of amino acid 589.

39. The nucleic acid of claim 38, operably linked to at least one transcriptional regulatory element.

40. A vector comprising the nucleic acid of claim 39.

* * * * *

SEQUENCE LISTING

<160> NUMBER OF SEQ ID NOS: 33

<210> SEQ ID NO 1
<211> LENGTH: 3270
<212> TYPE: DNA
<213> ORGANISM: Homo sapiens
<220> FEATURE:
<221> NAME/KEY: CDS
<222> LOCATION: (1)..(3267)

<400> SEQUENCE: 1

```
atg ggg act tcc cat ccg gcg ttc ctg gtc tta ggc tgt ctt ctc aca        48
Met Gly Thr Ser His Pro Ala Phe Leu Val Leu Gly Cys Leu Leu Thr
  1               5                  10                  15 ggg ctg agc cta atc ctc tgc cag ctt tca tta ccc tct atc ctt cca        96
Gly Leu Ser Leu Ile Leu Cys Gln Leu Ser Leu Pro Ser Ile Leu Pro
              20                  25                  30 aat gaa aat gaa aag gtt gtg cag ctg aat tca tcc ttt tct ctg aga       144
Asn Glu Asn Glu Lys Val Val Gln Leu Asn Ser Ser Phe Ser Leu Arg
          35                  40                  45 tgc ttt ggg gag agt gaa gtg agc tgg cag tac ccc atg tct gaa gaa       192
Cys Phe Gly Glu Ser Glu Val Ser Trp Gln Tyr Pro Met Ser Glu Glu
      50                  55                  60 gag agc tcc gat gtg gaa atc aga aat gaa gaa aac aac agc ggc ctt       240
Glu Ser Ser Asp Val Glu Ile Arg Asn Glu Glu Asn Asn Ser Gly Leu
 65                  70                  75                  80 ttt gtg acg gtc ttg gaa gtg agc agt gcc tcg gcg gcc cac aca ggg       288
Phe Val Thr Val Leu Glu Val Ser Ser Ala Ser Ala Ala His Thr Gly
                  85                  90                  95 ttg tac act tgc tat tac aac cac act cag aca gaa gag aat gag ctt       336
Leu Tyr Thr Cys Tyr Tyr Asn His Thr Gln Thr Glu Glu Asn Glu Leu
             100                 105                 110 gaa ggc agg cac att tac atc tat gtg cca gac cca gat gta gcc ttt       384
Glu Gly Arg His Ile Tyr Ile Tyr Val Pro Asp Pro Asp Val Ala Phe
         115                 120                 125 gta cct cta gga atg acg gat tat tta gtc atc gtg gag gat gat gat       432
Val Pro Leu Gly Met Thr Asp Tyr Leu Val Ile Val Glu Asp Asp Asp
     130                 135                 140 tct gcc att ata cct tgt cgc aca act gat ccc gag act cct gta acc       480
Ser Ala Ile Ile Pro Cys Arg Thr Thr Asp Pro Glu Thr Pro Val Thr
145                 150                 155                 160 tta cac aac agt gag ggg gtg gta cct gcc tcc tac gac agc aga cag       528
Leu His Asn Ser Glu Gly Val Val Pro Ala Ser Tyr Asp Ser Arg Gln
                 165                 170                 175 ggc ttt aat ggg acc ttc act gta ggg ccc tat atc tgt gag gcc acc       576
Gly Phe Asn Gly Thr Phe Thr Val Gly Pro Tyr Ile Cys Glu Ala Thr
             180                 185                 190 gtc aaa gga aag aag ttc cag acc atc cca ttt aat gtt tat gct tta       624
Val Lys Gly Lys Lys Phe Gln Thr Ile Pro Phe Asn Val Tyr Ala Leu
         195                 200                 205 aaa gca aca tca gag ctg gat cta gaa atg gaa gct ctt aaa acc gtg       672
Lys Ala Thr Ser Glu Leu Asp Leu Glu Met Glu Ala Leu Lys Thr Val
     210                 215                 220
```

```
tat aag tca ggg gaa acg att gtg gtc acc tgt gct gtt ttt aac aat        720
Tyr Lys Ser Gly Glu Thr Ile Val Val Thr Cys Ala Val Phe Asn Asn
225             230                 235                 240 gag gtg gtt gac ctt caa tgg act tac cct gga gaa gtg aaa ggc aaa        768
Glu Val Val Asp Leu Gln Trp Thr Tyr Pro Gly Glu Val Lys Gly Lys
            245                 250                 255 ggc atc aca atg ctg gaa gaa atc aaa gtc cca tcc atc aaa ttg gtg        816
Gly Ile Thr Met Leu Glu Glu Ile Lys Val Pro Ser Ile Lys Leu Val
        260                 265                 270 tac act ttg acg gtc ccc gag gcc acg gtg aaa gac agt gga gat tac        864
Tyr Thr Leu Thr Val Pro Glu Ala Thr Val Lys Asp Ser Gly Asp Tyr
    275                 280                 285 gaa tgt gct gcc cgc cag gct acc agg gag gtc aaa gaa atg aag aaa        912
Glu Cys Ala Ala Arg Gln Ala Thr Arg Glu Val Lys Glu Met Lys Lys
290                 295                 300 gtc act att tct gtc cat gag aaa ggt ttc att gaa atc aaa ccc acc        960
Val Thr Ile Ser Val His Glu Lys Gly Phe Ile Glu Ile Lys Pro Thr
305                 310                 315                 320 ttc agc cag ttg gaa gct gtc aac ctg cat gaa gtc aaa cat ttt gtt       1008
Phe Ser Gln Leu Glu Ala Val Asn Leu His Glu Val Lys His Phe Val
            325                 330                 335 gta gag gtg cgg gcc tac cca cct ccc agg ata tcc tgg ctg aaa aac       1056
Val Glu Val Arg Ala Tyr Pro Pro Pro Arg Ile Ser Trp Leu Lys Asn
        340                 345                 350 aat ctg act ctg att gaa aat ctc act gag atc acc act gat gtg gaa       1104
Asn Leu Thr Leu Ile Glu Asn Leu Thr Glu Ile Thr Thr Asp Val Glu
    355                 360                 365 aag att cag gaa ata agg tat cga agc aaa tta aag ctg atc cgt gct       1152
Lys Ile Gln Glu Ile Arg Tyr Arg Ser Lys Leu Lys Leu Ile Arg Ala
370                 375                 380 aag gaa gaa gac agt ggc cat tat act att gta gct caa aat gaa gat       1200
Lys Glu Glu Asp Ser Gly His Tyr Thr Ile Val Ala Gln Asn Glu Asp
385                 390                 395                 400 gct gtg aag agc tat act ttt gaa ctg tta act caa gtt cct tca tcc       1248
Ala Val Lys Ser Tyr Thr Phe Glu Leu Leu Thr Gln Val Pro Ser Ser
            405                 410                 415 att ctg gac ttg gtc gat gat cac cat ggc tca act ggg gga cag acg       1296
Ile Leu Asp Leu Val Asp Asp His His Gly Ser Thr Gly Gly Gln Thr
        420                 425                 430 gtg agg tgc aca gct gaa ggc acg ccg ctt cct gat att gag tgg atg       1344
Val Arg Cys Thr Ala Glu Gly Thr Pro Leu Pro Asp Ile Glu Trp Met
    435                 440                 445 ata tgc aaa gat att aag aaa tgt aat aat gaa act tcc tgg act att       1392
Ile Cys Lys Asp Ile Lys Lys Cys Asn Asn Glu Thr Ser Trp Thr Ile
450                 455                 460 ttg gcc aac aat gtc tca aac atc atc acg gag atc cac tcc cga gac       1440
Leu Ala Asn Asn Val Ser Asn Ile Ile Thr Glu Ile His Ser Arg Asp
465                 470                 475                 480 agg agt acc gtg gag ggc cgt gtg act ttc gcc aaa gtg gag gag acc       1488
Arg Ser Thr Val Glu Gly Arg Val Thr Phe Ala Lys Val Glu Glu Thr
            485                 490                 495 atc gcc gtg cga tgc ctg gct aag aat ctc ctt gga gct gag aac cga       1536
Ile Ala Val Arg Cys Leu Ala Lys Asn Leu Leu Gly Ala Glu Asn Arg
        500                 505                 510 gag ctg aag ctg gtg gct ccc acc ctg cgt tct gaa ctc acg gtg gct       1584
Glu Leu Lys Leu Val Ala Pro Thr Leu Arg Ser Glu Leu Thr Val Ala
    515                 520                 525 gct gca gtc ctg gtg ctg ttg gtg att gtg atc atc tca ctt att gtc       1632
Ala Ala Val Leu Val Leu Leu Val Ile Val Ile Ile Ser Leu Ile Val
```

-continued

```
                530                 535                 540
ctg gtt gtc att tgg aaa cag aaa ccg agg tat gaa att cgc tgg agg      1680
Leu Val Val Ile Trp Lys Gln Lys Pro Arg Tyr Glu Ile Arg Trp Arg
545                 550                 555                 560 gtc att gaa tca atc agc ccg gat gga cat gaa tat att tat gtg gac      1728
Val Ile Glu Ser Ile Ser Pro Asp Gly His Glu Tyr Ile Tyr Val Asp
                565                 570                 575 ccg atg cag ctg cct tat gac tca aga tgg gag ttt cca aga gat gga      1776
Pro Met Gln Leu Pro Tyr Asp Ser Arg Trp Glu Phe Pro Arg Asp Gly
            580                 585                 590 cta gtg ctt ggt cgg gtc ttg ggg tct gga gcg ttt ggg aag gtg gtt      1824
Leu Val Leu Gly Arg Val Leu Gly Ser Gly Ala Phe Gly Lys Val Val
        595                 600                 605 gaa gga aca gcc tat gga tta agc cgg tcc caa cct gtc atg aaa gtt      1872
Glu Gly Thr Ala Tyr Gly Leu Ser Arg Ser Gln Pro Val Met Lys Val
    610                 615                 620 gca gtg aag atg cta aaa ccc acg gcc aga tcc agt gaa aaa caa gct      1920
Ala Val Lys Met Leu Lys Pro Thr Ala Arg Ser Ser Glu Lys Gln Ala
625                 630                 635                 640 ctc atg tct gaa ctg aag ata atg act cac ctg ggg cca cat ttg aac      1968
Leu Met Ser Glu Leu Lys Ile Met Thr His Leu Gly Pro His Leu Asn
                645                 650                 655 att gta aac ttg ctg gga gcc tgc acc aag tca ggc ccc att tac atc      2016
Ile Val Asn Leu Leu Gly Ala Cys Thr Lys Ser Gly Pro Ile Tyr Ile
            660                 665                 670 atc aca gag tat tgc ttc tat gga gat ttg gtc aac tat ttg cat aag      2064
Ile Thr Glu Tyr Cys Phe Tyr Gly Asp Leu Val Asn Tyr Leu His Lys
        675                 680                 685 aat agg gat agc ttc ctg agc cac cac cca gag aag cca aag aaa gag      2112
Asn Arg Asp Ser Phe Leu Ser His His Pro Glu Lys Pro Lys Lys Glu
    690                 695                 700 ctg gat atc ttt gga ttg aac cct gct gat gaa agc aca cgg agc tat      2160
Leu Asp Ile Phe Gly Leu Asn Pro Ala Asp Glu Ser Thr Arg Ser Tyr
705                 710                 715                 720 gtt att tta tct ttt gaa aac aat ggt gac tac atg gac atg aag cag      2208
Val Ile Leu Ser Phe Glu Asn Asn Gly Asp Tyr Met Asp Met Lys Gln
                725                 730                 735 gct gat act aca cag tat gtc ccc atg cta gaa agg aaa gag gtt tct      2256
Ala Asp Thr Thr Gln Tyr Val Pro Met Leu Glu Arg Lys Glu Val Ser
            740                 745                 750 aaa tat tcc gac atc cag aga tca ctc tat gat cgt cca gcc tca tat      2304
Lys Tyr Ser Asp Ile Gln Arg Ser Leu Tyr Asp Arg Pro Ala Ser Tyr
        755                 760                 765 aag aag aaa tct atg tta gac tca gaa gtc aaa aac ctc ctt tca gat      2352
Lys Lys Lys Ser Met Leu Asp Ser Glu Val Lys Asn Leu Leu Ser Asp
    770                 775                 780 gat aac tca gaa ggc ctt act tta ttg gat ttg ttg agc ttc acc tat      2400
Asp Asn Ser Glu Gly Leu Thr Leu Leu Asp Leu Leu Ser Phe Thr Tyr
785                 790                 795                 800 caa gtt gcc cga gga atg gag ttt ttg gct tca aaa aat tgt gtc cac      2448
Gln Val Ala Arg Gly Met Glu Phe Leu Ala Ser Lys Asn Cys Val His
                805                 810                 815 cgt gat ctg gct gct cgc aac gtc ctc ctg gca caa gga aaa att gtg      2496
Arg Asp Leu Ala Ala Arg Asn Val Leu Leu Ala Gln Gly Lys Ile Val
            820                 825                 830 aag atc tgt gac ttt ggc ctg gcc aga gac atc atg cat gat tcg aac      2544
Lys Ile Cys Asp Phe Gly Leu Ala Arg Asp Ile Met His Asp Ser Asn
        835                 840                 845 tat gtg tcg aaa ggc agt acc ttt ctg ccc gtg aag tgg atg gct cct      2592
Tyr Val Ser Lys Gly Ser Thr Phe Leu Pro Val Lys Trp Met Ala Pro
```

```
Tyr Val Ser Lys Gly Ser Thr Phe Leu Pro Val Lys Trp Met Ala Pro
    850                 855                 860 gag agc atc ttt gac aac ctc tac acc aca ctg agt gat gtc tgg tct    2640
Glu Ser Ile Phe Asp Asn Leu Tyr Thr Thr Leu Ser Asp Val Trp Ser
865                 870                 875                 880 tat ggc att ctg ctc tgg gag atc ttt tcc ctt ggt ggc acc cct tac    2688
Tyr Gly Ile Leu Leu Trp Glu Ile Phe Ser Leu Gly Gly Thr Pro Tyr
                885                 890                 895 ccc ggc atg atg gtg gat tct act ttc tac aat aag atc aag agt ggg    2736
Pro Gly Met Met Val Asp Ser Thr Phe Tyr Asn Lys Ile Lys Ser Gly
            900                 905                 910 tac cgg atg gcc aag cct gac cac gct acc agt gaa gtc tac gag atc    2784
Tyr Arg Met Ala Lys Pro Asp His Ala Thr Ser Glu Val Tyr Glu Ile
        915                 920                 925 atg gtg aaa tgc tgg aac agt gag ccg gag aag aga ccc tcc ttt tac    2832
Met Val Lys Cys Trp Asn Ser Glu Pro Glu Lys Arg Pro Ser Phe Tyr
    930                 935                 940 cac ctg agt gag att gtg gag aat ctg ctg cct gga caa tat aaa aag    2880
His Leu Ser Glu Ile Val Glu Asn Leu Leu Pro Gly Gln Tyr Lys Lys
945                 950                 955                 960 agt tat gaa aaa att cac ctg gac ttc ctg aag agt gac cat cct gct    2928
Ser Tyr Glu Lys Ile His Leu Asp Phe Leu Lys Ser Asp His Pro Ala
                965                 970                 975 gtg gca cgc atg cgt gtg gac tca gac aat gca tac att ggt gtc acc    2976
Val Ala Arg Met Arg Val Asp Ser Asp Asn Ala Tyr Ile Gly Val Thr
            980                 985                 990 tac aaa aac gag gaa gac aag ctg aag gac tgg gag ggt ggt ctg gat    3024
Tyr Lys Asn Glu Glu Asp Lys Leu Lys Asp Trp Glu Gly Gly Leu Asp
        995                 1000                1005 gag cag aga ctg agc gct gac agt ggc tac atc att cct ctg cct gac    3072
Glu Gln Arg Leu Ser Ala Asp Ser Gly Tyr Ile Ile Pro Leu Pro Asp
    1010                1015                1020 att gac cct gtc cct gag gag gag gac ctg ggc aag agg aac aga cac    3120
Ile Asp Pro Val Pro Glu Glu Glu Asp Leu Gly Lys Arg Asn Arg His
1025                1030                1035                1040 agc tcg cag acc tct gaa gag agt gcc att gag acg ggt tcc agc agt    3168
Ser Ser Gln Thr Ser Glu Glu Ser Ala Ile Glu Thr Gly Ser Ser Ser
                1045                1050                1055 tcc acc ttc atc aag aga gag gac gag acc att gaa gac atc gac atg    3216
Ser Thr Phe Ile Lys Arg Glu Asp Glu Thr Ile Glu Asp Ile Asp Met
            1060                1065                1070 atg gac gac atc ggc ata gac tct tca gac ctg gtg gaa gac agc ttc    3264
Met Asp Asp Ile Gly Ile Asp Ser Ser Asp Leu Val Glu Asp Ser Phe
        1075                1080                1085 ctg taa                                                             3270
Leu

<210> SEQ ID NO 2
<211> LENGTH: 1089
<212> TYPE: PRT
<213> ORGANISM: Homo sapiens

<400> SEQUENCE: 2

Met Gly Thr Ser His Pro Ala Phe Leu Val Leu Gly Cys Leu Leu Thr
1               5                   10                  15

Gly Leu Ser Leu Ile Leu Cys Gln Leu Ser Leu Pro Ser Ile Leu Pro
            20                  25                  30

Asn Glu Asn Glu Lys Val Val Gln Leu Asn Ser Ser Phe Ser Leu Arg
        35                  40                  45
```

-continued

```
Cys Phe Gly Glu Ser Glu Val Ser Trp Gln Tyr Pro Met Ser Glu Glu
         50                  55                  60

Glu Ser Ser Asp Val Glu Ile Arg Asn Glu Asn Ser Gly Leu
 65                  70                  75                  80

Phe Val Thr Val Leu Glu Val Ser Ser Ala Ser Ala His Thr Gly
                 85                  90                  95

Leu Tyr Thr Cys Tyr Tyr Asn His Thr Gln Thr Glu Glu Asn Glu Leu
             100                 105                 110

Glu Gly Arg His Ile Tyr Ile Tyr Val Pro Asp Pro Asp Val Ala Phe
             115                 120                 125

Val Pro Leu Gly Met Thr Asp Tyr Leu Val Ile Val Glu Asp Asp Asp
 130                 135                 140

Ser Ala Ile Ile Pro Cys Arg Thr Thr Asp Pro Glu Thr Pro Val Thr
 145                 150                 155                 160

Leu His Asn Ser Glu Gly Val Val Pro Ala Ser Tyr Asp Ser Arg Gln
                 165                 170                 175

Gly Phe Asn Gly Thr Phe Thr Val Gly Pro Tyr Ile Cys Glu Ala Thr
             180                 185                 190

Val Lys Gly Lys Lys Phe Gln Thr Ile Pro Phe Asn Val Tyr Ala Leu
     195                 200                 205

Lys Ala Thr Ser Glu Leu Asp Leu Glu Met Glu Ala Leu Lys Thr Val
 210                 215                 220

Tyr Lys Ser Gly Glu Thr Ile Val Val Thr Cys Ala Val Phe Asn Asn
 225                 230                 235                 240

Glu Val Val Asp Leu Gln Trp Thr Tyr Pro Gly Glu Val Lys Gly Lys
                 245                 250                 255

Gly Ile Thr Met Leu Glu Glu Ile Lys Val Pro Ser Ile Lys Leu Val
             260                 265                 270

Tyr Thr Leu Thr Val Pro Glu Ala Thr Val Lys Asp Ser Gly Asp Tyr
             275                 280                 285

Glu Cys Ala Ala Arg Gln Ala Thr Arg Glu Val Lys Glu Met Lys Lys
 290                 295                 300

Val Thr Ile Ser Val His Glu Lys Gly Phe Ile Glu Ile Lys Pro Thr
 305                 310                 315                 320

Phe Ser Gln Leu Glu Ala Val Asn Leu His Glu Val Lys His Phe Val
                 325                 330                 335

Val Glu Val Arg Ala Tyr Pro Pro Pro Arg Ile Ser Trp Leu Lys Asn
             340                 345                 350

Asn Leu Thr Leu Ile Glu Asn Leu Thr Glu Ile Thr Thr Asp Val Glu
             355                 360                 365

Lys Ile Gln Glu Ile Arg Tyr Arg Ser Lys Leu Lys Leu Ile Arg Ala
 370                 375                 380

Lys Glu Glu Asp Ser Gly His Tyr Thr Ile Val Ala Gln Asn Glu Asp
 385                 390                 395                 400

Ala Val Lys Ser Tyr Thr Phe Glu Leu Leu Thr Gln Val Pro Ser Ser
                 405                 410                 415

Ile Leu Asp Leu Val Asp Asp His Gly Ser Thr Gly Gly Gln Thr
             420                 425                 430

Val Arg Cys Thr Ala Glu Gly Thr Pro Leu Pro Asp Ile Glu Trp Met
     435                 440                 445

Ile Cys Lys Asp Ile Lys Lys Cys Asn Asn Glu Thr Ser Trp Thr Ile
 450                 455                 460

Leu Ala Asn Asn Val Ser Asn Ile Ile Thr Glu Ile His Ser Arg Asp
```

-continued

```
          465                 470                 475                 480
     Arg Ser Thr Val Glu Gly Arg Val Thr Phe Ala Lys Val Glu Glu Thr
                         485                 490                 495

Ile Ala Val Arg Cys Leu Ala Lys Asn Leu Leu Gly Ala Glu Asn Arg
                 500                 505                 510

Glu Leu Lys Leu Val Ala Pro Thr Leu Arg Ser Glu Leu Thr Val Ala
             515                 520                 525

Ala Ala Val Leu Val Leu Leu Val Ile Val Ile Ile Ser Leu Ile Val
         530                 535                 540

Leu Val Val Ile Trp Lys Gln Lys Pro Arg Tyr Glu Ile Arg Trp Arg
     545                 550                 555                 560

Val Ile Glu Ser Ile Ser Pro Asp Gly His Glu Tyr Ile Tyr Val Asp
                         565                 570                 575

Pro Met Gln Leu Pro Tyr Asp Ser Arg Trp Glu Phe Pro Arg Asp Gly
                 580                 585                 590

Leu Val Leu Gly Arg Val Leu Gly Ser Gly Ala Phe Gly Lys Val Val
             595                 600                 605

Glu Gly Thr Ala Tyr Gly Leu Ser Arg Ser Gln Pro Val Met Lys Val
         610                 615                 620

Ala Val Lys Met Leu Lys Pro Thr Ala Arg Ser Ser Glu Lys Gln Ala
     625                 630                 635                 640

Leu Met Ser Glu Leu Lys Ile Met Thr His Leu Gly Pro His Leu Asn
                         645                 650                 655

Ile Val Asn Leu Leu Gly Ala Cys Thr Lys Ser Gly Pro Ile Tyr Ile
                 660                 665                 670

Ile Thr Glu Tyr Cys Phe Tyr Gly Asp Leu Val Asn Tyr Leu His Lys
             675                 680                 685

Asn Arg Asp Ser Phe Leu Ser His His Pro Glu Lys Pro Lys Lys Glu
         690                 695                 700

Leu Asp Ile Phe Gly Leu Asn Pro Ala Asp Glu Ser Thr Arg Ser Tyr
     705                 710                 715                 720

Val Ile Leu Ser Phe Glu Asn Asn Gly Asp Tyr Met Asp Met Lys Gln
                         725                 730                 735

Ala Asp Thr Thr Gln Tyr Val Pro Met Leu Glu Arg Lys Glu Val Ser
                 740                 745                 750

Lys Tyr Ser Asp Ile Gln Arg Ser Leu Tyr Asp Arg Pro Ala Ser Tyr
             755                 760                 765

Lys Lys Lys Ser Met Leu Asp Ser Glu Val Lys Asn Leu Leu Ser Asp
         770                 775                 780

Asp Asn Ser Glu Gly Leu Thr Leu Leu Asp Leu Leu Ser Phe Thr Tyr
     785                 790                 795                 800

Gln Val Ala Arg Gly Met Glu Phe Leu Ala Ser Lys Asn Cys Val His
                         805                 810                 815

Arg Asp Leu Ala Ala Arg Asn Val Leu Leu Ala Gln Gly Lys Ile Val
                 820                 825                 830

Lys Ile Cys Asp Phe Gly Leu Ala Arg Asp Ile Met His Asp Ser Asn
             835                 840                 845

Tyr Val Ser Lys Gly Ser Thr Phe Leu Pro Val Lys Trp Met Ala Pro
         850                 855                 860

Glu Ser Ile Phe Asp Asn Leu Tyr Thr Thr Leu Ser Asp Val Trp Ser
     865                 870                 875                 880

Tyr Gly Ile Leu Leu Trp Glu Ile Phe Ser Leu Gly Gly Thr Pro Tyr
                         885                 890                 895
```

```
Pro Gly Met Met Val Asp Ser Thr Phe Tyr Asn Lys Ile Lys Ser Gly
            900                 905                 910
Tyr Arg Met Ala Lys Pro Asp His Ala Thr Ser Glu Val Tyr Glu Ile
        915                 920                 925
Met Val Lys Cys Trp Asn Ser Glu Pro Glu Lys Arg Pro Ser Phe Tyr
    930                 935                 940
His Leu Ser Glu Ile Val Glu Asn Leu Leu Pro Gly Gln Tyr Lys Lys
945                 950                 955                 960
Ser Tyr Glu Lys Ile His Leu Asp Phe Leu Lys Ser Asp His Pro Ala
                965                 970                 975
Val Ala Arg Met Arg Val Asp Ser Asp Asn Ala Tyr Ile Gly Val Thr
            980                 985                 990
Tyr Lys Asn Glu Glu Asp Lys Leu Lys Asp Trp Glu Gly Gly Leu Asp
        995                 1000                1005
Glu Gln Arg Leu Ser Ala Asp Ser Gly Tyr Ile Ile Pro Leu Pro Asp
    1010                1015                1020
Ile Asp Pro Val Pro Glu Glu Asp Leu Gly Lys Arg Asn Arg His
1025                1030                1035                1040
Ser Ser Gln Thr Ser Glu Glu Ser Ala Ile Glu Thr Gly Ser Ser Ser
                1045                1050                1055
Ser Thr Phe Ile Lys Arg Glu Asp Glu Thr Ile Glu Asp Ile Asp Met
            1060                1065                1070
Met Asp Asp Ile Gly Ile Asp Ser Ser Asp Leu Val Glu Asp Ser Phe
        1075                1080                1085
Leu

<210> SEQ ID NO 3
<211> LENGTH: 3270
<212> TYPE: DNA
<213> ORGANISM: Homo sapiens
<220> FEATURE:
<221> NAME/KEY: CDS
<222> LOCATION: (1)..(3267)

<400> SEQUENCE: 3 atg ggg act tcc cat ccg gcg ttc ctg gtc tta ggc tgt ctt ctc aca      48
Met Gly Thr Ser His Pro Ala Phe Leu Val Leu Gly Cys Leu Leu Thr
  1               5                  10                  15 ggg ctg agc cta atc ctc tgc cag ctt tca tta ccc tct atc ctt cca      96
Gly Leu Ser Leu Ile Leu Cys Gln Leu Ser Leu Pro Ser Ile Leu Pro
             20                  25                  30 aat gaa aat gaa aag gtt gtg cag ctg aat tca tcc ttt tct ctg aga     144
Asn Glu Asn Glu Lys Val Val Gln Leu Asn Ser Ser Phe Ser Leu Arg
         35                  40                  45 tgc ttt ggg gag agt gaa gtg agc tgg cag tac ccc atg tct gaa gaa     192
Cys Phe Gly Glu Ser Glu Val Ser Trp Gln Tyr Pro Met Ser Glu Glu
     50                  55                  60 gag agc tcc gat gtg gaa atc aga aat gaa gaa aac agc ggc ctt         240
Glu Ser Ser Asp Val Glu Ile Arg Asn Glu Glu Asn Asn Ser Gly Leu
 65                  70                  75                  80 ttt gtg acg gtc ttg gaa gtg agc agt gcc tcg gcg gcc cac aca ggg     288
Phe Val Thr Val Leu Glu Val Ser Ser Ala Ser Ala Ala His Thr Gly
                 85                  90                  95 ttg tac act tgc tat tac aac cac act cag aca gaa gag aat gag ctt     336
Leu Tyr Thr Cys Tyr Tyr Asn His Thr Gln Thr Glu Glu Asn Glu Leu
            100                 105                 110 gaa ggc agg cac att tac atc tat gtg cca gac cca gat gta gcc ttt     384
```

```
                                                          -continued

Glu Gly Arg His Ile Tyr Ile Tyr Val Pro Asp Pro Asp Val Ala Phe
            115                 120                 125 gta cct cta gga atg acg gat tat tta gtc atc gtg gag gat gat gat     432
Val Pro Leu Gly Met Thr Asp Tyr Leu Val Ile Val Glu Asp Asp Asp
130                 135                 140 tct gcc att ata cct tgt cgc aca act gat ccc gag act cct gta acc     480
Ser Ala Ile Ile Pro Cys Arg Thr Thr Asp Pro Glu Thr Pro Val Thr
145                 150                 155                 160 tta cac aac agt gag ggg gtg gta cct gcc tcc tac gac agc aga cag     528
Leu His Asn Ser Glu Gly Val Val Pro Ala Ser Tyr Asp Ser Arg Gln
                165                 170                 175 ggc ttt aat ggg acc ttc act gta ggg ccc tat atc tgt gag gcc acc     576
Gly Phe Asn Gly Thr Phe Thr Val Gly Pro Tyr Ile Cys Glu Ala Thr
            180                 185                 190 gtc aaa gga aag aag ttc cag acc atc cca ttt aat gtt tat gct tta     624
Val Lys Gly Lys Lys Phe Gln Thr Ile Pro Phe Asn Val Tyr Ala Leu
        195                 200                 205 aaa gca aca tca gag ctg gat cta gaa atg gaa gct ctt aaa acc gtg     672
Lys Ala Thr Ser Glu Leu Asp Leu Glu Met Glu Ala Leu Lys Thr Val
210                 215                 220 tat aag tca ggg gaa acg att gtg gtc acc tgt gct gtt ttt aac aat     720
Tyr Lys Ser Gly Glu Thr Ile Val Val Thr Cys Ala Val Phe Asn Asn
225                 230                 235                 240 gag gtg gtt gac ctt caa tgg act tac cct gga gaa gtg aaa ggc aaa     768
Glu Val Val Asp Leu Gln Trp Thr Tyr Pro Gly Glu Val Lys Gly Lys
                245                 250                 255 ggc atc aca atg ctg gaa gaa atc aaa gtc cca tcc atc aaa ttg gtg     816
Gly Ile Thr Met Leu Glu Glu Ile Lys Val Pro Ser Ile Lys Leu Val
            260                 265                 270 tac act ttg acg gtc ccc gag gcc acg gtg aaa gac agt gga gat tac     864
Tyr Thr Leu Thr Val Pro Glu Ala Thr Val Lys Asp Ser Gly Asp Tyr
        275                 280                 285 gaa tgt gct gcc cgc cag gct acc agg gag gtc aaa gaa atg aag aaa     912
Glu Cys Ala Ala Arg Gln Ala Thr Arg Glu Val Lys Glu Met Lys Lys
290                 295                 300 gtc act att tct gtc cat gag aaa ggt ttc att gaa atc aaa ccc acc     960
Val Thr Ile Ser Val His Glu Lys Gly Phe Ile Glu Ile Lys Pro Thr
305                 310                 315                 320 ttc agc cag ttg gaa gct gtc aac ctg cat gaa gtc aaa cat ttt gtt    1008
Phe Ser Gln Leu Glu Ala Val Asn Leu His Glu Val Lys His Phe Val
                325                 330                 335 gta gag gtg cgg gcc tac cca cct ccc agg ata tcc tgg ctg aaa aac    1056
Val Glu Val Arg Ala Tyr Pro Pro Pro Arg Ile Ser Trp Leu Lys Asn
            340                 345                 350 aat ctg act ctg att gaa aat ctc act gag atc acc act gat gtg gaa    1104
Asn Leu Thr Leu Ile Glu Asn Leu Thr Glu Ile Thr Thr Asp Val Glu
        355                 360                 365 aag att cag gaa ata agg tat cga agc aaa tta aag ctg atc cgt gct    1152
Lys Ile Gln Glu Ile Arg Tyr Arg Ser Lys Leu Lys Leu Ile Arg Ala
370                 375                 380 aag gaa gaa gac agt ggc cat tat act att gta gct caa aat gaa gat    1200
Lys Glu Glu Asp Ser Gly His Tyr Thr Ile Val Ala Gln Asn Glu Asp
385                 390                 395                 400 gct gtg aag agc tat act ttt gaa ctg tta act caa gtt cct tca tcc    1248
Ala Val Lys Ser Tyr Thr Phe Glu Leu Leu Thr Gln Val Pro Ser Ser
                405                 410                 415 att ctg gac ttg gtc gat gat cac cat ggc tca act ggg gga cag acg    1296
Ile Leu Asp Leu Val Asp Asp His His Gly Ser Thr Gly Gly Gln Thr
            420                 425                 430
```

|  |  |  |  |  |  |  |  |  |  |  |  |  |  |  |  |  |
|---|---|---|---|---|---|---|---|---|---|---|---|---|---|---|---|---|
| gtg | agg | tgc | aca | gct | gaa | ggc | acg | ccg | ctt | cct | gat | att | gag | tgg | atg | 1344 |
| Val | Arg | Cys | Thr | Ala | Glu | Gly | Thr | Pro | Leu | Pro | Asp | Ile | Glu | Trp | Met | |
| | 435 | | | | 440 | | | | | 445 | | | | | | |
| ata | tgc | aaa | gat | att | aag | aaa | tgt | aat | aat | gaa | act | tcc | tgg | act | att | 1392 |
| Ile | Cys | Lys | Asp | Ile | Lys | Lys | Cys | Asn | Asn | Glu | Thr | Ser | Trp | Thr | Ile | |
| 450 | | | | | 455 | | | | | 460 | | | | | | |
| ttg | gcc | aac | aat | gtc | tca | aac | atc | atc | acg | gag | atc | cac | tcc | cga | gac | 1440 |
| Leu | Ala | Asn | Asn | Val | Ser | Asn | Ile | Ile | Thr | Glu | Ile | His | Ser | Arg | Asp | |
| 465 | | | | 470 | | | | | 475 | | | | | 480 | | |
| agg | agt | acc | gtg | gag | ggc | cgt | gtg | act | ttc | gcc | aaa | gtg | gag | gag | acc | 1488 |
| Arg | Ser | Thr | Val | Glu | Gly | Arg | Val | Thr | Phe | Ala | Lys | Val | Glu | Glu | Thr | |
| | | | | 485 | | | | | 490 | | | | | 495 | | |
| atc | gcc | gtg | cga | tgc | ctg | gct | aag | aat | ctc | ctt | gga | gct | gag | aac | cga | 1536 |
| Ile | Ala | Val | Arg | Cys | Leu | Ala | Lys | Asn | Leu | Leu | Gly | Ala | Glu | Asn | Arg | |
| | | 500 | | | | | 505 | | | | | 510 | | | | |
| gag | ctg | aag | ctg | gtg | gct | ccc | acc | ctg | cgt | tct | gaa | ctc | acg | gtg | gct | 1584 |
| Glu | Leu | Lys | Leu | Val | Ala | Pro | Thr | Leu | Arg | Ser | Glu | Leu | Thr | Val | Ala | |
| | | 515 | | | | | 520 | | | | | 525 | | | | |
| gct | gca | gtc | ctg | gtg | ctg | ttg | gtg | att | gtg | atc | atc | tca | ctt | att | gtc | 1632 |
| Ala | Ala | Val | Leu | Val | Leu | Leu | Val | Ile | Val | Ile | Ile | Ser | Leu | Ile | Val | |
| | 530 | | | | | 535 | | | | | 540 | | | | | |
| ctg | gtt | gtc | att | tgg | aaa | cag | aaa | ccg | agg | tat | gaa | att | cgc | tgg | agg | 1680 |
| Leu | Val | Val | Ile | Trp | Lys | Gln | Lys | Pro | Arg | Tyr | Glu | Ile | Arg | Trp | Arg | |
| 545 | | | | 550 | | | | | 555 | | | | | 560 | | |
| gtc | att | gaa | tca | atc | agc | ccg | gat | gga | cat | gaa | tat | att | tat | gtg | gac | 1728 |
| Val | Ile | Glu | Ser | Ile | Ser | Pro | Asp | Gly | His | Glu | Tyr | Ile | Tyr | Val | Asp | |
| | | | 565 | | | | | 570 | | | | | 575 | | | |
| ccg | atg | cag | ctg | cct | tat | gac | tca | aga | tgg | aag | ttt | cca | aga | gat | gga | 1776 |
| Pro | Met | Gln | Leu | Pro | Tyr | Asp | Ser | Arg | Trp | Lys | Phe | Pro | Arg | Asp | Gly | |
| | | 580 | | | | | 585 | | | | | 590 | | | | |
| cta | gtg | ctt | ggt | cgg | gtc | ttg | ggg | tct | gga | gcg | ttt | ggg | aag | gtg | gtt | 1824 |
| Leu | Val | Leu | Gly | Arg | Val | Leu | Gly | Ser | Gly | Ala | Phe | Gly | Lys | Val | Val | |
| | 595 | | | | | 600 | | | | | 605 | | | | | |
| gaa | gga | aca | gcc | tat | gga | tta | agc | cgg | tcc | caa | cct | gtc | atg | aaa | gtt | 1872 |
| Glu | Gly | Thr | Ala | Tyr | Gly | Leu | Ser | Arg | Ser | Gln | Pro | Val | Met | Lys | Val | |
| 610 | | | | | 615 | | | | | 620 | | | | | | |
| gca | gtg | aag | atg | cta | aaa | ccc | acg | gcc | aga | tcc | agt | gaa | aaa | caa | gct | 1920 |
| Ala | Val | Lys | Met | Leu | Lys | Pro | Thr | Ala | Arg | Ser | Ser | Glu | Lys | Gln | Ala | |
| 625 | | | | 630 | | | | | 635 | | | | | 640 | | |
| ctc | atg | tct | gaa | ctg | aag | ata | atg | act | cac | ctg | ggg | cca | cat | ttg | aac | 1968 |
| Leu | Met | Ser | Glu | Leu | Lys | Ile | Met | Thr | His | Leu | Gly | Pro | His | Leu | Asn | |
| | | | 645 | | | | | 650 | | | | | 655 | | | |
| att | gta | aac | ttg | ctg | gga | gcc | tgc | acc | aag | tca | ggc | ccc | att | tac | atc | 2016 |
| Ile | Val | Asn | Leu | Leu | Gly | Ala | Cys | Thr | Lys | Ser | Gly | Pro | Ile | Tyr | Ile | |
| | | 660 | | | | | 665 | | | | | 670 | | | | |
| atc | aca | gag | tat | tgc | ttc | tat | gga | gat | ttg | gtc | aac | tat | ttg | cat | aag | 2064 |
| Ile | Thr | Glu | Tyr | Cys | Phe | Tyr | Gly | Asp | Leu | Val | Asn | Tyr | Leu | His | Lys | |
| | | 675 | | | | | 680 | | | | | 685 | | | | |
| aat | agg | gat | agc | ttc | ctg | agc | cac | cac | cca | gag | aag | cca | aag | aaa | gag | 2112 |
| Asn | Arg | Asp | Ser | Phe | Leu | Ser | His | His | Pro | Glu | Lys | Pro | Lys | Lys | Glu | |
| | 690 | | | | | 695 | | | | | 700 | | | | | |
| ctg | gat | atc | ttt | gga | ttg | aac | cct | gct | gat | gaa | agc | aca | cgg | agc | tat | 2160 |
| Leu | Asp | Ile | Phe | Gly | Leu | Asn | Pro | Ala | Asp | Glu | Ser | Thr | Arg | Ser | Tyr | |
| 705 | | | | 710 | | | | | 715 | | | | | 720 | | |
| gtt | att | tta | tct | ttt | gaa | aac | aat | ggt | gac | tac | atg | gac | atg | aag | cag | 2208 |
| Val | Ile | Leu | Ser | Phe | Glu | Asn | Asn | Gly | Asp | Tyr | Met | Asp | Met | Lys | Gln | |
| | | | 725 | | | | | 730 | | | | | 735 | | | |
| gct | gat | act | aca | cag | tat | gtc | ccc | atg | cta | gaa | agg | aaa | gag | gtt | tct | 2256 |
| Ala | Asp | Thr | Thr | Gln | Tyr | Val | Pro | Met | Leu | Glu | Arg | Lys | Glu | Val | Ser | |
| | | 740 | | | | | 745 | | | | | 750 | | | | |

```
aaa tat tcc gac atc cag aga tca ctc tat gat cgt cca gcc tca tat      2304
Lys Tyr Ser Asp Ile Gln Arg Ser Leu Tyr Asp Arg Pro Ala Ser Tyr
        755                 760                 765 aag aag aaa tct atg tta gac tca gaa gtc aaa aac ctc ctt tca gat      2352
Lys Lys Lys Ser Met Leu Asp Ser Glu Val Lys Asn Leu Leu Ser Asp
770                 775                 780 gat aac tca gaa ggc ctt act tta ttg gat ttg ttg agc ttc acc tat      2400
Asp Asn Ser Glu Gly Leu Thr Leu Leu Asp Leu Leu Ser Phe Thr Tyr
785                 790                 795                 800 caa gtt gcc cga gga atg gag ttt ttg gct tca aaa aat tgt gtc cac      2448
Gln Val Ala Arg Gly Met Glu Phe Leu Ala Ser Lys Asn Cys Val His
                805                 810                 815 cgt gat ctg gct gct cgc aac gtc ctc ctg gca caa gga aaa att gtg      2496
Arg Asp Leu Ala Ala Arg Asn Val Leu Leu Ala Gln Gly Lys Ile Val
            820                 825                 830 aag atc tgt gac ttt ggc ctg gcc aga gac atc atg cat gat tcg aac      2544
Lys Ile Cys Asp Phe Gly Leu Ala Arg Asp Ile Met His Asp Ser Asn
                835                 840                 845 tat gtg tcg aaa ggc agt acc ttt ctg ccc gtg aag tgg atg gct cct      2592
Tyr Val Ser Lys Gly Ser Thr Phe Leu Pro Val Lys Trp Met Ala Pro
850                 855                 860 gag agc atc ttt gac aac ctc tac acc aca ctg agt gat gtc tgg tct      2640
Glu Ser Ile Phe Asp Asn Leu Tyr Thr Thr Leu Ser Asp Val Trp Ser
865                 870                 875                 880 tat ggc att ctg ctc tgg gag atc ttt tcc ctt ggt ggc acc cct tac      2688
Tyr Gly Ile Leu Leu Trp Glu Ile Phe Ser Leu Gly Gly Thr Pro Tyr
                885                 890                 895 ccc ggc atg atg gtg gat tct act ttc tac aat aag atc aag agt ggg      2736
Pro Gly Met Met Val Asp Ser Thr Phe Tyr Asn Lys Ile Lys Ser Gly
                    900                 905                 910 tac cgg atg gcc aag cct gac cac gct acc agt gaa gtc tac gag atc      2784
Tyr Arg Met Ala Lys Pro Asp His Ala Thr Ser Glu Val Tyr Glu Ile
            915                 920                 925 atg gtg aaa tgc tgg aac agt gag ccg gag aag aga ccc tcc ttt tac      2832
Met Val Lys Cys Trp Asn Ser Glu Pro Glu Lys Arg Pro Ser Phe Tyr
930                 935                 940 cac ctg agt gag att gtg gag aat ctg ctg cct gga caa tat aaa aag      2880
His Leu Ser Glu Ile Val Glu Asn Leu Leu Pro Gly Gln Tyr Lys Lys
945                 950                 955                 960 agt tat gaa aaa att cac ctg gac ttc ctg aag agt gac cat cct gct      2928
Ser Tyr Glu Lys Ile His Leu Asp Phe Leu Lys Ser Asp His Pro Ala
                965                 970                 975 gtg gca cgc atg cgt gtg gac tca gac aat gca tac att ggt gtc acc      2976
Val Ala Arg Met Arg Val Asp Ser Asp Asn Ala Tyr Ile Gly Val Thr
                    980                 985                 990 tac aaa aac gag gaa gac aag ctg aag gac tgg gag ggt ggt ctg gat      3024
Tyr Lys Asn Glu Glu Asp Lys Leu Lys Asp Trp Glu Gly Gly Leu Asp
                995                 1000                1005 gag cag aga ctg agc gct gac agt ggc tac atc att cct ctg cct gac      3072
Glu Gln Arg Leu Ser Ala Asp Ser Gly Tyr Ile Ile Pro Leu Pro Asp
    1010                1015                1020 att gac cct gtc cct gag gag gag gac ctg ggc aag agg aac aga cac      3120
Ile Asp Pro Val Pro Glu Glu Glu Asp Leu Gly Lys Arg Asn Arg His
1025                1030                1035                1040 agc tcg cag acc tct gaa gag agt gcc att gag acg ggt tcc agc agt      3168
Ser Ser Gln Thr Ser Glu Glu Ser Ala Ile Glu Thr Gly Ser Ser Ser
                1045                1050                1055 tcc acc ttc atc aag aga gag gac gag acc att gaa gac atc gac atg      3216
Ser Thr Phe Ile Lys Arg Glu Asp Glu Thr Ile Glu Asp Ile Asp Met
```

-continued

```
                 1060               1065               1070
atg gac gac atc ggc ata gac tct tca gac ctg gtg gaa gac agc ttc    3264
Met Asp Asp Ile Gly Ile Asp Ser Ser Asp Leu Val Glu Asp Ser Phe
        1075               1080               1085 ctg taa                                                             3270
Leu
```

<210> SEQ ID NO 4
<211> LENGTH: 1089
<212> TYPE: PRT
<213> ORGANISM: Homo sapiens

<400> SEQUENCE: 4

```
Met Gly Thr Ser His Pro Ala Phe Leu Val Leu Gly Cys Leu Leu Thr
 1               5                  10                  15

Gly Leu Ser Leu Ile Leu Cys Gln Leu Ser Leu Pro Ser Ile Leu Pro
            20                  25                  30

Asn Glu Asn Glu Lys Val Val Gln Leu Asn Ser Ser Phe Ser Leu Arg
        35                  40                  45

Cys Phe Gly Glu Ser Glu Val Ser Trp Gln Tyr Pro Met Ser Glu Glu
    50                  55                  60

Glu Ser Ser Asp Val Glu Ile Arg Asn Glu Glu Asn Asn Ser Gly Leu
65                  70                  75                  80

Phe Val Thr Val Leu Glu Val Ser Ser Ala Ser Ala Ala His Thr Gly
                85                  90                  95

Leu Tyr Thr Cys Tyr Tyr Asn His Thr Gln Thr Glu Glu Asn Glu Leu
            100                 105                 110

Glu Gly Arg His Ile Tyr Ile Tyr Val Pro Asp Pro Asp Val Ala Phe
        115                 120                 125

Val Pro Leu Gly Met Thr Asp Tyr Leu Val Ile Val Glu Asp Asp Asp
    130                 135                 140

Ser Ala Ile Ile Pro Cys Arg Thr Thr Asp Pro Glu Thr Pro Val Thr
145                 150                 155                 160

Leu His Asn Ser Glu Gly Val Val Pro Ala Ser Tyr Asp Ser Arg Gln
                165                 170                 175

Gly Phe Asn Gly Thr Phe Thr Val Gly Pro Tyr Ile Cys Glu Ala Thr
            180                 185                 190

Val Lys Gly Lys Lys Phe Gln Thr Ile Pro Phe Asn Val Tyr Ala Leu
        195                 200                 205

Lys Ala Thr Ser Glu Leu Asp Leu Glu Met Glu Ala Leu Lys Thr Val
    210                 215                 220

Tyr Lys Ser Gly Glu Thr Ile Val Val Thr Cys Ala Val Phe Asn Asn
225                 230                 235                 240

Glu Val Val Asp Leu Gln Trp Thr Tyr Pro Gly Glu Val Lys Gly Lys
                245                 250                 255

Gly Ile Thr Met Leu Glu Glu Ile Lys Val Pro Ser Ile Lys Leu Val
            260                 265                 270

Tyr Thr Leu Thr Val Pro Glu Ala Thr Val Lys Asp Ser Gly Asp Tyr
        275                 280                 285

Glu Cys Ala Ala Arg Gln Ala Thr Arg Glu Val Lys Glu Met Lys Lys
    290                 295                 300

Val Thr Ile Ser Val His Glu Lys Gly Phe Ile Glu Ile Lys Pro Thr
305                 310                 315                 320

Phe Ser Gln Leu Glu Ala Val Asn Leu His Glu Val Lys His Phe Val
                325                 330                 335
```

```
Val Glu Val Arg Ala Tyr Pro Pro Arg Ile Ser Trp Leu Lys Asn
            340                 345                 350

Asn Leu Thr Leu Ile Glu Asn Leu Thr Glu Ile Thr Thr Asp Val Glu
            355                 360                 365

Lys Ile Gln Glu Ile Arg Tyr Arg Ser Lys Leu Lys Leu Ile Arg Ala
            370                 375                 380

Lys Glu Glu Asp Ser Gly His Tyr Thr Ile Val Ala Gln Asn Glu Asp
385                 390                 395                 400

Ala Val Lys Ser Tyr Thr Phe Glu Leu Leu Thr Gln Val Pro Ser Ser
                405                 410                 415

Ile Leu Asp Leu Val Asp Asp His His Gly Ser Thr Gly Gly Gln Thr
            420                 425                 430

Val Arg Cys Thr Ala Glu Gly Thr Pro Leu Pro Asp Ile Glu Trp Met
            435                 440                 445

Ile Cys Lys Asp Ile Lys Lys Cys Asn Asn Glu Thr Ser Trp Thr Ile
            450                 455                 460

Leu Ala Asn Asn Val Ser Asn Ile Ile Thr Glu Ile His Ser Arg Asp
465                 470                 475                 480

Arg Ser Thr Val Glu Gly Arg Val Thr Phe Ala Lys Val Glu Glu Thr
                485                 490                 495

Ile Ala Val Arg Cys Leu Ala Lys Asn Leu Leu Gly Ala Glu Asn Arg
            500                 505                 510

Glu Leu Lys Leu Val Ala Pro Thr Leu Arg Ser Glu Leu Thr Val Ala
            515                 520                 525

Ala Ala Val Leu Val Leu Leu Val Ile Val Ile Ile Ser Leu Ile Val
530                 535                 540

Leu Val Val Ile Trp Lys Gln Lys Pro Arg Tyr Glu Ile Arg Trp Arg
545                 550                 555                 560

Val Ile Glu Ser Ile Ser Pro Asp Gly His Glu Tyr Ile Tyr Val Asp
                565                 570                 575

Pro Met Gln Leu Pro Tyr Asp Ser Arg Trp Lys Phe Pro Arg Asp Gly
            580                 585                 590

Leu Val Leu Gly Arg Val Leu Gly Ser Gly Ala Phe Gly Lys Val Val
            595                 600                 605

Glu Gly Thr Ala Tyr Gly Leu Ser Arg Ser Gln Pro Val Met Lys Val
            610                 615                 620

Ala Val Lys Met Leu Lys Pro Thr Ala Arg Ser Ser Glu Lys Gln Ala
625                 630                 635                 640

Leu Met Ser Glu Leu Lys Ile Met Thr His Leu Gly Pro His Leu Asn
                645                 650                 655

Ile Val Asn Leu Leu Gly Ala Cys Thr Lys Ser Gly Pro Ile Tyr Ile
            660                 665                 670

Ile Thr Glu Tyr Cys Phe Tyr Gly Asp Leu Val Asn Tyr Leu His Lys
            675                 680                 685

Asn Arg Asp Ser Phe Leu Ser His His Pro Glu Lys Pro Lys Lys Glu
            690                 695                 700

Leu Asp Ile Phe Gly Leu Asn Pro Ala Asp Glu Ser Thr Arg Ser Tyr
705                 710                 715                 720

Val Ile Leu Ser Phe Glu Asn Asn Gly Asp Tyr Met Asp Met Lys Gln
                725                 730                 735

Ala Asp Thr Thr Gln Tyr Val Pro Met Leu Glu Arg Lys Glu Val Ser
            740                 745                 750
```

```
Lys Tyr Ser Asp Ile Gln Arg Ser Leu Tyr Asp Arg Pro Ala Ser Tyr
        755                 760                 765

Lys Lys Lys Ser Met Leu Asp Ser Glu Val Lys Asn Leu Leu Ser Asp
        770                 775                 780

Asp Asn Ser Glu Gly Leu Thr Leu Leu Asp Leu Leu Ser Phe Thr Tyr
785                 790                 795                 800

Gln Val Ala Arg Gly Met Glu Phe Leu Ala Ser Lys Asn Cys Val His
                805                 810                 815

Arg Asp Leu Ala Ala Arg Asn Val Leu Leu Ala Gln Gly Lys Ile Val
                820                 825                 830

Lys Ile Cys Asp Phe Gly Leu Ala Arg Asp Ile Met His Asp Ser Asn
        835                 840                 845

Tyr Val Ser Lys Gly Ser Thr Phe Leu Pro Val Lys Trp Met Ala Pro
        850                 855                 860

Glu Ser Ile Phe Asp Asn Leu Tyr Thr Thr Leu Ser Asp Val Trp Ser
865                 870                 875                 880

Tyr Gly Ile Leu Leu Trp Glu Ile Phe Ser Leu Gly Gly Thr Pro Tyr
                885                 890                 895

Pro Gly Met Met Val Asp Ser Thr Phe Tyr Asn Lys Ile Lys Ser Gly
                900                 905                 910

Tyr Arg Met Ala Lys Pro Asp His Ala Thr Ser Glu Val Tyr Glu Ile
        915                 920                 925

Met Val Lys Cys Trp Asn Ser Glu Pro Glu Lys Arg Pro Ser Phe Tyr
        930                 935                 940

His Leu Ser Glu Ile Val Glu Asn Leu Leu Pro Gly Gln Tyr Lys Lys
945                 950                 955                 960

Ser Tyr Glu Lys Ile His Leu Asp Phe Leu Lys Ser Asp His Pro Ala
                965                 970                 975

Val Ala Arg Met Arg Val Asp Ser Asp Asn Ala Tyr Ile Gly Val Thr
                980                 985                 990

Tyr Lys Asn Glu Glu Asp Lys Leu Lys Asp Trp Glu Gly Gly Leu Asp
        995                 1000                1005

Glu Gln Arg Leu Ser Ala Asp Ser Gly Tyr Ile Ile Pro Leu Pro Asp
    1010                1015                1020

Ile Asp Pro Val Pro Glu Glu Glu Asp Leu Gly Lys Arg Asn Arg His
1025                1030                1035                1040

Ser Ser Gln Thr Ser Glu Glu Ser Ala Ile Glu Thr Gly Ser Ser Ser
                1045                1050                1055

Ser Thr Phe Ile Lys Arg Glu Asp Glu Thr Ile Glu Asp Ile Asp Met
                1060                1065                1070

Met Asp Asp Ile Gly Ile Asp Ser Ser Asp Leu Val Glu Asp Ser Phe
        1075                1080                1085

Leu

<210> SEQ ID NO 5
<211> LENGTH: 3270
<212> TYPE: DNA
<213> ORGANISM: Homo sapiens
<220> FEATURE:
<221> NAME/KEY: CDS
<222> LOCATION: (1)..(3267)

<400> SEQUENCE: 5 atg ggg act tcc cat ccg gcg ttc ctg gtc tta ggc tgt ctt ctc aca      48
Met Gly Thr Ser His Pro Ala Phe Leu Val Leu Gly Cys Leu Leu Thr
  1               5                  10                  15
```

```
ggg ctg agc cta atc ctc tgc cag ctt tca tta ccc tct atc ctt cca       96
Gly Leu Ser Leu Ile Leu Cys Gln Leu Ser Leu Pro Ser Ile Leu Pro
             20                  25                  30 aat gaa aat gaa aag gtt gtg cag ctg aat tca tcc ttt tct ctg aga      144
Asn Glu Asn Glu Lys Val Val Gln Leu Asn Ser Ser Phe Ser Leu Arg
             35                  40                  45 tgc ttt ggg gag agt gaa gtg agc tgg cag tac ccc atg tct gaa gaa      192
Cys Phe Gly Glu Ser Glu Val Ser Trp Gln Tyr Pro Met Ser Glu Glu
         50                  55                  60 gag agc tcc gat gtg gaa atc aga aat gaa gaa aac aac agc ggc ctt      240
Glu Ser Ser Asp Val Glu Ile Arg Asn Glu Glu Asn Asn Ser Gly Leu
 65                  70                  75                  80 ttt gtg acg gtc ttg gaa gtg agc agt gcc tcg gcg gcc cac aca ggg      288
Phe Val Thr Val Leu Glu Val Ser Ser Ala Ser Ala Ala His Thr Gly
                 85                  90                  95 ttg tac act tgc tat tac aac cac act cag aca gaa gag aat gag ctt      336
Leu Tyr Thr Cys Tyr Tyr Asn His Thr Gln Thr Glu Glu Asn Glu Leu
                100                 105                 110 gaa ggc agg cac att tac atc tat gtg cca gac cca gat gta gcc ttt      384
Glu Gly Arg His Ile Tyr Ile Tyr Val Pro Asp Pro Asp Val Ala Phe
            115                 120                 125 gta cct cta gga atg acg gat tat tta gtc atc gtg gag gat gat gat      432
Val Pro Leu Gly Met Thr Asp Tyr Leu Val Ile Val Glu Asp Asp Asp
        130                 135                 140 tct gcc att ata cct tgt cgc aca act gat ccc gag act cct gta acc      480
Ser Ala Ile Ile Pro Cys Arg Thr Thr Asp Pro Glu Thr Pro Val Thr
145                 150                 155                 160 tta cac aac agt gag ggg gtg gta cct gcc tcc tac gac agc aga cag      528
Leu His Asn Ser Glu Gly Val Val Pro Ala Ser Tyr Asp Ser Arg Gln
                165                 170                 175 ggc ttt aat ggg acc ttc act gta ggg ccc tat atc tgt gag gcc acc      576
Gly Phe Asn Gly Thr Phe Thr Val Gly Pro Tyr Ile Cys Glu Ala Thr
            180                 185                 190 gtc aaa gga aag aag ttc cag acc atc cca ttt aat gtt tat gct tta      624
Val Lys Gly Lys Lys Phe Gln Thr Ile Pro Phe Asn Val Tyr Ala Leu
        195                 200                 205 aaa gca aca tca gag ctg gat cta gaa atg gaa gct ctt aaa acc gtg      672
Lys Ala Thr Ser Glu Leu Asp Leu Glu Met Glu Ala Leu Lys Thr Val
210                 215                 220 tat aag tca ggg gaa acg att gtg gtc acc tgt gct gtt ttt aac aat      720
Tyr Lys Ser Gly Glu Thr Ile Val Val Thr Cys Ala Val Phe Asn Asn
225                 230                 235                 240 gag gtg gtt gac ctt caa tgg act tac cct gga gaa gtg aaa ggc aaa      768
Glu Val Val Asp Leu Gln Trp Thr Tyr Pro Gly Glu Val Lys Gly Lys
                245                 250                 255 ggc atc aca atg ctg gaa gaa atc aaa gtc cca tcc atc aaa ttg gtg      816
Gly Ile Thr Met Leu Glu Glu Ile Lys Val Pro Ser Ile Lys Leu Val
            260                 265                 270 tac act ttg acg gtc ccc gag gcc acg gtg aaa gac agt gga gat tac      864
Tyr Thr Leu Thr Val Pro Glu Ala Thr Val Lys Asp Ser Gly Asp Tyr
        275                 280                 285 gaa tgt gct gcc cgc cag gct acc agg gag gtc aaa gaa atg aag aaa      912
Glu Cys Ala Ala Arg Gln Ala Thr Arg Glu Val Lys Glu Met Lys Lys
    290                 295                 300 gtc act att tct gtc cat gag aaa ggt ttc att gaa atc aaa ccc acc      960
Val Thr Ile Ser Val His Glu Lys Gly Phe Ile Glu Ile Lys Pro Thr
305                 310                 315                 320 ttc agc cag ttg gaa gct gtc aac ctg cat gaa gtc aaa cat ttt gtt     1008
Phe Ser Gln Leu Glu Ala Val Asn Leu His Glu Val Lys His Phe Val
```

-continued

|     |     |     | 325 |     |     |     | 330 |     |     |     | 335 |     |     |     |      |
|-----|-----|-----|-----|-----|-----|-----|-----|-----|-----|-----|-----|-----|-----|-----|------|
| gta | gag | gtg | cgg | gcc | tac | cca | cct | ccc | agg | ata | tcc | tgg | ctg | aaa | aac  | 1056 |
| Val | Glu | Val | Arg | Ala | Tyr | Pro | Pro | Pro | Arg | Ile | Ser | Trp | Leu | Lys | Asn  |
|     |     |     | 340 |     |     |     | 345 |     |     |     | 350 |     |     |     |      | aat ctg act ctg att gaa aat ctc act gag atc acc act gat gtg gaa    1104
Asn Leu Thr Leu Ile Glu Asn Leu Thr Glu Ile Thr Thr Asp Val Glu
            355                 360                 365 aag att cag gaa ata agg tat cga agc aaa tta aag ctg atc cgt gct    1152
Lys Ile Gln Glu Ile Arg Tyr Arg Ser Lys Leu Lys Leu Ile Arg Ala
    370                 375                 380 aag gaa gaa gac agt ggc cat tat act att gta gct caa aat gaa gat    1200
Lys Glu Glu Asp Ser Gly His Tyr Thr Ile Val Ala Gln Asn Glu Asp
385                 390                 395                 400 gct gtg aag agc tat act ttt gaa ctg tta act caa gtt cct tca tcc    1248
Ala Val Lys Ser Tyr Thr Phe Glu Leu Leu Thr Gln Val Pro Ser Ser
            405                 410                 415 att ctg gac ttg gtc gat gat cac cat ggc tca act ggg gga cag acg    1296
Ile Leu Asp Leu Val Asp Asp His His Gly Ser Thr Gly Gly Gln Thr
            420                 425                 430 gtg agg tgc aca gct gaa ggc acg ccg ctt cct gat att gag tgg atg    1344
Val Arg Cys Thr Ala Glu Gly Thr Pro Leu Pro Asp Ile Glu Trp Met
        435                 440                 445 ata tgc aaa gat att aag aaa tgt aat aat gaa act tcc tgg act att    1392
Ile Cys Lys Asp Ile Lys Lys Cys Asn Asn Glu Thr Ser Trp Thr Ile
    450                 455                 460 ttg gcc aac aat gtc tca aac atc atc acg gag atc cac tcc cga gac    1440
Leu Ala Asn Asn Val Ser Asn Ile Ile Thr Glu Ile His Ser Arg Asp
465                 470                 475                 480 agg agt acc gtg gag ggc cgt gtg act ttc gcc aaa gtg gag gag acc    1488
Arg Ser Thr Val Glu Gly Arg Val Thr Phe Ala Lys Val Glu Glu Thr
            485                 490                 495 atc gcc gtg cga tgc ctg gct aag aat ctc ctt gga gct gag aac cga    1536
Ile Ala Val Arg Cys Leu Ala Lys Asn Leu Leu Gly Ala Glu Asn Arg
            500                 505                 510 gag ctg aag ctg gtg gct ccc acc ctg cgt tct gaa ctc acg gtg gct    1584
Glu Leu Lys Leu Val Ala Pro Thr Leu Arg Ser Glu Leu Thr Val Ala
        515                 520                 525 gct gca gtc ctg gtg ctg ttg gtg att gtg atc atc tca ctt att gtc    1632
Ala Ala Val Leu Val Leu Leu Val Ile Val Ile Ile Ser Leu Ile Val
    530                 535                 540 ctg gtt gtc att tgg aaa cag aaa ccg agg tat gaa att cgc tgg agg    1680
Leu Val Val Ile Trp Lys Gln Lys Pro Arg Tyr Glu Ile Arg Trp Arg
545                 550                 555                 560 gtc att gaa tca atc agc ccg gat gga cat gaa tat att tat gtg gac    1728
Val Ile Glu Ser Ile Ser Pro Asp Gly His Glu Tyr Ile Tyr Val Asp
            565                 570                 575 ccg atg cag ctg cct tat gac tca aga tgg gag ttt cca aga gat gga    1776
Pro Met Gln Leu Pro Tyr Asp Ser Arg Trp Glu Phe Pro Arg Asp Gly
            580                 585                 590 cta gtg ctt ggt cgg gtc ttg ggg tct gga gcg ttt ggg aag gtg gtt    1824
Leu Val Leu Gly Arg Val Leu Gly Ser Gly Ala Phe Gly Lys Val Val
        595                 600                 605 gaa gga aca gcc tat gga tta agc cgg tcc caa cct gtc atg aaa gtt    1872
Glu Gly Thr Ala Tyr Gly Leu Ser Arg Ser Gln Pro Val Met Lys Val
    610                 615                 620 gca gtg aag atg cta aaa ccc acg gcc aga tcc agt gaa aaa caa gct    1920
Ala Val Lys Met Leu Lys Pro Thr Ala Arg Ser Ser Glu Lys Gln Ala
625                 630                 635                 640 ctc atg tct gaa ctg aag ata atg act cac ctg ggg cca cat ttg aac    1968

-continued

```
Leu Met Ser Glu Leu Lys Ile Met Thr His Leu Gly Pro His Leu Asn
                645                 650                 655 att gta aac ttg ctg gga gcc tgc atg aag tca ggc ccc att tac atc      2016
Ile Val Asn Leu Leu Gly Ala Cys Met Lys Ser Gly Pro Ile Tyr Ile
            660                 665                 670 atc aca gag tat tgc ttc tat gga gat ttg gtc aac tat ttg cat aag      2064
Ile Thr Glu Tyr Cys Phe Tyr Gly Asp Leu Val Asn Tyr Leu His Lys
        675                 680                 685 aat agg gat agc ttc ctg agc cac cac cca gag aag cca aag aaa gag      2112
Asn Arg Asp Ser Phe Leu Ser His His Pro Glu Lys Pro Lys Lys Glu
    690                 695                 700 ctg gat atc ttt gga ttg aac cct gct gat gaa agc aca cgg agc tat      2160
Leu Asp Ile Phe Gly Leu Asn Pro Ala Asp Glu Ser Thr Arg Ser Tyr
705                 710                 715                 720 gtt att tta tct ttt gaa aac aat ggt gac tac atg gac atg aag cag      2208
Val Ile Leu Ser Phe Glu Asn Asn Gly Asp Tyr Met Asp Met Lys Gln
                725                 730                 735 gct gat act aca cag tat gtc ccc atg cta gaa agg aaa gag gtt tct      2256
Ala Asp Thr Thr Gln Tyr Val Pro Met Leu Glu Arg Lys Glu Val Ser
            740                 745                 750 aaa tat tcc gac atc cag aga tca ctc tat gat cgt cca gcc tca tat      2304
Lys Tyr Ser Asp Ile Gln Arg Ser Leu Tyr Asp Arg Pro Ala Ser Tyr
        755                 760                 765 aag aag aaa tct atg tta gac tca gaa gtc aaa aac ctc ctt tca gat      2352
Lys Lys Lys Ser Met Leu Asp Ser Glu Val Lys Asn Leu Leu Ser Asp
    770                 775                 780 gat aac tca gaa ggc ctt act tta ttg gat ttg ttg agc ttc acc tat      2400
Asp Asn Ser Glu Gly Leu Thr Leu Leu Asp Leu Leu Ser Phe Thr Tyr
785                 790                 795                 800 caa gtt gcc cga gga atg gag ttt ttg gct tca aaa aat tgt gtc cac      2448
Gln Val Ala Arg Gly Met Glu Phe Leu Ala Ser Lys Asn Cys Val His
                805                 810                 815 cgt gat ctg gct gct cgc aac gtc ctc ctg gca caa gga aaa att gtg      2496
Arg Asp Leu Ala Ala Arg Asn Val Leu Leu Ala Gln Gly Lys Ile Val
            820                 825                 830 aag atc tgt gac ttt ggc ctg gcc aga gac atc atg cat gat tcg aac      2544
Lys Ile Cys Asp Phe Gly Leu Ala Arg Asp Ile Met His Asp Ser Asn
        835                 840                 845 tat gtg tcg aaa ggc agt acc ttt ctg ccc gtg aag tgg atg gct cct      2592
Tyr Val Ser Lys Gly Ser Thr Phe Leu Pro Val Lys Trp Met Ala Pro
    850                 855                 860 gag agc atc ttt gac aac ctc tac acc aca ctg agt gat gtc tgg tct      2640
Glu Ser Ile Phe Asp Asn Leu Tyr Thr Thr Leu Ser Asp Val Trp Ser
865                 870                 875                 880 tat ggc att ctg ctc tgg gag atc ttt tcc ctt ggt ggc acc cct tac      2688
Tyr Gly Ile Leu Leu Trp Glu Ile Phe Ser Leu Gly Gly Thr Pro Tyr
                885                 890                 895 ccc ggc atg atg gtg gat tct act ttc tac aat aag atc aag agt ggg      2736
Pro Gly Met Met Val Asp Ser Thr Phe Tyr Asn Lys Ile Lys Ser Gly
            900                 905                 910 tac cgg atg gcc aag cct gac cac gct acc agt gaa gtc tac gag atc      2784
Tyr Arg Met Ala Lys Pro Asp His Ala Thr Ser Glu Val Tyr Glu Ile
        915                 920                 925 atg gtg aaa tgc tgg aac agt gag ccg gag aag aga ccc tcc ttt tac      2832
Met Val Lys Cys Trp Asn Ser Glu Pro Glu Lys Arg Pro Ser Phe Tyr
    930                 935                 940 cac ctg agt gag att gtg gag aat ctg ctg cct gga caa tat aaa aag      2880
His Leu Ser Glu Ile Val Glu Asn Leu Leu Pro Gly Gln Tyr Lys Lys
945                 950                 955                 960
```

-continued

| | |
|---|---|
| agt tat gaa aaa att cac ctg gac ttc ctg aag agt gac cat cct gct<br>Ser Tyr Glu Lys Ile His Leu Asp Phe Leu Lys Ser Asp His Pro Ala<br>                  965                      970                  975 | 2928 |
| gtg gca cgc atg cgt gtg gac tca gac aat gca tac att ggt gtc acc<br>Val Ala Arg Met Arg Val Asp Ser Asp Asn Ala Tyr Ile Gly Val Thr<br>                  980                      985                  990 | 2976 |
| tac aaa aac gag gaa gac aag ctg aag gac tgg gag ggt ggt ctg gat<br>Tyr Lys Asn Glu Glu Asp Lys Leu Lys Asp Trp Glu Gly Gly Leu Asp<br>                  995                      1000              1005 | 3024 |
| gag cag aga ctg agc gct gac agt ggc tac atc att cct ctg cct gac<br>Glu Gln Arg Leu Ser Ala Asp Ser Gly Tyr Ile Ile Pro Leu Pro Asp<br>    1010                      1015                      1020 | 3072 |
| att gac cct gtc cct gag gag gag gac ctg ggc aag agg aac aga cac<br>Ile Asp Pro Val Pro Glu Glu Glu Asp Leu Gly Lys Arg Asn Arg His<br>1025                      1030                      1035                      1040 | 3120 |
| agc tcg cag acc tct gaa gag agt gcc att gag acg ggt tcc agc agt<br>Ser Ser Gln Thr Ser Glu Glu Ser Ala Ile Glu Thr Gly Ser Ser Ser<br>                  1045                      1050                      1055 | 3168 |
| tcc acc ttc atc aag aga gag gac gag acc att gaa gac atc gac atg<br>Ser Thr Phe Ile Lys Arg Glu Asp Glu Thr Ile Glu Asp Ile Asp Met<br>    1060                      1065                      1070 | 3216 |
| atg gac gac atc ggc ata gac tct tca gac ctg gtg gaa gac agc ttc<br>Met Asp Asp Ile Gly Ile Asp Ser Ser Asp Leu Val Glu Asp Ser Phe<br>            1075                      1080                      1085 | 3264 |
| ctg taa<br>Leu | 3270 |

<210> SEQ ID NO 6
<211> LENGTH: 1089
<212> TYPE: PRT
<213> ORGANISM: Homo sapiens

<400> SEQUENCE: 6

Met Gly Thr Ser His Pro Ala Phe Leu Val Leu Gly Cys Leu Leu Thr
 1               5                  10                  15

Gly Leu Ser Leu Ile Leu Cys Gln Leu Ser Leu Pro Ser Ile Leu Pro
            20                  25                  30

Asn Glu Asn Glu Lys Val Val Gln Leu Asn Ser Ser Phe Ser Leu Arg
        35                  40                  45

Cys Phe Gly Glu Ser Glu Val Ser Trp Gln Tyr Pro Met Ser Glu Glu
    50                  55                  60

Glu Ser Ser Asp Val Glu Ile Arg Asn Glu Glu Asn Ser Gly Leu
65                  70                  75                  80

Phe Val Thr Val Leu Glu Val Ser Ser Ala Ser Ala Ala His Thr Gly
                85                  90                  95

Leu Tyr Thr Cys Tyr Tyr Asn His Thr Gln Thr Glu Glu Asn Glu Leu
            100                 105                 110

Glu Gly Arg His Ile Tyr Ile Tyr Val Pro Asp Pro Asp Val Ala Phe
        115                 120                 125

Val Pro Leu Gly Met Thr Asp Tyr Leu Val Ile Val Glu Asp Asp Asp
    130                 135                 140

Ser Ala Ile Ile Pro Cys Arg Thr Thr Asp Pro Glu Thr Pro Val Thr
145                 150                 155                 160

Leu His Asn Ser Glu Gly Val Val Pro Ala Ser Tyr Asp Ser Arg Gln
                165                 170                 175

Gly Phe Asn Gly Thr Phe Thr Val Gly Pro Tyr Ile Cys Glu Ala Thr
            180                 185                 190

```
                    -continued

Val Lys Gly Lys Lys Phe Gln Thr Ile Pro Phe Asn Val Tyr Ala Leu
            195                 200                 205

Lys Ala Thr Ser Glu Leu Asp Leu Glu Met Glu Ala Leu Lys Thr Val
210                 215                 220

Tyr Lys Ser Gly Glu Thr Ile Val Val Thr Cys Ala Val Phe Asn Asn
225                 230                 235                 240

Glu Val Val Asp Leu Gln Trp Thr Tyr Pro Gly Glu Val Lys Gly Lys
            245                 250                 255

Gly Ile Thr Met Leu Glu Glu Ile Lys Val Pro Ser Ile Lys Leu Val
            260                 265                 270

Tyr Thr Leu Thr Val Pro Glu Ala Thr Val Lys Asp Ser Gly Asp Tyr
            275                 280                 285

Glu Cys Ala Ala Arg Gln Ala Thr Arg Glu Val Lys Glu Met Lys Lys
            290                 295                 300

Val Thr Ile Ser Val His Glu Lys Gly Phe Ile Glu Ile Lys Pro Thr
305                 310                 315                 320

Phe Ser Gln Leu Glu Ala Val Asn Leu His Glu Val Lys His Phe Val
            325                 330                 335

Val Glu Val Arg Ala Tyr Pro Pro Arg Ile Ser Trp Leu Lys Asn
            340                 345                 350

Asn Leu Thr Leu Ile Glu Asn Leu Thr Glu Ile Thr Thr Asp Val Glu
            355                 360                 365

Lys Ile Gln Glu Ile Arg Tyr Arg Ser Lys Leu Lys Leu Ile Arg Ala
370                 375                 380

Lys Glu Glu Asp Ser Gly His Tyr Thr Ile Val Ala Gln Asn Glu Asp
385                 390                 395                 400

Ala Val Lys Ser Tyr Thr Phe Glu Leu Leu Thr Gln Val Pro Ser Ser
            405                 410                 415

Ile Leu Asp Leu Val Asp Asp His His Gly Ser Thr Gly Gly Gln Thr
            420                 425                 430

Val Arg Cys Thr Ala Glu Gly Thr Pro Leu Pro Asp Ile Glu Trp Met
            435                 440                 445

Ile Cys Lys Asp Ile Lys Lys Cys Asn Asn Glu Thr Ser Trp Thr Ile
450                 455                 460

Leu Ala Asn Asn Val Ser Asn Ile Ile Thr Glu Ile His Ser Arg Asp
465                 470                 475                 480

Arg Ser Thr Val Glu Gly Arg Val Thr Phe Ala Lys Val Glu Glu Thr
            485                 490                 495

Ile Ala Val Arg Cys Leu Ala Lys Asn Leu Leu Gly Ala Glu Asn Arg
            500                 505                 510

Glu Leu Lys Leu Val Ala Pro Thr Leu Arg Ser Glu Leu Thr Val Ala
            515                 520                 525

Ala Ala Val Leu Val Leu Leu Val Ile Val Ile Ile Ser Leu Ile Val
530                 535                 540

Leu Val Val Ile Trp Lys Gln Lys Pro Arg Tyr Glu Ile Arg Trp Arg
545                 550                 555                 560

Val Ile Glu Ser Ile Ser Pro Asp Gly His Glu Tyr Ile Tyr Val Asp
            565                 570                 575

Pro Met Gln Leu Pro Tyr Asp Ser Arg Trp Glu Phe Pro Arg Asp Gly
            580                 585                 590

Leu Val Leu Gly Arg Val Leu Gly Ser Gly Ala Phe Gly Lys Val Val
            595                 600                 605

Glu Gly Thr Ala Tyr Gly Leu Ser Arg Ser Gln Pro Val Met Lys Val
```

-continued

```
            610                 615                 620
Ala Val Lys Met Leu Lys Pro Thr Ala Arg Ser Ser Glu Lys Gln Ala
625                 630                 635                 640
Leu Met Ser Glu Leu Lys Ile Met Thr His Leu Gly Pro His Leu Asn
                    645                 650                 655
Ile Val Asn Leu Leu Gly Ala Cys Met Lys Ser Gly Pro Ile Tyr Ile
                660                 665                 670
Ile Thr Glu Tyr Cys Phe Tyr Gly Asp Leu Val Asn Tyr Leu His Lys
                675                 680                 685
Asn Arg Asp Ser Phe Leu Ser His His Pro Glu Lys Pro Lys Lys Glu
            690                 695                 700
Leu Asp Ile Phe Gly Leu Asn Pro Ala Asp Glu Ser Thr Arg Ser Tyr
705                 710                 715                 720
Val Ile Leu Ser Phe Glu Asn Asn Gly Asp Tyr Met Asp Met Lys Gln
                    725                 730                 735
Ala Asp Thr Thr Gln Tyr Val Pro Met Leu Glu Arg Lys Glu Val Ser
                740                 745                 750
Lys Tyr Ser Asp Ile Gln Arg Ser Leu Tyr Asp Arg Pro Ala Ser Tyr
                755                 760                 765
Lys Lys Lys Ser Met Leu Asp Ser Glu Val Lys Asn Leu Leu Ser Asp
            770                 775                 780
Asp Asn Ser Glu Gly Leu Thr Leu Leu Asp Leu Leu Ser Phe Thr Tyr
785                 790                 795                 800
Gln Val Ala Arg Gly Met Glu Phe Leu Ala Ser Lys Asn Cys Val His
                    805                 810                 815
Arg Asp Leu Ala Ala Arg Asn Val Leu Leu Ala Gln Gly Lys Ile Val
                820                 825                 830
Lys Ile Cys Asp Phe Gly Leu Ala Arg Asp Ile Met His Asp Ser Asn
            835                 840                 845
Tyr Val Ser Lys Gly Ser Thr Phe Leu Pro Val Lys Trp Met Ala Pro
            850                 855                 860
Glu Ser Ile Phe Asp Asn Leu Tyr Thr Thr Leu Ser Asp Val Trp Ser
865                 870                 875                 880
Tyr Gly Ile Leu Leu Trp Glu Ile Phe Ser Leu Gly Gly Thr Pro Tyr
                    885                 890                 895
Pro Gly Met Met Val Asp Ser Thr Phe Tyr Asn Lys Ile Lys Ser Gly
                900                 905                 910
Tyr Arg Met Ala Lys Pro Asp His Ala Thr Ser Glu Val Tyr Glu Ile
                915                 920                 925
Met Val Lys Cys Trp Asn Ser Glu Pro Glu Lys Arg Pro Ser Phe Tyr
930                 935                 940
His Leu Ser Glu Ile Val Glu Asn Leu Leu Pro Gly Gln Tyr Lys Lys
945                 950                 955                 960
Ser Tyr Glu Lys Ile His Leu Asp Phe Leu Lys Ser Asp His Pro Ala
                965                 970                 975
Val Ala Arg Met Arg Val Asp Ser Asp Asn Ala Tyr Ile Gly Val Thr
                980                 985                 990
Tyr Lys Asn Glu Glu Asp Lys Leu Lys Asp Trp Glu Gly Gly Leu Asp
            995                 1000                1005
Glu Gln Arg Leu Ser Ala Asp Ser Gly Tyr Ile Ile Pro Leu Pro Asp
        1010                1015                1020
Ile Asp Pro Val Pro Glu Glu Asp Leu Gly Lys Arg Asn Arg His
1025                1030                1035                1040
```

US 6,667,173 B2

101                                                                                                                                                                                  102

-continued

```
Ser Ser Gln Thr Ser Glu Glu Ser Ala Ile Glu Thr Gly Ser Ser Ser
            1045                1050                1055

Ser Thr Phe Ile Lys Arg Glu Asp Thr Ile Glu Asp Ile Asp Met
            1060                1065                1070

Met Asp Asp Ile Gly Ile Asp Ser Ser Asp Leu Val Glu Asp Ser Phe
        1075                1080                1085

Leu

<210> SEQ ID NO 7
<211> LENGTH: 3270
<212> TYPE: DNA
<213> ORGANISM: Homo sapiens
<220> FEATURE:
<221> NAME/KEY: CDS
<222> LOCATION: (1)..(3267)

<400> SEQUENCE: 7 atg ggg act tcc cat ccg gcg ttc ctg gtc tta ggc tgt ctt ctc aca      48
Met Gly Thr Ser His Pro Ala Phe Leu Val Leu Gly Cys Leu Leu Thr
 1               5                  10                  15 ggg ctg agc cta atc ctc tgc cag ctt tca tta ccc tct atc ctt cca      96
Gly Leu Ser Leu Ile Leu Cys Gln Leu Ser Leu Pro Ser Ile Leu Pro
            20                  25                  30 aat gaa aat gaa aag gtt gtg cag ctg aat tca tcc ttt tct ctg aga     144
Asn Glu Asn Glu Lys Val Val Gln Leu Asn Ser Ser Phe Ser Leu Arg
        35                  40                  45 tgc ttt ggg gag agt gaa gtg agc tgg cag tac ccc atg tct gaa gaa     192
Cys Phe Gly Glu Ser Glu Val Ser Trp Gln Tyr Pro Met Ser Glu Glu
    50                  55                  60 gag agc tcc gat gtg gaa atc aga aat gaa gaa aac aac agc ggc ctt     240
Glu Ser Ser Asp Val Glu Ile Arg Asn Glu Glu Asn Asn Ser Gly Leu
65                  70                  75                  80 ttt gtg acg gtc ttg gaa gtg agc agt gcc tcg gcg gcc cac aca ggg     288
Phe Val Thr Val Leu Glu Val Ser Ser Ala Ser Ala Ala His Thr Gly
                85                  90                  95 ttg tac act tgc tat tac aac cac act cag aca gaa gag aat gag ctt     336
Leu Tyr Thr Cys Tyr Tyr Asn His Thr Gln Thr Glu Glu Asn Glu Leu
            100                 105                 110 gaa ggc agg cac att tac atc tat gtg cca gac cca gat gta gcc ttt     384
Glu Gly Arg His Ile Tyr Ile Tyr Val Pro Asp Pro Asp Val Ala Phe
        115                 120                 125 gta cct cta gga atg acg gat tat tta gtc atc gtg gag gat gat gat     432
Val Pro Leu Gly Met Thr Asp Tyr Leu Val Ile Val Glu Asp Asp Asp
    130                 135                 140 tct gcc att ata cct tgt cgc aca act gat ccc gag act cct gta acc     480
Ser Ala Ile Ile Pro Cys Arg Thr Thr Asp Pro Glu Thr Pro Val Thr
145                 150                 155                 160 tta cac aac agt gag ggg gtg gta cct gcc tcc tac gac agc aga cag     528
Leu His Asn Ser Glu Gly Val Val Pro Ala Ser Tyr Asp Ser Arg Gln
                165                 170                 175 ggc ttt aat ggg acc ttc act gta ggg ccc tat atc tgt gag gcc acc     576
Gly Phe Asn Gly Thr Phe Thr Val Gly Pro Tyr Ile Cys Glu Ala Thr
            180                 185                 190 gtc aaa gga aag aag ttc cag acc atc cca ttt aat gtt tat gct tta     624
Val Lys Gly Lys Lys Phe Gln Thr Ile Pro Phe Asn Val Tyr Ala Leu
        195                 200                 205 aaa gca aca tca gag ctg gat cta gaa atg gaa gct ctt aaa acc gtg     672
Lys Ala Thr Ser Glu Leu Asp Leu Glu Met Glu Ala Leu Lys Thr Val
    210                 215                 220
```

```
tat aag tca ggg gaa acg att gtg gtc acc tgt gct gtt ttt aac aat      720
Tyr Lys Ser Gly Glu Thr Ile Val Val Thr Cys Ala Val Phe Asn Asn
225                 230                 235                 240 gag gtg gtt gac ctt caa tgg act tac cct gga gaa gtg aaa ggc aaa      768
Glu Val Val Asp Leu Gln Trp Thr Tyr Pro Gly Glu Val Lys Gly Lys
            245                 250                 255 ggc atc aca atg ctg gaa gaa atc aaa gtc cca tcc atc aaa ttg gtg      816
Gly Ile Thr Met Leu Glu Glu Ile Lys Val Pro Ser Ile Lys Leu Val
        260                 265                 270 tac act ttg acg gtc ccc gag gcc acg gtg aaa gac agt gga gat tac      864
Tyr Thr Leu Thr Val Pro Glu Ala Thr Val Lys Asp Ser Gly Asp Tyr
    275                 280                 285 gaa tgt gct gcc cgc cag gct acc agg gag gtc aaa gaa atg aag aaa      912
Glu Cys Ala Ala Arg Gln Ala Thr Arg Glu Val Lys Glu Met Lys Lys
290                 295                 300 gtc act att tct gtc cat gag aaa ggt ttc att gaa atc aaa ccc acc      960
Val Thr Ile Ser Val His Glu Lys Gly Phe Ile Glu Ile Lys Pro Thr
305                 310                 315                 320 ttc agc cag ttg gaa gct gtc aac ctg cat gaa gtc aaa cat ttt gtt     1008
Phe Ser Gln Leu Glu Ala Val Asn Leu His Glu Val Lys His Phe Val
            325                 330                 335 gta gag gtg cgg gcc tac cca cct ccc agg ata tcc tgg ctg aaa aac     1056
Val Glu Val Arg Ala Tyr Pro Pro Pro Arg Ile Ser Trp Leu Lys Asn
        340                 345                 350 aat ctg act ctg att gaa aat ctc act gag atc acc act gat gtg gaa     1104
Asn Leu Thr Leu Ile Glu Asn Leu Thr Glu Ile Thr Thr Asp Val Glu
    355                 360                 365 aag att cag gaa ata agg tat cga agc aaa tta aag ctg atc cgt gct     1152
Lys Ile Gln Glu Ile Arg Tyr Arg Ser Lys Leu Lys Leu Ile Arg Ala
370                 375                 380 aag gaa gaa gac agt ggc cat tat act att gta gct caa aat gaa gat     1200
Lys Glu Glu Asp Ser Gly His Tyr Thr Ile Val Ala Gln Asn Glu Asp
385                 390                 395                 400 gct gtg aag agc tat act ttt gaa ctg tta act caa gtt cct tca tcc     1248
Ala Val Lys Ser Tyr Thr Phe Glu Leu Leu Thr Gln Val Pro Ser Ser
            405                 410                 415 att ctg gac ttg gtc gat gat cac cat ggc tca act ggg gga cag acg     1296
Ile Leu Asp Leu Val Asp Asp His His Gly Ser Thr Gly Gly Gln Thr
        420                 425                 430 gtg agg tgc aca gct gaa ggc acg ccg ctt cct gat att gag tgg atg     1344
Val Arg Cys Thr Ala Glu Gly Thr Pro Leu Pro Asp Ile Glu Trp Met
    435                 440                 445 ata tgc aaa gat att aag aaa tgt aat aat gaa act tcc tgg act att     1392
Ile Cys Lys Asp Ile Lys Lys Cys Asn Asn Glu Thr Ser Trp Thr Ile
450                 455                 460 ttg gcc aac aat gtc tca aac atc atc acg gag atc cac tcc cga gac     1440
Leu Ala Asn Asn Val Ser Asn Ile Ile Thr Glu Ile His Ser Arg Asp
465                 470                 475                 480 agg agt acc gtg gag ggc cgt gtg act ttc gcc aaa gtg gag gag acc     1488
Arg Ser Thr Val Glu Gly Arg Val Thr Phe Ala Lys Val Glu Glu Thr
            485                 490                 495 atc gcc gtg cga tgc ctg gct aag aat ctc ctt gga gct gag aac cga     1536
Ile Ala Val Arg Cys Leu Ala Lys Asn Leu Leu Gly Ala Glu Asn Arg
        500                 505                 510 gag ctg aag ctg gtg gct ccc acc ctg cgt tct gaa ctc acg gtg gct     1584
Glu Leu Lys Leu Val Ala Pro Thr Leu Arg Ser Glu Leu Thr Val Ala
    515                 520                 525 gct gca gtc ctg gtg ctg ttg gtg att gtg atc atc tca ctt att gtc     1632
Ala Ala Val Leu Val Leu Leu Val Ile Val Ile Ile Ser Leu Ile Val
530                 535                 540
```

```
ctg gtt gtc att tgg aaa cag aaa ccg agg tat gaa att cgc tgg agg    1680
Leu Val Val Ile Trp Lys Gln Lys Pro Arg Tyr Glu Ile Arg Trp Arg
545                 550                 555                 560 gtc att gaa tca atc agc ccg gat gga cat gaa tat att tat gtg gac    1728
Val Ile Glu Ser Ile Ser Pro Asp Gly His Glu Tyr Ile Tyr Val Asp
                565                 570                 575 ccg atg cag ctg cct tat gac tca aga tgg gag ttt cca aga gat gga    1776
Pro Met Gln Leu Pro Tyr Asp Ser Arg Trp Glu Phe Pro Arg Asp Gly
            580                 585                 590 cta gtg ctt ggt cgg gtc ttg ggg tct gga gcg ttt ggg aag gtg gtt    1824
Leu Val Leu Gly Arg Val Leu Gly Ser Gly Ala Phe Gly Lys Val Val
        595                 600                 605 gaa gga aca gcc tat gga tta agc cgg tcc caa cct gtc atg aaa gtt    1872
Glu Gly Thr Ala Tyr Gly Leu Ser Arg Ser Gln Pro Val Met Lys Val
    610                 615                 620 gca gtg aag atg cta aaa ccc acg gcc aga tcc agt gaa aaa caa gct    1920
Ala Val Lys Met Leu Lys Pro Thr Ala Arg Ser Ser Glu Lys Gln Ala
625                 630                 635                 640 ctc atg tct gaa ctg aag ata atg act cac ctg ggg cca cat ttg aac    1968
Leu Met Ser Glu Leu Lys Ile Met Thr His Leu Gly Pro His Leu Asn
                645                 650                 655 att gta aac ttg ctg gga gcc tgc acc aag tca ggc ccc att tac atc    2016
Ile Val Asn Leu Leu Gly Ala Cys Thr Lys Ser Gly Pro Ile Tyr Ile
            660                 665                 670 atc aca gag tat tgc ttc tat gga gat ttg gtc aac tat ttg cat aag    2064
Ile Thr Glu Tyr Cys Phe Tyr Gly Asp Leu Val Asn Tyr Leu His Lys
        675                 680                 685 aat agg gat agc ttc ctg agc cac cac cca gag aag cca aag aaa gag    2112
Asn Arg Asp Ser Phe Leu Ser His His Pro Glu Lys Pro Lys Lys Glu
    690                 695                 700 ctg gat atc ttt gga ttg aac cct gct gat gaa agc aca cgg agc tat    2160
Leu Asp Ile Phe Gly Leu Asn Pro Ala Asp Glu Ser Thr Arg Ser Tyr
705                 710                 715                 720 gtt att tta tct ttt gaa aac aat ggt gac tac atg gac atg aag cag    2208
Val Ile Leu Ser Phe Glu Asn Asn Gly Asp Tyr Met Asp Met Lys Gln
                725                 730                 735 gct gat act aca cag tat gtc ccc atg cta gaa agg aaa gag gtt tct    2256
Ala Asp Thr Thr Gln Tyr Val Pro Met Leu Glu Arg Lys Glu Val Ser
            740                 745                 750 aaa tat tcc gac atc cag aga tca ctc tat gat cgt cca gcc tca tat    2304
Lys Tyr Ser Asp Ile Gln Arg Ser Leu Tyr Asp Arg Pro Ala Ser Tyr
        755                 760                 765 aag aag aaa tct atg tta gac tca gaa gtc aaa aac ctc ctt tca gat    2352
Lys Lys Lys Ser Met Leu Asp Ser Glu Val Lys Asn Leu Leu Ser Asp
    770                 775                 780 gat aac tca gaa ggc ctt act tta ttg gat ttg ttg agc ttc acc tat    2400
Asp Asn Ser Glu Gly Leu Thr Leu Leu Asp Leu Leu Ser Phe Thr Tyr
785                 790                 795                 800 caa gtt gcc cga gga atg gag ttt ttg gct tca aaa aat tgt gtc cac    2448
Gln Val Ala Arg Gly Met Glu Phe Leu Ala Ser Lys Asn Cys Val His
                805                 810                 815 cgt aat ctg gct gct cgc aac gtc ctc ctg gca caa gga aaa att gtg    2496
Arg Asn Leu Ala Ala Arg Asn Val Leu Leu Ala Gln Gly Lys Ile Val
            820                 825                 830 aag atc tgt gac ttt ggc ctg gcc aga gac atc atg cat gat tcg aac    2544
Lys Ile Cys Asp Phe Gly Leu Ala Arg Asp Ile Met His Asp Ser Asn
        835                 840                 845 tat gtg tcg aaa ggc agt acc ttt ctg ccc gtg aag tgg atg gct cct    2592
Tyr Val Ser Lys Gly Ser Thr Phe Leu Pro Val Lys Trp Met Ala Pro
```

-continued

```
                 850                 855                 860
gag agc atc ttt gac aac ctc tac acc aca ctg agt gat gtc tgg tct         2640
Glu Ser Ile Phe Asp Asn Leu Tyr Thr Thr Leu Ser Asp Val Trp Ser
865                 870                 875                 880 tat ggc att ctg ctc tgg gag atc ttt tcc ctt ggt ggc acc cct tac         2688
Tyr Gly Ile Leu Leu Trp Glu Ile Phe Ser Leu Gly Gly Thr Pro Tyr
                885                 890                 895 ccc ggc atg atg gtg gat tct act ttc tac aat aag atc aag agt ggg         2736
Pro Gly Met Met Val Asp Ser Thr Phe Tyr Asn Lys Ile Lys Ser Gly
            900                 905                 910 tac cgg atg gcc aag cct gac cac gct acc agt gaa gtc tac gag atc         2784
Tyr Arg Met Ala Lys Pro Asp His Ala Thr Ser Glu Val Tyr Glu Ile
        915                 920                 925 atg gtg aaa tgc tgg aac agt gag ccg gag aag aga ccc tcc ttt tac         2832
Met Val Lys Cys Trp Asn Ser Glu Pro Glu Lys Arg Pro Ser Phe Tyr
930                 935                 940 cac ctg agt gag att gtg gag aat ctg ctg cct gga caa tat aaa aag         2880
His Leu Ser Glu Ile Val Glu Asn Leu Leu Pro Gly Gln Tyr Lys Lys
945                 950                 955                 960 agt tat gaa aaa att cac ctg gac ttc ctg aag agt gac cat cct gct         2928
Ser Tyr Glu Lys Ile His Leu Asp Phe Leu Lys Ser Asp His Pro Ala
                965                 970                 975 gtg gca cgc atg cgt gtg gac tca gac aat gca tac att ggt gtc acc         2976
Val Ala Arg Met Arg Val Asp Ser Asp Asn Ala Tyr Ile Gly Val Thr
            980                 985                 990 tac aaa aac gag gaa gac aag ctg aag gac tgg gag ggt ggt ctg gat         3024
Tyr Lys Asn Glu Glu Asp Lys Leu Lys Asp Trp Glu Gly Gly Leu Asp
        995                 1000                1005 gag cag aga ctg agc gct gac agt ggc tac atc att cct ctg cct gac         3072
Glu Gln Arg Leu Ser Ala Asp Ser Gly Tyr Ile Ile Pro Leu Pro Asp
    1010                1015                1020 att gac cct gtc cct gag gag gag gac ctg ggc aag agg aac aga cac         3120
Ile Asp Pro Val Pro Glu Glu Glu Asp Leu Gly Lys Arg Asn Arg His
1025                1030                1035                1040 agc tcg cag acc tct gaa gag agt gcc att gag acg ggt tcc agc agt         3168
Ser Ser Gln Thr Ser Glu Glu Ser Ala Ile Glu Thr Gly Ser Ser Ser
                1045                1050                1055 tcc acc ttc atc aag aga gag gac gag acc att gaa gac atc gac atg         3216
Ser Thr Phe Ile Lys Arg Glu Asp Glu Thr Ile Glu Asp Ile Asp Met
            1060                1065                1070 atg gac gac atc ggc ata gac tct tca gac ctg gtg gaa gac agc ttc         3264
Met Asp Asp Ile Gly Ile Asp Ser Ser Asp Leu Val Glu Asp Ser Phe
        1075                1080                1085 ctg taa                                                                  3270
Leu <210> SEQ ID NO 8
<211> LENGTH: 1089
<212> TYPE: PRT
<213> ORGANISM: Homo sapiens

<400> SEQUENCE: 8

Met Gly Thr Ser His Pro Ala Phe Leu Val Leu Gly Cys Leu Leu Thr
 1               5                  10                  15

Gly Leu Ser Leu Ile Leu Cys Gln Leu Ser Leu Pro Ser Ile Leu Pro
            20                  25                  30

Asn Glu Asn Glu Lys Val Val Gln Leu Asn Ser Ser Phe Ser Leu Arg
        35                  40                  45

Cys Phe Gly Glu Ser Glu Val Ser Trp Gln Tyr Pro Met Ser Glu Glu
```

```
                50                    55                    60
Glu Ser Ser Asp Val Glu Ile Arg Asn Glu Glu Asn Ser Gly Leu
65                   70                    75                   80

Phe Val Thr Val Leu Glu Val Ser Ser Ala Ser Ala Ala His Thr Gly
                    85                    90                    95

Leu Tyr Thr Cys Tyr Tyr Asn His Thr Gln Thr Glu Glu Asn Glu Leu
                100                   105                   110

Glu Gly Arg His Ile Tyr Ile Tyr Val Pro Asp Pro Asp Val Ala Phe
                115                   120                   125

Val Pro Leu Gly Met Thr Asp Tyr Leu Val Ile Val Glu Asp Asp Asp
130                  135                   140

Ser Ala Ile Ile Pro Cys Arg Thr Thr Asp Pro Glu Thr Pro Val Thr
145                  150                   155                   160

Leu His Asn Ser Glu Gly Val Val Pro Ala Ser Tyr Asp Ser Arg Gln
                165                   170                   175

Gly Phe Asn Gly Thr Phe Thr Val Gly Pro Tyr Ile Cys Glu Ala Thr
                180                   185                   190

Val Lys Gly Lys Lys Phe Gln Thr Ile Pro Phe Asn Val Tyr Ala Leu
                195                   200                   205

Lys Ala Thr Ser Glu Leu Asp Leu Glu Met Glu Ala Leu Lys Thr Val
210                  215                   220

Tyr Lys Ser Gly Glu Thr Ile Val Val Thr Cys Ala Val Phe Asn Asn
225                  230                   235                   240

Glu Val Val Asp Leu Gln Trp Thr Tyr Pro Gly Glu Val Lys Gly Lys
                245                   250                   255

Gly Ile Thr Met Leu Glu Glu Ile Lys Val Pro Ser Ile Lys Leu Val
                260                   265                   270

Tyr Thr Leu Thr Val Pro Glu Ala Thr Val Lys Asp Ser Gly Asp Tyr
                275                   280                   285

Glu Cys Ala Ala Arg Gln Ala Thr Arg Glu Val Lys Glu Met Lys Lys
                290                   295                   300

Val Thr Ile Ser Val His Glu Lys Gly Phe Ile Glu Ile Lys Pro Thr
305                  310                   315                   320

Phe Ser Gln Leu Glu Ala Val Asn Leu His Glu Val Lys His Phe Val
                325                   330                   335

Val Glu Val Arg Ala Tyr Pro Pro Arg Ile Ser Trp Leu Lys Asn
                340                   345                   350

Asn Leu Thr Leu Ile Glu Asn Leu Thr Glu Ile Thr Thr Asp Val Glu
                355                   360                   365

Lys Ile Gln Glu Ile Arg Tyr Arg Ser Lys Leu Lys Leu Ile Arg Ala
370                  375                   380

Lys Glu Glu Asp Ser Gly His Tyr Thr Ile Val Ala Gln Asn Glu Asp
385                  390                   395                   400

Ala Val Lys Ser Tyr Thr Phe Glu Leu Leu Thr Gln Val Pro Ser Ser
                405                   410                   415

Ile Leu Asp Leu Val Asp Asp His Gly Ser Thr Gly Gly Gln Thr
                420                   425                   430

Val Arg Cys Thr Ala Glu Gly Thr Pro Leu Pro Asp Ile Glu Trp Met
                435                   440                   445

Ile Cys Lys Asp Ile Lys Lys Cys Asn Asn Glu Thr Ser Trp Thr Ile
                450                   455                   460

Leu Ala Asn Asn Val Ser Asn Ile Ile Thr Glu Ile His Ser Arg Asp
465                  470                   475                   480
```

-continued

```
Arg Ser Thr Val Glu Arg Val Thr Phe Ala Lys Val Glu Glu Thr
            485                 490                 495

Ile Ala Val Arg Cys Leu Ala Lys Asn Leu Leu Gly Ala Glu Asn Arg
            500                 505                 510

Glu Leu Lys Leu Val Ala Pro Thr Leu Arg Ser Glu Leu Thr Val Ala
            515                 520                 525

Ala Ala Val Leu Val Leu Leu Val Ile Val Ile Ile Ser Leu Ile Val
            530                 535                 540

Leu Val Val Ile Trp Lys Gln Lys Pro Arg Tyr Glu Ile Arg Trp Arg
545                 550                 555                 560

Val Ile Glu Ser Ile Ser Pro Asp Gly His Glu Tyr Ile Tyr Val Asp
                565                 570                 575

Pro Met Gln Leu Pro Tyr Asp Ser Arg Trp Glu Phe Pro Arg Asp Gly
            580                 585                 590

Leu Val Leu Gly Arg Val Leu Gly Ser Gly Ala Phe Gly Lys Val Val
            595                 600                 605

Glu Gly Thr Ala Tyr Gly Leu Ser Arg Ser Gln Pro Val Met Lys Val
            610                 615                 620

Ala Val Lys Met Leu Lys Pro Thr Ala Arg Ser Ser Glu Lys Gln Ala
625                 630                 635                 640

Leu Met Ser Glu Leu Lys Ile Met Thr His Leu Gly Pro His Leu Asn
                645                 650                 655

Ile Val Asn Leu Leu Gly Ala Cys Thr Lys Ser Gly Pro Ile Tyr Ile
            660                 665                 670

Ile Thr Glu Tyr Cys Phe Tyr Gly Asp Leu Val Asn Tyr Leu His Lys
            675                 680                 685

Asn Arg Asp Ser Phe Leu Ser His His Pro Glu Lys Pro Lys Lys Glu
690                 695                 700

Leu Asp Ile Phe Gly Leu Asn Pro Ala Asp Glu Ser Thr Arg Ser Tyr
705                 710                 715                 720

Val Ile Leu Ser Phe Glu Asn Asn Gly Asp Tyr Met Asp Met Lys Gln
                725                 730                 735

Ala Asp Thr Thr Gln Tyr Val Pro Met Leu Glu Arg Lys Glu Val Ser
            740                 745                 750

Lys Tyr Ser Asp Ile Gln Arg Ser Leu Tyr Asp Arg Pro Ala Ser Tyr
            755                 760                 765

Lys Lys Lys Ser Met Leu Asp Ser Glu Val Lys Asn Leu Leu Ser Asp
            770                 775                 780

Asp Asn Ser Glu Gly Leu Thr Leu Leu Asp Leu Leu Ser Phe Thr Tyr
785                 790                 795                 800

Gln Val Ala Arg Gly Met Glu Phe Leu Ala Ser Lys Asn Cys Val His
            805                 810                 815

Arg Asn Leu Ala Ala Arg Asn Val Leu Leu Ala Gln Gly Lys Ile Val
            820                 825                 830

Lys Ile Cys Asp Phe Gly Leu Ala Arg Asp Ile Met His Asp Ser Asn
            835                 840                 845

Tyr Val Ser Lys Gly Ser Thr Phe Leu Pro Val Lys Trp Met Ala Pro
            850                 855                 860

Glu Ser Ile Phe Asp Asn Leu Tyr Thr Thr Leu Ser Asp Val Trp Ser
865                 870                 875                 880

Tyr Gly Ile Leu Leu Trp Glu Ile Phe Ser Leu Gly Gly Thr Pro Tyr
                885                 890                 895
```

```
Pro Gly Met Met Val Asp Ser Thr Phe Tyr Asn Lys Ile Lys Ser Gly
            900                 905                 910

Tyr Arg Met Ala Lys Pro Asp His Ala Thr Ser Glu Val Tyr Glu Ile
        915                 920                 925

Met Val Lys Cys Trp Asn Ser Glu Pro Glu Lys Arg Pro Ser Phe Tyr
    930                 935                 940

His Leu Ser Glu Ile Val Glu Asn Leu Leu Pro Gly Gln Tyr Lys Lys
945                 950                 955                 960

Ser Tyr Glu Lys Ile His Leu Asp Phe Leu Lys Ser Asp His Pro Ala
                965                 970                 975

Val Ala Arg Met Arg Val Asp Ser Asp Asn Ala Tyr Ile Gly Val Thr
            980                 985                 990

Tyr Lys Asn Glu Glu Asp Lys Leu Lys Asp Trp Glu Gly Gly Leu Asp
        995                 1000                1005

Glu Gln Arg Leu Ser Ala Asp Ser Gly Tyr Ile Ile Pro Leu Pro Asp
    1010                1015                1020

Ile Asp Pro Val Pro Glu Glu Asp Leu Gly Lys Arg Asn Arg His
1025                1030                1035                1040

Ser Ser Gln Thr Ser Glu Glu Ser Ala Ile Glu Thr Gly Ser Ser Ser
                1045                1050                1055

Ser Thr Phe Ile Lys Arg Glu Asp Glu Thr Ile Glu Asp Ile Asp Met
            1060                1065                1070

Met Asp Asp Ile Gly Ile Asp Ser Ser Asp Leu Val Glu Asp Ser Phe
        1075                1080                1085

Leu
```

<210> SEQ ID NO 9
<211> LENGTH: 3270
<212> TYPE: DNA
<213> ORGANISM: Homo sapiens
<220> FEATURE:
<221> NAME/KEY: CDS
<222> LOCATION: (1)..(3267)

<400> SEQUENCE: 9

```
atg ggg act tcc cat ccg gcg ttc ctg gtc tta ggc tgt ctt ctc aca      48
Met Gly Thr Ser His Pro Ala Phe Leu Val Leu Gly Cys Leu Leu Thr
1               5                   10                  15 ggg ctg agc cta atc ctc tgc cag ctt tca tta ccc tct atc ctt cca      96
Gly Leu Ser Leu Ile Leu Cys Gln Leu Ser Leu Pro Ser Ile Leu Pro
            20                  25                  30 aat gaa aat gaa aag gtt gtg cag ctg aat tca tcc ttt tct ctg aga     144
Asn Glu Asn Glu Lys Val Val Gln Leu Asn Ser Ser Phe Ser Leu Arg
        35                  40                  45 tgc ttt ggg gag agt gaa gtg agc tgg cag tac ccc atg tct gaa gaa     192
Cys Phe Gly Glu Ser Glu Val Ser Trp Gln Tyr Pro Met Ser Glu Glu
    50                  55                  60 gag agc tcc gat gtg gaa atc aga aat gaa gaa aac agc ggc ctt         240
Glu Ser Ser Asp Val Glu Ile Arg Asn Glu Glu Asn Asn Ser Gly Leu
65                  70                  75                  80 ttt gtg acg gtc ttg gaa gtg agc agt gcc tcg gcg gcc cac aca ggg     288
Phe Val Thr Val Leu Glu Val Ser Ser Ala Ser Ala Ala His Thr Gly
                85                  90                  95 ttg tac act tgc tat tac aac cac act cag aca gaa gag aat gag ctt     336
Leu Tyr Thr Cys Tyr Tyr Asn His Thr Gln Thr Glu Glu Asn Glu Leu
            100                 105                 110 gaa ggc agg cac att tac atc tat gtg cca gac cca gat gta gcc ttt     384
Glu Gly Arg His Ile Tyr Ile Tyr Val Pro Asp Pro Asp Val Ala Phe
```

-continued

|     | 115 |     |     |     | 120 |     |     |     | 125 |     |     |     |     |      |
|-----|-----|-----|-----|-----|-----|-----|-----|-----|-----|-----|-----|-----|-----|------|
| gta | cct | cta | gga | atg | acg | gat | tat | tta | gtc | atc | gtg | gag | gat | gat | gat |      432 |
| Val | Pro | Leu | Gly | Met | Thr | Asp | Tyr | Leu | Val | Ile | Val | Glu | Asp | Asp | Asp |
|     | 130 |     |     |     | 135 |     |     |     | 140 |     |     |     |     |      |

```
gta cct cta gga atg acg gat tat tta gtc atc gtg gag gat gat gat    432
Val Pro Leu Gly Met Thr Asp Tyr Leu Val Ile Val Glu Asp Asp Asp
    130                 135                 140 tct gcc att ata cct tgt cgc aca act gat ccc gag act cct gta acc    480
Ser Ala Ile Ile Pro Cys Arg Thr Thr Asp Pro Glu Thr Pro Val Thr
145                 150                 155                 160 tta cac aac agt gag ggg gtg gta cct gcc tcc tac gac agc aga cag    528
Leu His Asn Ser Glu Gly Val Val Pro Ala Ser Tyr Asp Ser Arg Gln
                165                 170                 175 ggc ttt aat ggg acc ttc act gta ggg ccc tat atc tgt gag gcc acc    576
Gly Phe Asn Gly Thr Phe Thr Val Gly Pro Tyr Ile Cys Glu Ala Thr
            180                 185                 190 gtc aaa gga aag aag ttc cag acc atc cca ttt aat gtt tat gct tta    624
Val Lys Gly Lys Lys Phe Gln Thr Ile Pro Phe Asn Val Tyr Ala Leu
        195                 200                 205 aaa gca aca tca gag ctg gat cta gaa atg gaa gct ctt aaa acc gtg    672
Lys Ala Thr Ser Glu Leu Asp Leu Glu Met Glu Ala Leu Lys Thr Val
    210                 215                 220 tat aag tca ggg gaa acg att gtg gtc acc tgt gct gtt ttt aac aat    720
Tyr Lys Ser Gly Glu Thr Ile Val Val Thr Cys Ala Val Phe Asn Asn
225                 230                 235                 240 gag gtg gtt gac ctt caa tgg act tac cct gga gaa gtg aaa ggc aaa    768
Glu Val Val Asp Leu Gln Trp Thr Tyr Pro Gly Glu Val Lys Gly Lys
                245                 250                 255 ggc atc aca atg ctg gaa gaa atc aaa gtc cca tcc atc aaa ttg gtg    816
Gly Ile Thr Met Leu Glu Glu Ile Lys Val Pro Ser Ile Lys Leu Val
            260                 265                 270 tac act ttg acg gtc ccc gag gcc acg gtg aaa gac agt gga gat tac    864
Tyr Thr Leu Thr Val Pro Glu Ala Thr Val Lys Asp Ser Gly Asp Tyr
        275                 280                 285 gaa tgt gct gcc cgc cag gct acc agg gag gtc aaa gaa atg aag aaa    912
Glu Cys Ala Ala Arg Gln Ala Thr Arg Glu Val Lys Glu Met Lys Lys
    290                 295                 300 gtc act att tct gtc cat gag aaa ggt ttc att gaa atc aaa ccc acc    960
Val Thr Ile Ser Val His Glu Lys Gly Phe Ile Glu Ile Lys Pro Thr
305                 310                 315                 320 ttc agc cag ttg gaa gct gtc aac ctg cat gaa gtc aaa cat ttt gtt   1008
Phe Ser Gln Leu Glu Ala Val Asn Leu His Glu Val Lys His Phe Val
                325                 330                 335 gta gag gtg cgg gcc tac cca cct ccc agg ata tcc tgg ctg aaa aac   1056
Val Glu Val Arg Ala Tyr Pro Pro Pro Arg Ile Ser Trp Leu Lys Asn
            340                 345                 350 aat ctg act ctg att gaa aat ctc act gag atc acc act gat gtg gaa   1104
Asn Leu Thr Leu Ile Glu Asn Leu Thr Glu Ile Thr Thr Asp Val Glu
        355                 360                 365 aag att cag gaa ata agg tat cga agc aaa tta aag ctg atc cgt gct   1152
Lys Ile Gln Glu Ile Arg Tyr Arg Ser Lys Leu Lys Leu Ile Arg Ala
    370                 375                 380 aag gaa gaa gac agt ggc cat tat act att gta gct caa aat gaa gat   1200
Lys Glu Glu Asp Ser Gly His Tyr Thr Ile Val Ala Gln Asn Glu Asp
385                 390                 395                 400 gct gtg aag agc tat act ttt gaa ctg tta act caa gtt cct tca tcc   1248
Ala Val Lys Ser Tyr Thr Phe Glu Leu Leu Thr Gln Val Pro Ser Ser
                405                 410                 415 att ctg gac ttg gtc gat gat cac cat ggc tca act ggg gga cag acg   1296
Ile Leu Asp Leu Val Asp Asp His His Gly Ser Thr Gly Gly Gln Thr
            420                 425                 430 gtg agg tgc aca gct gaa ggc acg ccg ctt cct gat att gag tgg atg   1344
```

-continued

| | | | | | | | | | | | | | | |
|---|---|---|---|---|---|---|---|---|---|---|---|---|---|---|
| Val | Arg | Cys | Thr | Ala | Glu | Gly | Thr | Pro | Leu | Pro | Asp | Ile | Glu | Trp | Met |
| | | 435 | | | | | 440 | | | | | 445 | | | |

```
ata tgc aaa gat att aag aaa tgt aat aat gaa act tcc tgg act att      1392
Ile Cys Lys Asp Ile Lys Lys Cys Asn Asn Glu Thr Ser Trp Thr Ile
450                 455                 460 ttg gcc aac aat gtc tca aac atc atc acg gag atc cac tcc cga gac      1440
Leu Ala Asn Asn Val Ser Asn Ile Ile Thr Glu Ile His Ser Arg Asp
465                 470                 475                 480 agg agt acc gtg gag ggc cgt gtg act ttc gcc aaa gtg gag gag acc      1488
Arg Ser Thr Val Glu Gly Arg Val Thr Phe Ala Lys Val Glu Glu Thr
            485                 490                 495 atc gcc gtg cga tgc ctg gct aag aat ctc ctt gga gct gag aac cga      1536
Ile Ala Val Arg Cys Leu Ala Lys Asn Leu Leu Gly Ala Glu Asn Arg
        500                 505                 510 gag ctg aag ctg gtg gct ccc acc ctg cgt tct gaa ctc acg gtg gct      1584
Glu Leu Lys Leu Val Ala Pro Thr Leu Arg Ser Glu Leu Thr Val Ala
    515                 520                 525 gct gca gtc ctg gtg ctg ttg gtg att gtg atc atc tca ctt att gtc      1632
Ala Ala Val Leu Val Leu Leu Val Ile Val Ile Ile Ser Leu Ile Val
530                 535                 540 ctg gtt gtc att tgg aaa cag aaa ccg agg tat gaa att cgc tgg agg      1680
Leu Val Val Ile Trp Lys Gln Lys Pro Arg Tyr Glu Ile Arg Trp Arg
545                 550                 555                 560 gtc att gaa tca atc agc ccg gat gga cat gaa tat att tat gtg gac      1728
Val Ile Glu Ser Ile Ser Pro Asp Gly His Glu Tyr Ile Tyr Val Asp
                565                 570                 575 ccg atg cag ctg cct tat gac tca aga tgg gag ttt cca aga gat gga      1776
Pro Met Gln Leu Pro Tyr Asp Ser Arg Trp Glu Phe Pro Arg Asp Gly
            580                 585                 590 cta gtg ctt ggt cgg gtc ttg ggg tct gga gcg ttt ggg aag gtg gtt      1824
Leu Val Leu Gly Arg Val Leu Gly Ser Gly Ala Phe Gly Lys Val Val
        595                 600                 605 gaa gga aca gcc tat gga tta agc cgg tcc caa cct gtc atg aaa gtt      1872
Glu Gly Thr Ala Tyr Gly Leu Ser Arg Ser Gln Pro Val Met Lys Val
    610                 615                 620 gca gtg aag atg cta aaa ccc acg gcc aga tcc agt gaa aaa caa gct      1920
Ala Val Lys Met Leu Lys Pro Thr Ala Arg Ser Ser Glu Lys Gln Ala
625                 630                 635                 640 ctc atg tct gaa ctg aag ata atg act cac ctg ggg cca cat ttg aac      1968
Leu Met Ser Glu Leu Lys Ile Met Thr His Leu Gly Pro His Leu Asn
                645                 650                 655 att gta aac ttg ctg gga gcc tgc acc aag tca ggc ccc att tac atc      2016
Ile Val Asn Leu Leu Gly Ala Cys Thr Lys Ser Gly Pro Ile Tyr Ile
            660                 665                 670 atc aca gag tat tgc ttc tat gga gat ttg gtc aac tat ttg cat aag      2064
Ile Thr Glu Tyr Cys Phe Tyr Gly Asp Leu Val Asn Tyr Leu His Lys
        675                 680                 685 aat agg gat agc ttc ctg agc cac cac cca gag aag cca aag aaa gag      2112
Asn Arg Asp Ser Phe Leu Ser His His Pro Glu Lys Pro Lys Lys Glu
    690                 695                 700 ctg gat atc ttt gga ttg aac cct gct gat gaa agc aca cgg agc tat      2160
Leu Asp Ile Phe Gly Leu Asn Pro Ala Asp Glu Ser Thr Arg Ser Tyr
705                 710                 715                 720 gtt att tta tct ttt gaa aac aat ggt gac tac atg gac atg aag cag      2208
Val Ile Leu Ser Phe Glu Asn Asn Gly Asp Tyr Met Asp Met Lys Gln
                725                 730                 735 gct gat act aca cag tat gtc ccc atg cta gaa agg aaa gag gtt tct      2256
Ala Asp Thr Thr Gln Tyr Val Pro Met Leu Glu Arg Lys Glu Val Ser
            740                 745                 750
```

```
aaa tat tcc gac atc cag aga tca ctc tat gat cgt cca gcc tca tat    2304
Lys Tyr Ser Asp Ile Gln Arg Ser Leu Tyr Asp Arg Pro Ala Ser Tyr
        755                 760                 765 aag aag aaa tct atg tta gac tca gaa gtc aaa aac ctc ctt tca gat    2352
Lys Lys Lys Ser Met Leu Asp Ser Glu Val Lys Asn Leu Leu Ser Asp
770             775                 780 gat aac tca gaa ggc ctt act tta ttg gat ttg ttg agc ttc acc tat    2400
Asp Asn Ser Glu Gly Leu Thr Leu Leu Asp Leu Leu Ser Phe Thr Tyr
785             790                 795                 800 caa gtt gcc cga gga atg gag ttt ttg gct tca aaa aat tgt gtc cac    2448
Gln Val Ala Arg Gly Met Glu Phe Leu Ala Ser Lys Asn Cys Val His
                805                 810                 815 cgt gat ctg gct gct cgc aac gtc ctc ctg gca caa gga aaa att gtg    2496
Arg Asp Leu Ala Ala Arg Asn Val Leu Leu Ala Gln Gly Lys Ile Val
            820                 825                 830 aag atc tgt gac ttt ggc ctg gcc aga gac atc atg cat gat tcg aac    2544
Lys Ile Cys Asp Phe Gly Leu Ala Arg Asp Ile Met His Asp Ser Asn
            835                 840                 845 tat gtg tcg aaa ggc agt acc ttt ctg ccc atg aag tgg atg gct cct    2592
Tyr Val Ser Lys Gly Ser Thr Phe Leu Pro Met Lys Trp Met Ala Pro
850                 855                 860 gag agc atc ttt gac aac ctc tac acc aca ctg agt gat gtc tgg tct    2640
Glu Ser Ile Phe Asp Asn Leu Tyr Thr Thr Leu Ser Asp Val Trp Ser
865                 870                 875                 880 tat ggc att ctg ctc tgg gag atc ttt tcc ctt ggt ggc acc cct tac    2688
Tyr Gly Ile Leu Leu Trp Glu Ile Phe Ser Leu Gly Gly Thr Pro Tyr
                885                 890                 895 ccc ggc atg atg gtg gat tct act ttc tac aat aag atc aag agt ggg    2736
Pro Gly Met Met Val Asp Ser Thr Phe Tyr Asn Lys Ile Lys Ser Gly
            900                 905                 910 tac cgg atg gcc aag cct gac cac gct acc agt gaa gtc tac gag atc    2784
Tyr Arg Met Ala Lys Pro Asp His Ala Thr Ser Glu Val Tyr Glu Ile
            915                 920                 925 atg gtg aaa tgc tgg aac agt gag ccg gag aag aga ccc tcc ttt tac    2832
Met Val Lys Cys Trp Asn Ser Glu Pro Glu Lys Arg Pro Ser Phe Tyr
930                 935                 940 cac ctg agt gag att gtg gag aat ctg ctg cct gga caa tat aaa aag    2880
His Leu Ser Glu Ile Val Glu Asn Leu Leu Pro Gly Gln Tyr Lys Lys
945                 950                 955                 960 agt tat gaa aaa att cac ctg gac ttc ctg aag agt gac cat cct gct    2928
Ser Tyr Glu Lys Ile His Leu Asp Phe Leu Lys Ser Asp His Pro Ala
                965                 970                 975 gtg gca cgc atg cgt gtg gac tca gac aat gca tac att ggt gtc acc    2976
Val Ala Arg Met Arg Val Asp Ser Asp Asn Ala Tyr Ile Gly Val Thr
            980                 985                 990 tac aaa aac gag gaa gac aag ctg aag gac tgg gag ggt ggt ctg gat    3024
Tyr Lys Asn Glu Glu Asp Lys Leu Lys Asp Trp Glu Gly Gly Leu Asp
        995                 1000                1005 gag cag aga ctg agc gct gac agt ggc tac atc att cct ctg cct gac    3072
Glu Gln Arg Leu Ser Ala Asp Ser Gly Tyr Ile Ile Pro Leu Pro Asp
1010            1015                1020 att gac cct gtc cct gag gag gag gac ctg ggc aag agg aac aga cac    3120
Ile Asp Pro Val Pro Glu Glu Glu Asp Leu Gly Lys Arg Asn Arg His
1025            1030                1035                1040 agc tcg cag acc tct gaa gag agt gcc att gag acg ggt tcc agc agt    3168
Ser Ser Gln Thr Ser Glu Glu Ser Ala Ile Glu Thr Gly Ser Ser Ser
                1045                1050                1055 tcc acc ttc atc aag aga gag gac gag acc att gaa gac atc gac atg    3216
Ser Thr Phe Ile Lys Arg Glu Asp Glu Thr Ile Glu Asp Ile Asp Met
            1060                1065                1070
```

```
          atg gac gac atc ggc ata gac tct tca gac ctg gtg gaa gac agc ttc    3264
          Met Asp Asp Ile Gly Ile Asp Ser Ser Asp Leu Val Glu Asp Ser Phe
                   1075                1080                1085 ctg taa                                                             3270
          Leu <210> SEQ ID NO 10
          <211> LENGTH: 1089
          <212> TYPE: PRT
          <213> ORGANISM: Homo sapiens

<400> SEQUENCE: 10

Met Gly Thr Ser His Pro Ala Phe Leu Val Leu Gly Cys Leu Leu Thr
           1               5                  10                  15

Gly Leu Ser Leu Ile Leu Cys Gln Leu Ser Leu Pro Ser Ile Leu Pro
                          20                  25                  30

Asn Glu Asn Glu Lys Val Val Gln Leu Asn Ser Ser Phe Ser Leu Arg
                      35                  40                  45

Cys Phe Gly Glu Ser Glu Val Ser Trp Gln Tyr Pro Met Ser Glu Glu
                  50                  55                  60

Glu Ser Ser Asp Val Glu Ile Arg Asn Glu Glu Asn Asn Ser Gly Leu
           65                  70                  75                  80

Phe Val Thr Val Leu Glu Val Ser Ser Ala Ser Ala Ala His Thr Gly
                          85                  90                  95

Leu Tyr Thr Cys Tyr Tyr Asn His Thr Gln Thr Glu Glu Asn Glu Leu
                         100                 105                 110

Glu Gly Arg His Ile Tyr Ile Tyr Val Pro Asp Pro Asp Val Ala Phe
                     115                 120                 125

Val Pro Leu Gly Met Thr Asp Tyr Leu Val Ile Val Glu Asp Asp Asp
                 130                 135                 140

Ser Ala Ile Ile Pro Cys Arg Thr Thr Asp Pro Glu Thr Pro Val Thr
          145                 150                 155                 160

Leu His Asn Ser Glu Gly Val Val Pro Ala Ser Tyr Asp Ser Arg Gln
                         165                 170                 175

Gly Phe Asn Gly Thr Phe Thr Val Gly Pro Tyr Ile Cys Glu Ala Thr
                     180                 185                 190

Val Lys Gly Lys Lys Phe Gln Thr Ile Pro Phe Asn Val Tyr Ala Leu
                 195                 200                 205

Lys Ala Thr Ser Glu Leu Asp Leu Glu Met Glu Ala Leu Lys Thr Val
              210                 215                 220

Tyr Lys Ser Gly Glu Thr Ile Val Val Thr Cys Ala Val Phe Asn Asn
          225                 230                 235                 240

Glu Val Val Asp Leu Gln Trp Thr Tyr Pro Gly Glu Val Lys Gly Lys
                         245                 250                 255

Gly Ile Thr Met Leu Glu Glu Ile Lys Val Pro Ser Ile Lys Leu Val
                     260                 265                 270

Tyr Thr Leu Thr Val Pro Glu Ala Thr Val Lys Asp Ser Gly Asp Tyr
                 275                 280                 285

Glu Cys Ala Ala Arg Gln Ala Thr Arg Glu Val Lys Glu Met Lys Lys
              290                 295                 300

Val Thr Ile Ser Val His Glu Lys Gly Phe Ile Glu Ile Lys Pro Thr
          305                 310                 315                 320

Phe Ser Gln Leu Glu Ala Val Asn Leu His Glu Val Lys His Phe Val
                         325                 330                 335
```

-continued

```
Val Glu Val Arg Ala Tyr Pro Pro Arg Ile Ser Trp Leu Lys Asn
            340             345             350

Asn Leu Thr Leu Ile Glu Asn Leu Thr Glu Ile Thr Thr Asp Val Glu
            355             360             365

Lys Ile Gln Glu Ile Arg Tyr Arg Ser Lys Leu Lys Leu Ile Arg Ala
            370             375             380

Lys Glu Glu Asp Ser Gly His Tyr Thr Ile Val Ala Gln Asn Glu Asp
385             390             395             400

Ala Val Lys Ser Tyr Thr Phe Glu Leu Leu Thr Gln Val Pro Ser Ser
            405             410             415

Ile Leu Asp Leu Val Asp His His Gly Ser Thr Gly Gly Gln Thr
            420             425             430

Val Arg Cys Thr Ala Glu Gly Thr Pro Leu Pro Asp Ile Glu Trp Met
            435             440             445

Ile Cys Lys Asp Ile Lys Lys Cys Asn Asn Glu Thr Ser Trp Thr Ile
            450             455             460

Leu Ala Asn Asn Val Ser Asn Ile Ile Thr Glu Ile His Ser Arg Asp
465             470             475             480

Arg Ser Thr Val Glu Gly Arg Val Thr Phe Ala Lys Val Glu Glu Thr
            485             490             495

Ile Ala Val Arg Cys Leu Ala Lys Asn Leu Leu Gly Ala Glu Asn Arg
            500             505             510

Glu Leu Lys Leu Val Ala Pro Thr Leu Arg Ser Glu Leu Thr Val Ala
            515             520             525

Ala Ala Val Leu Val Leu Leu Val Ile Val Ile Ile Ser Leu Ile Val
            530             535             540

Leu Val Val Ile Trp Lys Gln Lys Pro Arg Tyr Glu Ile Arg Trp Arg
545             550             555             560

Val Ile Glu Ser Ile Ser Pro Asp Gly His Glu Tyr Ile Tyr Val Asp
            565             570             575

Pro Met Gln Leu Pro Tyr Asp Ser Arg Trp Glu Phe Pro Arg Asp Gly
            580             585             590

Leu Val Leu Gly Arg Val Leu Gly Ser Gly Ala Phe Gly Lys Val Val
            595             600             605

Glu Gly Thr Ala Tyr Gly Leu Ser Arg Ser Gln Pro Val Met Lys Val
            610             615             620

Ala Val Lys Met Leu Lys Pro Thr Ala Arg Ser Ser Glu Lys Gln Ala
625             630             635             640

Leu Met Ser Glu Leu Lys Ile Met Thr His Leu Gly Pro His Leu Asn
            645             650             655

Ile Val Asn Leu Leu Gly Ala Cys Thr Lys Ser Gly Pro Ile Tyr Ile
            660             665             670

Ile Thr Glu Tyr Cys Phe Tyr Gly Asp Leu Val Asn Tyr Leu His Lys
            675             680             685

Asn Arg Asp Ser Phe Leu Ser His His Pro Glu Lys Pro Lys Lys Glu
            690             695             700

Leu Asp Ile Phe Gly Leu Asn Pro Ala Asp Glu Ser Thr Arg Ser Tyr
705             710             715             720

Val Ile Leu Ser Phe Glu Asn Asn Gly Asp Tyr Met Asp Met Lys Gln
            725             730             735

Ala Asp Thr Thr Gln Tyr Val Pro Met Leu Glu Arg Lys Glu Val Ser
            740             745             750

Lys Tyr Ser Asp Ile Gln Arg Ser Leu Tyr Asp Arg Pro Ala Ser Tyr
```

755                 760                 765
Lys Lys Lys Ser Met Leu Asp Ser Glu Val Lys Asn Leu Leu Ser Asp
    770                 775                 780

Asp Asn Ser Glu Gly Leu Thr Leu Leu Asp Leu Leu Ser Phe Thr Tyr
785                 790                 795                 800

Gln Val Ala Arg Gly Met Glu Phe Leu Ala Ser Lys Asn Cys Val His
                805                 810                 815

Arg Asp Leu Ala Ala Arg Asn Val Leu Leu Ala Gln Gly Lys Ile Val
            820                 825                 830

Lys Ile Cys Asp Phe Gly Leu Ala Arg Asp Ile Met His Asp Ser Asn
        835                 840                 845

Tyr Val Ser Lys Gly Ser Thr Phe Leu Pro Met Lys Trp Met Ala Pro
    850                 855                 860

Glu Ser Ile Phe Asp Asn Leu Tyr Thr Thr Leu Ser Asp Val Trp Ser
865                 870                 875                 880

Tyr Gly Ile Leu Leu Trp Glu Ile Phe Ser Leu Gly Gly Thr Pro Tyr
                885                 890                 895

Pro Gly Met Met Val Asp Ser Thr Phe Tyr Asn Lys Ile Lys Ser Gly
            900                 905                 910

Tyr Arg Met Ala Lys Pro Asp His Ala Thr Ser Glu Val Tyr Glu Ile
        915                 920                 925

Met Val Lys Cys Trp Asn Ser Glu Pro Glu Lys Arg Pro Ser Phe Tyr
    930                 935                 940

His Leu Ser Glu Ile Val Glu Asn Leu Leu Pro Gly Gln Tyr Lys Lys
945                 950                 955                 960

Ser Tyr Glu Lys Ile His Leu Asp Phe Leu Lys Ser Asp His Pro Ala
                965                 970                 975

Val Ala Arg Met Arg Val Asp Ser Asp Asn Ala Tyr Ile Gly Val Thr
            980                 985                 990

Tyr Lys Asn Glu Glu Asp Lys Leu Lys Asp Trp Glu Gly Gly Leu Asp
        995                 1000                1005

Glu Gln Arg Leu Ser Ala Asp Ser Gly Tyr Ile Ile Pro Leu Pro Asp
    1010                1015                1020

Ile Asp Pro Val Pro Glu Glu Glu Asp Leu Gly Lys Arg Asn Arg His
1025                1030                1035                1040

Ser Ser Gln Thr Ser Glu Glu Ser Ala Ile Glu Thr Gly Ser Ser Ser
                1045                1050                1055

Ser Thr Phe Ile Lys Arg Glu Asp Glu Thr Ile Glu Asp Ile Asp Met
            1060                1065                1070

Met Asp Asp Ile Gly Ile Asp Ser Ser Asp Leu Val Glu Asp Ser Phe
        1075                1080                1085

Leu

<210> SEQ ID NO 11
<211> LENGTH: 1767
<212> TYPE: DNA
<213> ORGANISM: Homo sapiens
<220> FEATURE:
<221> NAME/KEY: CDS
<222> LOCATION: (1)..(1767)

<400> SEQUENCE: 11 atg ggg act tcc cat ccg gcg ttc ctg gtc tta ggc tgt ctt ctc aca    48
Met Gly Thr Ser His Pro Ala Phe Leu Val Leu Gly Cys Leu Leu Thr
1               5                   10                  15

-continued

| | |
|---|---|
| ggg ctg agc cta atc ctc tgc cag ctt tca tta ccc tct atc ctt cca<br>Gly Leu Ser Leu Ile Leu Cys Gln Leu Ser Leu Pro Ser Ile Leu Pro<br>          20                   25                  30 | 96 |
| aat gaa aat gaa aag gtt gtg cag ctg aat tca tcc ttt tct ctg aga<br>Asn Glu Asn Glu Lys Val Val Gln Leu Asn Ser Ser Phe Ser Leu Arg<br>          35                   40                  45 | 144 |
| tgc ttt ggg gag agt gaa gtg agc tgg cag tac ccc atg tct gaa gaa<br>Cys Phe Gly Glu Ser Glu Val Ser Trp Gln Tyr Pro Met Ser Glu Glu<br>50                   55                   60 | 192 |
| gag agc tcc gat gtg gaa atc aga aat gaa gaa aac aac agc ggc ctt<br>Glu Ser Ser Asp Val Glu Ile Arg Asn Glu Glu Asn Asn Ser Gly Leu<br>65                   70                   75                80 | 240 |
| ttt gtg acg gtc ttg gaa gtg agc agt gcc tcg gcg gcc cac aca ggg<br>Phe Val Thr Val Leu Glu Val Ser Ser Ala Ser Ala Ala His Thr Gly<br>                  85                   90                  95 | 288 |
| ttg tac act tgc tat tac aac cac act cag aca gaa gag aat gag ctt<br>Leu Tyr Thr Cys Tyr Tyr Asn His Thr Gln Thr Glu Glu Asn Glu Leu<br>          100                  105               110 | 336 |
| gaa ggc agg cac att tac atc tat gtg cca gac cca gat gta gcc ttt<br>Glu Gly Arg His Ile Tyr Ile Tyr Val Pro Asp Pro Asp Val Ala Phe<br>          115                  120               125 | 384 |
| gta cct cta gga atg acg gat tat tta gtc atc gtg gag gat gat gat<br>Val Pro Leu Gly Met Thr Asp Tyr Leu Val Ile Val Glu Asp Asp Asp<br>130                   135                   140 | 432 |
| tct gcc att ata cct tgt cgc aca act gat ccc gag act cct gta acc<br>Ser Ala Ile Ile Pro Cys Arg Thr Thr Asp Pro Glu Thr Pro Val Thr<br>145                   150                   155               160 | 480 |
| tta cac aac agt gag ggg gtg gta cct gcc tcc tac gac agc aga cag<br>Leu His Asn Ser Glu Gly Val Val Pro Ala Ser Tyr Asp Ser Arg Gln<br>                  165                  170               175 | 528 |
| ggc ttt aat ggg acc ttc act gta ggg ccc tat atc tgt gag gcc acc<br>Gly Phe Asn Gly Thr Phe Thr Val Gly Pro Tyr Ile Cys Glu Ala Thr<br>          180                  185               190 | 576 |
| gtc aaa gga aag aag ttc cag acc atc cca ttt aat gtt tat gct tta<br>Val Lys Gly Lys Lys Phe Gln Thr Ile Pro Phe Asn Val Tyr Ala Leu<br>          195                  200               205 | 624 |
| aaa gca aca tca gag ctg gat cta gaa atg gaa gct ctt aaa acc gtg<br>Lys Ala Thr Ser Glu Leu Asp Leu Glu Met Glu Ala Leu Lys Thr Val<br>210                   215                   220 | 672 |
| tat aag tca ggg gaa acg att gtg gtc acc tgt gct gtt ttt aac aat<br>Tyr Lys Ser Gly Glu Thr Ile Val Val Thr Cys Ala Val Phe Asn Asn<br>225                   230                   235               240 | 720 |
| gag gtg gtt gac ctt caa tgg act tac cct gga gaa gtg aaa ggc aaa<br>Glu Val Val Asp Leu Gln Trp Thr Tyr Pro Gly Glu Val Lys Gly Lys<br>                  245                  250               255 | 768 |
| ggc atc aca atg ctg gaa gaa atc aaa gtc cca tcc atc aaa ttg gtg<br>Gly Ile Thr Met Leu Glu Glu Ile Lys Val Pro Ser Ile Lys Leu Val<br>          260                  265               270 | 816 |
| tac act ttg acg gtc ccc gag gcc acg gtg aaa gac agt gga gat tac<br>Tyr Thr Leu Thr Val Pro Glu Ala Thr Val Lys Asp Ser Gly Asp Tyr<br>          275                  280               285 | 864 |
| gaa tgt gct gcc cgc cag gct acc agg gag gtc aaa gaa atg aag aaa<br>Glu Cys Ala Ala Arg Gln Ala Thr Arg Glu Val Lys Glu Met Lys Lys<br>290                   295                   300 | 912 |
| gtc act att tct gtc cat gag aaa ggt ttc att gaa atc aaa ccc acc<br>Val Thr Ile Ser Val His Glu Lys Gly Phe Ile Glu Ile Lys Pro Thr<br>305                   310                   315               320 | 960 |
| ttc agc cag ttg gaa gct gtc aac ctg cat gaa gtc aaa cat ttt gtt<br>Phe Ser Gln Leu Glu Ala Val Asn Leu His Glu Val Lys His Phe Val<br>          325                  330               335 | 1008 |

-continued

```
gta gag gtg cgg gcc tac cca cct ccc agg ata tcc tgg ctg aaa aac      1056
Val Glu Val Arg Ala Tyr Pro Pro Pro Arg Ile Ser Trp Leu Lys Asn
            340                 345                 350 aat ctg act ctg att gaa aat ctc act gag atc acc act gat gtg gaa      1104
Asn Leu Thr Leu Ile Glu Asn Leu Thr Glu Ile Thr Thr Asp Val Glu
            355                 360                 365 aag att cag gaa ata agg tat cga agc aaa tta aag ctg atc cgt gct      1152
Lys Ile Gln Glu Ile Arg Tyr Arg Ser Lys Leu Lys Leu Ile Arg Ala
    370                 375                 380 aag gaa gaa gac agt ggc cat tat act att gta gct caa aat gaa gat      1200
Lys Glu Glu Asp Ser Gly His Tyr Thr Ile Val Ala Gln Asn Glu Asp
385                 390                 395                 400 gct gtg aag agc tat act ttt gaa ctg tta act caa gtt cct tca tcc      1248
Ala Val Lys Ser Tyr Thr Phe Glu Leu Leu Thr Gln Val Pro Ser Ser
            405                 410                 415 att ctg gac ttg gtc gat gat cac cat ggc tca act ggg gga cag acg      1296
Ile Leu Asp Leu Val Asp Asp His His Gly Ser Thr Gly Gly Gln Thr
            420                 425                 430 gtg agg tgc aca gct gaa ggc acg ccg ctt cct gat att gag tgg atg      1344
Val Arg Cys Thr Ala Glu Gly Thr Pro Leu Pro Asp Ile Glu Trp Met
            435                 440                 445 ata tgc aaa gat att aag aaa tgt aat aat gaa act tcc tgg act att      1392
Ile Cys Lys Asp Ile Lys Lys Cys Asn Asn Glu Thr Ser Trp Thr Ile
450                 455                 460 ttg gcc aac aat gtc tca aac atc atc acg gag atc cac tcc cga gac      1440
Leu Ala Asn Asn Val Ser Asn Ile Ile Thr Glu Ile His Ser Arg Asp
465                 470                 475                 480 agg agt acc gtg gag ggc cgt gtg act ttc gcc aaa gtg gag gag acc      1488
Arg Ser Thr Val Glu Gly Arg Val Thr Phe Ala Lys Val Glu Glu Thr
            485                 490                 495 atc gcc gtg cga tgc ctg gct aag aat ctc ctt gga gct gag aac cga      1536
Ile Ala Val Arg Cys Leu Ala Lys Asn Leu Leu Gly Ala Glu Asn Arg
            500                 505                 510 gag ctg aag ctg gtg gct ccc acc ctg cgt tct gaa ctc acg gtg gct      1584
Glu Leu Lys Leu Val Ala Pro Thr Leu Arg Ser Glu Leu Thr Val Ala
            515                 520                 525 gct gca gtc ctg gtg ctg ttg gtg att gtg atc atc tca ctt att gtc      1632
Ala Ala Val Leu Val Leu Leu Val Ile Val Ile Ile Ser Leu Ile Val
            530                 535                 540 ctg gtt gtc att tgg aaa cag aaa ccg agg tat gaa att cgc tgg agg      1680
Leu Val Val Ile Trp Lys Gln Lys Pro Arg Tyr Glu Ile Arg Trp Arg
545                 550                 555                 560 gtc att gaa tca atc agc ccg gat gga cat gaa tat att tat gtg gac      1728
Val Ile Glu Ser Ile Ser Pro Asp Gly His Glu Tyr Ile Tyr Val Asp
            565                 570                 575 ccg atg cag ctg cct tat gac tca aga tgg gag ttt cca                  1767
Pro Met Gln Leu Pro Tyr Asp Ser Arg Trp Glu Phe Pro
            580                 585

<210> SEQ ID NO 12
<211> LENGTH: 589
<212> TYPE: PRT
<213> ORGANISM: Homo sapiens

<400> SEQUENCE: 12

Met Gly Thr Ser His Pro Ala Phe Leu Val Leu Gly Cys Leu Leu Thr
  1               5                  10                  15

Gly Leu Ser Leu Ile Leu Cys Gln Leu Ser Leu Pro Ser Ile Leu Pro
             20                  25                  30
```

-continued

```
Asn Glu Asn Glu Lys Val Val Gln Leu Asn Ser Ser Phe Ser Leu Arg
         35                  40                  45
Cys Phe Gly Glu Ser Glu Val Ser Trp Gln Tyr Pro Met Ser Glu Glu
     50                  55                  60
Glu Ser Ser Asp Val Glu Ile Arg Asn Glu Asn Asn Ser Gly Leu
 65              70                  75                  80
Phe Val Thr Val Leu Glu Val Ser Ala Ser Ala Ala His Thr Gly
             85                  90                  95
Leu Tyr Thr Cys Tyr Tyr Asn His Thr Gln Thr Glu Glu Asn Glu Leu
            100                 105                 110
Glu Gly Arg His Ile Tyr Ile Tyr Val Pro Asp Pro Asp Val Ala Phe
            115                 120                 125
Val Pro Leu Gly Met Thr Asp Tyr Leu Val Ile Val Glu Asp Asp Asp
130                 135                 140
Ser Ala Ile Ile Pro Cys Arg Thr Thr Asp Pro Glu Thr Pro Val Thr
145                 150                 155                 160
Leu His Asn Ser Glu Gly Val Val Pro Ala Ser Tyr Asp Ser Arg Gln
                165                 170                 175
Gly Phe Asn Gly Thr Phe Thr Val Gly Pro Tyr Ile Cys Glu Ala Thr
            180                 185                 190
Val Lys Gly Lys Lys Phe Gln Thr Ile Pro Phe Asn Val Tyr Ala Leu
            195                 200                 205
Lys Ala Thr Ser Glu Leu Asp Leu Glu Met Glu Ala Leu Lys Thr Val
210                 215                 220
Tyr Lys Ser Gly Glu Thr Ile Val Val Thr Cys Ala Val Phe Asn Asn
225                 230                 235                 240
Glu Val Val Asp Leu Gln Trp Thr Tyr Pro Gly Glu Val Lys Gly Lys
                245                 250                 255
Gly Ile Thr Met Leu Glu Glu Ile Lys Val Pro Ser Ile Lys Leu Val
            260                 265                 270
Tyr Thr Leu Thr Val Pro Glu Ala Thr Val Lys Asp Ser Gly Asp Tyr
            275                 280                 285
Glu Cys Ala Ala Arg Gln Ala Thr Arg Glu Val Lys Glu Met Lys Lys
            290                 295                 300
Val Thr Ile Ser Val His Glu Lys Gly Phe Ile Glu Ile Lys Pro Thr
305                 310                 315                 320
Phe Ser Gln Leu Glu Ala Val Asn Leu His Glu Val Lys His Phe Val
                325                 330                 335
Val Glu Val Arg Ala Tyr Pro Pro Arg Ile Ser Trp Leu Lys Asn
                340                 345                 350
Asn Leu Thr Leu Ile Glu Asn Leu Thr Glu Ile Thr Thr Asp Val Glu
            355                 360                 365
Lys Ile Gln Glu Ile Arg Tyr Arg Ser Lys Leu Lys Leu Ile Arg Ala
            370                 375                 380
Lys Glu Glu Asp Ser Gly His Tyr Thr Ile Val Ala Gln Asn Glu Asp
385                 390                 395                 400
Ala Val Lys Ser Tyr Thr Phe Glu Leu Leu Thr Gln Val Pro Ser Ser
                405                 410                 415
Ile Leu Asp Leu Val Asp His His Gly Ser Thr Gly Gly Gln Thr
            420                 425                 430
Val Arg Cys Thr Ala Glu Gly Thr Pro Leu Pro Asp Ile Glu Trp Met
            435                 440                 445
Ile Cys Lys Asp Ile Lys Lys Cys Asn Asn Glu Thr Ser Trp Thr Ile
```

-continued

```
                    450                 455                 460
Leu Ala Asn Asn Val Ser Asn Ile Ile Thr Glu Ile His Ser Arg Asp
465                 470                 475                 480

Arg Ser Thr Val Glu Gly Arg Val Thr Phe Ala Lys Val Glu Glu Thr
                    485                 490                 495

Ile Ala Val Arg Cys Leu Ala Lys Asn Leu Leu Gly Ala Glu Asn Arg
                500                 505                 510

Glu Leu Lys Leu Val Ala Pro Thr Leu Arg Ser Glu Leu Thr Val Ala
            515                 520                 525

Ala Ala Val Leu Val Leu Leu Val Ile Val Ile Ser Leu Ile Val
        530                 535                 540

Leu Val Val Ile Trp Lys Gln Lys Pro Arg Tyr Glu Ile Arg Trp Arg
545                 550                 555                 560

Val Ile Glu Ser Ile Ser Pro Asp Gly His Glu Tyr Ile Tyr Val Asp
                565                 570                 575

Pro Met Gln Leu Pro Tyr Asp Ser Arg Trp Glu Phe Pro
            580                 585

<210> SEQ ID NO 13
<211> LENGTH: 3321
<212> TYPE: DNA
<213> ORGANISM: Homo sapiens
<220> FEATURE:
<221> NAME/KEY: CDS
<222> LOCATION: (1)..(3270)

<400> SEQUENCE: 13 atg cgg ctt ccg ggt gcg atg cca gct ctg gcc ctc aaa ggc gag ctg        48
Met Arg Leu Pro Gly Ala Met Pro Ala Leu Ala Leu Lys Gly Glu Leu
  1               5                  10                  15 ctg ttg ctg tct ctc ctg tta ctt ctg gaa cca cag atc tct cag ggc        96
Leu Leu Leu Ser Leu Leu Leu Leu Glu Pro Gln Ile Ser Gln Gly
             20                  25                  30 ctg gtc gtc aca ccc ccg ggg cca gag ctt gtc ctc aat gtc tcc agc       144
Leu Val Val Thr Pro Pro Gly Pro Glu Leu Val Leu Asn Val Ser Ser
         35                  40                  45 acc ttc gtt ctg acc tgc tcg ggt tca gct ccg gtg gtg tgg gaa cgg       192
Thr Phe Val Leu Thr Cys Ser Gly Ser Ala Pro Val Val Trp Glu Arg
 50                  55                  60 atg tcc cag gag ccc cca cag gaa atg gcc aag gcc cag gat ggc acc       240
Met Ser Gln Glu Pro Pro Gln Glu Met Ala Lys Ala Gln Asp Gly Thr
 65                  70                  75                  80 ttc tcc agc gtg ctc aca ctg acc aac ctc act ggg cta gac acg gga       288
Phe Ser Ser Val Leu Thr Leu Thr Asn Leu Thr Gly Leu Asp Thr Gly
                 85                  90                  95 gaa tac ttt tgc acc cac aat gac tcc cgt gga ctg gag acc gat gag       336
Glu Tyr Phe Cys Thr His Asn Asp Ser Arg Gly Leu Glu Thr Asp Glu
            100                 105                 110 cgg aaa cgg ctc tac atc ttt gtg cca gat ccc acc gtg ggc ttc ctc       384
Arg Lys Arg Leu Tyr Ile Phe Val Pro Asp Pro Thr Val Gly Phe Leu
        115                 120                 125 cct aat gat gcc gag gaa cta ttc atc ttt ctc acg gaa ata act gag       432
Pro Asn Asp Ala Glu Glu Leu Phe Ile Phe Leu Thr Glu Ile Thr Glu
    130                 135                 140 atc acc att cca tgc cga gta aca gac cca cag ctg gtg gtg aca ctg       480
Ile Thr Ile Pro Cys Arg Val Thr Asp Pro Gln Leu Val Val Thr Leu
145                 150                 155                 160 cac gag aag aaa ggg gac gtt gca ctg cct gtc ccc tat gat cac caa       528
His Glu Lys Lys Gly Asp Val Ala Leu Pro Val Pro Tyr Asp His Gln
```

-continued

|     |     |     |     |     |     |     |     |     |     |     |     |     |     |     |     |      |
|-----|-----|-----|-----|-----|-----|-----|-----|-----|-----|-----|-----|-----|-----|-----|-----|------|
|     |     |     |     | 165 |     |     |     |     | 170 |     |     |     |     | 175 |     |      |
| cgt | ggc | ttt | tct | ggt | atc | ttt | gag | gac | aga | agc | tac | atc | tgc | aaa | acc | 576  |
| Arg | Gly | Phe | Ser | Gly | Ile | Phe | Glu | Asp | Arg | Ser | Tyr | Ile | Cys | Lys | Thr |      |
|     |     |     | 180 |     |     |     |     | 185 |     |     |     |     | 190 |     |     |      |
| acc | att | ggg | gac | agg | gag | gtg | gat | tct | gat | gcc | tac | tat | gtc | tac | aga | 624  |
| Thr | Ile | Gly | Asp | Arg | Glu | Val | Asp | Ser | Asp | Ala | Tyr | Tyr | Val | Tyr | Arg |      |
|     |     | 195 |     |     |     |     | 200 |     |     |     |     | 205 |     |     |     |      |
| ctc | cag | gtg | tca | tcc | atc | aac | gtc | tct | gtg | aac | gca | gtg | cag | act | gtg | 672  |
| Leu | Gln | Val | Ser | Ser | Ile | Asn | Val | Ser | Val | Asn | Ala | Val | Gln | Thr | Val |      |
|     | 210 |     |     |     |     | 215 |     |     |     |     | 220 |     |     |     |     |      |
| gtc | cgc | cag | ggt | gag | aac | atc | acc | ctc | atg | tgc | att | gtg | atc | ggg | aat | 720  |
| Val | Arg | Gln | Gly | Glu | Asn | Ile | Thr | Leu | Met | Cys | Ile | Val | Ile | Gly | Asn |      |
| 225 |     |     |     |     | 230 |     |     |     |     | 235 |     |     |     |     | 240 |      |
| gag | gtg | gtc | aac | ttc | gag | tgg | aca | tac | ccc | cgc | aaa | gaa | agt | ggg | cgg | 768  |
| Glu | Val | Val | Asn | Phe | Glu | Trp | Thr | Tyr | Pro | Arg | Lys | Glu | Ser | Gly | Arg |      |
|     |     |     |     | 245 |     |     |     |     | 250 |     |     |     |     | 255 |     |      |
| ctg | gtg | gag | ccg | gtg | act | gac | ttc | ctc | ttg | gat | atg | cct | tac | cac | atc | 816  |
| Leu | Val | Glu | Pro | Val | Thr | Asp | Phe | Leu | Leu | Asp | Met | Pro | Tyr | His | Ile |      |
|     |     |     | 260 |     |     |     |     | 265 |     |     |     |     | 270 |     |     |      |
| cgc | tcc | atc | ctg | cac | atc | ccc | agt | gcc | gag | tta | gaa | gac | tcg | ggg | acc | 864  |
| Arg | Ser | Ile | Leu | His | Ile | Pro | Ser | Ala | Glu | Leu | Glu | Asp | Ser | Gly | Thr |      |
|     |     | 275 |     |     |     |     | 280 |     |     |     |     | 285 |     |     |     |      |
| tac | acc | tgc | aat | gtg | acg | gag | agt | gtg | aat | gac | cat | cag | gat | gaa | aag | 912  |
| Tyr | Thr | Cys | Asn | Val | Thr | Glu | Ser | Val | Asn | Asp | His | Gln | Asp | Glu | Lys |      |
|     | 290 |     |     |     |     | 295 |     |     |     |     | 300 |     |     |     |     |      |
| gcc | atc | aac | atc | acc | gtg | gtt | gag | agc | ggc | tac | gtg | cgg | ctc | ctg | gga | 960  |
| Ala | Ile | Asn | Ile | Thr | Val | Val | Glu | Ser | Gly | Tyr | Val | Arg | Leu | Leu | Gly |      |
| 305 |     |     |     |     | 310 |     |     |     |     | 315 |     |     |     |     | 320 |      |
| gag | gtg | ggc | aca | cta | caa | ttt | gct | gag | ctg | cat | cgg | agc | cgg | aca | ctg | 1008 |
| Glu | Val | Gly | Thr | Leu | Gln | Phe | Ala | Glu | Leu | His | Arg | Ser | Arg | Thr | Leu |      |
|     |     |     |     | 325 |     |     |     |     | 330 |     |     |     |     | 335 |     |      |
| cag | gta | gtg | ttc | gag | gcc | tac | cca | ccg | ccc | act | gtc | ctg | tgg | ttc | aaa | 1056 |
| Gln | Val | Val | Phe | Glu | Ala | Tyr | Pro | Pro | Pro | Thr | Val | Leu | Trp | Phe | Lys |      |
|     |     |     | 340 |     |     |     |     | 345 |     |     |     |     | 350 |     |     |      |
| gac | aac | cgc | acc | ctg | ggc | gac | tcc | agc | gct | ggc | gaa | atc | gcc | ctg | tcc | 1104 |
| Asp | Asn | Arg | Thr | Leu | Gly | Asp | Ser | Ser | Ala | Gly | Glu | Ile | Ala | Leu | Ser |      |
|     |     | 355 |     |     |     |     | 360 |     |     |     |     | 365 |     |     |     |      |
| acg | cgc | aac | gtg | tcg | gag | acc | cgg | tat | gtg | tca | gag | ctg | aca | ctg | gtt | 1152 |
| Thr | Arg | Asn | Val | Ser | Glu | Thr | Arg | Tyr | Val | Ser | Glu | Leu | Thr | Leu | Val |      |
|     | 370 |     |     |     |     | 375 |     |     |     |     | 380 |     |     |     |     |      |
| cgc | gtg | aag | gtg | gca | gag | gct | ggc | cac | tac | acc | atg | cgg | gcc | ttc | cat | 1200 |
| Arg | Val | Lys | Val | Ala | Glu | Ala | Gly | His | Tyr | Thr | Met | Arg | Ala | Phe | His |      |
| 385 |     |     |     |     | 390 |     |     |     |     | 395 |     |     |     |     | 400 |      |
| gag | gat | gct | gag | gtc | cag | ctc | tcc | ttc | cag | cta | cag | atc | aat | gtc | cct | 1248 |
| Glu | Asp | Ala | Glu | Val | Gln | Leu | Ser | Phe | Gln | Leu | Gln | Ile | Asn | Val | Pro |      |
|     |     |     |     | 405 |     |     |     |     | 410 |     |     |     |     | 415 |     |      |
| gtc | cga | gtg | ctg | gag | cta | agt | gag | agc | cac | cct | gac | agt | ggg | gaa | cag | 1296 |
| Val | Arg | Val | Leu | Glu | Leu | Ser | Glu | Ser | His | Pro | Asp | Ser | Gly | Glu | Gln |      |
|     |     |     | 420 |     |     |     |     | 425 |     |     |     |     | 430 |     |     |      |
| aca | gtc | cgc | tgt | cgt | ggc | cgg | ggc | atg | ccc | cag | ccg | aac | atc | atc | tgg | 1344 |
| Thr | Val | Arg | Cys | Arg | Gly | Arg | Gly | Met | Pro | Gln | Pro | Asn | Ile | Ile | Trp |      |
|     |     | 435 |     |     |     |     | 440 |     |     |     |     | 445 |     |     |     |      |
| tct | gcc | tgc | aga | gac | ctc | aaa | agg | tgt | cca | cgt | gag | ctg | ccg | ccc | acg | 1392 |
| Ser | Ala | Cys | Arg | Asp | Leu | Lys | Arg | Cys | Pro | Arg | Glu | Leu | Pro | Pro | Thr |      |
|     | 450 |     |     |     |     | 455 |     |     |     |     | 460 |     |     |     |     |      |
| ctg | ctg | ggg | aac | agt | tcc | gaa | gag | gag | agc | cag | ctg | gag | act | aac | gtg | 1440 |
| Leu | Leu | Gly | Asn | Ser | Ser | Glu | Glu | Glu | Ser | Gln | Leu | Glu | Thr | Asn | Val |      |
| 465 |     |     |     |     | 470 |     |     |     |     | 475 |     |     |     |     | 480 |      |
| acg | tac | tgg | gag | gag | gag | cag | gag | ttt | gag | gtg | gtg | agc | aca | ctg | cgt | 1488 |

```
Thr Tyr Trp Glu Glu Glu Gln Glu Phe Glu Val Val Ser Thr Leu Arg
            485                 490                 495 ctg cag cac gtg gat cgg cca ctg tcg gtg cgc tgc acg ctg cgc aac     1536
Leu Gln His Val Asp Arg Pro Leu Ser Val Arg Cys Thr Leu Arg Asn
        500                 505                 510 gct gtg ggc cag gac acg cag gag gtc atc gtg gtg cca cac tcc ttg     1584
Ala Val Gly Gln Asp Thr Gln Glu Val Ile Val Val Pro His Ser Leu
515                 520                 525 ccc ttt aag gtg gtg gtg atc tca gcc atc ctg gcc ctg gtg gtg ctc     1632
Pro Phe Lys Val Val Val Ile Ser Ala Ile Leu Ala Leu Val Val Leu
    530                 535                 540 acc atc atc tcc ctt atc atc ctc atc atg ctt tgg cag aag aag cca     1680
Thr Ile Ile Ser Leu Ile Ile Leu Ile Met Leu Trp Gln Lys Lys Pro
545                 550                 555                 560 cgt tac gag atc cga tgg aag gtg att gag tct gtg agc tct gac ggc     1728
Arg Tyr Glu Ile Arg Trp Lys Val Ile Glu Ser Val Ser Ser Asp Gly
                565                 570                 575 cat gag tac atc tac gtg gac ccc atg cag ctg ccc tat gac tcc acg     1776
His Glu Tyr Ile Tyr Val Asp Pro Met Gln Leu Pro Tyr Asp Ser Thr
            580                 585                 590 tgg gag ctg ccg cgg gac cag ctt gtg ctg gga cgc acc ctc ggc tct     1824
Trp Glu Leu Pro Arg Asp Gln Leu Val Leu Gly Arg Thr Leu Gly Ser
        595                 600                 605 ggg gcc ttt ggg cag gtg gtg gag gcc acg gct cat ggc ctg agc cat     1872
Gly Ala Phe Gly Gln Val Val Glu Ala Thr Ala His Gly Leu Ser His
    610                 615                 620 tct cag gcc acg atg aaa gtg gcc gtc aag atg ctt aaa tcc aca gcc     1920
Ser Gln Ala Thr Met Lys Val Ala Val Lys Met Leu Lys Ser Thr Ala
625                 630                 635                 640 cgc agc agt gag aag caa gcc ctt atg tcg gag ctg aag atc atg agt     1968
Arg Ser Ser Glu Lys Gln Ala Leu Met Ser Glu Leu Lys Ile Met Ser
                645                 650                 655 cac ctt ggg ccc cac ctg aac gtg gtc aac ctg ttg ggg gcc tgc acc     2016
His Leu Gly Pro His Leu Asn Val Val Asn Leu Leu Gly Ala Cys Thr
            660                 665                 670 aaa gga gga ccc atc tat atc atc act gag tac tgc cgc tac gga gac     2064
Lys Gly Gly Pro Ile Tyr Ile Ile Thr Glu Tyr Cys Arg Tyr Gly Asp
        675                 680                 685 ctg gtg gac tac ctg cac cgc aac aaa cac acc ttc ctg cag cac cac     2112
Leu Val Asp Tyr Leu His Arg Asn Lys His Thr Phe Leu Gln His His
    690                 695                 700 tcc gac aag cgc cgc ccg ccc agc gcg gag ctc tac agc aat gct ctg     2160
Ser Asp Lys Arg Arg Pro Pro Ser Ala Glu Leu Tyr Ser Asn Ala Leu
705                 710                 715                 720 ccc gtt ggg ctc ccc ctg ccc agc cat gtg tcc ttg acc ggg gag agc     2208
Pro Val Gly Leu Pro Leu Pro Ser His Val Ser Leu Thr Gly Glu Ser
                725                 730                 735 gac ggt ggc tac atg gac atg agc aag gac gag tcg gtg gac tat gtg     2256
Asp Gly Gly Tyr Met Asp Met Ser Lys Asp Glu Ser Val Asp Tyr Val
            740                 745                 750 ccc atg ctg gac atg aaa gga gac gtc aaa tat gca gac atc gag tcc     2304
Pro Met Leu Asp Met Lys Gly Asp Val Lys Tyr Ala Asp Ile Glu Ser
        755                 760                 765 tcc aac tac atg gcc cct tac gat aac tac gtt ccc tct gcc cct gag     2352
Ser Asn Tyr Met Ala Pro Tyr Asp Asn Tyr Val Pro Ser Ala Pro Glu
    770                 775                 780 agg acc tgc cga gca act ttg atc aac gag tct cca gtg cta agc tac     2400
Arg Thr Cys Arg Ala Thr Leu Ile Asn Glu Ser Pro Val Leu Ser Tyr
785                 790                 795                 800
```

-continued

| | | |
|---|---|---|
| atg gac ctc gtg ggc ttc agc tac cag gtg gcc aat ggc atg gag ttt<br>Met Asp Leu Val Gly Phe Ser Tyr Gln Val Ala Asn Gly Met Glu Phe<br>805 810 815 | | 2448 |
| ctg gcc tcc aag aac tgc gtc cac aga gac ctg gcg gct agg aac gtg<br>Leu Ala Ser Lys Asn Cys Val His Arg Asp Leu Ala Ala Arg Asn Val<br>820 825 830 | | 2496 |
| ctc atc tgt gaa ggc aag ctg gtc aag atc tgt gac ttt ggc ctg gct<br>Leu Ile Cys Glu Gly Lys Leu Val Lys Ile Cys Asp Phe Gly Leu Ala<br>835 840 845 | | 2544 |
| cga gac atc atg cgg gac tcg aat tac atc tcc aaa ggc agc acc ttt<br>Arg Asp Ile Met Arg Asp Ser Asn Tyr Ile Ser Lys Gly Ser Thr Phe<br>850 855 860 | | 2592 |
| ttg cct tta aag tgg atg gct ccg gag agc atc ttc aac agc ctc tac<br>Leu Pro Leu Lys Trp Met Ala Pro Glu Ser Ile Phe Asn Ser Leu Tyr<br>865 870 875 880 | | 2640 |
| acc acc ctg agc gac gtg tgg tcc ttc ggg atc ctg ctc tgg gag atc<br>Thr Thr Leu Ser Asp Val Trp Ser Phe Gly Ile Leu Leu Trp Glu Ile<br>885 890 895 | | 2688 |
| ttc acc ttg ggt ggc acc cct tac cca gag ctg ccc atg aac gag cag<br>Phe Thr Leu Gly Gly Thr Pro Tyr Pro Glu Leu Pro Met Asn Glu Gln<br>900 905 910 | | 2736 |
| ttc tac aat gcc atc aaa cgg ggt tac cgc atg gcc cag cct gcc cat<br>Phe Tyr Asn Ala Ile Lys Arg Gly Tyr Arg Met Ala Gln Pro Ala His<br>915 920 925 | | 2784 |
| gcc tcc gac gag atc tat gag atc atg cag aag tgc tgg gaa gag aag<br>Ala Ser Asp Glu Ile Tyr Glu Ile Met Gln Lys Cys Trp Glu Glu Lys<br>930 935 940 | | 2832 |
| ttt gag att cgg ccc ccc ttc tcc cag ctg gtg ctg ctt ctc gag aga<br>Phe Glu Ile Arg Pro Pro Phe Ser Gln Leu Val Leu Leu Leu Glu Arg<br>945 950 955 960 | | 2880 |
| ctg ttg ggc gaa ggt tac aaa aag aag tac cag cag gtg gat gag gag<br>Leu Leu Gly Glu Gly Tyr Lys Lys Lys Tyr Gln Gln Val Asp Glu Glu<br>965 970 975 | | 2928 |
| ttt ctg agg agt gac cac cca gcc atc ctt cgg tcc cag gcc cgc ttg<br>Phe Leu Arg Ser Asp His Pro Ala Ile Leu Arg Ser Gln Ala Arg Leu<br>980 985 990 | | 2976 |
| cct ggg ttc cat ggc ctc cga tct ccc ctg gac acc agc tcc gtc ctc<br>Pro Gly Phe His Gly Leu Arg Ser Pro Leu Asp Thr Ser Ser Val Leu<br>995 1000 1005 | | 3024 |
| tat act gcc gtg cag ccc aat gag ggt gac aac gac tat atc atc ccc<br>Tyr Thr Ala Val Gln Pro Asn Glu Gly Asp Asn Asp Tyr Ile Ile Pro<br>1010 1015 1020 | | 3072 |
| ctg cct gac ccc aaa ccc gag gtt gct gac gag ggc cca ctg gag ggt<br>Leu Pro Asp Pro Lys Pro Glu Val Ala Asp Glu Gly Pro Leu Glu Gly<br>1025 1030 1035 1040 | | 3120 |
| tcc ccc agc cta gcc agc tcc acc ctg aat gaa gtc aac acc tcc tca<br>Ser Pro Ser Leu Ala Ser Ser Thr Leu Asn Glu Val Asn Thr Ser Ser<br>1045 1050 1055 | | 3168 |
| acc atc tcc tgt gac agc ccc ctg gag ccc cag gac gaa cca gag cca<br>Thr Ile Ser Cys Asp Ser Pro Leu Glu Pro Gln Asp Glu Pro Glu Pro<br>1060 1065 1070 | | 3216 |
| gag ccc cag ctt gag ctc cag gtg gag ccg gag cca gag ctg gaa cag<br>Glu Pro Gln Leu Glu Leu Gln Val Glu Pro Glu Pro Glu Leu Glu Gln<br>1075 1080 1085 | | 3264 |
| ttg ccg gattcggggt gccctgcgcc tcgggcggaa gcagaggata gcttcctgta g<br>Leu Pro<br>1090 | | 3321 |

<210> SEQ ID NO 14
<211> LENGTH: 1090

```
<212> TYPE: PRT
<213> ORGANISM: Homo sapiens

<400> SEQUENCE: 14

Met Arg Leu Pro Gly Ala Met Pro Ala Leu Ala Leu Lys Gly Glu Leu
  1               5                  10                  15

Leu Leu Leu Ser Leu Leu Leu Leu Glu Pro Gln Ile Ser Gln Gly
             20                  25                  30

Leu Val Val Thr Pro Pro Gly Pro Glu Leu Val Leu Asn Val Ser Ser
             35                  40                  45

Thr Phe Val Leu Thr Cys Ser Gly Ser Ala Pro Val Val Trp Glu Arg
         50                  55                  60

Met Ser Gln Glu Pro Pro Gln Glu Met Ala Lys Ala Gln Asp Gly Thr
 65                  70                  75                  80

Phe Ser Ser Val Leu Thr Leu Thr Asn Leu Thr Gly Leu Asp Thr Gly
                 85                  90                  95

Glu Tyr Phe Cys Thr His Asn Asp Ser Arg Gly Leu Glu Thr Asp Glu
                100                 105                 110

Arg Lys Arg Leu Tyr Ile Phe Val Pro Asp Pro Thr Val Gly Phe Leu
            115                 120                 125

Pro Asn Asp Ala Glu Glu Leu Phe Ile Phe Leu Thr Glu Ile Thr Glu
        130                 135                 140

Ile Thr Ile Pro Cys Arg Val Thr Asp Pro Gln Leu Val Val Thr Leu
145                 150                 155                 160

His Glu Lys Lys Gly Asp Val Ala Leu Pro Val Pro Tyr Asp His Gln
                165                 170                 175

Arg Gly Phe Ser Gly Ile Phe Glu Asp Arg Ser Tyr Ile Cys Lys Thr
            180                 185                 190

Thr Ile Gly Asp Arg Glu Val Asp Ser Asp Ala Tyr Tyr Val Tyr Arg
        195                 200                 205

Leu Gln Val Ser Ser Ile Asn Val Ser Val Asn Ala Val Gln Thr Val
        210                 215                 220

Val Arg Gln Gly Glu Asn Ile Thr Leu Met Cys Ile Val Ile Gly Asn
225                 230                 235                 240

Glu Val Val Asn Phe Glu Trp Thr Tyr Pro Arg Lys Glu Ser Gly Arg
                245                 250                 255

Leu Val Glu Pro Val Thr Asp Phe Leu Leu Asp Met Pro Tyr His Ile
            260                 265                 270

Arg Ser Ile Leu His Ile Pro Ser Ala Glu Leu Glu Asp Ser Gly Thr
        275                 280                 285

Tyr Thr Cys Asn Val Thr Glu Ser Val Asn Asp His Gln Asp Glu Lys
        290                 295                 300

Ala Ile Asn Ile Thr Val Val Glu Ser Gly Tyr Val Arg Leu Leu Gly
305                 310                 315                 320

Glu Val Gly Thr Leu Gln Phe Ala Glu Leu His Arg Ser Arg Thr Leu
                325                 330                 335

Gln Val Val Phe Glu Ala Tyr Pro Pro Pro Thr Val Leu Trp Phe Lys
            340                 345                 350

Asp Asn Arg Thr Leu Gly Asp Ser Ser Ala Gly Glu Ile Ala Leu Ser
        355                 360                 365

Thr Arg Asn Val Ser Glu Thr Arg Tyr Val Ser Glu Leu Thr Leu Val
        370                 375                 380

Arg Val Lys Val Ala Glu Ala Gly His Tyr Thr Met Arg Ala Phe His
385                 390                 395                 400
```

-continued

```
Glu Asp Ala Glu Val Gln Leu Ser Phe Gln Leu Gln Ile Asn Val Pro
                405                 410                 415
Val Arg Val Leu Glu Leu Ser Glu Ser His Pro Asp Ser Gly Glu Gln
            420                 425                 430
Thr Val Arg Cys Arg Gly Arg Gly Met Pro Gln Pro Asn Ile Ile Trp
        435                 440                 445
Ser Ala Cys Arg Asp Leu Lys Arg Cys Pro Arg Glu Leu Pro Pro Thr
    450                 455                 460
Leu Leu Gly Asn Ser Ser Glu Glu Ser Gln Leu Glu Thr Asn Val
465                 470                 475                 480
Thr Tyr Trp Glu Glu Gln Glu Phe Glu Val Val Ser Thr Leu Arg
                485                 490                 495
Leu Gln His Val Asp Arg Pro Leu Ser Val Arg Cys Thr Leu Arg Asn
            500                 505                 510
Ala Val Gly Gln Asp Thr Gln Glu Val Ile Val Pro His Ser Leu
        515                 520                 525
Pro Phe Lys Val Val Ile Ser Ala Ile Leu Ala Leu Val Val Leu
    530                 535                 540
Thr Ile Ile Ser Leu Ile Ile Leu Ile Met Leu Trp Gln Lys Lys Pro
545                 550                 555                 560
Arg Tyr Glu Ile Arg Trp Lys Val Ile Glu Ser Val Ser Ser Asp Gly
                565                 570                 575
His Glu Tyr Ile Tyr Val Asp Pro Met Gln Leu Pro Tyr Asp Ser Thr
            580                 585                 590
Trp Glu Leu Pro Arg Asp Gln Leu Val Leu Gly Arg Thr Leu Gly Ser
        595                 600                 605
Gly Ala Phe Gly Gln Val Val Glu Ala Thr Ala His Gly Leu Ser His
    610                 615                 620
Ser Gln Ala Thr Met Lys Val Ala Val Lys Met Leu Lys Ser Thr Ala
625                 630                 635                 640
Arg Ser Ser Glu Lys Gln Ala Leu Met Ser Glu Leu Lys Ile Met Ser
                645                 650                 655
His Leu Gly Pro His Leu Asn Val Val Asn Leu Leu Gly Ala Cys Thr
            660                 665                 670
Lys Gly Gly Pro Ile Tyr Ile Ile Thr Glu Tyr Cys Arg Tyr Gly Asp
        675                 680                 685
Leu Val Asp Tyr Leu His Arg Asn Lys His Thr Phe Leu Gln His His
    690                 695                 700
Ser Asp Lys Arg Arg Pro Pro Ser Ala Glu Leu Tyr Ser Asn Ala Leu
705                 710                 715                 720
Pro Val Gly Leu Pro Leu Pro Ser His Val Ser Leu Thr Gly Glu Ser
                725                 730                 735
Asp Gly Gly Tyr Met Asp Met Ser Lys Asp Glu Ser Val Asp Tyr Val
            740                 745                 750
Pro Met Leu Asp Met Lys Gly Asp Val Lys Tyr Ala Asp Ile Glu Ser
        755                 760                 765
Ser Asn Tyr Met Ala Pro Tyr Asp Asn Tyr Val Pro Ser Ala Pro Glu
    770                 775                 780
Arg Thr Cys Arg Ala Thr Leu Ile Asn Glu Ser Pro Val Leu Ser Tyr
785                 790                 795                 800
Met Asp Leu Val Gly Phe Ser Tyr Gln Val Ala Asn Gly Met Glu Phe
                805                 810                 815
```

-continued

```
Leu Ala Ser Lys Asn Cys Val His Arg Asp Leu Ala Ala Arg Asn Val
            820                 825                 830
Leu Ile Cys Glu Gly Lys Leu Val Lys Ile Cys Asp Phe Gly Leu Ala
        835                 840                 845
Arg Asp Ile Met Arg Asp Ser Asn Tyr Ile Ser Lys Gly Ser Thr Phe
    850                 855                 860
Leu Pro Leu Lys Trp Met Ala Pro Glu Ser Ile Phe Asn Ser Leu Tyr
865                 870                 875                 880
Thr Thr Leu Ser Asp Val Trp Ser Phe Gly Ile Leu Leu Trp Glu Ile
                885                 890                 895
Phe Thr Leu Gly Gly Thr Pro Tyr Pro Glu Leu Pro Met Asn Glu Gln
            900                 905                 910
Phe Tyr Asn Ala Ile Lys Arg Gly Tyr Arg Met Ala Gln Pro Ala His
        915                 920                 925
Ala Ser Asp Glu Ile Tyr Glu Ile Met Gln Lys Cys Trp Glu Glu Lys
    930                 935                 940
Phe Glu Ile Arg Pro Pro Phe Ser Gln Leu Val Leu Leu Leu Glu Arg
945                 950                 955                 960
Leu Leu Gly Glu Gly Tyr Lys Lys Tyr Gln Gln Val Asp Glu Glu
                965                 970                 975
Phe Leu Arg Ser Asp His Pro Ala Ile Leu Arg Ser Gln Ala Arg Leu
            980                 985                 990
Pro Gly Phe His Gly Leu Arg Ser Pro Leu Asp Thr Ser Ser Val Leu
        995                 1000                1005
Tyr Thr Ala Val Gln Pro Asn Glu Gly Asp Asn Asp Tyr Ile Ile Pro
    1010                1015                1020
Leu Pro Asp Pro Lys Pro Glu Val Ala Asp Glu Gly Pro Leu Glu Gly
1025                1030                1035                1040
Ser Pro Ser Leu Ala Ser Ser Thr Leu Asn Glu Val Asn Thr Ser Ser
                1045                1050                1055
Thr Ile Ser Cys Asp Ser Pro Leu Glu Pro Gln Asp Glu Pro Glu Pro
            1060                1065                1070
Glu Pro Gln Leu Glu Leu Gln Val Glu Pro Glu Pro Glu Leu Glu Gln
        1075                1080                1085
Leu Pro
    1090

<210> SEQ ID NO 15
<211> LENGTH: 3321
<212> TYPE: DNA
<213> ORGANISM: Homo sapiens
<220> FEATURE:
<221> NAME/KEY: CDS
<222> LOCATION: (1)..(3318)

<400> SEQUENCE: 15 atg cgg ctt ccg ggt gcg atg cca gct ctg gcc ctc aaa ggc gag ctg      48
Met Arg Leu Pro Gly Ala Met Pro Ala Leu Ala Leu Lys Gly Glu Leu
1               5                   10                  15 ctg ttg ctg tct ctc ctg tta ctt ctg gaa cca cag atc tct cag ggc      96
Leu Leu Leu Ser Leu Leu Leu Leu Leu Glu Pro Gln Ile Ser Gln Gly
            20                  25                  30 ctg gtc gtc aca ccc ccg ggg cca gag ctt gtc ctc aat gtc tcc agc     144
Leu Val Val Thr Pro Pro Gly Pro Glu Leu Val Leu Asn Val Ser Ser
        35                  40                  45 acc ttc gtt ctg acc tgc tcg ggt tca gct ccg gtg gtg tgg gaa cgg     192
Thr Phe Val Leu Thr Cys Ser Gly Ser Ala Pro Val Val Trp Glu Arg
```

```
                50                    55                    60
atg tcc cag gag ccc cca cag gaa atg gcc aag gcc cag gat ggc acc        240
Met Ser Gln Glu Pro Pro Gln Glu Met Ala Lys Ala Gln Asp Gly Thr
 65                  70                  75                  80 ttc tcc agc gtg ctc aca ctg acc aac ctc act ggg cta gac acg gga        288
Phe Ser Ser Val Leu Thr Leu Thr Asn Leu Thr Gly Leu Asp Thr Gly
                     85                  90                  95 gaa tac ttt tgc acc cac aat gac tcc cgt gga ctg gag acc gat gag        336
Glu Tyr Phe Cys Thr His Asn Asp Ser Arg Gly Leu Glu Thr Asp Glu
                    100                 105                 110 cgg aaa cgg ctc tac atc ttt gtg cca gat ccc acc gtg ggc ttc ctc        384
Arg Lys Arg Leu Tyr Ile Phe Val Pro Asp Pro Thr Val Gly Phe Leu
                115                 120                 125 cct aat gat gcc gag gaa cta ttc atc ttt ctc acg gaa ata act gag        432
Pro Asn Asp Ala Glu Glu Leu Phe Ile Phe Leu Thr Glu Ile Thr Glu
    130                 135                 140 atc acc att cca tgc cga gta aca gac cca cag ctg gtg gtg aca ctg        480
Ile Thr Ile Pro Cys Arg Val Thr Asp Pro Gln Leu Val Val Thr Leu
145                 150                 155                 160 cac gag aag aaa ggg gac gtt gca ctg cct gtc ccc tat gat cac caa        528
His Glu Lys Lys Gly Asp Val Ala Leu Pro Val Pro Tyr Asp His Gln
                165                 170                 175 cgt ggc ttt tct ggt atc ttt gag gac aga agc tac atc tgc aaa acc        576
Arg Gly Phe Ser Gly Ile Phe Glu Asp Arg Ser Tyr Ile Cys Lys Thr
                180                 185                 190 acc att ggg gac agg gag gtg gat tct gat gcc tac tat gtc tac aga        624
Thr Ile Gly Asp Arg Glu Val Asp Ser Asp Ala Tyr Tyr Val Tyr Arg
            195                 200                 205 ctc cag gtg tca tcc atc aac gtc tct gtg aac gca gtg cag act gtg        672
Leu Gln Val Ser Ser Ile Asn Val Ser Val Asn Ala Val Gln Thr Val
        210                 215                 220 gtc cgc cag ggt gag aac atc acc ctc atg tgc att gtg atc ggg aat        720
Val Arg Gln Gly Glu Asn Ile Thr Leu Met Cys Ile Val Ile Gly Asn
225                 230                 235                 240 gag gtg gtc aac ttc gag tgg aca tac ccc cgc aaa gaa agt ggg cgg        768
Glu Val Val Asn Phe Glu Trp Thr Tyr Pro Arg Lys Glu Ser Gly Arg
                245                 250                 255 ctg gtg gag ccg gtg act gac ttc ctc ttg gat atg cct tac cac atc        816
Leu Val Glu Pro Val Thr Asp Phe Leu Leu Asp Met Pro Tyr His Ile
            260                 265                 270 cgc tcc atc ctg cac atc ccc agt gcc gag tta gaa gac tcg ggg acc        864
Arg Ser Ile Leu His Ile Pro Ser Ala Glu Leu Glu Asp Ser Gly Thr
        275                 280                 285 tac acc tgc aat gtg acg gag agt gtg aat gac cat cag gat gaa aag        912
Tyr Thr Cys Asn Val Thr Glu Ser Val Asn Asp His Gln Asp Glu Lys
    290                 295                 300 gcc atc aac atc acc gtg gtt gag agc ggc tac gtg cgg ctc ctg gga        960
Ala Ile Asn Ile Thr Val Val Glu Ser Gly Tyr Val Arg Leu Leu Gly
305                 310                 315                 320 gag gtg ggc aca cta caa ttt gct gag ctg cat cgg agc cgg aca ctg       1008
Glu Val Gly Thr Leu Gln Phe Ala Glu Leu His Arg Ser Arg Thr Leu
                325                 330                 335 cag gta gtg ttc gag gcc tac cca ccg ccc act gtc ctg tgg ttc aaa       1056
Gln Val Val Phe Glu Ala Tyr Pro Pro Pro Thr Val Leu Trp Phe Lys
            340                 345                 350 gac aac cgc acc ctg ggc gac tcc agc gct ggc gaa atc gcc ctg tcc       1104
Asp Asn Arg Thr Leu Gly Asp Ser Ser Ala Gly Glu Ile Ala Leu Ser
        355                 360                 365 acg cgc aac gtg tcg gag acc cgg tat gtg tca gag ctg aca ctg gtt       1152
```

-continued

```
                Thr Arg Asn Val Ser Glu Thr Arg Tyr Val Ser Glu Leu Thr Leu Val
                    370                 375                 380 cgc gtg aag gtg gca gag gct ggc cac tac acc atg cgg gcc ttc cat        1200
Arg Val Lys Val Ala Glu Ala Gly His Tyr Thr Met Arg Ala Phe His
385                 390                 395                 400 gag gat gct gag gtc cag ctc tcc ttc cag cta cag atc aat gtc cct        1248
Glu Asp Ala Glu Val Gln Leu Ser Phe Gln Leu Gln Ile Asn Val Pro
                    405                 410                 415 gtc cga gtg ctg gag cta agt gag agc cac cct gac agt ggg gaa cag        1296
Val Arg Val Leu Glu Leu Ser Glu Ser His Pro Asp Ser Gly Glu Gln
                420                 425                 430 aca gtc cgc tgt cgt ggc cgg ggc atg ccc cag ccg aac atc atc tgg        1344
Thr Val Arg Cys Arg Gly Arg Gly Met Pro Gln Pro Asn Ile Ile Trp
            435                 440                 445 tct gcc tgc aga gac ctc aaa agg tgt cca cgt gag ctg ccg ccc acg        1392
Ser Ala Cys Arg Asp Leu Lys Arg Cys Pro Arg Glu Leu Pro Pro Thr
450                 455                 460 ctg ctg ggg aac agt tcc gaa gag gag agc cag ctg gag act aac gtg        1440
Leu Leu Gly Asn Ser Ser Glu Glu Glu Ser Gln Leu Glu Thr Asn Val
465                 470                 475                 480 acg tac tgg gag gag gag cag gag ttt gag gtg gtg agc aca ctg cgt        1488
Thr Tyr Trp Glu Glu Glu Gln Glu Phe Glu Val Val Ser Thr Leu Arg
                    485                 490                 495 ctg cag cac gtg gat cgg cca ctg tcg gtg cgc tgc acg ctg cgc aac        1536
Leu Gln His Val Asp Arg Pro Leu Ser Val Arg Cys Thr Leu Arg Asn
                500                 505                 510 gct gtg ggc cag gac acg cag gag gtc atc gtg gtg cca cac tcc ttg        1584
Ala Val Gly Gln Asp Thr Gln Glu Val Ile Val Val Pro His Ser Leu
            515                 520                 525 ccc ttt aag gtg gtg gtg atc tca gcc atc ctg gcc ctg gtg gtg ctc        1632
Pro Phe Lys Val Val Val Ile Ser Ala Ile Leu Ala Leu Val Val Leu
530                 535                 540 acc atc atc tcc ctt atc atc ctc atc atg ctt tgg cag aag aag cca        1680
Thr Ile Ile Ser Leu Ile Ile Leu Ile Met Leu Trp Gln Lys Lys Pro
545                 550                 555                 560 cgt tac gag atc cga tgg aag gtg att gag tct gtg agc tct gac ggc        1728
Arg Tyr Glu Ile Arg Trp Lys Val Ile Glu Ser Val Ser Ser Asp Gly
                    565                 570                 575 cat gag tac atc tac gtg gac ccc atg cag ctg ccc tat gac tcc acg        1776
His Glu Tyr Ile Tyr Val Asp Pro Met Gln Leu Pro Tyr Asp Ser Thr
                580                 585                 590 tgg aag ctg ccg cgg gac cag ctt gtg ctg gga cgc acc ctc ggc tct        1824
Trp Lys Leu Pro Arg Asp Gln Leu Val Leu Gly Arg Thr Leu Gly Ser
            595                 600                 605 ggg gcc ttt ggg cag gtg gtg gag gcc acg gct cat ggc ctg agc cat        1872
Gly Ala Phe Gly Gln Val Val Glu Ala Thr Ala His Gly Leu Ser His
610                 615                 620 tct cag gcc acg atg aaa gtg gcc gtc aag atg ctt aaa tcc aca gcc        1920
Ser Gln Ala Thr Met Lys Val Ala Val Lys Met Leu Lys Ser Thr Ala
625                 630                 635                 640 cgc agc agt gag aag caa gcc ctt atg tcg gag ctg aag atc atg agt        1968
Arg Ser Ser Glu Lys Gln Ala Leu Met Ser Glu Leu Lys Ile Met Ser
                    645                 650                 655 cac ctt ggg ccc cac ctg aac gtg gtc aac ctg ttg ggg gcc tgc acc        2016
His Leu Gly Pro His Leu Asn Val Val Asn Leu Leu Gly Ala Cys Thr
                660                 665                 670 aaa gga gga ccc atc tat atc atc act gag tac tgc cgc tac gga gac        2064
Lys Gly Gly Pro Ile Tyr Ile Ile Thr Glu Tyr Cys Arg Tyr Gly Asp
            675                 680                 685
```

-continued

| | |
|---|---|
| ctg gtg gac tac ctg cac cgc aac aaa cac acc ttc ctg cag cac cac<br>Leu Val Asp Tyr Leu His Arg Asn Lys His Thr Phe Leu Gln His His<br>690                    695                  700 | 2112 |
| tcc gac aag cgc cgc ccg ccc agc gcg gag ctc tac agc aat gct ctg<br>Ser Asp Lys Arg Arg Pro Pro Ser Ala Glu Leu Tyr Ser Asn Ala Leu<br>705                    710                  715                  720 | 2160 |
| ccc gtt ggg ctc ccc ctg ccc agc cat gtg tcc ttg acc ggg gag agc<br>Pro Val Gly Leu Pro Leu Pro Ser His Val Ser Leu Thr Gly Glu Ser<br>             725                  730                  735 | 2208 |
| gac ggt ggc tac atg gac atg agc aag gac gag tcg gtg gac tat gtg<br>Asp Gly Gly Tyr Met Asp Met Ser Lys Asp Glu Ser Val Asp Tyr Val<br>740                    745                  750 | 2256 |
| ccc atg ctg gac atg aaa gga gac gtc aaa tat gca gac atc gag tcc<br>Pro Met Leu Asp Met Lys Gly Asp Val Lys Tyr Ala Asp Ile Glu Ser<br>             755                  760                  765 | 2304 |
| tcc aac tac atg gcc cct tac gat aac tac gtt ccc tct gcc cct gag<br>Ser Asn Tyr Met Ala Pro Tyr Asp Asn Tyr Val Pro Ser Ala Pro Glu<br>770                    775                  780 | 2352 |
| agg acc tgc cga gca act ttg atc aac gag tct cca gtg cta agc tac<br>Arg Thr Cys Arg Ala Thr Leu Ile Asn Glu Ser Pro Val Leu Ser Tyr<br>785                    790                  795                  800 | 2400 |
| atg gac ctc gtg ggc ttc agc tac cag gtg gcc aat ggc atg gag ttt<br>Met Asp Leu Val Gly Phe Ser Tyr Gln Val Ala Asn Gly Met Glu Phe<br>             805                  810                  815 | 2448 |
| ctg gcc tcc aag aac tgc gtc cac aga gac ctg gcg gct agg aac gtg<br>Leu Ala Ser Lys Asn Cys Val His Arg Asp Leu Ala Ala Arg Asn Val<br>820                    825                  830 | 2496 |
| ctc atc tgt gaa ggc aag ctg gtc aag atc tgt gac ttt ggc ctg gct<br>Leu Ile Cys Glu Gly Lys Leu Val Lys Ile Cys Asp Phe Gly Leu Ala<br>             835                  840                  845 | 2544 |
| cga gac atc atg cgg gac tcg aat tac atc tcc aaa ggc agc acc ttt<br>Arg Asp Ile Met Arg Asp Ser Asn Tyr Ile Ser Lys Gly Ser Thr Phe<br>850                    855                  860 | 2592 |
| ttg cct tta aag tgg atg gct ccg gag agc atc ttc aac agc ctc tac<br>Leu Pro Leu Lys Trp Met Ala Pro Glu Ser Ile Phe Asn Ser Leu Tyr<br>865                    870                  875                  880 | 2640 |
| acc acc ctg agc gac gtg tgg tcc ttc ggg atc ctg ctc tgg gag atc<br>Thr Thr Leu Ser Asp Val Trp Ser Phe Gly Ile Leu Leu Trp Glu Ile<br>             885                  890                  895 | 2688 |
| ttc acc ttg ggt ggc acc cct tac cca gag ctg ccc atg aac gag cag<br>Phe Thr Leu Gly Gly Thr Pro Tyr Pro Glu Leu Pro Met Asn Glu Gln<br>900                    905                  910 | 2736 |
| ttc tac aat gcc atc aaa cgg ggt tac cgc atg gcc cag cct gcc cat<br>Phe Tyr Asn Ala Ile Lys Arg Gly Tyr Arg Met Ala Gln Pro Ala His<br>             915                  920                  925 | 2784 |
| gcc tcc gac gag atc tat gag atc atg cag aag tgc tgg gaa gag aag<br>Ala Ser Asp Glu Ile Tyr Glu Ile Met Gln Lys Cys Trp Glu Glu Lys<br>930                    935                  940 | 2832 |
| ttt gag att cgg ccc ccc ttc tcc cag ctg gtg ctg ctt ctc gag aga<br>Phe Glu Ile Arg Pro Pro Phe Ser Gln Leu Val Leu Leu Leu Glu Arg<br>945                    950                  955                  960 | 2880 |
| ctg ttg ggc gaa ggt tac aaa aag aag tac cag cag gtg gat gag gag<br>Leu Leu Gly Glu Gly Tyr Lys Lys Lys Tyr Gln Gln Val Asp Glu Glu<br>             965                  970                  975 | 2928 |
| ttt ctg agg agt gac cac cca gcc atc ctt cgg tcc cag gcc cgc ttg<br>Phe Leu Arg Ser Asp His Pro Ala Ile Leu Arg Ser Gln Ala Arg Leu<br>980                    985                  990 | 2976 |
| cct ggg ttc cat ggc ctc cga tct ccc ctg gac acc agc tcc gtc ctc<br>Pro Gly Phe His Gly Leu Arg Ser Pro Leu Asp Thr Ser Ser Val Leu<br>             995                  1000              1005 | 3024 |

```
tat act gcc gtg cag ccc aat gag ggt gac aac gac tat atc atc ccc    3072
Tyr Thr Ala Val Gln Pro Asn Glu Gly Asp Asn Asp Tyr Ile Ile Pro
    1010                1015                1020 ctg cct gac ccc aaa ccc gag gtt gct gac gag ggc cca ctg gag ggt    3120
Leu Pro Asp Pro Lys Pro Glu Val Ala Asp Glu Gly Pro Leu Glu Gly
1025                1030                1035                1040 tcc ccc agc cta gcc agc tcc acc ctg aat gaa gtc aac acc tcc tca    3168
Ser Pro Ser Leu Ala Ser Ser Thr Leu Asn Glu Val Asn Thr Ser Ser
                1045                1050                1055 acc atc tcc tgt gac agc ccc ctg gag ccc cag gac gaa cca gag cca    3216
Thr Ile Ser Cys Asp Ser Pro Leu Glu Pro Gln Asp Glu Pro Glu Pro
            1060                1065                1070 gag ccc cag ctt gag ctc cag gtg gag ccg gag cca gag ctg gaa cag    3264
Glu Pro Gln Leu Glu Leu Gln Val Glu Pro Glu Pro Glu Leu Glu Gln
        1075                1080                1085 ttg ccg gat tcg ggg tgc cct gcg cct cgg gcg gaa gca gag gat agc    3312
Leu Pro Asp Ser Gly Cys Pro Ala Pro Arg Ala Glu Ala Glu Asp Ser
    1090                1095                1100 ttc ctg tag                                                         3321
Phe Leu
1105

<210> SEQ ID NO 16
<211> LENGTH: 1106
<212> TYPE: PRT
<213> ORGANISM: Homo sapiens

<400> SEQUENCE: 16

Met Arg Leu Pro Gly Ala Met Pro Ala Leu Ala Leu Lys Gly Glu Leu
1               5                   10                  15

Leu Leu Leu Ser Leu Leu Leu Leu Glu Pro Gln Ile Ser Gln Gly
            20                  25                  30

Leu Val Val Thr Pro Pro Gly Pro Glu Leu Val Leu Asn Val Ser Ser
        35                  40                  45

Thr Phe Val Leu Thr Cys Ser Gly Ser Ala Pro Val Val Trp Glu Arg
    50                  55                  60

Met Ser Gln Glu Pro Pro Gln Glu Met Ala Lys Ala Gln Asp Gly Thr
65                  70                  75                  80

Phe Ser Ser Val Leu Thr Leu Thr Asn Leu Thr Gly Leu Asp Thr Gly
                85                  90                  95

Glu Tyr Phe Cys Thr His Asn Asp Ser Arg Gly Leu Glu Thr Asp Glu
            100                 105                 110

Arg Lys Arg Leu Tyr Ile Phe Val Pro Asp Pro Thr Val Gly Phe Leu
        115                 120                 125

Pro Asn Asp Ala Glu Glu Leu Phe Ile Phe Leu Thr Glu Ile Thr Glu
    130                 135                 140

Ile Thr Ile Pro Cys Arg Val Thr Asp Pro Gln Leu Val Val Thr Leu
145                 150                 155                 160

His Glu Lys Lys Gly Asp Val Ala Leu Pro Val Pro Tyr Asp His Gln
                165                 170                 175

Arg Gly Phe Ser Gly Ile Phe Glu Asp Arg Ser Tyr Ile Cys Lys Thr
            180                 185                 190

Thr Ile Gly Asp Arg Glu Val Asp Ser Asp Ala Tyr Tyr Val Tyr Arg
        195                 200                 205

Leu Gln Val Ser Ser Ile Asn Val Ser Val Asn Ala Val Gln Thr Val
    210                 215                 220
```

-continued

Val Arg Gln Gly Glu Asn Ile Thr Leu Met Cys Ile Val Ile Gly Asn
225                 230                 235                 240

Glu Val Val Asn Phe Glu Trp Thr Tyr Pro Arg Lys Glu Ser Gly Arg
            245                 250                 255

Leu Val Glu Pro Val Thr Asp Phe Leu Leu Asp Met Pro Tyr His Ile
            260                 265                 270

Arg Ser Ile Leu His Ile Pro Ser Ala Glu Leu Glu Asp Ser Gly Thr
        275                 280                 285

Tyr Thr Cys Asn Val Thr Glu Ser Val Asn Asp His Gln Asp Glu Lys
        290                 295                 300

Ala Ile Asn Ile Thr Val Val Glu Ser Gly Tyr Val Arg Leu Leu Gly
305                 310                 315                 320

Glu Val Gly Thr Leu Gln Phe Ala Glu Leu His Arg Ser Arg Thr Leu
            325                 330                 335

Gln Val Val Phe Glu Ala Tyr Pro Pro Pro Thr Val Leu Trp Phe Lys
            340                 345                 350

Asp Asn Arg Thr Leu Gly Asp Ser Ser Ala Gly Glu Ile Ala Leu Ser
        355                 360                 365

Thr Arg Asn Val Ser Glu Thr Arg Tyr Val Ser Glu Leu Thr Leu Val
370                 375                 380

Arg Val Lys Val Ala Glu Ala Gly His Tyr Thr Met Arg Ala Phe His
385                 390                 395                 400

Glu Asp Ala Glu Val Gln Leu Ser Phe Gln Leu Gln Ile Asn Val Pro
            405                 410                 415

Val Arg Val Leu Glu Leu Ser Glu Ser His Pro Asp Ser Gly Glu Gln
            420                 425                 430

Thr Val Arg Cys Arg Gly Arg Gly Met Pro Gln Pro Asn Ile Ile Trp
        435                 440                 445

Ser Ala Cys Arg Asp Leu Lys Arg Cys Pro Arg Glu Leu Pro Pro Thr
450                 455                 460

Leu Leu Gly Asn Ser Ser Glu Glu Glu Ser Gln Leu Glu Thr Asn Val
465                 470                 475                 480

Thr Tyr Trp Glu Glu Glu Gln Glu Phe Glu Val Val Ser Thr Leu Arg
            485                 490                 495

Leu Gln His Val Asp Arg Pro Leu Ser Val Arg Cys Thr Leu Arg Asn
        500                 505                 510

Ala Val Gly Gln Asp Thr Gln Glu Val Ile Val Val Pro His Ser Leu
        515                 520                 525

Pro Phe Lys Val Val Ile Ser Ala Ile Leu Ala Leu Val Val Leu
530                 535                 540

Thr Ile Ile Ser Leu Ile Ile Leu Ile Met Leu Trp Gln Lys Lys Pro
545                 550                 555                 560

Arg Tyr Glu Ile Arg Trp Lys Val Ile Glu Ser Val Ser Ser Asp Gly
            565                 570                 575

His Glu Tyr Ile Tyr Val Asp Pro Met Gln Leu Pro Tyr Asp Ser Thr
        580                 585                 590

Trp Lys Leu Pro Arg Asp Gln Leu Val Leu Gly Arg Thr Leu Gly Ser
        595                 600                 605

Gly Ala Phe Gly Gln Val Val Glu Ala Thr Ala His Gly Leu Ser His
        610                 615                 620

Ser Gln Ala Thr Met Lys Val Ala Val Lys Met Leu Lys Ser Thr Ala
625                 630                 635                 640

Arg Ser Ser Glu Lys Gln Ala Leu Met Ser Glu Leu Lys Ile Met Ser

-continued

```
                645                 650                 655
His Leu Gly Pro His Leu Asn Val Val Asn Leu Leu Gly Ala Cys Thr
            660                 665                 670
Lys Gly Gly Pro Ile Tyr Ile Ile Thr Glu Tyr Cys Arg Tyr Gly Asp
            675                 680                 685
Leu Val Asp Tyr Leu His Arg Asn Lys His Thr Phe Leu Gln His His
            690                 695                 700
Ser Asp Lys Arg Arg Pro Pro Ser Ala Glu Leu Tyr Ser Asn Ala Leu
705                 710                 715                 720
Pro Val Gly Leu Pro Leu Pro Ser His Val Ser Leu Thr Gly Glu Ser
                725                 730                 735
Asp Gly Gly Tyr Met Asp Met Ser Lys Asp Glu Ser Val Asp Tyr Val
                740                 745                 750
Pro Met Leu Asp Met Lys Gly Asp Val Lys Tyr Ala Asp Ile Glu Ser
            755                 760                 765
Ser Asn Tyr Met Ala Pro Tyr Asp Asn Tyr Val Pro Ser Ala Pro Glu
770                 775                 780
Arg Thr Cys Arg Ala Thr Leu Ile Asn Glu Ser Pro Val Leu Ser Tyr
785                 790                 795                 800
Met Asp Leu Val Gly Phe Ser Tyr Gln Val Ala Asn Gly Met Glu Phe
                805                 810                 815
Leu Ala Ser Lys Asn Cys Val His Arg Asp Leu Ala Ala Arg Asn Val
            820                 825                 830
Leu Ile Cys Glu Gly Lys Leu Val Lys Ile Cys Asp Phe Gly Leu Ala
            835                 840                 845
Arg Asp Ile Met Arg Asp Ser Asn Tyr Ile Ser Lys Gly Ser Thr Phe
850                 855                 860
Leu Pro Leu Lys Trp Met Ala Pro Glu Ser Ile Phe Asn Ser Leu Tyr
865                 870                 875                 880
Thr Thr Leu Ser Asp Val Trp Ser Phe Gly Ile Leu Leu Trp Glu Ile
                885                 890                 895
Phe Thr Leu Gly Gly Thr Pro Tyr Pro Glu Leu Pro Met Asn Glu Gln
                900                 905                 910
Phe Tyr Asn Ala Ile Lys Arg Gly Tyr Arg Met Ala Gln Pro Ala His
            915                 920                 925
Ala Ser Asp Glu Ile Tyr Glu Ile Met Gln Lys Cys Trp Glu Glu Lys
            930                 935                 940
Phe Glu Ile Arg Pro Pro Phe Ser Gln Leu Val Leu Leu Leu Glu Arg
945                 950                 955                 960
Leu Leu Gly Glu Gly Tyr Lys Lys Lys Tyr Gln Gln Val Asp Glu Glu
                965                 970                 975
Phe Leu Arg Ser Asp His Pro Ala Ile Leu Arg Ser Gln Ala Arg Leu
            980                 985                 990
Pro Gly Phe His Gly Leu Arg Ser Pro Leu Asp Thr Ser Ser Val Leu
            995                 1000                1005
Tyr Thr Ala Val Gln Pro Asn Glu Gly Asp Asn Asp Tyr Ile Ile Pro
    1010                1015                1020
Leu Pro Asp Pro Lys Pro Glu Val Ala Asp Glu Gly Pro Leu Glu Gly
1025                1030                1035                1040
Ser Pro Ser Leu Ala Ser Ser Thr Leu Asn Glu Val Asn Thr Ser Ser
                1045                1050                1055
Thr Ile Ser Cys Asp Ser Pro Leu Glu Pro Gln Asp Glu Pro Glu Pro
            1060                1065                1070
```

```
Glu Pro Gln Leu Glu Leu Gln Val Glu Pro Pro Glu Leu Gln
        1075                1080                1085

Leu Pro Asp Ser Gly Cys Pro Ala Pro Arg Ala Glu Ala Glu Asp Ser
    1090                1095                1100

Phe Leu
1105

<210> SEQ ID NO 17
<211> LENGTH: 3321
<212> TYPE: DNA
<213> ORGANISM: Homo sapiens
<220> FEATURE:
<221> NAME/KEY: CDS
<222> LOCATION: (1)..(3318)

<400> SEQUENCE: 17 atg cgg ctt ccg ggt gcg atg cca gct ctg gcc ctc aaa ggc gag ctg         48
Met Arg Leu Pro Gly Ala Met Pro Ala Leu Ala Leu Lys Gly Glu Leu
  1               5                  10                  15 ctg ttg ctg tct ctc ctg tta ctt ctg gaa cca cag atc tct cag ggc         96
Leu Leu Leu Ser Leu Leu Leu Leu Glu Pro Gln Ile Ser Gln Gly
             20                  25                  30 ctg gtc gtc aca ccc ccg ggg cca gag ctt gtc ctc aat gtc tcc agc        144
Leu Val Val Thr Pro Pro Gly Pro Glu Leu Val Leu Asn Val Ser Ser
         35                  40                  45 acc ttc gtt ctg acc tgc tcg ggt tca gct ccg gtg gtg tgg gaa cgg        192
Thr Phe Val Leu Thr Cys Ser Gly Ser Ala Pro Val Val Trp Glu Arg
 50                  55                  60 atg tcc cag gag ccc cca cag gaa atg gcc aag gcc cag gat ggc acc        240
Met Ser Gln Glu Pro Pro Gln Glu Met Ala Lys Ala Gln Asp Gly Thr
 65                  70                  75                  80 ttc tcc agc gtg ctc aca ctg acc aac ctc act ggg cta gac acg gga        288
Phe Ser Ser Val Leu Thr Leu Thr Asn Leu Thr Gly Leu Asp Thr Gly
             85                  90                  95 gaa tac ttt tgc acc cac aat gac tcc cgt gga ctg gag acc gat gag        336
Glu Tyr Phe Cys Thr His Asn Asp Ser Arg Gly Leu Glu Thr Asp Glu
            100                 105                 110 cgg aaa cgg ctc tac atc ttt gtg cca gat ccc acc gtg ggc ttc ctc        384
Arg Lys Arg Leu Tyr Ile Phe Val Pro Asp Pro Thr Val Gly Phe Leu
        115                 120                 125 cct aat gat gcc gag gaa cta ttc atc ttt ctc acg gaa ata act gag        432
Pro Asn Asp Ala Glu Glu Leu Phe Ile Phe Leu Thr Glu Ile Thr Glu
    130                 135                 140 atc acc att cca tgc cga gta aca gac cca cag ctg gtg gtg aca ctg        480
Ile Thr Ile Pro Cys Arg Val Thr Asp Pro Gln Leu Val Val Thr Leu
145                 150                 155                 160 cac gag aag aaa ggg gac gtt gca ctg cct gtc ccc tat gat cac caa        528
His Glu Lys Lys Gly Asp Val Ala Leu Pro Val Pro Tyr Asp His Gln
                165                 170                 175 cgt ggc ttt tct ggt atc ttt gag gac aga agc tac atc tgc aaa acc        576
Arg Gly Phe Ser Gly Ile Phe Glu Asp Arg Ser Tyr Ile Cys Lys Thr
            180                 185                 190 acc att ggg gac agg gag gtg gat tct gat gcc tac tat gtc tac aga        624
Thr Ile Gly Asp Arg Glu Val Asp Ser Asp Ala Tyr Tyr Val Tyr Arg
        195                 200                 205 ctc cag gtg tca tcc atc aac gtc tct gtg aac gca gtg cag act gtg        672
Leu Gln Val Ser Ser Ile Asn Val Ser Val Asn Ala Val Gln Thr Val
    210                 215                 220 gtc cgc cag ggt gag aac atc acc ctc atg tgc att gtg atc ggg aat        720
Val Arg Gln Gly Glu Asn Ile Thr Leu Met Cys Ile Val Ile Gly Asn
```

```
              225                 230                 235                 240
gag gtg gtc aac ttc gag tgg aca tac ccc cgc aaa gaa agt ggg cgg         768
Glu Val Val Asn Phe Glu Trp Thr Tyr Pro Arg Lys Glu Ser Gly Arg
                245                 250                 255 ctg gtg gag ccg gtg act gac ttc ctc ttg gat atg cct tac cac atc         816
Leu Val Glu Pro Val Thr Asp Phe Leu Leu Asp Met Pro Tyr His Ile
                260                 265                 270 cgc tcc atc ctg cac atc ccc agt gcc gag tta gaa gac tcg ggg acc         864
Arg Ser Ile Leu His Ile Pro Ser Ala Glu Leu Glu Asp Ser Gly Thr
                275                 280                 285 tac acc tgc aat gtg acg gag agt gtg aat gac cat cag gat gaa aag         912
Tyr Thr Cys Asn Val Thr Glu Ser Val Asn Asp His Gln Asp Glu Lys
                290                 295                 300 gcc atc aac atc acc gtg gtt gag agc ggc tac gtg cgg ctc ctg gga         960
Ala Ile Asn Ile Thr Val Val Glu Ser Gly Tyr Val Arg Leu Leu Gly
305                 310                 315                 320 gag gtg ggc aca cta caa ttt gct gag ctg cat cgg agc cgg aca ctg        1008
Glu Val Gly Thr Leu Gln Phe Ala Glu Leu His Arg Ser Arg Thr Leu
                325                 330                 335 cag gta gtg ttc gag gcc tac cca ccg ccc act gtc ctg tgg ttc aaa        1056
Gln Val Val Phe Glu Ala Tyr Pro Pro Pro Thr Val Leu Trp Phe Lys
                340                 345                 350 gac aac cgc acc ctg ggc gac tcc agc gct ggc gaa atc gcc ctg tcc        1104
Asp Asn Arg Thr Leu Gly Asp Ser Ser Ala Gly Glu Ile Ala Leu Ser
                355                 360                 365 acg cgc aac gtg tcg gag acc cgg tat gtg tca gag ctg aca ctg gtt        1152
Thr Arg Asn Val Ser Glu Thr Arg Tyr Val Ser Glu Leu Thr Leu Val
                370                 375                 380 cgc gtg aag gtg gca gag gct ggc cac tac acc atg cgg gcc ttc cat        1200
Arg Val Lys Val Ala Glu Ala Gly His Tyr Thr Met Arg Ala Phe His
385                 390                 395                 400 gag gat gct gag gtc cag ctc tcc ttc cag cta cag atc aat gtc cct        1248
Glu Asp Ala Glu Val Gln Leu Ser Phe Gln Leu Gln Ile Asn Val Pro
                405                 410                 415 gtc cga gtg ctg gag cta agt gag agc cac cct gac agt ggg gaa cag        1296
Val Arg Val Leu Glu Leu Ser Glu Ser His Pro Asp Ser Gly Glu Gln
                420                 425                 430 aca gtc cgc tgt cgt ggc cgg ggc atg ccc cag ccg aac atc atc tgg        1344
Thr Val Arg Cys Arg Gly Arg Gly Met Pro Gln Pro Asn Ile Ile Trp
                435                 440                 445 tct gcc tgc aga gac ctc aaa agg tgt cca cgt gag ctg ccg ccc acg        1392
Ser Ala Cys Arg Asp Leu Lys Arg Cys Pro Arg Glu Leu Pro Pro Thr
                450                 455                 460 ctg ctg ggg aac agt tcc gaa gag gag agc cag ctg gag act aac gtg        1440
Leu Leu Gly Asn Ser Ser Glu Glu Glu Ser Gln Leu Glu Thr Asn Val
465                 470                 475                 480 acg tac tgg gag gag gag cag gag ttt gag gtg gtg agc aca ctg cgt        1488
Thr Tyr Trp Glu Glu Glu Gln Glu Phe Glu Val Val Ser Thr Leu Arg
                485                 490                 495 ctg cag cac gtg gat cgg cca ctg tcg gtg cgc tgc acg ctg cgc aac        1536
Leu Gln His Val Asp Arg Pro Leu Ser Val Arg Cys Thr Leu Arg Asn
                500                 505                 510 gct gtg ggc cag gac acg cag gag gtc atc gtg gtg cca cac tcc ttg        1584
Ala Val Gly Gln Asp Thr Gln Glu Val Ile Val Val Pro His Ser Leu
                515                 520                 525 ccc ttt aag gtg gtg gtg atc tca gcc atc ctg gcc ctg gtg gtg ctc        1632
Pro Phe Lys Val Val Val Ile Ser Ala Ile Leu Ala Leu Val Val Leu
                530                 535                 540 acc atc atc tcc ctt atc atc ctc atc atg ctt tgg cag aag aag cca        1680
```

-continued

```
Thr Ile Ile Ser Leu Ile Ile Leu Ile Met Leu Trp Gln Lys Lys Pro
545                 550                 555                 560 cgt tac gag atc cga tgg aag gtg att gag tct gtg agc tct gac ggc        1728
Arg Tyr Glu Ile Arg Trp Lys Val Ile Glu Ser Val Ser Ser Asp Gly
                565                 570                 575 cat gag tac atc tac gtg gac ccc atg cag ctg ccc tat gac tcc acg        1776
His Glu Tyr Ile Tyr Val Asp Pro Met Gln Leu Pro Tyr Asp Ser Thr
            580                 585                 590 tgg gag ctg ccg cgg gac cag ctt gtg ctg gga cgc acc ctc ggc tct        1824
Trp Glu Leu Pro Arg Asp Gln Leu Val Leu Gly Arg Thr Leu Gly Ser
        595                 600                 605 ggg gcc ttt ggg cag gtg gtg gag gcc acg gct cat ggc ctg agc cat        1872
Gly Ala Phe Gly Gln Val Val Glu Ala Thr Ala His Gly Leu Ser His
    610                 615                 620 tct cag gcc acg atg aaa gtg gcc gtc aag atg ctt aaa tcc aca gcc        1920
Ser Gln Ala Thr Met Lys Val Ala Val Lys Met Leu Lys Ser Thr Ala
625                 630                 635                 640 cgc agc agt gag aag caa gcc ctt atg tcg gag ctg aag atc atg agt        1968
Arg Ser Ser Glu Lys Gln Ala Leu Met Ser Glu Leu Lys Ile Met Ser
                645                 650                 655 cac ctt ggg ccc cac ctg aac gtg gtc aac ctg ttg ggg gcc tgc atg        2016
His Leu Gly Pro His Leu Asn Val Val Asn Leu Leu Gly Ala Cys Met
            660                 665                 670 aaa gga gga ccc atc tat atc atc act gag tac tgc cgc tac gga gac        2064
Lys Gly Gly Pro Ile Tyr Ile Ile Thr Glu Tyr Cys Arg Tyr Gly Asp
        675                 680                 685 ctg gtg gac tac ctg cac cgc aac aaa cac acc ttc ctg cag cac cac        2112
Leu Val Asp Tyr Leu His Arg Asn Lys His Thr Phe Leu Gln His His
    690                 695                 700 tcc gac aag cgc cgc ccg ccc agc gcg gag ctc tac agc aat gct ctg        2160
Ser Asp Lys Arg Arg Pro Pro Ser Ala Glu Leu Tyr Ser Asn Ala Leu
705                 710                 715                 720 ccc gtt ggg ctc ccc ctg ccc agc cat gtg tcc ttg acc ggg gag agc        2208
Pro Val Gly Leu Pro Leu Pro Ser His Val Ser Leu Thr Gly Glu Ser
                725                 730                 735 gac ggt ggc tac atg gac atg agc aag gac gag tcg gtg gac tat gtg        2256
Asp Gly Gly Tyr Met Asp Met Ser Lys Asp Glu Ser Val Asp Tyr Val
            740                 745                 750 ccc atg ctg gac atg aaa gga gac gtc aaa tat gca gac atc gag tcc        2304
Pro Met Leu Asp Met Lys Gly Asp Val Lys Tyr Ala Asp Ile Glu Ser
        755                 760                 765 tcc aac tac atg gcc cct tac gat aac tac gtt ccc tct gcc cct gag        2352
Ser Asn Tyr Met Ala Pro Tyr Asp Asn Tyr Val Pro Ser Ala Pro Glu
    770                 775                 780 agg acc tgc cga gca act ttg atc aac gag tct cca gtg cta agc tac        2400
Arg Thr Cys Arg Ala Thr Leu Ile Asn Glu Ser Pro Val Leu Ser Tyr
785                 790                 795                 800 atg gac ctc gtg ggc ttc agc tac cag gtg gcc aat ggc atg gag ttt        2448
Met Asp Leu Val Gly Phe Ser Tyr Gln Val Ala Asn Gly Met Glu Phe
                805                 810                 815 ctg gcc tcc aag aac tgc gtc cac aga gac ctg gcg gct agg aac gtg        2496
Leu Ala Ser Lys Asn Cys Val His Arg Asp Leu Ala Ala Arg Asn Val
            820                 825                 830 ctc atc tgt gaa ggc aag ctg gtc aag atc tgt gac ttt ggc ctg gct        2544
Leu Ile Cys Glu Gly Lys Leu Val Lys Ile Cys Asp Phe Gly Leu Ala
        835                 840                 845 cga gac atc atg cgg gac tcg aat tac atc tcc aaa ggc agc acc ttt        2592
Arg Asp Ile Met Arg Asp Ser Asn Tyr Ile Ser Lys Gly Ser Thr Phe
    850                 855                 860
```

```
ttg cct tta aag tgg atg gct ccg gag agc atc ttc aac agc ctc tac    2640
Leu Pro Leu Lys Trp Met Ala Pro Glu Ser Ile Phe Asn Ser Leu Tyr
865                 870                 875                 880 acc acc ctg agc gac gtg tgg tcc ttc ggg atc ctg ctc tgg gag atc    2688
Thr Thr Leu Ser Asp Val Trp Ser Phe Gly Ile Leu Leu Trp Glu Ile
                885                 890                 895 ttc acc ttg ggt ggc acc cct tac cca gag ctg ccc atg aac gag cag    2736
Phe Thr Leu Gly Gly Thr Pro Tyr Pro Glu Leu Pro Met Asn Glu Gln
            900                 905                 910 ttc tac aat gcc atc aaa cgg ggt tac cgc atg gcc cag cct gcc cat    2784
Phe Tyr Asn Ala Ile Lys Arg Gly Tyr Arg Met Ala Gln Pro Ala His
        915                 920                 925 gcc tcc gac gag atc tat gag atc atg cag aag tgc tgg gaa gag aag    2832
Ala Ser Asp Glu Ile Tyr Glu Ile Met Gln Lys Cys Trp Glu Glu Lys
    930                 935                 940 ttt gag att cgg ccc ccc ttc tcc cag ctg gtg ctg ctt ctc gag aga    2880
Phe Glu Ile Arg Pro Pro Phe Ser Gln Leu Val Leu Leu Leu Glu Arg
945                 950                 955                 960 ctg ttg ggc gaa ggt tac aaa aag aag tac cag cag gtg gat gag gag    2928
Leu Leu Gly Glu Gly Tyr Lys Lys Lys Tyr Gln Gln Val Asp Glu Glu
                965                 970                 975 ttt ctg agg agt gac cac cca gcc atc ctt cgg tcc cag gcc cgc ttg    2976
Phe Leu Arg Ser Asp His Pro Ala Ile Leu Arg Ser Gln Ala Arg Leu
            980                 985                 990 cct ggg ttc cat ggc ctc cga tct ccc ctg gac acc agc tcc gtc ctc    3024
Pro Gly Phe His Gly Leu Arg Ser Pro Leu Asp Thr Ser Ser Val Leu
        995                 1000                1005 tat act gcc gtg cag ccc aat gag ggt gac aac gac tat atc atc ccc    3072
Tyr Thr Ala Val Gln Pro Asn Glu Gly Asp Asn Asp Tyr Ile Ile Pro
    1010                1015                1020 ctg cct gac ccc aaa ccc gag gtt gct gac gag ggc cca ctg gag ggt    3120
Leu Pro Asp Pro Lys Pro Glu Val Ala Asp Glu Gly Pro Leu Glu Gly
1025                1030                1035                1040 tcc ccc agc cta gcc agc tcc acc ctg aat gaa gtc aac acc tcc tca    3168
Ser Pro Ser Leu Ala Ser Ser Thr Leu Asn Glu Val Asn Thr Ser Ser
                1045                1050                1055 acc atc tcc tgt gac agc ccc ctg gag ccc cag gac gaa cca gag cca    3216
Thr Ile Ser Cys Asp Ser Pro Leu Glu Pro Gln Asp Glu Pro Glu Pro
            1060                1065                1070 gag ccc cag ctt gag ctc cag gtg gag ccg gag cca gag ctg gaa cag    3264
Glu Pro Gln Leu Glu Leu Gln Val Glu Pro Glu Pro Glu Leu Glu Gln
        1075                1080                1085 ttg ccg gat tcg ggg tgc cct gcg cct cgg gcg gaa gca gag gat agc    3312
Leu Pro Asp Ser Gly Cys Pro Ala Pro Arg Ala Glu Ala Glu Asp Ser
    1090                1095                1100 ttc ctg tag                                                         3321
Phe Leu
1105

<210> SEQ ID NO 18
<211> LENGTH: 1106
<212> TYPE: PRT
<213> ORGANISM: Homo sapiens

<400> SEQUENCE: 18

Met Arg Leu Pro Gly Ala Met Pro Ala Leu Ala Leu Lys Gly Glu Leu
1               5                   10                  15

Leu Leu Leu Ser Leu Leu Leu Leu Glu Pro Gln Ile Ser Gln Gly
            20                  25                  30

Leu Val Val Thr Pro Pro Gly Pro Glu Leu Val Leu Asn Val Ser Ser
```

-continued

```
                35                  40                  45
Thr Phe Val Leu Thr Cys Ser Gly Ser Ala Pro Val Val Trp Glu Arg
 50                  55                  60
Met Ser Gln Glu Pro Gln Glu Met Ala Lys Ala Gln Asp Gly Thr
 65                  70                  75                  80
Phe Ser Ser Val Leu Thr Leu Thr Asn Leu Thr Gly Leu Asp Thr Gly
                 85                  90                  95
Glu Tyr Phe Cys Thr His Asn Asp Ser Arg Gly Leu Glu Thr Asp Glu
                100                 105                 110
Arg Lys Arg Leu Tyr Ile Phe Val Pro Asp Pro Thr Val Gly Phe Leu
                115                 120                 125
Pro Asn Asp Ala Glu Glu Leu Phe Ile Phe Leu Thr Glu Ile Thr Glu
130                 135                 140
Ile Thr Ile Pro Cys Arg Val Thr Asp Pro Gln Leu Val Val Thr Leu
145                 150                 155                 160
His Glu Lys Lys Gly Asp Val Ala Leu Pro Val Pro Tyr Asp His Gln
                165                 170                 175
Arg Gly Phe Ser Gly Ile Phe Glu Asp Arg Ser Tyr Ile Cys Lys Thr
                180                 185                 190
Thr Ile Gly Asp Arg Glu Val Asp Ser Asp Ala Tyr Tyr Val Tyr Arg
                195                 200                 205
Leu Gln Val Ser Ser Ile Asn Val Ser Val Asn Ala Val Gln Thr Val
210                 215                 220
Val Arg Gln Gly Glu Asn Ile Thr Leu Met Cys Ile Val Ile Gly Asn
225                 230                 235                 240
Glu Val Val Asn Phe Glu Trp Thr Tyr Pro Arg Lys Glu Ser Gly Arg
                245                 250                 255
Leu Val Glu Pro Val Thr Asp Phe Leu Leu Asp Met Pro Tyr His Ile
                260                 265                 270
Arg Ser Ile Leu His Ile Pro Ser Ala Glu Leu Glu Asp Ser Gly Thr
                275                 280                 285
Tyr Thr Cys Asn Val Thr Glu Ser Val Asn Asp His Gln Asp Glu Lys
                290                 295                 300
Ala Ile Asn Ile Thr Val Val Glu Ser Gly Tyr Val Arg Leu Leu Gly
305                 310                 315                 320
Glu Val Gly Thr Leu Gln Phe Ala Glu Leu His Arg Ser Arg Thr Leu
                325                 330                 335
Gln Val Val Phe Glu Ala Tyr Pro Pro Pro Thr Val Leu Trp Phe Lys
                340                 345                 350
Asp Asn Arg Thr Leu Gly Asp Ser Ser Ala Gly Glu Ile Ala Leu Ser
                355                 360                 365
Thr Arg Asn Val Ser Glu Thr Arg Tyr Val Ser Glu Leu Thr Leu Val
                370                 375                 380
Arg Val Lys Val Ala Glu Ala Gly His Tyr Thr Met Arg Ala Phe His
385                 390                 395                 400
Glu Asp Ala Glu Val Gln Leu Ser Phe Gln Leu Gln Ile Asn Val Pro
                405                 410                 415
Val Arg Val Leu Glu Leu Ser Glu Ser His Pro Asp Ser Gly Glu Gln
                420                 425                 430
Thr Val Arg Cys Arg Gly Arg Gly Met Pro Gln Pro Asn Ile Ile Trp
                435                 440                 445
Ser Ala Cys Arg Asp Leu Lys Arg Cys Pro Arg Glu Leu Pro Pro Thr
450                 455                 460
```

-continued

```
Leu Leu Gly Asn Ser Ser Glu Glu Ser Gln Leu Glu Thr Asn Val
465                 470                 475                 480

Thr Tyr Trp Glu Glu Glu Gln Glu Phe Glu Val Val Ser Thr Leu Arg
                485                 490                 495

Leu Gln His Val Asp Arg Pro Leu Ser Val Arg Cys Thr Leu Arg Asn
            500                 505                 510

Ala Val Gly Gln Asp Thr Gln Glu Val Ile Val Val Pro His Ser Leu
            515                 520                 525

Pro Phe Lys Val Val Ile Ser Ala Ile Leu Ala Leu Val Val Leu
    530                 535                 540

Thr Ile Ile Ser Leu Ile Ile Leu Ile Met Leu Trp Gln Lys Lys Pro
545                 550                 555                 560

Arg Tyr Glu Ile Arg Trp Lys Val Ile Glu Ser Val Ser Ser Asp Gly
                565                 570                 575

His Glu Tyr Ile Tyr Val Asp Pro Met Gln Leu Pro Tyr Asp Ser Thr
            580                 585                 590

Trp Glu Leu Pro Arg Asp Gln Leu Val Leu Gly Arg Thr Leu Gly Ser
            595                 600                 605

Gly Ala Phe Gly Gln Val Val Glu Ala Thr Ala His Gly Leu Ser His
    610                 615                 620

Ser Gln Ala Thr Met Lys Val Ala Val Lys Met Leu Lys Ser Thr Ala
625                 630                 635                 640

Arg Ser Ser Glu Lys Gln Ala Leu Met Ser Glu Leu Lys Ile Met Ser
                645                 650                 655

His Leu Gly Pro His Leu Asn Val Val Asn Leu Leu Gly Ala Cys Met
            660                 665                 670

Lys Gly Gly Pro Ile Tyr Ile Ile Thr Glu Tyr Cys Arg Tyr Gly Asp
            675                 680                 685

Leu Val Asp Tyr Leu His Arg Asn Lys His Thr Phe Leu Gln His His
    690                 695                 700

Ser Asp Lys Arg Arg Pro Pro Ser Ala Glu Leu Tyr Ser Asn Ala Leu
705                 710                 715                 720

Pro Val Gly Leu Pro Leu Pro Ser His Val Ser Leu Thr Gly Glu Ser
                725                 730                 735

Asp Gly Gly Tyr Met Asp Met Ser Lys Asp Glu Ser Val Asp Tyr Val
            740                 745                 750

Pro Met Leu Asp Met Lys Gly Asp Val Lys Tyr Ala Asp Ile Glu Ser
            755                 760                 765

Ser Asn Tyr Met Ala Pro Tyr Asp Asn Tyr Val Pro Ser Ala Pro Glu
770                 775                 780

Arg Thr Cys Arg Ala Thr Leu Ile Asn Glu Ser Pro Val Leu Ser Tyr
785                 790                 795                 800

Met Asp Leu Val Gly Phe Ser Tyr Gln Val Ala Asn Gly Met Glu Phe
                805                 810                 815

Leu Ala Ser Lys Asn Cys Val His Arg Asp Leu Ala Ala Arg Asn Val
            820                 825                 830

Leu Ile Cys Glu Gly Lys Leu Val Lys Ile Cys Asp Phe Gly Leu Ala
            835                 840                 845

Arg Asp Ile Met Arg Asp Ser Asn Tyr Ile Ser Lys Gly Ser Thr Phe
    850                 855                 860

Leu Pro Leu Lys Trp Met Ala Pro Glu Ser Ile Phe Asn Ser Leu Tyr
865                 870                 875                 880
```

```
Thr Thr Leu Ser Asp Val Trp Ser Phe Gly Ile Leu Leu Trp Glu Ile
            885                 890                 895

Phe Thr Leu Gly Gly Thr Pro Tyr Pro Glu Leu Pro Met Asn Glu Gln
            900                 905                 910

Phe Tyr Asn Ala Ile Lys Arg Gly Tyr Arg Met Ala Gln Pro Ala His
            915                 920                 925

Ala Ser Asp Glu Ile Tyr Glu Ile Met Gln Lys Cys Trp Glu Lys
        930                 935                 940

Phe Glu Ile Arg Pro Pro Phe Ser Gln Leu Val Leu Leu Glu Arg
945                 950                 955                 960

Leu Leu Gly Glu Gly Tyr Lys Lys Tyr Gln Gln Val Asp Glu Glu
            965                 970                 975

Phe Leu Arg Ser Asp His Pro Ala Ile Leu Arg Ser Gln Ala Arg Leu
            980                 985                 990

Pro Gly Phe His Gly Leu Arg Ser Pro Leu Asp Thr Ser Ser Val Leu
            995                 1000                1005

Tyr Thr Ala Val Gln Pro Asn Glu Gly Asp Asn Asp Tyr Ile Ile Pro
        1010                1015                1020

Leu Pro Asp Pro Lys Pro Glu Val Ala Asp Glu Gly Pro Leu Glu Gly
1025                1030                1035                1040

Ser Pro Ser Leu Ala Ser Ser Thr Leu Asn Glu Val Asn Thr Ser Ser
            1045                1050                1055

Thr Ile Ser Cys Asp Ser Pro Leu Glu Pro Gln Asp Glu Pro Glu Pro
            1060                1065                1070

Glu Pro Gln Leu Glu Leu Gln Val Glu Pro Glu Pro Glu Leu Glu Gln
        1075                1080                1085

Leu Pro Asp Ser Gly Cys Pro Ala Pro Arg Ala Glu Ala Glu Asp Ser
    1090                1095                1100

Phe Leu
1105

<210> SEQ ID NO 19
<211> LENGTH: 3321
<212> TYPE: DNA
<213> ORGANISM: Homo sapiens
<220> FEATURE:
<221> NAME/KEY: CDS
<222> LOCATION: (1)..(3318)

<400> SEQUENCE: 19 atg cgg ctt ccg ggt gcg atg cca gct ctg gcc ctc aaa ggc gag ctg      48
Met Arg Leu Pro Gly Ala Met Pro Ala Leu Ala Leu Lys Gly Glu Leu
  1               5                  10                  15 ctg ttg ctg tct ctc ctg tta ctt ctg gaa cca cag atc tct cag ggc      96
Leu Leu Leu Ser Leu Leu Leu Leu Leu Glu Pro Gln Ile Ser Gln Gly
             20                  25                  30 ctg gtc gtc aca ccc ccg ggg cca gag ctt gtc ctc aat gtc tcc agc     144
Leu Val Val Thr Pro Pro Gly Pro Glu Leu Val Leu Asn Val Ser Ser
         35                  40                  45 acc ttc gtt ctg acc tgc tcg ggt tca gct ccg gtg gtg tgg gaa cgg     192
Thr Phe Val Leu Thr Cys Ser Gly Ser Ala Pro Val Val Trp Glu Arg
     50                  55                  60 atg tcc cag gag ccc cca cag gaa atg gcc aag gcc cag gat ggc acc     240
Met Ser Gln Glu Pro Pro Gln Glu Met Ala Lys Ala Gln Asp Gly Thr
 65                  70                  75                  80 ttc tcc agc gtg ctc aca ctg acc aac ctc act ggg cta gac acg gga     288
Phe Ser Ser Val Leu Thr Leu Thr Asn Leu Thr Gly Leu Asp Thr Gly
                 85                  90                  95
```

-continued

```
gaa tac ttt tgc acc cac aat gac tcc cgt gga ctg gag acc gat gag    336
Glu Tyr Phe Cys Thr His Asn Asp Ser Arg Gly Leu Glu Thr Asp Glu
            100                 105                 110 cgg aaa cgg ctc tac atc ttt gtg cca gat ccc acc gtg ggc ttc ctc    384
Arg Lys Arg Leu Tyr Ile Phe Val Pro Asp Pro Thr Val Gly Phe Leu
        115                 120                 125 cct aat gat gcc gag gaa cta ttc atc ttt ctc acg gaa ata act gag    432
Pro Asn Asp Ala Glu Glu Leu Phe Ile Phe Leu Thr Glu Ile Thr Glu
    130                 135                 140 atc acc att cca tgc cga gta aca gac cca cag ctg gtg gtg aca ctg    480
Ile Thr Ile Pro Cys Arg Val Thr Asp Pro Gln Leu Val Val Thr Leu
145                 150                 155                 160 cac gag aag aaa ggg gac gtt gca ctg cct gtc ccc tat gat cac caa    528
His Glu Lys Lys Gly Asp Val Ala Leu Pro Val Pro Tyr Asp His Gln
                165                 170                 175 cgt ggc ttt tct ggt atc ttt gag gac aga agc tac atc tgc aaa acc    576
Arg Gly Phe Ser Gly Ile Phe Glu Asp Arg Ser Tyr Ile Cys Lys Thr
            180                 185                 190 acc att ggg gac agg gag gtg gat tct gat gcc tac tat gtc tac aga    624
Thr Ile Gly Asp Arg Glu Val Asp Ser Asp Ala Tyr Tyr Val Tyr Arg
        195                 200                 205 ctc cag gtg tca tcc atc aac gtc tct gtg aac gca gtg cag act gtg    672
Leu Gln Val Ser Ser Ile Asn Val Ser Val Asn Ala Val Gln Thr Val
    210                 215                 220 gtc cgc cag ggt gag aac atc acc ctc atg tgc att gtg atc ggg aat    720
Val Arg Gln Gly Glu Asn Ile Thr Leu Met Cys Ile Val Ile Gly Asn
225                 230                 235                 240 gag gtg gtc aac ttc gag tgg aca tac ccc cgc aaa gaa agt ggg cgg    768
Glu Val Val Asn Phe Glu Trp Thr Tyr Pro Arg Lys Glu Ser Gly Arg
                245                 250                 255 ctg gtg gag ccg gtg act gac ttc ctc ttg gat atg cct tac cac atc    816
Leu Val Glu Pro Val Thr Asp Phe Leu Leu Asp Met Pro Tyr His Ile
            260                 265                 270 cgc tcc atc ctg cac atc ccc agt gcc gag tta gaa gac tcg ggg acc    864
Arg Ser Ile Leu His Ile Pro Ser Ala Glu Leu Glu Asp Ser Gly Thr
        275                 280                 285 tac acc tgc aat gtg acg gag agt gtg aat gac cat cag gat gaa aag    912
Tyr Thr Cys Asn Val Thr Glu Ser Val Asn Asp His Gln Asp Glu Lys
    290                 295                 300 gcc atc aac atc acc gtg gtt gag agc ggc tac gtg cgg ctc ctg gga    960
Ala Ile Asn Ile Thr Val Val Glu Ser Gly Tyr Val Arg Leu Leu Gly
305                 310                 315                 320 gag gtg ggc aca cta caa ttt gct gag ctg cat cgg agc cgg aca ctg    1008
Glu Val Gly Thr Leu Gln Phe Ala Glu Leu His Arg Ser Arg Thr Leu
                325                 330                 335 cag gta gtg ttc gag gcc tac cca ccg ccc act gtc ctg tgg ttc aaa    1056
Gln Val Val Phe Glu Ala Tyr Pro Pro Pro Thr Val Leu Trp Phe Lys
            340                 345                 350 gac aac cgc acc ctg ggc gac tcc agc gct ggc gaa atc gcc ctg tcc    1104
Asp Asn Arg Thr Leu Gly Asp Ser Ser Ala Gly Glu Ile Ala Leu Ser
        355                 360                 365 acg cgc aac gtg tcg gag acc cgg tat gtg tca gag ctg aca ctg gtt    1152
Thr Arg Asn Val Ser Glu Thr Arg Tyr Val Ser Glu Leu Thr Leu Val
    370                 375                 380 cgc gtg aag gtg gca gag gct ggc cac tac acc atg cgg gcc ttc cat    1200
Arg Val Lys Val Ala Glu Ala Gly His Tyr Thr Met Arg Ala Phe His
385                 390                 395                 400 gag gat gct gag gtc cag ctc tcc ttc cag cta cag atc aat gtc cct    1248
Glu Asp Ala Glu Val Gln Leu Ser Phe Gln Leu Gln Ile Asn Val Pro
```

```
                    405                 410                 415
gtc cga gtg ctg gag cta agt gag agc cac cct gac agt ggg gaa cag    1296
Val Arg Val Leu Glu Leu Ser Glu Ser His Pro Asp Ser Gly Glu Gln
            420                 425                 430 aca gtc cgc tgt cgt ggc cgg ggc atg ccc cag ccg aac atc atc tgg    1344
Thr Val Arg Cys Arg Gly Arg Gly Met Pro Gln Pro Asn Ile Ile Trp
            435                 440                 445 tct gcc tgc aga gac ctc aaa agg tgt cca cgt gag ctg ccg ccc acg    1392
Ser Ala Cys Arg Asp Leu Lys Arg Cys Pro Arg Glu Leu Pro Pro Thr
450                 455                 460 ctg ctg ggg aac agt tcc gaa gag gag agc cag ctg gag act aac gtg    1440
Leu Leu Gly Asn Ser Ser Glu Glu Glu Ser Gln Leu Glu Thr Asn Val
465                 470                 475                 480 acg tac tgg gag gag gag cag gag ttt gag gtg gtg agc aca ctg cgt    1488
Thr Tyr Trp Glu Glu Glu Gln Glu Phe Glu Val Val Ser Thr Leu Arg
                485                 490                 495 ctg cag cac gtg gat cgg cca ctg tcg gtg cgc tgc acg ctg cgc aac    1536
Leu Gln His Val Asp Arg Pro Leu Ser Val Arg Cys Thr Leu Arg Asn
            500                 505                 510 gct gtg ggc cag gac acg cag gag gtc atc gtg gtg cca cac tcc ttg    1584
Ala Val Gly Gln Asp Thr Gln Glu Val Ile Val Val Pro His Ser Leu
            515                 520                 525 ccc ttt aag gtg gtg gtg atc tca gcc atc ctg gcc ctg gtg gtg ctc    1632
Pro Phe Lys Val Val Val Ile Ser Ala Ile Leu Ala Leu Val Val Leu
530                 535                 540 acc atc atc tcc ctt atc atc ctc atc atg ctt tgg cag aag aag cca    1680
Thr Ile Ile Ser Leu Ile Ile Leu Ile Met Leu Trp Gln Lys Lys Pro
545                 550                 555                 560 cgt tac gag atc cga tgg aag gtg att gag tct gtg agc tct gac ggc    1728
Arg Tyr Glu Ile Arg Trp Lys Val Ile Glu Ser Val Ser Ser Asp Gly
                565                 570                 575 cat gag tac atc tac gtg gac ccc atg cag ctg ccc tat gac tcc acg    1776
His Glu Tyr Ile Tyr Val Asp Pro Met Gln Leu Pro Tyr Asp Ser Thr
            580                 585                 590 tgg gag ctg ccg cgg gac cag ctt gtg ctg gga cgc acc ctc ggc tct    1824
Trp Glu Leu Pro Arg Asp Gln Leu Val Leu Gly Arg Thr Leu Gly Ser
            595                 600                 605 ggg gcc ttt ggg cag gtg gtg gag gcc acg gct cat ggc ctg agc cat    1872
Gly Ala Phe Gly Gln Val Val Glu Ala Thr Ala His Gly Leu Ser His
            610                 615                 620 tct cag gcc acg atg aaa gtg gcc gtc aag atg ctt aaa tcc aca gcc    1920
Ser Gln Ala Thr Met Lys Val Ala Val Lys Met Leu Lys Ser Thr Ala
625                 630                 635                 640 cgc agc agt gag aag caa gcc ctt atg tcg gag ctg aag atc atg agt    1968
Arg Ser Ser Glu Lys Gln Ala Leu Met Ser Glu Leu Lys Ile Met Ser
                645                 650                 655 cac ctt ggg ccc cac ctg aac gtg gtc aac ctg ttg ggg gcc tgc acc    2016
His Leu Gly Pro His Leu Asn Val Val Asn Leu Leu Gly Ala Cys Thr
            660                 665                 670 aaa gga gga ccc atc tat atc atc act gag tac tgc cgc tac gga gac    2064
Lys Gly Gly Pro Ile Tyr Ile Ile Thr Glu Tyr Cys Arg Tyr Gly Asp
            675                 680                 685 ctg gtg gac tac ctg cac cgc aac aaa cac acc ttc ctg cag cac cac    2112
Leu Val Asp Tyr Leu His Arg Asn Lys His Thr Phe Leu Gln His His
            690                 695                 700 tcc gac aag cgc cgc ccg ccc agc gcg gag ctc tac agc aat gct ctg    2160
Ser Asp Lys Arg Arg Pro Pro Ser Ala Glu Leu Tyr Ser Asn Ala Leu
705                 710                 715                 720 ccc gtt ggg ctc ccc ctg ccc agc cat gtg tcc ttg acc ggg gag agc    2208
```

-continued

| | | | | | | | | | | | | |
|---|---|---|---|---|---|---|---|---|---|---|---|---|
|Pro|Val|Gly|Leu|Pro|Leu|Pro|Ser|His|Val|Ser|Leu|Thr|Gly|Glu|Ser|
| | | |725| | | |730| | | |735| |

```
gac ggt ggc tac atg gac atg agc aag gac gag tcg gtg gac tat gtg     2256
Asp Gly Gly Tyr Met Asp Met Ser Lys Asp Glu Ser Val Asp Tyr Val
        740                 745                 750 ccc atg ctg gac atg aaa gga gac gtc aaa tat gca gac atc gag tcc     2304
Pro Met Leu Asp Met Lys Gly Asp Val Lys Tyr Ala Asp Ile Glu Ser
        755                 760                 765 tcc aac tac atg gcc cct tac gat aac tac gtt ccc tct gcc cct gag     2352
Ser Asn Tyr Met Ala Pro Tyr Asp Asn Tyr Val Pro Ser Ala Pro Glu
770                 775                 780 agg acc tgc cga gca act ttg atc aac gag tct cca gtg cta agc tac     2400
Arg Thr Cys Arg Ala Thr Leu Ile Asn Glu Ser Pro Val Leu Ser Tyr
785                 790                 795                 800 atg gac ctc gtg ggc ttc agc tac cag gtg gcc aat ggc atg gag ttt     2448
Met Asp Leu Val Gly Phe Ser Tyr Gln Val Ala Asn Gly Met Glu Phe
            805                 810                 815 ctg gcc tcc aag aac tgc gtc cac aga aac ctg gcg gct agg aac gtg     2496
Leu Ala Ser Lys Asn Cys Val His Arg Asn Leu Ala Ala Arg Asn Val
            820                 825                 830 ctc atc tgt gaa ggc aag ctg gtc aag atc tgt gac ttt ggc ctg gct     2544
Leu Ile Cys Glu Gly Lys Leu Val Lys Ile Cys Asp Phe Gly Leu Ala
            835                 840                 845 cga gac atc atg cgg gac tcg aat tac atc tcc aaa ggc agc acc ttt     2592
Arg Asp Ile Met Arg Asp Ser Asn Tyr Ile Ser Lys Gly Ser Thr Phe
850                 855                 860 ttg cct tta aag tgg atg gct ccg gag agc atc ttc aac agc ctc tac     2640
Leu Pro Leu Lys Trp Met Ala Pro Glu Ser Ile Phe Asn Ser Leu Tyr
865                 870                 875                 880 acc acc ctg agc gac gtg tgg tcc ttc ggg atc ctc ctc tgg gag atc     2688
Thr Thr Leu Ser Asp Val Trp Ser Phe Gly Ile Leu Leu Trp Glu Ile
            885                 890                 895 ttc acc ttg ggt ggc acc cct tac cca gag ctg ccc atg aac gag cag     2736
Phe Thr Leu Gly Gly Thr Pro Tyr Pro Glu Leu Pro Met Asn Glu Gln
            900                 905                 910 ttc tac aat gcc atc aaa cgg ggt tac cgc atg gcc cag cct gcc cat     2784
Phe Tyr Asn Ala Ile Lys Arg Gly Tyr Arg Met Ala Gln Pro Ala His
            915                 920                 925 gcc tcc gac gag atc tat gag atc atg cag aag tgc tgg gaa gag aag     2832
Ala Ser Asp Glu Ile Tyr Glu Ile Met Gln Lys Cys Trp Glu Glu Lys
930                 935                 940 ttt gag att cgg ccc ccc ttc tcc cag ctg gtg ctg ctt ctc gag aga     2880
Phe Glu Ile Arg Pro Pro Phe Ser Gln Leu Val Leu Leu Leu Glu Arg
945                 950                 955                 960 ctg ttg ggc gaa ggt tac aaa aag aag tac cag cag gtg gat gag gag     2928
Leu Leu Gly Glu Gly Tyr Lys Lys Lys Tyr Gln Gln Val Asp Glu Glu
            965                 970                 975 ttt ctg agg agt gac cac cca gcc atc ctt cgg tcc cag gcc cgc ttg     2976
Phe Leu Arg Ser Asp His Pro Ala Ile Leu Arg Ser Gln Ala Arg Leu
            980                 985                 990 cct ggg ttc cat ggc ctc cga tct ccc ctg gac acc agc tcc gtc ctc     3024
Pro Gly Phe His Gly Leu Arg Ser Pro Leu Asp Thr Ser Ser Val Leu
            995                 1000                1005 tat act gcc gtg cag ccc aat gag ggt gac aac gac tat atc atc ccc     3072
Tyr Thr Ala Val Gln Pro Asn Glu Gly Asp Asn Asp Tyr Ile Ile Pro
        1010                1015                1020 ctg cct gac ccc aaa ccc gag gtt gct gac gag ggc cca ctg gag ggt     3120
Leu Pro Asp Pro Lys Pro Glu Val Ala Asp Glu Gly Pro Leu Glu Gly
1025                1030                1035                1040
```

-continued

| | | | | | | | | | | | | |
|---|---|---|---|---|---|---|---|---|---|---|---|---|
| tcc | ccc | agc | cta | gcc | agc | tcc | acc | ctg | aat | gaa | gtc | aac | acc | tcc | tca | 3168 |
| Ser | Pro | Ser | Leu | Ala | Ser | Ser | Thr | Leu | Asn | Glu | Val | Asn | Thr | Ser | Ser | |
| | | | 1045 | | | | | 1050 | | | | | 1055 | | | |

| acc | atc | tcc | tgt | gac | agc | ccc | ctg | gag | ccc | cag | gac | gaa | cca | gag | cca | 3216 |
| Thr | Ile | Ser | Cys | Asp | Ser | Pro | Leu | Glu | Pro | Gln | Asp | Glu | Pro | Glu | Pro | |
| | | | 1060 | | | | | 1065 | | | | | 1070 | | | |

| gag | ccc | cag | ctt | gag | ctc | cag | gtg | gag | ccg | gag | cca | gag | ctg | gaa | cag | 3264 |
| Glu | Pro | Gln | Leu | Glu | Leu | Gln | Val | Glu | Pro | Glu | Pro | Glu | Leu | Glu | Gln | |
| | | | 1075 | | | | | 1080 | | | | | 1085 | | | |

| ttg | ccg | gat | tcg | ggg | tgc | cct | gcg | cct | cgg | gcg | gaa | gca | gag | gat | agc | 3312 |
| Leu | Pro | Asp | Ser | Gly | Cys | Pro | Ala | Pro | Arg | Ala | Glu | Ala | Glu | Asp | Ser | |
| | | | 1090 | | | | | 1095 | | | | | 1100 | | | |

| ttc | ctg | tag | | | | | | | | | | | | | | 3321 |
| Phe | Leu | | | | | | | | | | | | | | | |
| 1105 | | | | | | | | | | | | | | | | |

<210> SEQ ID NO 20
<211> LENGTH: 1106
<212> TYPE: PRT
<213> ORGANISM: Homo sapiens

<400> SEQUENCE: 20

Met Arg Leu Pro Gly Ala Met Pro Ala Leu Ala Leu Lys Gly Glu Leu
 1               5                  10                  15

Leu Leu Leu Ser Leu Leu Leu Leu Glu Pro Gln Ile Ser Gln Gly
            20                  25                  30

Leu Val Val Thr Pro Pro Gly Pro Glu Leu Val Leu Asn Val Ser Ser
            35                  40                  45

Thr Phe Val Leu Thr Cys Ser Gly Ser Ala Pro Val Val Trp Glu Arg
    50                  55                  60

Met Ser Gln Glu Pro Pro Gln Glu Met Ala Lys Ala Gln Asp Gly Thr
65                  70                  75                  80

Phe Ser Ser Val Leu Thr Leu Thr Asn Leu Thr Gly Leu Asp Thr Gly
                85                  90                  95

Glu Tyr Phe Cys Thr His Asn Asp Ser Arg Gly Leu Glu Thr Asp Glu
            100                 105                 110

Arg Lys Arg Leu Tyr Ile Phe Val Pro Asp Pro Thr Val Gly Phe Leu
        115                 120                 125

Pro Asn Asp Ala Glu Glu Leu Phe Ile Phe Leu Thr Glu Ile Thr Glu
    130                 135                 140

Ile Thr Ile Pro Cys Arg Val Thr Asp Pro Gln Leu Val Val Thr Leu
145                 150                 155                 160

His Glu Lys Lys Gly Asp Val Ala Leu Pro Val Pro Tyr Asp His Gln
                165                 170                 175

Arg Gly Phe Ser Gly Ile Phe Glu Asp Arg Ser Tyr Ile Cys Lys Thr
            180                 185                 190

Thr Ile Gly Asp Arg Glu Val Asp Ser Asp Ala Tyr Tyr Val Tyr Arg
        195                 200                 205

Leu Gln Val Ser Ser Ile Asn Val Ser Val Asn Ala Val Gln Thr Val
    210                 215                 220

Val Arg Gln Gly Glu Asn Ile Thr Leu Met Cys Ile Val Ile Gly Asn
225                 230                 235                 240

Glu Val Val Asn Phe Glu Trp Thr Tyr Pro Arg Lys Glu Ser Gly Arg
                245                 250                 255

Leu Val Glu Pro Val Thr Asp Phe Leu Leu Asp Met Pro Tyr His Ile
            260                 265                 270

-continued

```
Arg Ser Ile Leu His Ile Pro Ser Ala Glu Leu Glu Asp Ser Gly Thr
            275                 280                 285

Tyr Thr Cys Asn Val Thr Glu Ser Val Asn Asp His Gln Asp Glu Lys
            290                 295                 300

Ala Ile Asn Ile Thr Val Val Glu Ser Gly Tyr Val Arg Leu Leu Gly
305                 310                 315                 320

Glu Val Gly Thr Leu Gln Phe Ala Glu Leu His Arg Ser Arg Thr Leu
                325                 330                 335

Gln Val Val Phe Glu Ala Tyr Pro Pro Thr Val Leu Trp Phe Lys
                340                 345                 350

Asp Asn Arg Thr Leu Gly Asp Ser Ser Ala Gly Glu Ile Ala Leu Ser
                355                 360                 365

Thr Arg Asn Val Ser Glu Thr Arg Tyr Val Ser Glu Leu Thr Leu Val
370                 375                 380

Arg Val Lys Val Ala Glu Ala Gly His Tyr Thr Met Arg Ala Phe His
385                 390                 395                 400

Glu Asp Ala Glu Val Gln Leu Ser Phe Gln Leu Gln Ile Asn Val Pro
                405                 410                 415

Val Arg Val Leu Glu Leu Ser Glu Ser His Pro Asp Ser Gly Glu Gln
                420                 425                 430

Thr Val Arg Cys Arg Gly Arg Gly Met Pro Gln Pro Asn Ile Ile Trp
            435                 440                 445

Ser Ala Cys Arg Asp Leu Lys Arg Cys Pro Arg Glu Leu Pro Pro Thr
450                 455                 460

Leu Leu Gly Asn Ser Ser Glu Glu Ser Gln Leu Glu Thr Asn Val
465                 470                 475                 480

Thr Tyr Trp Glu Glu Glu Gln Glu Phe Glu Val Val Ser Thr Leu Arg
                485                 490                 495

Leu Gln His Val Asp Arg Pro Leu Ser Val Arg Cys Thr Leu Arg Asn
            500                 505                 510

Ala Val Gly Gln Asp Thr Gln Glu Val Ile Val Val Pro His Ser Leu
            515                 520                 525

Pro Phe Lys Val Val Ile Ser Ala Ile Leu Ala Leu Val Val Leu
530                 535                 540

Thr Ile Ile Ser Leu Ile Ile Leu Ile Met Leu Trp Gln Lys Lys Pro
545                 550                 555                 560

Arg Tyr Glu Ile Arg Trp Lys Val Ile Glu Ser Val Ser Ser Asp Gly
                565                 570                 575

His Glu Tyr Ile Tyr Val Asp Pro Met Gln Leu Pro Tyr Asp Ser Thr
            580                 585                 590

Trp Glu Leu Pro Arg Asp Gln Leu Val Leu Gly Arg Thr Leu Gly Ser
            595                 600                 605

Gly Ala Phe Gly Gln Val Val Glu Ala Thr Ala His Gly Leu Ser His
    610                 615                 620

Ser Gln Ala Thr Met Lys Val Ala Val Lys Met Leu Lys Ser Thr Ala
625                 630                 635                 640

Arg Ser Ser Glu Lys Gln Ala Leu Met Ser Glu Leu Lys Ile Met Ser
                645                 650                 655

His Leu Gly Pro His Leu Asn Val Val Asn Leu Leu Gly Ala Cys Thr
            660                 665                 670

Lys Gly Gly Pro Ile Tyr Ile Ile Thr Glu Tyr Cys Arg Tyr Gly Asp
            675                 680                 685

Leu Val Asp Tyr Leu His Arg Asn Lys His Thr Phe Leu Gln His His
```

-continued

```
            690                 695                 700
Ser Asp Lys Arg Arg Pro Ser Ala Glu Leu Tyr Ser Asn Ala Leu
705                 710                 715                 720
Pro Val Gly Leu Pro Leu Pro Ser His Val Ser Leu Thr Gly Glu Ser
                725                 730                 735
Asp Gly Gly Tyr Met Asp Met Ser Lys Asp Glu Ser Val Asp Tyr Val
                740                 745                 750
Pro Met Leu Asp Met Lys Gly Asp Val Lys Tyr Ala Asp Ile Glu Ser
                755                 760                 765
Ser Asn Tyr Met Ala Pro Tyr Asp Asn Tyr Val Pro Ser Ala Pro Glu
770                 775                 780
Arg Thr Cys Arg Ala Thr Leu Ile Asn Glu Ser Pro Val Leu Ser Tyr
785                 790                 795                 800
Met Asp Leu Val Gly Phe Ser Tyr Gln Val Ala Asn Gly Met Glu Phe
                805                 810                 815
Leu Ala Ser Lys Asn Cys Val His Arg Asn Leu Ala Ala Arg Asn Val
                820                 825                 830
Leu Ile Cys Glu Gly Lys Leu Val Lys Ile Cys Asp Phe Gly Leu Ala
                835                 840                 845
Arg Asp Ile Met Arg Asp Ser Asn Tyr Ile Ser Lys Gly Ser Thr Phe
850                 855                 860
Leu Pro Leu Lys Trp Met Ala Pro Glu Ser Ile Phe Asn Ser Leu Tyr
865                 870                 875                 880
Thr Thr Leu Ser Asp Val Trp Ser Phe Gly Ile Leu Leu Trp Glu Ile
                885                 890                 895
Phe Thr Leu Gly Gly Thr Pro Tyr Pro Glu Leu Pro Met Asn Glu Gln
                900                 905                 910
Phe Tyr Asn Ala Ile Lys Arg Gly Tyr Arg Met Ala Gln Pro Ala His
                915                 920                 925
Ala Ser Asp Glu Ile Tyr Glu Ile Met Gln Lys Cys Trp Glu Glu Lys
930                 935                 940
Phe Glu Ile Arg Pro Pro Phe Ser Gln Leu Val Leu Leu Leu Glu Arg
945                 950                 955                 960
Leu Leu Gly Glu Gly Tyr Lys Lys Lys Tyr Gln Gln Val Asp Glu Glu
                965                 970                 975
Phe Leu Arg Ser Asp His Pro Ala Ile Leu Arg Ser Gln Ala Arg Leu
                980                 985                 990
Pro Gly Phe His Gly Leu Arg Ser Pro Leu Asp Thr Ser Ser Val Leu
                995                 1000                1005
Tyr Thr Ala Val Gln Pro Asn Glu Gly Asp Asn Asp Tyr Ile Ile Pro
1010                1015                1020
Leu Pro Asp Pro Lys Pro Glu Val Ala Asp Glu Gly Pro Leu Glu Gly
1025                1030                1035                1040
Ser Pro Ser Leu Ala Ser Ser Thr Leu Asn Glu Val Asn Thr Ser Ser
                1045                1050                1055
Thr Ile Ser Cys Asp Ser Pro Leu Glu Pro Gln Asp Glu Pro Glu Pro
                1060                1065                1070
Glu Pro Gln Leu Glu Leu Gln Val Glu Pro Glu Pro Glu Leu Glu Gln
                1075                1080                1085
Leu Pro Asp Ser Gly Cys Pro Ala Pro Arg Ala Glu Ala Glu Asp Ser
                1090                1095                1100
Phe Leu
1105
```

<210> SEQ ID NO 21
<211> LENGTH: 3321
<212> TYPE: DNA
<213> ORGANISM: Homo sapiens
<220> FEATURE:
<221> NAME/KEY: CDS
<222> LOCATION: (1)..(3318)

<400> SEQUENCE: 21

| | | | | | | | | | | | | | | | | |
|---|---|---|---|---|---|---|---|---|---|---|---|---|---|---|---|---|
| atg | cgg | ctt | ccg | ggt | gcg | atg | cca | gct | ctg | gcc | ctc | aaa | ggc | gag | ctg | 48 |
| Met | Arg | Leu | Pro | Gly | Ala | Met | Pro | Ala | Leu | Ala | Leu | Lys | Gly | Glu | Leu | |
| 1 | | | | 5 | | | | | 10 | | | | | 15 | | |
| ctg | ttg | ctg | tct | ctc | ctg | tta | ctt | ctg | gaa | cca | cag | atc | tct | cag | ggc | 96 |
| Leu | Leu | Leu | Ser | Leu | Leu | Leu | Leu | Leu | Glu | Pro | Gln | Ile | Ser | Gln | Gly | |
| | | | 20 | | | | | 25 | | | | | 30 | | | |
| ctg | gtc | gtc | aca | ccc | ccg | ggg | cca | gag | ctt | gtc | ctc | aat | gtc | tcc | agc | 144 |
| Leu | Val | Val | Thr | Pro | Pro | Gly | Pro | Glu | Leu | Val | Leu | Asn | Val | Ser | Ser | |
| | | 35 | | | | | 40 | | | | | 45 | | | | |
| acc | ttc | gtt | ctg | acc | tgc | tcg | ggt | tca | gct | ccg | gtg | gtg | tgg | gaa | cgg | 192 |
| Thr | Phe | Val | Leu | Thr | Cys | Ser | Gly | Ser | Ala | Pro | Val | Val | Trp | Glu | Arg | |
| | 50 | | | | | 55 | | | | | 60 | | | | | |
| atg | tcc | cag | gag | ccc | cca | cag | gaa | atg | gcc | aag | gcc | cag | gat | ggc | acc | 240 |
| Met | Ser | Gln | Glu | Pro | Pro | Gln | Glu | Met | Ala | Lys | Ala | Gln | Asp | Gly | Thr | |
| 65 | | | | | 70 | | | | | 75 | | | | | 80 | |
| ttc | tcc | agc | gtg | ctc | aca | ctg | acc | aac | ctc | act | ggg | cta | gac | acg | gga | 288 |
| Phe | Ser | Ser | Val | Leu | Thr | Leu | Thr | Asn | Leu | Thr | Gly | Leu | Asp | Thr | Gly | |
| | | | | 85 | | | | | 90 | | | | | 95 | | |
| gaa | tac | ttt | tgc | acc | cac | aat | gac | tcc | cgt | gga | ctg | gag | acc | gat | gag | 336 |
| Glu | Tyr | Phe | Cys | Thr | His | Asn | Asp | Ser | Arg | Gly | Leu | Glu | Thr | Asp | Glu | |
| | | | 100 | | | | | 105 | | | | | 110 | | | |
| cgg | aaa | cgg | ctc | tac | atc | ttt | gtg | cca | gat | ccc | acc | gtg | ggc | ttc | ctc | 384 |
| Arg | Lys | Arg | Leu | Tyr | Ile | Phe | Val | Pro | Asp | Pro | Thr | Val | Gly | Phe | Leu | |
| | | 115 | | | | | 120 | | | | | 125 | | | | |
| cct | aat | gat | gcc | gag | gaa | cta | ttc | att | ttt | ctc | acg | gaa | ata | act | gag | 432 |
| Pro | Asn | Asp | Ala | Glu | Glu | Leu | Phe | Ile | Phe | Leu | Thr | Glu | Ile | Thr | Glu | |
| | 130 | | | | | 135 | | | | | 140 | | | | | |
| atc | acc | att | cca | tgc | cga | gta | aca | gac | cca | cag | ctg | gtg | gtg | aca | ctg | 480 |
| Ile | Thr | Ile | Pro | Cys | Arg | Val | Thr | Asp | Pro | Gln | Leu | Val | Val | Thr | Leu | |
| 145 | | | | | 150 | | | | | 155 | | | | | 160 | |
| cac | gag | aag | aaa | ggg | gac | gtt | gca | ctg | cct | gtc | ccc | tat | gat | cac | caa | 528 |
| His | Glu | Lys | Lys | Gly | Asp | Val | Ala | Leu | Pro | Val | Pro | Tyr | Asp | His | Gln | |
| | | | | 165 | | | | | 170 | | | | | 175 | | |
| cgt | ggc | ttt | tct | ggt | atc | ttt | gag | gac | aga | agc | tac | atc | tgc | aaa | acc | 576 |
| Arg | Gly | Phe | Ser | Gly | Ile | Phe | Glu | Asp | Arg | Ser | Tyr | Ile | Cys | Lys | Thr | |
| | | | 180 | | | | | 185 | | | | | 190 | | | |
| acc | att | ggg | gac | agg | gag | gtg | gat | tct | gat | gcc | tac | tat | gtc | tac | aga | 624 |
| Thr | Ile | Gly | Asp | Arg | Glu | Val | Asp | Ser | Asp | Ala | Tyr | Tyr | Val | Tyr | Arg | |
| | | 195 | | | | | 200 | | | | | 205 | | | | |
| ctc | cag | gtg | tca | tcc | atc | aac | gtc | tct | gtg | aac | gca | gtg | cag | act | gtg | 672 |
| Leu | Gln | Val | Ser | Ser | Ile | Asn | Val | Ser | Val | Asn | Ala | Val | Gln | Thr | Val | |
| | 210 | | | | | 215 | | | | | 220 | | | | | |
| gtc | cgc | cag | ggt | gag | aac | atc | acc | ctc | atg | tgc | att | gtg | atc | ggg | aat | 720 |
| Val | Arg | Gln | Gly | Glu | Asn | Ile | Thr | Leu | Met | Cys | Ile | Val | Ile | Gly | Asn | |
| 225 | | | | | 230 | | | | | 235 | | | | | 240 | |
| gag | gtg | gtc | aac | ttc | gag | tgg | aca | tac | ccc | cgc | aaa | gaa | agt | ggg | cgg | 768 |
| Glu | Val | Val | Asn | Phe | Glu | Trp | Thr | Tyr | Pro | Arg | Lys | Glu | Ser | Gly | Arg | |
| | | | | 245 | | | | | 250 | | | | | 255 | | |
| ctg | gtg | gag | ccg | gtg | act | gac | ttc | ctc | ttg | gat | atg | cct | tac | cac | atc | 816 |
| Leu | Val | Glu | Pro | Val | Thr | Asp | Phe | Leu | Leu | Asp | Met | Pro | Tyr | His | Ile | |
| | | | 260 | | | | | 265 | | | | | 270 | | | |

-continued

```
cgc tcc atc ctg cac atc ccc agt gcc gag tta gaa gac tcg ggg acc        864
Arg Ser Ile Leu His Ile Pro Ser Ala Glu Leu Glu Asp Ser Gly Thr
        275                 280                 285 tac acc tgc aat gtg acg gag agt gtg aat gac cat cag gat gaa aag        912
Tyr Thr Cys Asn Val Thr Glu Ser Val Asn Asp His Gln Asp Glu Lys
        290                 295                 300 gcc atc aac atc acc gtg gtt gag agc ggc tac gtg cgg ctc ctg gga        960
Ala Ile Asn Ile Thr Val Val Glu Ser Gly Tyr Val Arg Leu Leu Gly
305                 310                 315                 320 gag gtg ggc aca cta caa ttt gct gag ctg cat cgg agc cgg aca ctg       1008
Glu Val Gly Thr Leu Gln Phe Ala Glu Leu His Arg Ser Arg Thr Leu
                325                 330                 335 cag gta gtg ttc gag gcc tac cca ccg ccc act gtc ctg tgg ttc aaa       1056
Gln Val Val Phe Glu Ala Tyr Pro Pro Pro Thr Val Leu Trp Phe Lys
            340                 345                 350 gac aac cgc acc ctg ggc gac tcc agc gct ggc gaa atc gcc ctg tcc       1104
Asp Asn Arg Thr Leu Gly Asp Ser Ser Ala Gly Glu Ile Ala Leu Ser
        355                 360                 365 acg cgc aac gtg tcg gag acc cgg tat gtg tca gag ctg aca ctg gtt       1152
Thr Arg Asn Val Ser Glu Thr Arg Tyr Val Ser Glu Leu Thr Leu Val
        370                 375                 380 cgc gtg aag gtg gca gag gct ggc cac tac acc atg cgg gcc ttc cat       1200
Arg Val Lys Val Ala Glu Ala Gly His Tyr Thr Met Arg Ala Phe His
385                 390                 395                 400 gag gat gct gag gtc cag ctc tcc ttc cag cta cag atc aat gtc cct       1248
Glu Asp Ala Glu Val Gln Leu Ser Phe Gln Leu Gln Ile Asn Val Pro
                405                 410                 415 gtc cga gtg ctg gag cta agt gag agc cac cct gac agt ggg gaa cag       1296
Val Arg Val Leu Glu Leu Ser Glu Ser His Pro Asp Ser Gly Glu Gln
            420                 425                 430 aca gtc cgc tgt cgt ggc cgg ggc atg ccc cag ccg aac atc atc tgg       1344
Thr Val Arg Cys Arg Gly Arg Gly Met Pro Gln Pro Asn Ile Ile Trp
        435                 440                 445 tct gcc tgc aga gac ctc aaa agg tgt cca cgt gag ctg ccg ccc acg       1392
Ser Ala Cys Arg Asp Leu Lys Arg Cys Pro Arg Glu Leu Pro Pro Thr
450                 455                 460 ctg ctg ggg aac agt tcc gaa gag gag agc cag ctg gag act aac gtg       1440
Leu Leu Gly Asn Ser Ser Glu Glu Glu Ser Gln Leu Glu Thr Asn Val
465                 470                 475                 480 acg tac tgg gag gag gag cag gag ttt gag gtg gtg agc aca ctg cgt       1488
Thr Tyr Trp Glu Glu Glu Gln Glu Phe Glu Val Val Ser Thr Leu Arg
                485                 490                 495 ctg cag cac gtg gat cgg cca ctg tcg gtg cgc tgc acg ctg cgc aac       1536
Leu Gln His Val Asp Arg Pro Leu Ser Val Arg Cys Thr Leu Arg Asn
            500                 505                 510 gct gtg ggc cag gac acg cag gag gtc atc gtg gtg cca cac tcc ttg       1584
Ala Val Gly Gln Asp Thr Gln Glu Val Ile Val Val Pro His Ser Leu
        515                 520                 525 ccc ttt aag gtg gtg gtg atc tca gcc atc ctg gcc ctg gtg gtg ctc       1632
Pro Phe Lys Val Val Val Ile Ser Ala Ile Leu Ala Leu Val Val Leu
530                 535                 540 acc atc atc tcc ctt atc atc ctc atc atg ctt tgg cag aag aag cca       1680
Thr Ile Ile Ser Leu Ile Ile Leu Ile Met Leu Trp Gln Lys Lys Pro
545                 550                 555                 560 cgt tac gag atc cga tgg aag gtg att gag tct gtg agc tct gac ggc       1728
Arg Tyr Glu Ile Arg Trp Lys Val Ile Glu Ser Val Ser Ser Asp Gly
                565                 570                 575 cat gag tac atc tac gtg gac ccc atg cag ctg ccc tat gac tcc acg       1776
His Glu Tyr Ile Tyr Val Asp Pro Met Gln Leu Pro Tyr Asp Ser Thr
```

```
                580                      585                      590
tgg gag ctg ccg cgg gac cag ctt gtg ctg gga cgc acc ctc ggc tct   1824
Trp Glu Leu Pro Arg Asp Gln Leu Val Leu Gly Arg Thr Leu Gly Ser
            595                      600                      605 ggg gcc ttt ggg cag gtg gtg gag gcc acg gct cat ggc ctg agc cat   1872
Gly Ala Phe Gly Gln Val Val Glu Ala Thr Ala His Gly Leu Ser His
    610                      615                      620 tct cag gcc acg atg aaa gtg gcc gtc aag atg ctt aaa tcc aca gcc   1920
Ser Gln Ala Thr Met Lys Val Ala Val Lys Met Leu Lys Ser Thr Ala
625                      630                      635                      640 cgc agc agt gag aag caa gcc ctt atg tcg gag ctg aag atc atg agt   1968
Arg Ser Ser Glu Lys Gln Ala Leu Met Ser Glu Leu Lys Ile Met Ser
                645                      650                      655 cac ctt ggg ccc cac ctg aac gtg gtc aac ctg ttg ggg gcc tgc acc   2016
His Leu Gly Pro His Leu Asn Val Val Asn Leu Leu Gly Ala Cys Thr
            660                      665                      670 aaa gga gga ccc atc tat atc atc act gag tac tgc cgc tac gga gac   2064
Lys Gly Gly Pro Ile Tyr Ile Ile Thr Glu Tyr Cys Arg Tyr Gly Asp
        675                      680                      685 ctg gtg gac tac ctg cac cgc aac aaa cac acc ttc ctg cag cac cac   2112
Leu Val Asp Tyr Leu His Arg Asn Lys His Thr Phe Leu Gln His His
    690                      695                      700 tcc gac aag cgc cgc ccg ccc agc gcg gag ctc tac agc aat gct ctg   2160
Ser Asp Lys Arg Arg Pro Pro Ser Ala Glu Leu Tyr Ser Asn Ala Leu
705                      710                      715                      720 ccc gtt ggg ctc ccc ctg ccc agc cat gtg tcc ttg acc ggg gag agc   2208
Pro Val Gly Leu Pro Leu Pro Ser His Val Ser Leu Thr Gly Glu Ser
                725                      730                      735 gac ggt ggc tac atg gac atg agc aag gac gag tcg gtg gac tat gtg   2256
Asp Gly Gly Tyr Met Asp Met Ser Lys Asp Glu Ser Val Asp Tyr Val
            740                      745                      750 ccc atg ctg gac atg aaa gga gac gtc aaa tat gca gac atc gag tcc   2304
Pro Met Leu Asp Met Lys Gly Asp Val Lys Tyr Ala Asp Ile Glu Ser
        755                      760                      765 tcc aac tac atg gcc cct tac gat aac tac gtt ccc tct gcc cct gag   2352
Ser Asn Tyr Met Ala Pro Tyr Asp Asn Tyr Val Pro Ser Ala Pro Glu
    770                      775                      780 agg acc tgc cga gca act ttg atc aac gag tct cca gtg cta agc tac   2400
Arg Thr Cys Arg Ala Thr Leu Ile Asn Glu Ser Pro Val Leu Ser Tyr
785                      790                      795                      800 atg gac ctc gtg ggc ttc agc tac cag gtg gcc aat ggc atg gag ttt   2448
Met Asp Leu Val Gly Phe Ser Tyr Gln Val Ala Asn Gly Met Glu Phe
                805                      810                      815 ctg gcc tcc aag aac tgc gtc cac aga gac ctg gcg gct agg aac gtg   2496
Leu Ala Ser Lys Asn Cys Val His Arg Asp Leu Ala Ala Arg Asn Val
            820                      825                      830 ctc atc tgt gaa ggc aag ctg gtc aag atc tgt gac ttt ggc ctg gct   2544
Leu Ile Cys Glu Gly Lys Leu Val Lys Ile Cys Asp Phe Gly Leu Ala
        835                      840                      845 cga gac atc atg cgg gac tcg aat tac atc tcc aaa ggc agc acc ttt   2592
Arg Asp Ile Met Arg Asp Ser Asn Tyr Ile Ser Lys Gly Ser Thr Phe
    850                      855                      860 ttg cct atg aag tgg atg gct ccg gag agc atc ttc aac agc ctc tac   2640
Leu Pro Met Lys Trp Met Ala Pro Glu Ser Ile Phe Asn Ser Leu Tyr
865                      870                      875                      880 acc acc ctg agc gac gtg tgg tcc ttc ggg atc ctg ctc tgg gag atc   2688
Thr Thr Leu Ser Asp Val Trp Ser Phe Gly Ile Leu Leu Trp Glu Ile
                885                      890                      895 ttc acc ttg ggt ggc acc cct tac cca gag ctg ccc atg aac gag cag   2736
```

```
Phe Thr Leu Gly Gly Thr Pro Tyr Pro Glu Leu Pro Met Asn Glu Gln
                900                 905                 910 ttc tac aat gcc atc aaa cgg ggt tac cgc atg gcc cag cct gcc cat       2784
Phe Tyr Asn Ala Ile Lys Arg Gly Tyr Arg Met Ala Gln Pro Ala His
        915                 920                 925 gcc tcc gac gag atc tat gag atc atg cag aag tgc tgg gaa gag aag       2832
Ala Ser Asp Glu Ile Tyr Glu Ile Met Gln Lys Cys Trp Glu Glu Lys
    930                 935                 940 ttt gag att cgg ccc ccc ttc tcc cag ctg gtg ctg ctt ctc gag aga       2880
Phe Glu Ile Arg Pro Pro Phe Ser Gln Leu Val Leu Leu Leu Glu Arg
945                 950                 955                 960 ctg ttg ggc gaa ggt tac aaa aag aag tac cag cag gtg gat gag gag       2928
Leu Leu Gly Glu Gly Tyr Lys Lys Lys Tyr Gln Gln Val Asp Glu Glu
                965                 970                 975 ttt ctg agg agt gac cac cca gcc atc ctt cgg tcc cag gcc cgc ttg       2976
Phe Leu Arg Ser Asp His Pro Ala Ile Leu Arg Ser Gln Ala Arg Leu
        980                 985                 990 cct ggg ttc cat ggc ctc cga tct ccc ctg gac acc agc tcc gtc ctc       3024
Pro Gly Phe His Gly Leu Arg Ser Pro Leu Asp Thr Ser Ser Val Leu
    995                 1000                1005 tat act gcc gtg cag ccc aat gag ggt gac aac gac tat atc atc ccc       3072
Tyr Thr Ala Val Gln Pro Asn Glu Gly Asp Asn Asp Tyr Ile Ile Pro
   1010                 1015                1020 ctg cct gac ccc aaa ccc gag gtt gct gac gag ggc cca ctg gag ggt       3120
Leu Pro Asp Pro Lys Pro Glu Val Ala Asp Glu Gly Pro Leu Glu Gly
1025                1030                1035                1040 tcc ccc agc cta gcc agc tcc acc ctg aat gaa gtc aac acc tcc tca       3168
Ser Pro Ser Leu Ala Ser Ser Thr Leu Asn Glu Val Asn Thr Ser Ser
                1045                1050                1055 acc atc tcc tgt gac agc ccc ctg gag ccc cag gac gaa cca gag cca       3216
Thr Ile Ser Cys Asp Ser Pro Leu Glu Pro Gln Asp Glu Pro Glu Pro
        1060                1065                1070 gag ccc cag ctt gag ctc cag gtg gag ccg gag cca gag ctg gaa cag       3264
Glu Pro Gln Leu Glu Leu Gln Val Glu Pro Glu Pro Glu Leu Glu Gln
    1075                1080                1085 ttg ccg gat tcg ggg tgc cct gcg cct cgg gcg gaa gca gag gat agc       3312
Leu Pro Asp Ser Gly Cys Pro Ala Pro Arg Ala Glu Ala Glu Asp Ser
1090                1095                1100 ttc ctg tag                                                           3321
Phe Leu
1105

<210> SEQ ID NO 22
<211> LENGTH: 1106
<212> TYPE: PRT
<213> ORGANISM: Homo sapiens

<400> SEQUENCE: 22

Met Arg Leu Pro Gly Ala Met Pro Ala Leu Ala Leu Lys Gly Glu Leu
  1               5                  10                  15

Leu Leu Leu Ser Leu Leu Leu Leu Glu Pro Gln Ile Ser Gln Gly
                 20                  25                  30

Leu Val Val Thr Pro Pro Gly Pro Glu Leu Val Leu Asn Val Ser Ser
             35                  40                  45

Thr Phe Val Leu Thr Cys Ser Gly Ser Ala Pro Val Val Trp Glu Arg
         50                  55                  60

Met Ser Gln Glu Pro Pro Gln Glu Met Ala Lys Ala Gln Asp Gly Thr
 65                  70                  75                  80

Phe Ser Ser Val Leu Thr Leu Thr Asn Leu Thr Gly Leu Asp Thr Gly
```

-continued

```
                85                  90                  95
Glu Tyr Phe Cys Thr His Asn Asp Ser Arg Gly Leu Glu Thr Asp Glu
                    100                 105                 110

Arg Lys Arg Leu Tyr Ile Phe Val Pro Asp Pro Thr Val Gly Phe Leu
            115                 120                 125

Pro Asn Asp Ala Glu Glu Leu Phe Ile Phe Leu Thr Glu Ile Thr Glu
        130                 135                 140

Ile Thr Ile Pro Cys Arg Val Thr Asp Pro Gln Leu Val Val Thr Leu
145                 150                 155                 160

His Glu Lys Lys Gly Asp Val Ala Leu Pro Val Pro Tyr Asp His Gln
                165                 170                 175

Arg Gly Phe Ser Gly Ile Phe Glu Asp Arg Ser Tyr Ile Cys Lys Thr
            180                 185                 190

Thr Ile Gly Asp Arg Glu Val Asp Ser Asp Ala Tyr Tyr Val Tyr Arg
        195                 200                 205

Leu Gln Val Ser Ser Ile Asn Val Ser Val Asn Ala Val Gln Thr Val
    210                 215                 220

Val Arg Gln Gly Glu Asn Ile Thr Leu Met Cys Ile Val Ile Gly Asn
225                 230                 235                 240

Glu Val Val Asn Phe Glu Trp Thr Tyr Pro Arg Lys Glu Ser Gly Arg
                245                 250                 255

Leu Val Glu Pro Val Thr Asp Phe Leu Leu Asp Met Pro Tyr His Ile
            260                 265                 270

Arg Ser Ile Leu His Ile Pro Ser Ala Glu Leu Glu Asp Ser Gly Thr
        275                 280                 285

Tyr Thr Cys Asn Val Thr Glu Ser Val Asn Asp His Gln Asp Glu Lys
    290                 295                 300

Ala Ile Asn Ile Thr Val Val Glu Ser Gly Tyr Val Arg Leu Leu Gly
305                 310                 315                 320

Glu Val Gly Thr Leu Gln Phe Ala Glu Leu His Arg Ser Arg Thr Leu
                325                 330                 335

Gln Val Val Phe Glu Ala Tyr Pro Pro Pro Thr Val Leu Trp Phe Lys
            340                 345                 350

Asp Asn Arg Thr Leu Gly Asp Ser Ser Ala Gly Glu Ile Ala Leu Ser
        355                 360                 365

Thr Arg Asn Val Ser Glu Thr Arg Tyr Val Ser Glu Leu Thr Leu Val
    370                 375                 380

Arg Val Lys Val Ala Glu Ala Gly His Tyr Thr Met Arg Ala Phe His
385                 390                 395                 400

Glu Asp Ala Glu Val Gln Leu Ser Phe Gln Leu Gln Ile Asn Val Pro
                405                 410                 415

Val Arg Val Leu Glu Leu Ser Glu Ser His Pro Asp Ser Gly Glu Gln
            420                 425                 430

Thr Val Arg Cys Arg Gly Arg Gly Met Pro Gln Pro Asn Ile Ile Trp
        435                 440                 445

Ser Ala Cys Arg Asp Leu Lys Arg Cys Pro Arg Glu Leu Pro Pro Thr
    450                 455                 460

Leu Leu Gly Asn Ser Ser Glu Glu Ser Gln Leu Glu Thr Asn Val
465                 470                 475                 480

Thr Tyr Trp Glu Glu Glu Gln Glu Phe Glu Val Val Ser Thr Leu Arg
                485                 490                 495

Leu Gln His Val Asp Arg Pro Leu Ser Val Arg Cys Thr Leu Arg Asn
            500                 505                 510
```

-continued

```
Ala Val Gly Gln Asp Thr Gln Glu Val Ile Val Pro His Ser Leu
        515                 520                 525
Pro Phe Lys Val Val Ile Ser Ala Ile Leu Ala Leu Val Val Leu
        530                 535                 540
Thr Ile Ile Ser Leu Ile Ile Leu Ile Met Leu Trp Gln Lys Lys Pro
545                 550                 555                 560
Arg Tyr Glu Ile Arg Trp Lys Val Ile Glu Ser Val Ser Ser Asp Gly
                565                 570                 575
His Glu Tyr Ile Tyr Val Asp Pro Met Gln Leu Pro Tyr Asp Ser Thr
                580                 585                 590
Trp Glu Leu Pro Arg Asp Gln Leu Val Leu Gly Arg Thr Leu Gly Ser
                595                 600                 605
Gly Ala Phe Gly Gln Val Val Glu Ala Thr Ala His Gly Leu Ser His
                610                 615                 620
Ser Gln Ala Thr Met Lys Val Ala Val Lys Met Leu Lys Ser Thr Ala
625                 630                 635                 640
Arg Ser Ser Glu Lys Gln Ala Leu Met Ser Glu Leu Lys Ile Met Ser
                645                 650                 655
His Leu Gly Pro His Leu Asn Val Val Asn Leu Leu Gly Ala Cys Thr
                660                 665                 670
Lys Gly Gly Pro Ile Tyr Ile Ile Thr Glu Tyr Cys Arg Tyr Gly Asp
                675                 680                 685
Leu Val Asp Tyr Leu His Arg Asn Lys His Thr Phe Leu Gln His His
                690                 695                 700
Ser Asp Lys Arg Arg Pro Pro Ser Ala Glu Leu Tyr Ser Asn Ala Leu
705                 710                 715                 720
Pro Val Gly Leu Pro Leu Pro Ser His Val Ser Leu Thr Gly Glu Ser
                725                 730                 735
Asp Gly Gly Tyr Met Asp Met Ser Lys Asp Glu Ser Val Asp Tyr Val
                740                 745                 750
Pro Met Leu Asp Met Lys Gly Asp Val Lys Tyr Ala Asp Ile Glu Ser
                755                 760                 765
Ser Asn Tyr Met Ala Pro Tyr Asp Asn Tyr Val Pro Ser Ala Pro Glu
770                 775                 780
Arg Thr Cys Arg Ala Thr Leu Ile Asn Glu Ser Pro Val Leu Ser Tyr
785                 790                 795                 800
Met Asp Leu Val Gly Phe Ser Tyr Gln Val Ala Asn Gly Met Glu Phe
                805                 810                 815
Leu Ala Ser Lys Asn Cys Val His Arg Asp Leu Ala Ala Arg Asn Val
                820                 825                 830
Leu Ile Cys Glu Gly Lys Leu Val Lys Ile Cys Asp Phe Gly Leu Ala
                835                 840                 845
Arg Asp Ile Met Arg Asp Ser Asn Tyr Ile Ser Lys Gly Ser Thr Phe
                850                 855                 860
Leu Pro Met Lys Trp Met Ala Pro Glu Ser Ile Phe Asn Ser Leu Tyr
865                 870                 875                 880
Thr Thr Leu Ser Asp Val Trp Ser Phe Gly Ile Leu Leu Trp Glu Ile
                885                 890                 895
Phe Thr Leu Gly Gly Thr Pro Tyr Pro Glu Leu Pro Met Asn Glu Gln
                900                 905                 910
Phe Tyr Asn Ala Ile Lys Arg Gly Tyr Arg Met Ala Gln Pro Ala His
                915                 920                 925
```

```
Ala Ser Asp Glu Ile Tyr Glu Ile Met Gln Lys Cys Trp Glu Glu Lys
    930                 935                 940

Phe Glu Ile Arg Pro Pro Phe Ser Gln Leu Val Leu Leu Glu Arg
945                 950                 955                 960

Leu Leu Gly Glu Gly Tyr Lys Lys Tyr Gln Gln Val Asp Glu Glu
                965                 970                 975

Phe Leu Arg Ser Asp His Pro Ala Ile Leu Arg Ser Gln Ala Arg Leu
            980                 985                 990

Pro Gly Phe His Gly Leu Arg Ser Pro Leu Asp Thr Ser Ser Val Leu
        995                 1000                1005

Tyr Thr Ala Val Gln Pro Asn Glu Gly Asp Asn Asp Tyr Ile Ile Pro
    1010                1015                1020

Leu Pro Asp Pro Lys Pro Glu Val Ala Asp Glu Gly Pro Leu Glu Gly
1025                1030                1035                1040

Ser Pro Ser Leu Ala Ser Ser Thr Leu Asn Glu Val Asn Thr Ser Ser
                1045                1050                1055

Thr Ile Ser Cys Asp Ser Pro Leu Glu Pro Gln Asp Glu Pro Glu Pro
                1060                1065                1070

Glu Pro Gln Leu Glu Leu Gln Val Glu Pro Glu Pro Glu Leu Glu Gln
            1075                1080                1085

Leu Pro Asp Ser Gly Cys Pro Ala Pro Arg Ala Glu Ala Glu Asp Ser
    1090                1095                1100

Phe Leu
1105

<210> SEQ ID NO 23
<211> LENGTH: 1683
<212> TYPE: DNA
<213> ORGANISM: Homo sapiens
<220> FEATURE:
<221> NAME/KEY: CDS
<222> LOCATION: (1)..(1683)

<400> SEQUENCE: 23 atg cgg ctt ccg ggt gcg atg cca gct ctg gcc ctc aaa ggc gag ctg      48
Met Arg Leu Pro Gly Ala Met Pro Ala Leu Ala Leu Lys Gly Glu Leu
 1               5                  10                  15 ctg ttg ctg tct ctc ctg tta ctt ctg gaa cca cag atc tct cag ggc      96
Leu Leu Leu Ser Leu Leu Leu Leu Glu Pro Gln Ile Ser Gln Gly
             20                  25                  30 ctg gtc gtc aca ccc ccg ggg cca gag ctt gtc ctc aat gtc tcc agc     144
Leu Val Val Thr Pro Pro Gly Pro Glu Leu Val Leu Asn Val Ser Ser
         35                  40                  45 acc ttc gtt ctg acc tgc tcg ggt tca gct ccg gtg gtg tgg gaa cgg     192
Thr Phe Val Leu Thr Cys Ser Gly Ser Ala Pro Val Val Trp Glu Arg
     50                  55                  60 atg tcc cag gag ccc cca cag gaa atg gcc aag gcc cag gat ggc acc     240
Met Ser Gln Glu Pro Pro Gln Glu Met Ala Lys Ala Gln Asp Gly Thr
 65                  70                  75                  80 ttc tcc agc gtg ctc aca ctg acc aac ctc act ggg cta gac acg gga     288
Phe Ser Ser Val Leu Thr Leu Thr Asn Leu Thr Gly Leu Asp Thr Gly
                 85                  90                  95 gaa tac ttt tgc acc cac aat gac tcc cgt gga ctg gag acc gat gag     336
Glu Tyr Phe Cys Thr His Asn Asp Ser Arg Gly Leu Glu Thr Asp Glu
            100                 105                 110 cgg aaa cgg ctc tac atc ttt gtg cca gat ccc acc gtg ggc ttc ctc     384
Arg Lys Arg Leu Tyr Ile Phe Val Pro Asp Pro Thr Val Gly Phe Leu
        115                 120                 125
```

```
cct aat gat gcc gag gaa cta ttc atc ttt ctc acg gaa ata act gag      432
Pro Asn Asp Ala Glu Glu Leu Phe Ile Phe Leu Thr Glu Ile Thr Glu
    130                 135                 140 atc acc att cca tgc cga gta aca gac cca cag ctg gtg gtg aca ctg      480
Ile Thr Ile Pro Cys Arg Val Thr Asp Pro Gln Leu Val Val Thr Leu
145                 150                 155                 160 cac gag aag aaa ggg gac gtt gca ctg cct gtc ccc tat gat cac caa      528
His Glu Lys Lys Gly Asp Val Ala Leu Pro Val Pro Tyr Asp His Gln
                165                 170                 175 cgt ggc ttt tct ggt atc ttt gag gac aga agc tac atc tgc aaa acc      576
Arg Gly Phe Ser Gly Ile Phe Glu Asp Arg Ser Tyr Ile Cys Lys Thr
            180                 185                 190 acc att ggg gac agg gag gtg gat tct gat gcc tac tat gtc tac aga      624
Thr Ile Gly Asp Arg Glu Val Asp Ser Asp Ala Tyr Tyr Val Tyr Arg
        195                 200                 205 ctc cag gtg tca tcc atc aac gtc tct gtg aac gca gtg cag act gtg      672
Leu Gln Val Ser Ser Ile Asn Val Ser Val Asn Ala Val Gln Thr Val
    210                 215                 220 gtc cgc cag ggt gag aac atc acc ctc atg tgc att gtg atc ggg aat      720
Val Arg Gln Gly Glu Asn Ile Thr Leu Met Cys Ile Val Ile Gly Asn
225                 230                 235                 240 gag gtg gtc aac ttc gag tgg aca tac ccc cgc aaa gaa agt ggg cgg      768
Glu Val Val Asn Phe Glu Trp Thr Tyr Pro Arg Lys Glu Ser Gly Arg
                245                 250                 255 ctg gtg gag ccg gtg act gac ttc ctc ttg gat atg cct tac cac atc      816
Leu Val Glu Pro Val Thr Asp Phe Leu Leu Asp Met Pro Tyr His Ile
            260                 265                 270 cgc tcc atc ctg cac atc ccc agt gcc gag tta gaa gac tcg ggg acc      864
Arg Ser Ile Leu His Ile Pro Ser Ala Glu Leu Glu Asp Ser Gly Thr
        275                 280                 285 tac acc tgc aat gtg acg gag agt gtg aat gac cat cag gat gaa aag      912
Tyr Thr Cys Asn Val Thr Glu Ser Val Asn Asp His Gln Asp Glu Lys
    290                 295                 300 gcc atc aac atc acc gtg gtt gag agc ggc tac gtg cgg ctc ctg gga      960
Ala Ile Asn Ile Thr Val Val Glu Ser Gly Tyr Val Arg Leu Leu Gly
305                 310                 315                 320 gag gtg ggc aca cta caa ttt gct gag ctg cat cgg agc cgg aca ctg     1008
Glu Val Gly Thr Leu Gln Phe Ala Glu Leu His Arg Ser Arg Thr Leu
                325                 330                 335 cag gta gtg ttc gag gcc tac cca ccg ccc act gtc ctg tgg ttc aaa     1056
Gln Val Val Phe Glu Ala Tyr Pro Pro Pro Thr Val Leu Trp Phe Lys
            340                 345                 350 gac aac cgc acc ctg ggc gac tcc agc gct ggc gaa atc gcc ctg tcc     1104
Asp Asn Arg Thr Leu Gly Asp Ser Ser Ala Gly Glu Ile Ala Leu Ser
        355                 360                 365 acg cgc aac gtg tcg gag acc cgg tat gtg tca gag ctg aca ctg gtt     1152
Thr Arg Asn Val Ser Glu Thr Arg Tyr Val Ser Glu Leu Thr Leu Val
    370                 375                 380 cgc gtg aag gtg gca gag gct ggc cac tac acc atg cgg gcc ttc cat     1200
Arg Val Lys Val Ala Glu Ala Gly His Tyr Thr Met Arg Ala Phe His
385                 390                 395                 400 gag gat gct gag gtc cag ctc tcc ttc cag cta cag atc aat gtc cct     1248
Glu Asp Ala Glu Val Gln Leu Ser Phe Gln Leu Gln Ile Asn Val Pro
                405                 410                 415 gtc cga gtg ctg gag cta agt gag agc cac cct gac agt ggg gaa cag     1296
Val Arg Val Leu Glu Leu Ser Glu Ser His Pro Asp Ser Gly Glu Gln
            420                 425                 430 aca gtc cgc tgt cgt ggc cgg ggc atg ccc cag ccg aac atc atc tgg     1344
Thr Val Arg Cys Arg Gly Arg Gly Met Pro Gln Pro Asn Ile Ile Trp
        435                 440                 445
```

```
tct gcc tgc aga gac ctc aaa agg tgt cca cgt gag ctg ccg ccc acg      1392
Ser Ala Cys Arg Asp Leu Lys Arg Cys Pro Arg Glu Leu Pro Pro Thr
    450                 455                 460 ctg ctg ggg aac agt tcc gaa gag gag agc cag ctg gag act aac gtg      1440
Leu Leu Gly Asn Ser Ser Glu Glu Glu Ser Gln Leu Glu Thr Asn Val
465                 470                 475                 480 acg tac tgg gag gag gag cag gag ttt gag gtg gtg agc aca ctg cgt      1488
Thr Tyr Trp Glu Glu Glu Gln Glu Phe Glu Val Val Ser Thr Leu Arg
                485                 490                 495 ctg cag cac gtg gat cgg cca ctg tcg gtg cgc tgc acg ctg cgc aac      1536
Leu Gln His Val Asp Arg Pro Leu Ser Val Arg Cys Thr Leu Arg Asn
            500                 505                 510 gct gtg ggc cag gac acg cag gag gtc atc gtg gtg cca cac tcc ttg      1584
Ala Val Gly Gln Asp Thr Gln Glu Val Ile Val Val Pro His Ser Leu
        515                 520                 525 ccc ttt aag gtg gtg gtg atc tca gcc atc ctg gcc ctg gtg gtg ctc      1632
Pro Phe Lys Val Val Val Ile Ser Ala Ile Leu Ala Leu Val Val Leu
    530                 535                 540 acc atc atc tcc ctt atc atc ctc atc atg ctt tgg cag aag aag cca      1680
Thr Ile Ile Ser Leu Ile Ile Leu Ile Met Leu Trp Gln Lys Lys Pro
545                 550                 555                 560 cgt                                                                   1683
Arg

<210> SEQ ID NO 24
<211> LENGTH: 561
<212> TYPE: PRT
<213> ORGANISM: Homo sapiens

<400> SEQUENCE: 24

Met Arg Leu Pro Gly Ala Met Pro Ala Leu Ala Leu Lys Gly Glu Leu
1               5                   10                  15

Leu Leu Leu Ser Leu Leu Leu Leu Glu Pro Gln Ile Ser Gln Gly
                20                  25                  30

Leu Val Val Thr Pro Pro Gly Pro Glu Leu Val Leu Asn Val Ser Ser
            35                  40                  45

Thr Phe Val Leu Thr Cys Ser Gly Ser Ala Pro Val Val Trp Glu Arg
        50                  55                  60

Met Ser Gln Glu Pro Pro Gln Glu Met Ala Lys Ala Gln Asp Gly Thr
65                  70                  75                  80

Phe Ser Ser Val Leu Thr Leu Thr Asn Leu Thr Gly Leu Asp Thr Gly
                85                  90                  95

Glu Tyr Phe Cys Thr His Asn Asp Ser Arg Gly Leu Glu Thr Asp Glu
                100                 105                 110

Arg Lys Arg Leu Tyr Ile Phe Val Pro Asp Pro Thr Val Gly Phe Leu
            115                 120                 125

Pro Asn Asp Ala Glu Glu Leu Phe Ile Phe Leu Thr Glu Ile Thr Glu
        130                 135                 140

Ile Thr Ile Pro Cys Arg Val Thr Asp Pro Gln Leu Val Val Thr Leu
145                 150                 155                 160

His Glu Lys Lys Gly Asp Val Ala Leu Pro Val Pro Tyr Asp His Gln
                165                 170                 175

Arg Gly Phe Ser Gly Ile Phe Glu Asp Arg Ser Tyr Ile Cys Lys Thr
            180                 185                 190

Thr Ile Gly Asp Arg Glu Val Asp Ser Asp Ala Tyr Tyr Val Tyr Arg
        195                 200                 205
```

-continued

```
Leu Gln Val Ser Ser Ile Asn Val Ser Val Asn Ala Val Gln Thr Val
        210                 215                 220

Val Arg Gln Gly Glu Asn Ile Thr Leu Met Cys Ile Val Ile Gly Asn
225                 230                 235                 240

Glu Val Val Asn Phe Glu Trp Thr Tyr Pro Arg Lys Glu Ser Gly Arg
                245                 250                 255

Leu Val Glu Pro Val Thr Asp Phe Leu Leu Asp Met Pro Tyr His Ile
            260                 265                 270

Arg Ser Ile Leu His Ile Pro Ser Ala Glu Leu Glu Asp Ser Gly Thr
        275                 280                 285

Tyr Thr Cys Asn Val Thr Glu Ser Val Asn Asp His Gln Asp Glu Lys
    290                 295                 300

Ala Ile Asn Ile Thr Val Val Glu Ser Gly Tyr Val Arg Leu Leu Gly
305                 310                 315                 320

Glu Val Gly Thr Leu Gln Phe Ala Glu Leu His Arg Ser Arg Thr Leu
                325                 330                 335

Gln Val Val Phe Glu Ala Tyr Pro Pro Pro Thr Val Leu Trp Phe Lys
            340                 345                 350

Asp Asn Arg Thr Leu Gly Asp Ser Ser Ala Gly Glu Ile Ala Leu Ser
        355                 360                 365

Thr Arg Asn Val Ser Glu Thr Arg Tyr Val Ser Glu Leu Thr Leu Val
    370                 375                 380

Arg Val Lys Val Ala Glu Ala Gly His Tyr Thr Met Arg Ala Phe His
385                 390                 395                 400

Glu Asp Ala Glu Val Gln Leu Ser Phe Gln Leu Gln Ile Asn Val Pro
                405                 410                 415

Val Arg Val Leu Glu Leu Ser Glu Ser His Pro Asp Ser Gly Glu Gln
            420                 425                 430

Thr Val Arg Cys Arg Gly Arg Gly Met Pro Gln Pro Asn Ile Ile Trp
        435                 440                 445

Ser Ala Cys Arg Asp Leu Lys Arg Cys Pro Arg Glu Leu Pro Pro Thr
450                 455                 460

Leu Leu Gly Asn Ser Ser Glu Glu Glu Ser Gln Leu Glu Thr Asn Val
465                 470                 475                 480

Thr Tyr Trp Glu Glu Glu Gln Glu Phe Glu Val Val Ser Thr Leu Arg
                485                 490                 495

Leu Gln His Val Asp Arg Pro Leu Ser Val Arg Cys Thr Leu Arg Asn
            500                 505                 510

Ala Val Gly Gln Asp Thr Gln Glu Val Ile Val Val Pro His Ser Leu
        515                 520                 525

Pro Phe Lys Val Val Val Ile Ser Ala Ile Leu Ala Leu Val Val Leu
    530                 535                 540

Thr Ile Ile Ser Leu Ile Ile Leu Ile Met Leu Trp Gln Lys Lys Pro
545                 550                 555                 560

Arg

<210> SEQ ID NO 25
<211> LENGTH: 7
<212> TYPE: PRT
<213> ORGANISM: Homo sapiens

<400> SEQUENCE: 25

Asp Ser Arg Trp Glu Phe Pro
  1               5
```

<210> SEQ ID NO 26
<211> LENGTH: 9
<212> TYPE: PRT
<213> ORGANISM: Homo sapiens

<400> SEQUENCE: 26

Asp Ser Arg Trp Glu Phe Pro Arg Asp
 1               5

<210> SEQ ID NO 27
<211> LENGTH: 9
<212> TYPE: PRT
<213> ORGANISM: Homo sapiens

<400> SEQUENCE: 27

Asp Ser Arg Trp Lys Phe Pro Arg Asp
 1               5

<210> SEQ ID NO 28
<211> LENGTH: 9
<212> TYPE: PRT
<213> ORGANISM: Homo sapiens

<400> SEQUENCE: 28

Leu Gly Ala Cys Thr Lys Ser Gly Pro
 1               5

<210> SEQ ID NO 29
<211> LENGTH: 8
<212> TYPE: PRT
<213> ORGANISM: Homo sapiens

<400> SEQUENCE: 29

Val His Arg Asp Leu Ala Ala Arg
 1               5

<210> SEQ ID NO 30
<211> LENGTH: 8
<212> TYPE: PRT
<213> ORGANISM: Homo sapiens

<400> SEQUENCE: 30

Val His Arg Asn Leu Ala Ala Arg
 1               5

<210> SEQ ID NO 31
<211> LENGTH: 9
<212> TYPE: PRT
<213> ORGANISM: Homo sapiens

<400> SEQUENCE: 31

Leu Pro Val Lys Trp Met Ala Pro Glu
 1               5

<210> SEQ ID NO 32
<211> LENGTH: 9
<212> TYPE: PRT
<213> ORGANISM: Homo sapiens

<400> SEQUENCE: 32

Leu Pro Met Lys Trp Met Ala Pro Glu
 1               5

<210> SEQ ID NO 33

```
<211> LENGTH: 9
<212> TYPE: PRT
<213> ORGANISM: Homo sapiens

<400> SEQUENCE: 33

Leu Gly Ala Cys Met Lys Ser Gly Pro
 1               5
```